US008680090B2

(12) United States Patent
Johnson et al.

(10) Patent No.: US 8,680,090 B2
(45) Date of Patent: Mar. 25, 2014

(54) SULFONYL CONTAINING BENZOTHIAZOLE INHIBITORS OF ENDOTHELIAL LIPASE

(71) Applicant: Bristol-Myers Squibb Company, Princeton, NJ (US)

(72) Inventors: James A. Johnson, Pennington, NJ (US); Ji Jiang, West Windsor, NJ (US); Soong-Hoon Kim, Titusville, NJ (US); Zulan Pi, Pennington, NJ (US); Jennifer X. Qiao, Princeton, NJ (US); George O. Tora, Langhorne, PA (US); Tammy C. Wang, Lawrenceville, NJ (US); Heather Finlay, Skillman, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 13/936,311

(22) Filed: Jul. 8, 2013

(65) Prior Publication Data
US 2014/0011799 A1 Jan. 9, 2014

Related U.S. Application Data

(60) Provisional application No. 61/669,222, filed on Jul. 9, 2012, provisional application No. 61/770,672, filed on Feb. 28, 2013.

(51) Int. Cl.
| | | |
|---|---|---|
| *A61K 31/397* | (2006.01) | |
| *A61K 31/5377* | (2006.01) | |
| *A61K 31/496* | (2006.01) | |
| *A61K 31/506* | (2006.01) | |
| *A61K 31/4436* | (2006.01) | |
| *A61K 31/4535* | (2006.01) | |
| *A61K 31/4245* | (2006.01) | |
| *A61K 31/433* | (2006.01) | |
| *C07D 417/14* | (2006.01) | |
| *C07D 413/14* | (2006.01) | |
| *C07D 401/14* | (2006.01) | |
| *C07D 285/12* | (2006.01) | |
| *C07D 271/10* | (2006.01) | |

(52) U.S. Cl.
USPC ............. 514/210.21; 514/233.8; 514/254.04; 514/256; 514/321; 514/338; 514/363; 514/364; 544/135; 544/333; 544/368; 546/198; 546/269.1; 548/136; 548/143

(58) Field of Classification Search
USPC .......... 514/210.21, 233.8, 254.04, 256, 321, 514/338, 363, 364; 544/135, 333, 368; 546/198, 269.1; 548/136, 143
See application file for complete search history.

(56) References Cited

U.S. PATENT DOCUMENTS

| | | |
|---|---|---|
| 7,217,727 B2 | 5/2007 | Eacho et al. |
| 7,595,403 B2 | 9/2009 | Eacho et al. |
| 2006/0211755 A1 | 9/2006 | Eacho et al. |
| 2008/0287448 A1 | 11/2008 | Zoller et al. |
| 2009/0054478 A1 | 2/2009 | Zoller et al. |
| 2009/0076068 A1 | 3/2009 | Zoller et al. |
| 2011/0251386 A1 | 10/2011 | Masuda et al. |
| 2012/0253040 A1 | 10/2012 | Masuda et al. |

FOREIGN PATENT DOCUMENTS

| | | |
|---|---|---|
| WO | WO99/32611 | 7/1999 |
| WO | WO2004/093872 | 11/2004 |
| WO | WO2004/094393 | 11/2004 |
| WO | WO2004/094394 | 11/2004 |
| WO | WO2007/042178 | 4/2007 |
| WO | WO2007/110215 | 10/2007 |
| WO | WO2007/110216 | 10/2007 |
| WO | WO2009/123164 | 10/2009 |
| WO | WO2009/133834 | 11/2009 |
| WO | WO 2012/081563 | 6/2012 |
| WO | WO2012/815663 | 6/2012 |
| WO | WO2012/173099 | 12/2012 |

OTHER PUBLICATIONS

Bevilacqua, M.P. et al., "Selectins, Perspectives", J. Clinical Invest., vol. 91(2), pp. 379-387 (1993).
Bundgaard, H. et al., "Glycolamide Esters as Biolabile Prodrugs of Carboxylic Acid Agents: Synthesis, Stability, Bioconversion, and Physicochemical Properties", J. of Pharmaceutical Sciences, vol. 77(4), pp. 285-298 (1988).
Bundgaard, H., "(C) Means to Enhance Penetration (1) Prodrugs as a means to improve the delivery of peptide drugs", Advanced Drug Delivery Reviews, vol. 8, pp. 1-38 (1992).
deLemos, A.S. et al., "Identification of Genetic Variants in Endothelial Lipase in Persons With Elevated High-Density Lipoprotein Cholesterol", Circulation, vol. 106(11), pp. 1321-1326 (2002).
Group Writing Members, et al., Heart Disease and Stroke Statistics-2012 Update: A Report From the American Heart Association, Circulation, vol. 125, pp. e2-e220, (2011).

(Continued)

Primary Examiner — Samantha Shterengarts
(74) Attorney, Agent, or Firm — Jing G. Sun

(57) ABSTRACT

The present invention provides compounds of Formula (I):

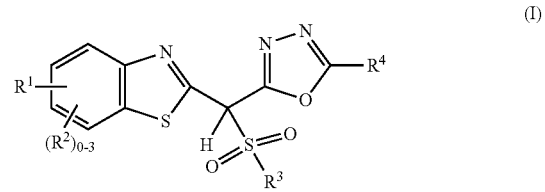

as defined in the specification and compositions comprising any of such novel compounds. These compounds are endothelial lipase inhibitors which may be used as medicaments.

12 Claims, No Drawings

(56) References Cited

OTHER PUBLICATIONS

Folkman, J. et al., "Angiogenesis, *Minireview*" The J. of Biological Chemistry, vol. 267(16), pp. 10931-10934, (1992).

Folkman, J. et al., "Angiogenic Factors", Science, vol. 235, pp. 442-447 (1987).

Gordon, D.J. et al., "High-Density Lipoprotein Cholesterol and Cardiovascular Disease" Circulation, vol. 79(1), pp. 8-15, (1989).

Gordon, D.J. et al., "High-Density Lipoprotein-The Clinical Implications of Recent Studies", New England J. Med., vol. 321(19), pp. 1311-1316 (1989).

Hirata, Ken-ichi, et al., "Cloning of a Unique Lipase from Endothelial Cells Extends the Lipase Gene Family", The J. of Biological Chemistry, vol. 274(20), pp. 14170-14175 (1999).

Janssens, S.P. et al., "Cloning and Expression of a cDNA Encoding Human Endothelium-deriving Relaxing Factor/Nitric Oxide Synthase", The J. of Biological Chemistry, Vo. 267(21), pp. 14519-14522 (1992).

Jaye, M. et al., "A novel endothelial-derived lipase that modulates HDL metabolism", Nature Genetics, vol. 21, pp. 424-428 (1999).

Jin, W. et al., "Lipases and HDL metabolism", *TRENDS* in Endocrinology & Metabolism, vol. 13(4), pp. 174-178 (2002).

Kakeya, N. et al., "Studies on Prodrugs of Cephalosporins. I.[1]) Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxlyic Acid", Chem. Pharm. Bulletin, vol. 32(2), pp. 692-698 (1984).

Lamas, S. et al., "Endothelial nitric oxide synthase: Molecular cloning and characterization of a distinct constitutive enzyme isoform", PNAS, vol. 89(14), pp. 6348-6352, (1992).

Lüscher, T.F. et al., "Endothelium-Derived Contracting Factors", Hypertension, vol. 19(2), pp. 117-130 (1992).

McCoy, M.G. et al., "Characterization of the lipolytic activity of endothelial lipase", Journal of Lipid Research, vol. 43, pp. 921-929 (2002).

Ross, R., "The pathogenesis of atherosclerosis: a perspective for the 1990s" Nature, vol. 362, pp. 801-809 (1993).

Strauss, Juliane G. et al., "Endothelial cell-derived lipase mediates uptake and binding of high-density lipoprotein (HDL) particles and the selective uptake of HDL-associated cholesterol esters independent of its enzymatic activity", Biochem. J., vol. 368, pp. 69-79 (2002).

Williams, T.J. et al., "Adhesion Molecules Involved in the MIcrovascular Inflammatory Response", Am Rev Respir Dis., vol. 146, pp. S45-S50 (1992).

Winum, J. et al., "*N*-(*tert*-Butoxycarbonyl)-*N*-[44-(dimethylazaniumylidene)-1,4-dihydropyridina-1-ylsulfonyl]azanide: A New Sulfamoylating Agent. Structure and Reactivity toward Amines", Organic Letters, vol. 3(14), pp. 2241-2243 (2001).

Wong, H. et al., "The lipase gene family" thematic review. J. of Lipid Research, vol. 43, pp. 993-999 (2002).

Yanagisawa, M. et al., "A novel potent vasoconstrictor peptide produced by vascular endothelial cells", Nature, vol. 332(6163), pp. 411-415 (1988).

U.S. Appl. No. 13/944,921, filed Jul. 18, 2013, Finlay, Heather et al.

SULFONYL CONTAINING BENZOTHIAZOLE INHIBITORS OF ENDOTHELIAL LIPASE

FIELD OF THE INVENTION

The present invention provides novel sulfonyl containing benzothiazole compounds and analogues, which are endothelial lipase (EL) inhibitors, compositions containing them, and methods of using them, for example, for the treatment and/or prophylaxis of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, R., Nature, 362(6423):801-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon, D. J. et al., N. Engl. J. Med., 321(19):1311-1316 (1989)).

The metabolism of HDL is influenced by several members of the phospholipase and triacylglycerol (TG) lipase family of proteins, which hydrolyze triglycerides, phospholipids (PL), and cholesteryl esters (CE), generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin, W. et al., Trends Endocrinol. Metab., 13(4):174-178 (2002); Wong, H. et al., J. Lipid Res., 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata, K. et al., J. Biol. Chem., 274(20):14170-14175 (1999); Jaye, M. et al., Nat. Genet., 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy, M. G. et al., J. Lipid Res., 43:921-929 (2002)). Overexpression of the human endothelial lipase gene in the livers of mice markedly reduces plasma concentrations of HDL cholesterol and its major protein, apolipoprotein A-I (apoA-I) (Jaye, M. et al., Nat. Genet., 21:424-428 (1999)).

Various types of compounds have been reported to modulate the expression of endothelial lipase, for example, 3-oxo-1,3-dihydro-indazole-2-carboxamides (WO 2004/093872, US 2006/0211755A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448A1) and imidazopyridin-2-one derivatives (WO 2007/110215, US 2009/0076068A1), and azolopyridin-3-one derivatives (WO 2007/110216, US 2009/0054478A1) by Sanofi-Aventis; heterocyclic derivatives (WO 2009/123164), keto-amide derivatives (WO 2009/133834), acetic acid amide derivatives (WO20/10/44441, US 2011/0251386A1), oxadiazole derivatives (WO 2011074560, US2012253040 A1), benzothiazole and azabenzothiazole derivatives (WO 2012081563) and amino derivatives (WO2012173099) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of inhibiting the activity of lipases, particularly endothelial lipase, that would constitute effective treatments to the diseases or disorders associated with the activity of such lipases.

SUMMARY OF THE INVENTION

The present disclosure provides sulfonyl containing benzothiazole compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of dyslipidemias and the sequelae thereof.

The compounds of the invention may be used in therapy.

The compounds of the invention may be used for the manufacture of a medicament for the treatment and/or prophylaxis of dyslipidemias and the sequelae thereof.

The compounds of the invention can be used alone, in combination with other compounds of the present invention, or in combination with one or more, preferably one to two, and other agent.

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

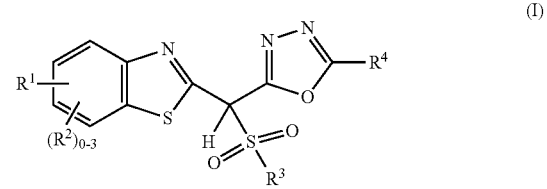

or a stereoisomer, a tautomer, a pharmaceutically acceptable salt, or a solvate thereof, wherein:

$R^1$ is independently selected from: halogen, CN, —CO—$R^j$, —CONH—$(CH_2)_m$—$R^j$, phenyl substituted with 0-3 $R^a$, and a 5- to 6-membered heterocycle comprising carbon atoms and 1-4 heteroatoms selected from N, $NR^c$, O, and $S(O)_p$; wherein heterocycle is substituted with 0-3 $R^{a1}$;

$R^2$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CN, $NH_2$, $NO_2$, $NH(C_{1-4}$ alkyl), $N(C_{1-4}$ alkyl)$_2$, $CO_2H$, $CO_2(C_{1-4}$ alkyl), and $CONH_2$;

$R^3$ is independently selected from: $C_{1-6}$ alkyl substituted with 0-2 $R^7$, $C_{2-6}$ alkenyl, $C_{1-6}$ haloalkyl, $C_{1-6}$ alkoxy, —$(CH_2)_m$—$(O)_n$—$(C_{3-6}$ carbocycle substituted with 0-3 $R^b$), —$(CH_2)_m$—$(O)_n$-(5- to 6-membered heterocycle comprising carbon atoms and 1-4 heteroatoms selected from N, $NR^c$, O, and $S(O)_p$; wherein said heterocycle is substituted with 0-2 $R^b$);

$R^4$ independently selected from:

$R^5$ is independently selected from: $CO_2(C_{1-4}$ alkyl), $NH_2$, $NH(C_{1-4}$ alkyl), $N(C_{1-4}$ alkyl)$_2$, $CONH_2$, $CONH(C_{1-4}$ alkyl), $CON(C_{1-4}$ alkyl)$_2$, $NHCOR^8$, $NHCONH(C_{1-4}$ alkyl), $SO_2R^9$, $NHSO_2NH_2$, $SO_2NHCO(C_{1-4}$ alkyl), $NHSO_2(C_{1-4}$ alkyl), $NHSO_2NHCO_2(C_{1-4}$ alkyl), $NHSO_2NHR^j$, $SO_2NHSO_2(C_{1-4}$ haloalkyl), $N(C_{1-4}$ alkyl)$SO_2NH_2$, $N(CO_2C_{1-4}$ alkyl)$SO_2$ $(C_{1-4}$ alkyl), $CONH(C_{3-6}$ cycloalkyl),

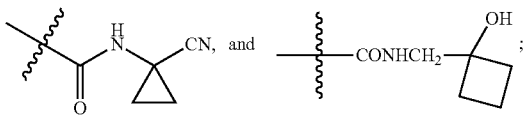

$R^6$ is independently selected from:

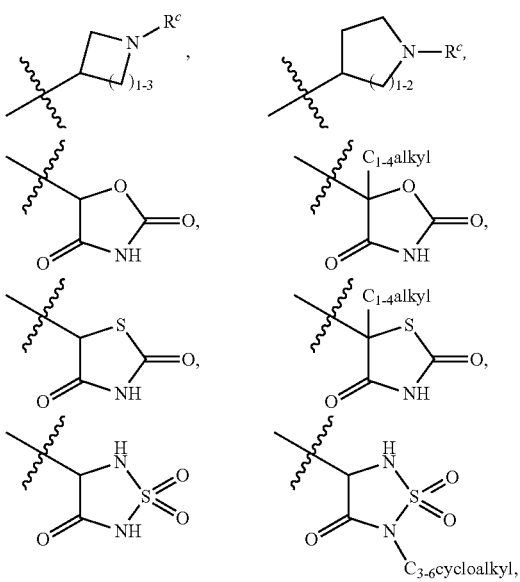

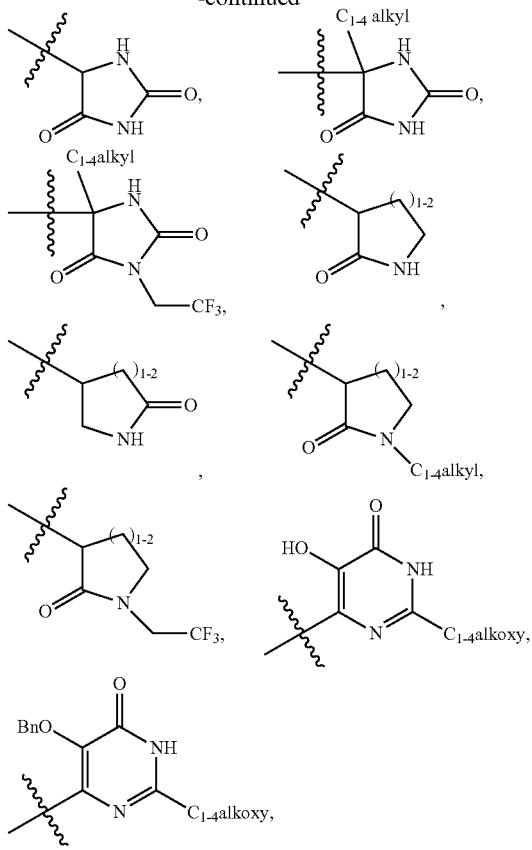

phenyl and a 5- to 6-membered heteroaryl comprising carbon atoms and 1-4 heteroatoms selected from N, $NR^c$, O, and $S(O)_p$; wherein said phenyl and heteroaryl are is substituted with 0-2 $R^f$;

$R^7$ is independently selected from: halogen, $C_{1-4}$ alkoxy, $C_{1-4}$ haloalkyl, $C_{1-4}$ haloalkoxy, $NH_2$, $CO_2H$, $CO_2(C_{1-4}$ alkyl), $SO_3H$, $CONHR^d$, $NHCONHR^d$, $NHCO_2R^d$,

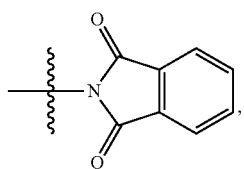

and 5- to 6-membered heterocycle comprising carbon atoms and 1-4 heteroatoms selected from N, $NR^g$, O, and $S(O)_p$;

$R^8$ is, independently selected from: $C_{1-4}$ alkyl, —$(CH_2)_{0-3}C_{1-4}$ alkoxy, —$CH(OH)(C_{1-4}$ alkyl), —$CH(OCON(C_{1-4}$ alkyl)$_2)(C_{1-4}$ alkyl), and —$(CH_2)_{1-3}CH(OH)(C_{1-4}$ alkyl);

$R^9$ is independently selected from: OH, $C_{1-6}$ alkyl, $C_{2-6}$ alkenyl, $NH_2$, $NH(C_{1-6}$ alkyl), $NH(C_{2-6}$ alkenyl), $NH(C_{1-4}$ haloalkyl), NHPh, and phenyl substituted with 0-2 halogens;

$R^a$ is, independently at each occurrence, selected from: halogen, $C_{1-6}$ alkyl substituted with 0-1 $R^f$, $C_{1-4}$ alkoxy substituted with 0-1 $R^f$, $C_{1-6}$ haloalkyl, $C_{1-6}$ haloalkoxy, OH, CN, $NO_2$, $CO_2H$, $CO_2(C_{1-4}$ alkyl), $NR^gR^h$, $CONR^gR^h$, $CONR^gR^j$, $NHCOR^i$, $NHCO_2R^i$, $SO_2NR^gR^h$, —$(O)_n$—$(CH_2)_t$—$R^j$, and —CO—$R^j$;

$R^{a1}$ is, independently selected from: =O and $R^a$;

$R^b$ is, independently at each occurrence, selected from: halogen, $C_{1-4}$ alkyl, $C_{1-4}$ alkoxy, $C_{1-4}$ haloalkyl, $C_{1-4}$ haloalkoxy, OH, CN, $NH_2$, $NO_2$, $NH(C_{1-4}$ alkyl), $N(C_{1-4}$ alkyl)$_2$, $CO_2H$, $CO_2(C_{1-4}$ alkyl), $SO_2(C_{1-4}$ alkyl), $SO_2NH_2$, $CONH_2$, and $CONH(C_{1-4}$ alkyl);

$R^c$ is, independently at each occurrence, selected from: H, $C_{1-6}$ alkyl substituted with 0-1 $R^e$, $CO(C_{1-4}$ alkyl), $CO_2(C_{1-4}$ alkyl), $CO_2Bn$, $CO_2Bn$, —$(CH_2)_t$-piperidinyl, —$(CH_2)_t$-morpholinyl, —$(CH_2)_t$-piperazinyl, pyrimidinyl and —$(CH_2)_t$—($C_{3-6}$ carbocycle substituted with 0-2 $R^e$);

$R^d$ is, independently at each occurrence, selected from: $C_{1-6}$ alkyl and —$(CH_2)_t$-(phenyl substituted with 0-2 $R^e$);

$R^e$ is, independently at each occurrence, selected from: halogen, $C_{1-4}$ alkyl, $C_{1-4}$ alkoxy, $C_{1-4}$ haloalkyl, and $C_{1-4}$ haloalkoxy;

$R^f$ is, independently at each occurrence, selected from: OH, halogen, $C_{1-4}$ alkyl, $C_{1-4}$ alkoxy, $C_{1-4}$ haloalkyl, and $C_{1-4}$ haloalkoxy;

$R^g$ is, independently at each occurrence, selected from: H and $C_{1-4}$ alkyl;

$R^h$ is, independently at each occurrence, selected from: H, $C_{1-6}$ haloalkyl and $C_{1-6}$ alkyl substituted with 0-1 $R^f$;

$R^i$ is, independently at each occurrence, selected from: $C_{1-4}$ haloalkyl and $C_{1-4}$ alkyl substituted with 0-1 $R^f$;

$R^j$ is, independently at each occurrence: $C_{3-6}$ carbocycle or a 4- to 6-membered heterocycle comprising carbon atoms and 1-4 heteroatoms selected from N, $NR^g$, O, and $S(O)_p$; wherein said carbocycle and heterocycle are substituted with 0-2 $R^f$;

m and t are, independently at each occurrence, selected from 0, 1, 2, and 3;

n is, independently at each occurrence, selected from 0 and 1;

p is, independently at each occurrence, selected from 0, 1, and 2; and s is, independently at each occurrence, selected from 1, 2, and 3.

In a second aspect, the present invention includes a compound of Formula (IIa) or (IIb):

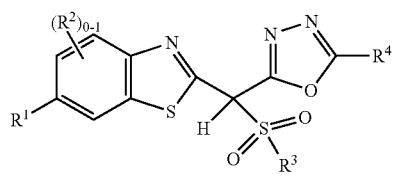

(IIa)

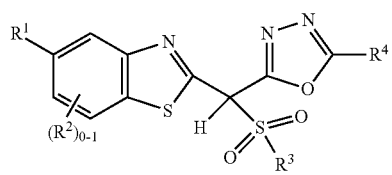

(IIb)

or a stereoisomer, a tautomer, a pharmaceutically acceptable salt, or a solvate thereof, within the scope of the first aspect; wherein:

$R^2$ is independently selected from: halogen, $C_{1-4}$ alkyl, $C_{1-4}$ alkoxy and $C_{1-4}$ haloalkyl.

In a third aspect, the present invention includes a compound of Formula (IIIa) or (IIIb):

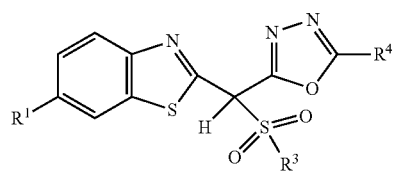

(IIIa)

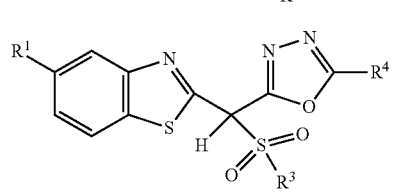

(IIIb)

or a stereoisomer, a tautomer, a pharmaceutically acceptable salt, or a solvate thereof, within the scope of any of the above aspects.

In a fourth aspect, the present invention includes a compound of Formula (I), (IIa), (IIb), (IIIa) or (IIIb), or a stereoisomer, a tautomer, a pharmaceutically acceptable salt, or a solvate thereof, within the scope of any of the above aspects, wherein:

$R^1$ is independently selected from: phenyl substituted with 0-2 $R^a$, pyridyl substituted with 0-2 $R^a$, pyrimidinyl substituted with 0-2 $R^a$,

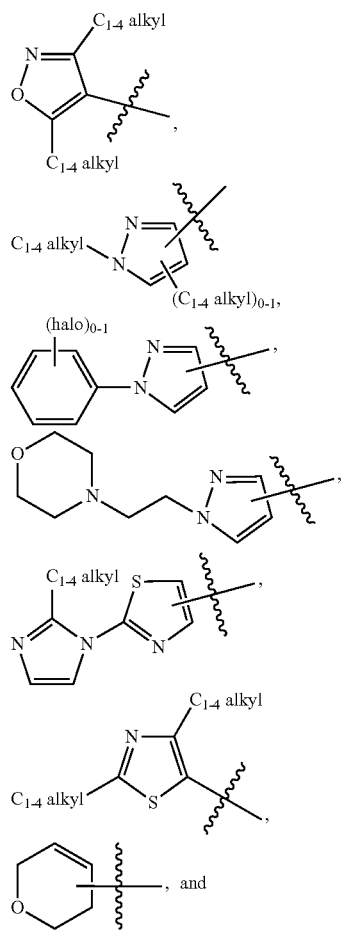

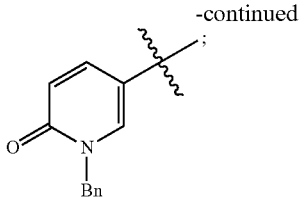
R³ is independently selected from: $C_{1-4}$ alkyl substituted with 0-2 R⁷, $C_{2-4}$ alkenyl, $C_{1-4}$ haloalkyl, —(CH₂)$_{0-1}$—($C_{3-6}$ cycloalkyl), —(CH₂)$_{0-3}$—(O)$_{0-1}$-(phenyl substituted with 0-2 R$^b$), —(CH₂)$_{0-3}$—(O)$_{0-1}$-(pyridyl substituted with 0-2 R$^b$),
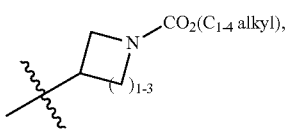
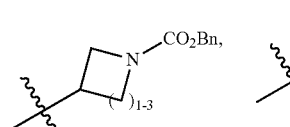 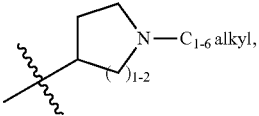
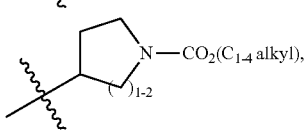
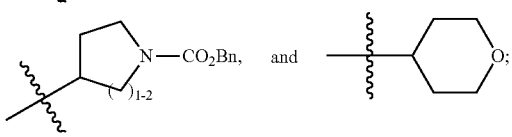
R⁴ independently selected from:
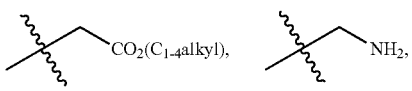
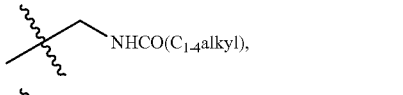
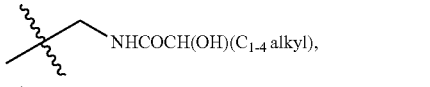
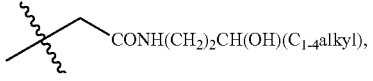
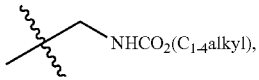
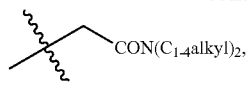
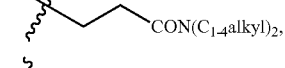
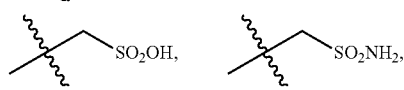 
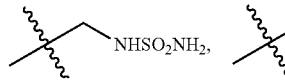
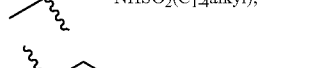
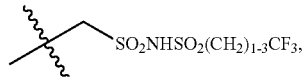
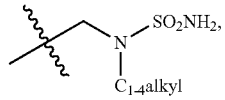
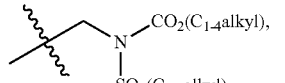
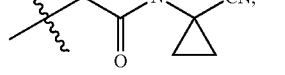
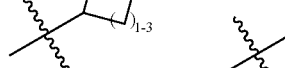
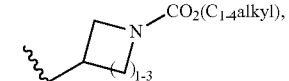
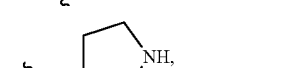
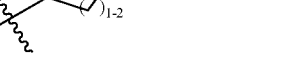

-continued

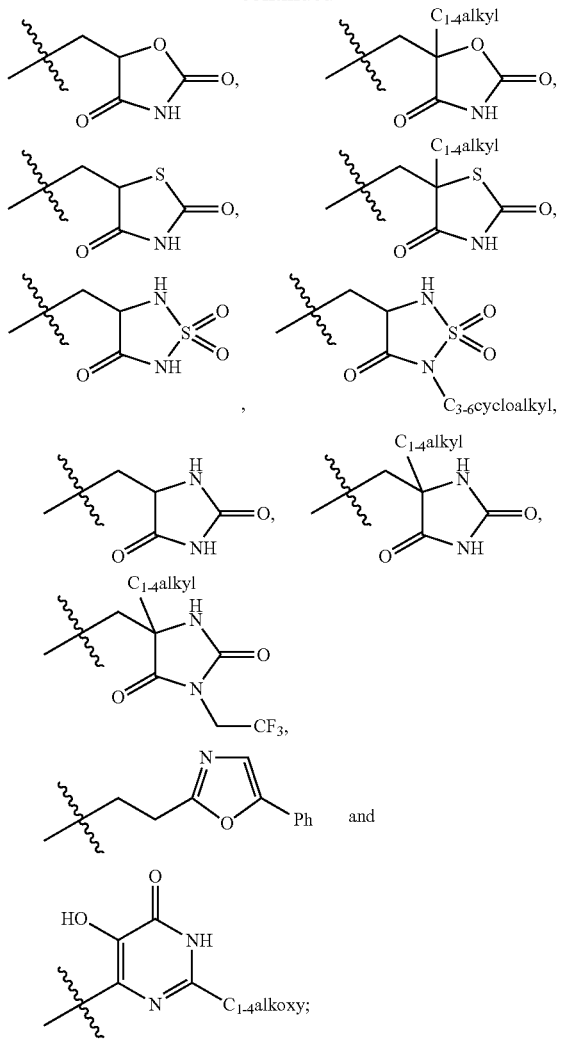

$R^7$ is independently selected from: $NH_2$, $C_{1-4}$ alkoxy, $C_{1-4}$ haloalkyl, $CO_2(C_{1-4}$ alkyl), NHCONHBn, NHCO$_2$Bn,

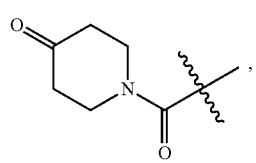

$R^a$ is, independently at each occurrence, selected from: OH, halogen, $C_{1-4}$ alkyl, $C_{1-4}$ alkoxy, $C_{1-4}$ haloalkyl, $CO_2H$, $CON(C_{1-4}$ alkyl)$_2$, $CONH(CH_2)_2OH$, $CONH(CH_2)_2O(C_{1-4}$ alkyl), $CONH(C_{1-4}$ haloalkyl), benzoxy,

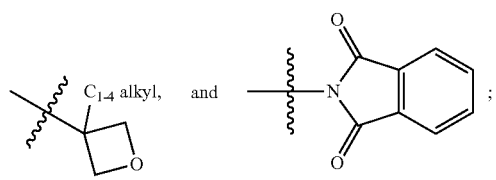

-continued

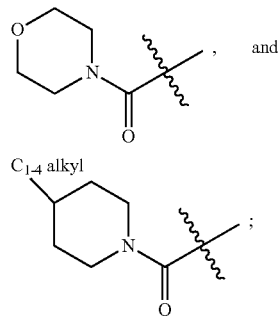

$R^b$ is independently selected from: halogen, $C_{1-4}$ alkyl, $C_{1-4}$ alkoxy, and $C_{1-4}$ haloalkyl.

In a fifth aspect, the present invention includes a compound of Formula (I), (IIa), (IIb), (IIIa) or (IIIb), or a stereoisomer, a tautomer, a pharmaceutically acceptable salt, or a solvate thereof, within the scope of any of the above aspects, wherein:

$R^1$ independently selected from: Ph, 3-halo-Ph, 4-halo-Ph, 4-$C_{1-4}$ haloalkyl-Ph, pyrimidinyl,

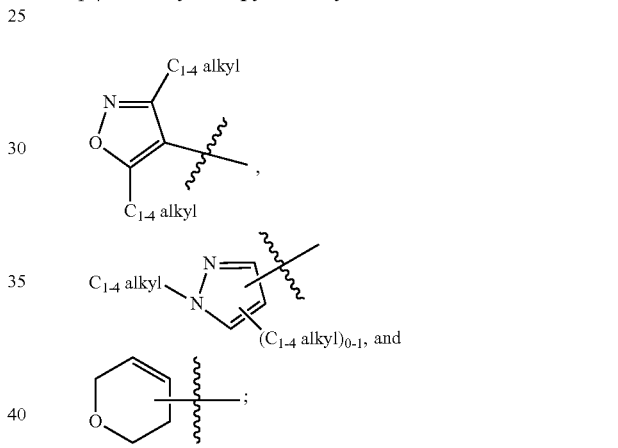

$R^3$ independently selected from: $C_{1-4}$ alkyl substituted with 0-2 $R^7$, $C_{2-4}$ alkenyl, $-(CH_2)_{0-3}-C_{3-6}$ cycloalkyl, $-(CH_2)_{1-3}-(O)_{0-1}$-(phenyl substituted with 0-2 $R^b$),

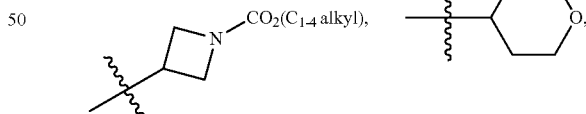

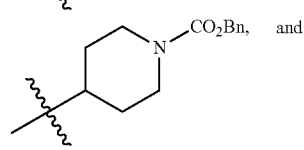

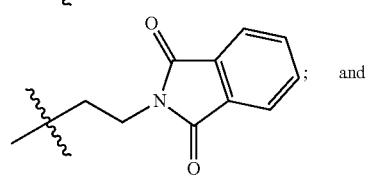

$R^4$ independently selected from:

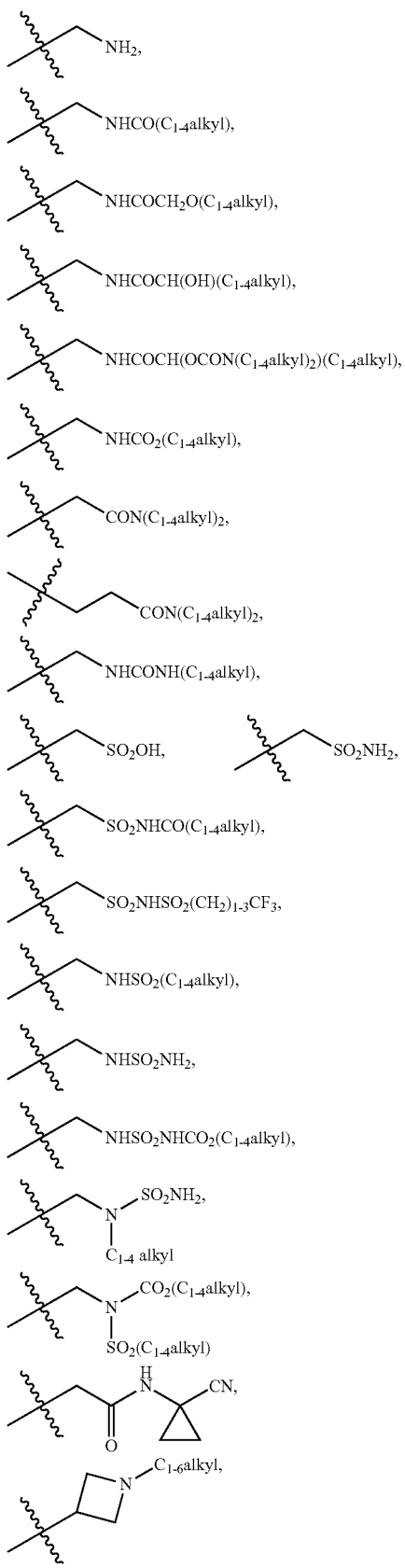
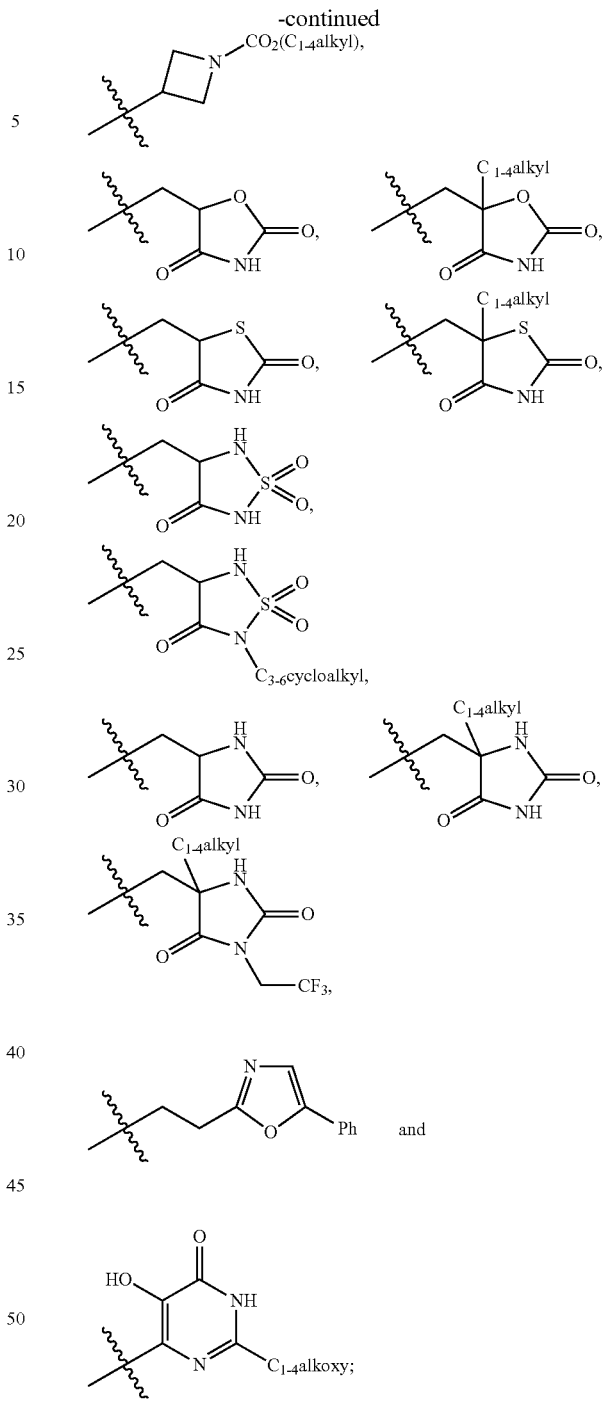

$R^b$ is independently selected from: halogen, $C_{1-4}$ alkyl, $C_{1-4}$ alkoxy, and $C_{1-4}$ haloalkyl; and $R^7$ is independently selected from: OH, $NH_2$, $C_{1-4}$ alkoxy, $C_{1-4}$ haloalkyl, $CO_2H$, $CO_2(C_{1-4}$ alkyl), and $NHCO_2Bn$.

In a sixth aspect, the present invention includes a compound of Formula (I), (IIa), (IIb), (IIIa) or (IIIb), or a stereoisomer, a tautomer, a pharmaceutically acceptable salt, or a solvate thereof, within the scope of any of the above aspects, wherein:

$R^1$ independently selected from: Ph, 4-F-Ph, 3-Cl-Ph, 4-Cl-Ph, 4-$CF_3$-Ph, pyrimidin-5-yl,

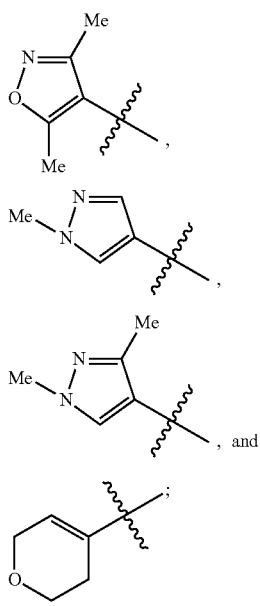
R³ is independently selected from: Me, Et, Pr, i-Pr, i-Bu, —CH₂—CH=CH₂, —CH₂CH(OH)Me, —CH₂CH(OH)CH₂OH, —(CH₂)₂OMe, —(CH₂)₂₋₃CF₃, —(CH₂)₂NH₂, —(CH₂)₂CO₂H, —(CH₂)₂CO₂Me, —(CH₂)₂NHCO₂Bn, cyclopropyl, cyclopropylmethyl, cyclopentyl, cyclohexylmethyl, Bn, 2-Me-Bn, 3-Me-Bn, 2-F-Bn, 3-F-Bn, 4-F-Bn, 3-Cl-Bn, 4-Cl-Bn, 3-Br-Bn, 3-CF₃-Bn, 4-CF₃-Bn, 3,4-diCl-Bn, 3,5-diCl-Bn,
3—CF₃—5—CF₃—Bn,
—CH₂CH₂CH₂Ph,
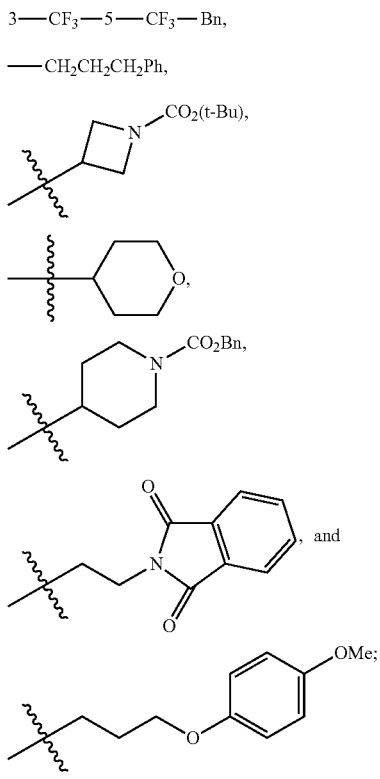
R⁴ is independently selected from:
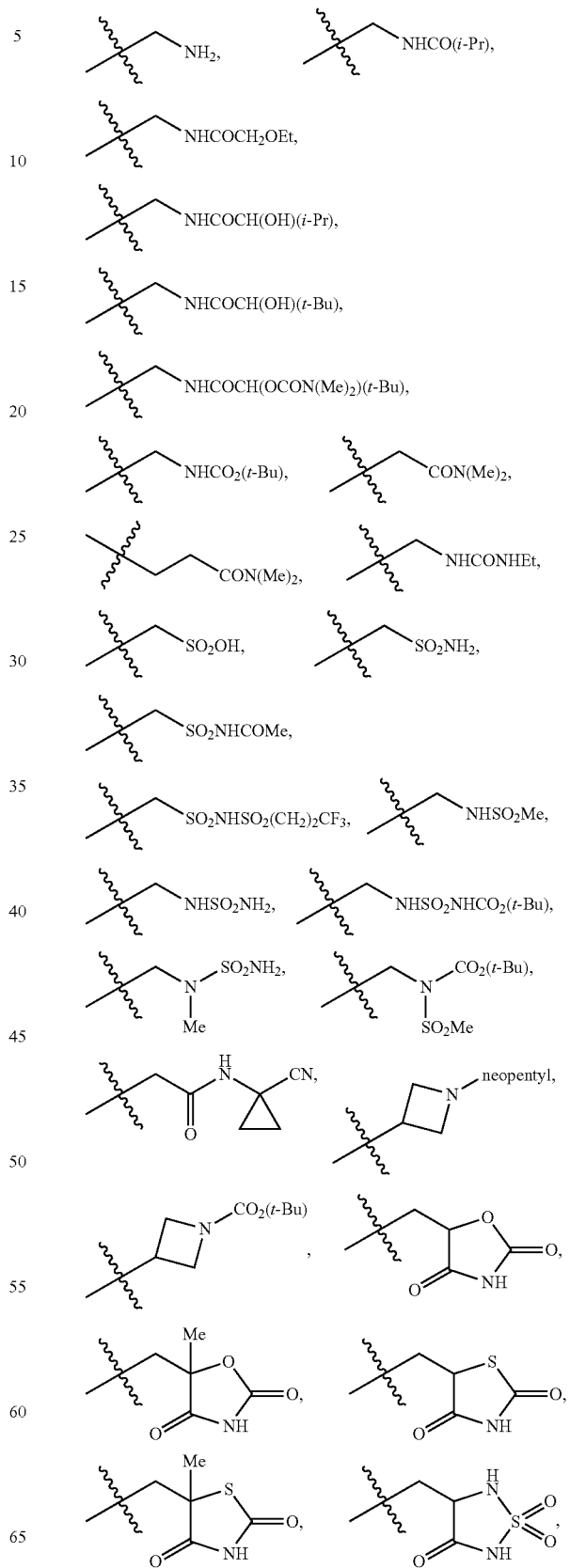

-continued

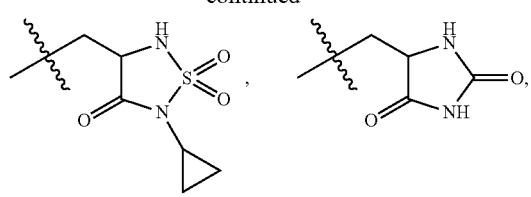

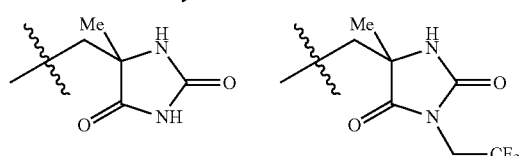

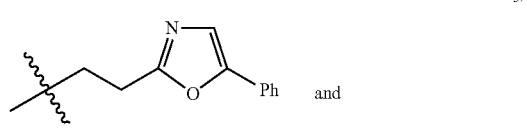

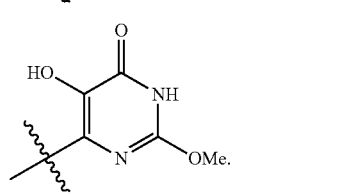

-continued

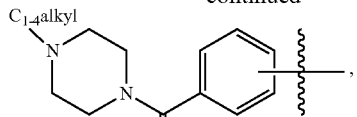

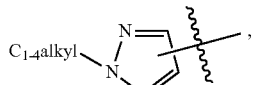

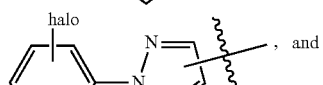

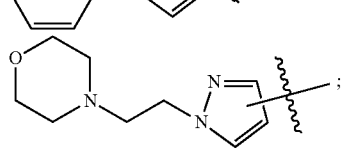

In a seventh aspect, the present invention includes a compound of Formula (I), (IIa), (IIb), (IIIa) or (IIIb), or a stereoisomer, a tautomer, a pharmaceutically acceptable salt, or a solvate thereof, within the scope of any of the first, second, third and fourth aspects, wherein:

$R^1$ is independently selected from: 3-CO$_2$H-Ph, 3-CONH(CH$_2$)$_2$OH-Ph, 3-CONH(CH$_2$)$_2$O(C$_{1-4}$ alkyl)-Ph, 3-halo-4-halo-Ph, 3-halo-5-halo-Ph, 3-halo-4-CON(C$_{1-4}$ alkyl)-2-Ph, 6-OH-pyrid-3-yl, 6-halo-pyrid-3-yl, 2-C$_{1-4}$ alkoxy-pyrid-4-yl, 2-halo-6-halo-pyrid-4-yl,

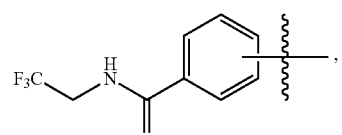

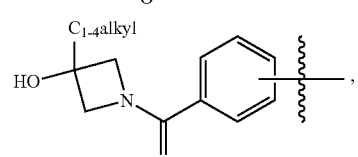

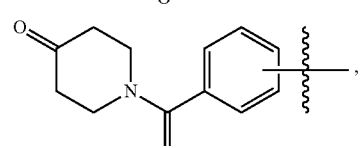

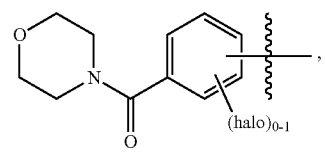

$R^3$ is independently selected from: C$_{1-4}$ alkyl substituted with 0-1 R$^7$, C$_{2-4}$ alkenyl, —CH$_2$—C$_{3-6}$ cycloalkyl, Bn, (6-halo-pyrid-3-yl)methyl, (6-CF$_3$-pyrid-3-yl)methyl, and

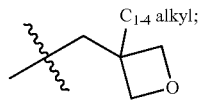

$R^4$ is independently selected from:

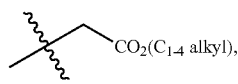 CO$_2$(C$_{1-4}$ alkyl),

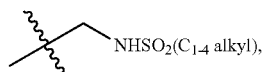 NHSO$_2$(C$_{1-4}$ alkyl),

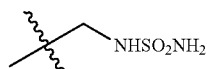 NHSO$_2$NH$_2$,

NHSO$_2$NHCO$_2$(C$_{1-4}$ alkyl), and

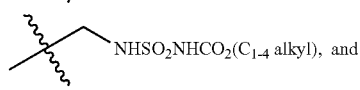 CONH(C$_{3-6}$ cycloalkyl);

and $R^7$ is independently selected from: NH$_2$, C$_{1-4}$ alkoxy, C$_{1-4}$ haloalkyl, and NHCO$_2$Bn.

In an eighth aspect, the present invention includes a compound of Formula (I), (IIa), (IIb), (IIIa) or (IIIb), or a stereoisomer, a tautomer, a pharmaceutically acceptable salt, or a solvate thereof, within the scope of any of the first, second, third, fourth and seventh aspects, wherein:

$R^1$ is independently selected from: 3-CO$_2$H-Ph, 3-CONH(CH$_2$)$_2$OH-Ph, 3-CONH(CH$_2$)$_2$OMe-Ph, 3-CONHCH$_2$CF$_3$-Ph, 3-F-4-Cl-Ph, 3-Cl-4-F-Ph, 3-Cl-4-Cl-Ph, 3-Cl-5-F-Ph, 3-Cl-5-Cl-Ph, 3-Cl-4-CON(Me)-2-Ph, 6-OH-pyrid-3-yl, 6-F-pyrid-3-yl, 2-OMe-pyrid-4-yl, 2,6-diF-pyrid-4-yl,

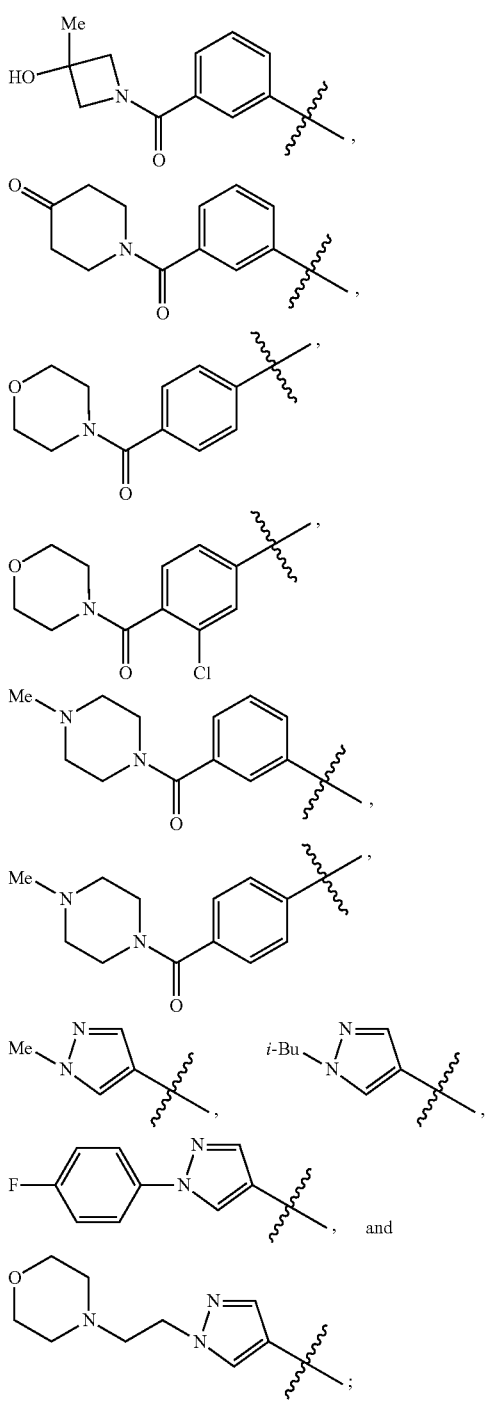

R³ is independently selected from: Me, —CH₂—CH═CH₂, —(CH₂)₂OMe, —(CH₂)₂NH₂, —(CH₂)₂CF₃, —(CH₂)₂NHCO₂Bn, cyclopropylmethyl, Bn, (6-F-pyrid-3-yl)methyl, (6-CF₃-pyrid-3-yl)methyl, and R⁴ is independently selected from:

$CO_2$(t-Bu), $NHSO_2$Me, $NHSO_2NH_2$, $NHSO_2NHCO_2$(t-Bu), and

CONH—cyclopentyl.

In a ninth aspect, the present invention includes a compound of Formula (I), (IIa), (IIb), (IIIa) or (IIIb), or a stereoisomer, a tautomer, a pharmaceutically acceptable salt, or a solvate thereof, within the scope of any of the first, second, third and fourth aspects, wherein:

R¹ is independently selected from: 4-OBn-Ph, 4-CO₂Bn-Ph, 2-halo-pyrid-4-yl, 6-halo-pyrid-3-yl, 2-CN-pyrid-4-yl, —CO-morpholinyl,

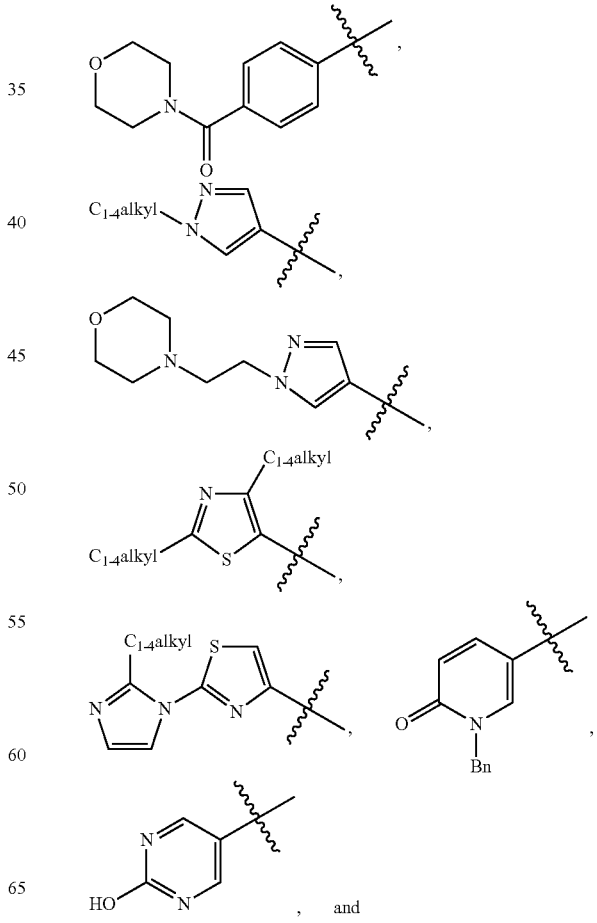

-continued

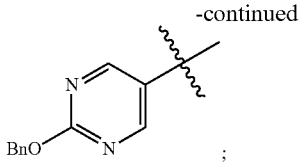

$R^3$ is independently selected from: $C_{1-4}$ alkyl substituted with 0-1 $R^7$, Bn and

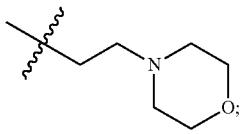 [SMILES: *CCN1CCOCC1]

$R^4$ is independently selected from:

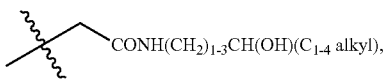CONH(CH$_2$)$_{1-3}$CH(OH)(C$_{1-4}$ alkyl),

CONH(CH$_2$)$_3$O(C$_{1-4}$ alkyl),

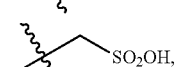SO$_2$OH,

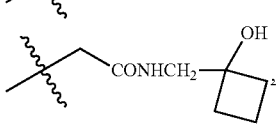

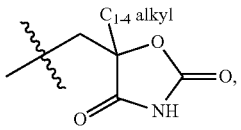

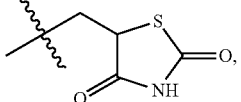

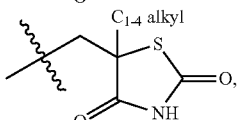

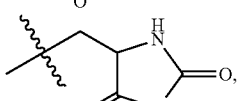

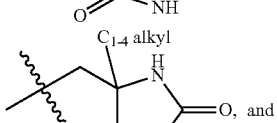, and

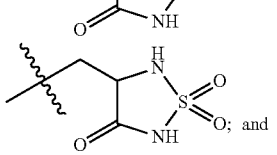; and $R^7$ is independently selected from: NH$_2$ and C$_{1-4}$ haloalkyl.

In a tenth aspect, the present invention includes a compound of Formula (I), (IIa), (IIb), (IIIa) or (IIIb), or a stereoisomer, a tautomer, a pharmaceutically acceptable salt, or a solvate thereof, within the scope of any of first, second, third, fourth and ninth aspects, wherein:

$R^1$ is independently selected from: 4-OBn-Ph, 4-CO$_2$Bn-Ph, 2-F-pyrid-4-yl, 6-F-pyrid-3-yl, 2-CN-pyrid-4-yl, —CO-morpholinyl,

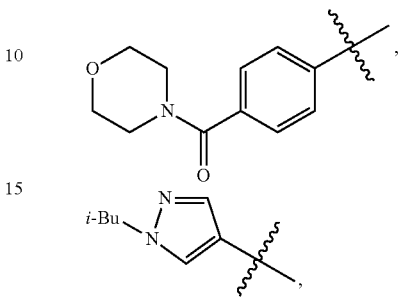

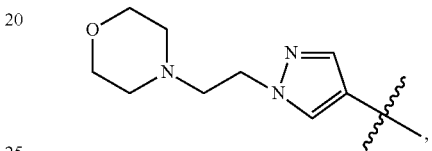

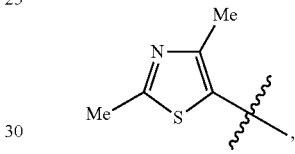

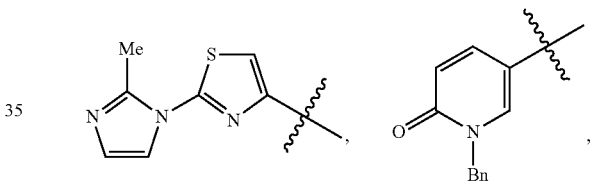

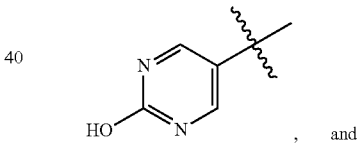

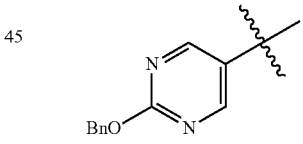, and

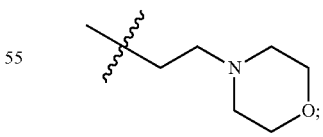;

$R^3$ is independently selected from: Me, —(CH$_2$)$_2$NH$_2$, —(CH$_2$)$_2$CF$_3$, Bn, and

;

and $R^4$ is independently selected from:

CONH(CH$_2$)$_{1-2}$CH(OH)Me,

-continued

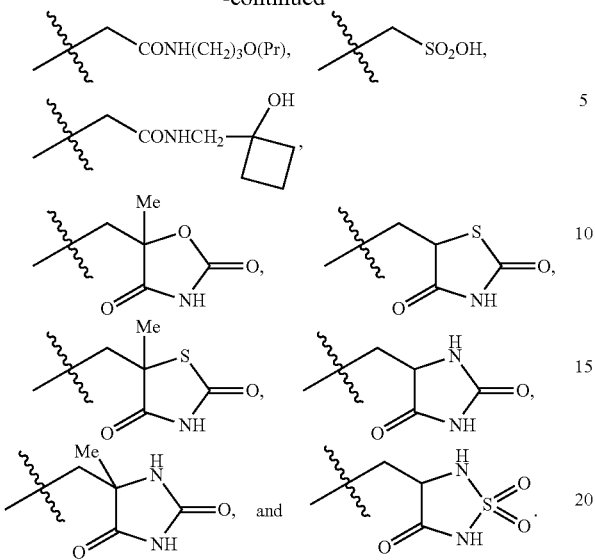

In another aspect, the present invention provides a compound of Formula (I), or a stereoisomer, a tautomer, a pharmaceutically acceptable salt, or a solvate thereof, wherein:

$R^1$ is independently selected from: halogen, CN, —CO—$R^j$, —CONH—$(CH_2)_m$—$R^j$, phenyl substituted with 0-3 $R^a$, and a 5- to 6-membered heterocycle comprising carbon atoms and 1-4 heteroatoms selected from N, $NR^c$, O, and $S(O)_p$; wherein heterocycle is substituted with 0-3 $R^{a1}$;

$R^2$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CN, $NH_2$, $NO_2$, $NH(C_{1-4}$ alkyl), $N(C_{1-4}$ alkyl$)_2$, $CO_2H$, $CO_2(C_{1-4}$ alkyl), and $CONH_2$;

$R^3$ is independently selected from: $C_{1-6}$ alkyl substituted with 0-2 $R^7$, $C_{2-6}$ alkenyl, $C_{1-6}$ haloalkyl, $C_{1-6}$ alkoxy, —$(CH_2)_m$—$(O)_n$—$(C_{3-6}$ carbocycle substituted with 0-3 $R^b$), —$(CH_2)_m$—$(O)_n$-(5- to 6-membered heterocycle comprising carbon atoms and 1-4 heteroatoms selected from N, $NR^c$, O, and $S(O)_p$; wherein said heterocycle is substituted with 0-2 $R^b$);

$R^4$ independently selected from:

$R^5$ is independently selected from: $CO_2(C_{1-4}$ alkyl), $NH_2$, $NH(C_{1-4}$ alkyl), $N(C_{1-4}$ alkyl$)_2$, $CONH_2$, $CONH(C_{1-4}$ alkyl substituted with 0-1 $R^f$), $CON(C_{1-4}$ alkyl$)_2$, $NHCOR^8$, $NHCONH(C_{1-4}$ alkyl), $SO_2R^9$, $NHSO_2NH_2$, $SO_2NHCO(C_{1-4}$ alkyl), $NHSO_2(C_{1-4}$ alkyl), $NHSO_2NHCO_2(C_{1-4}$ alkyl), $NHSO_2NHR^j$, $SO_2NHSO_2(C_{1-4}$ haloalkyl), $N(C_{1-4}$ alkyl)$SO_2NH_2$, $N(CO_2C_{1-4}$ alkyl)$SO_2(C_{1-4}$ alkyl), $CONH(C_{3-6}$ cycloalkyl),

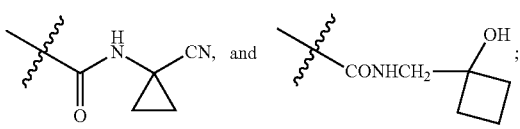

$R^6$ is independently selected from:

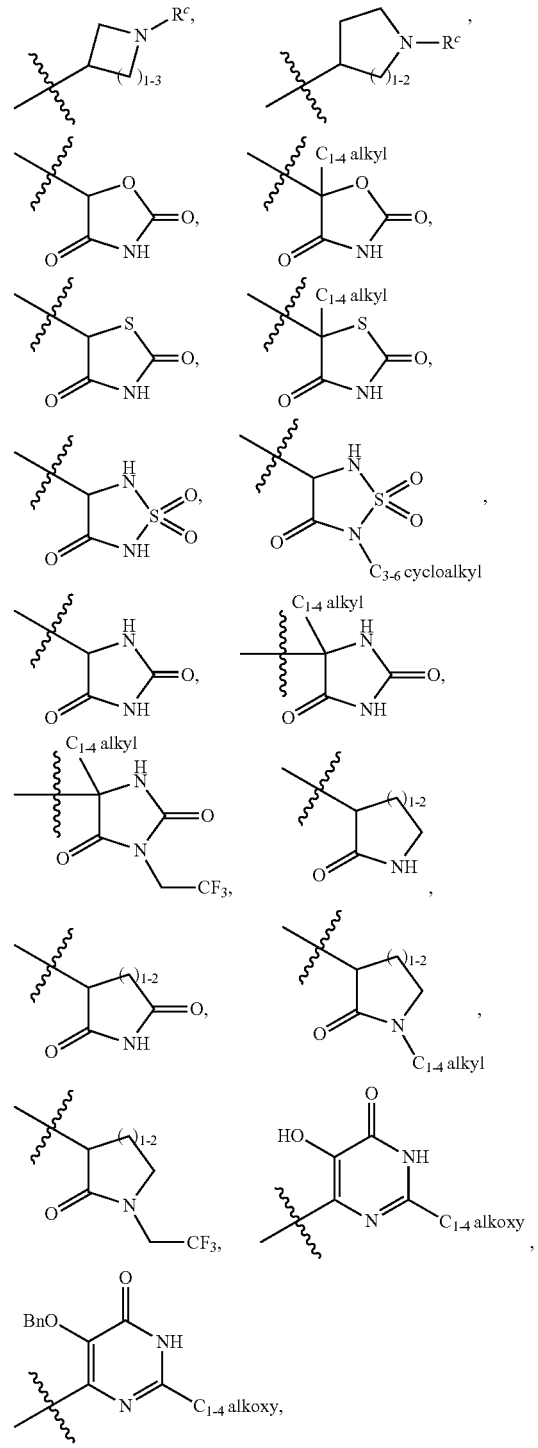

phenyl and a 5- to 6-membered heteroaryl comprising carbon atoms and 1-4 heteroatoms selected from N, $NR^c$, O, and $S(O)_p$; wherein said phenyl and heteroaryl are is substituted with 0-2 $R^{11}$;

$R^7$ is independently selected from: OH, halogen, $C_{1-4}$ alkoxy, $C_{1-4}$ haloalkyl, $C_{1-4}$ haloalkoxy, $NH_2$, $CO_2H$, $CO_2(C_{1-4}$ alkyl), $SO_3H$, $CONHR^d$, $NHCONHR^d$, $NHCO_2R^d$,

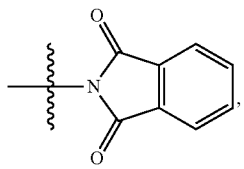 [SMILES: *N1C(=O)c2ccccc2C1=O]

and 5- to 6-membered heterocycle comprising carbon atoms and 1-4 heteroatoms selected from N, $NR^g$, O, and $S(O)_p$;

$R^8$ is, independently selected from: $C_{1-4}$ alkyl, $-(CH_2)_{0-3}C_{1-4}$ alkoxy, $-CH(OH)(C_{1-4}$ alkyl), $-CH(OCON(C_{1-4}$ alkyl$)_2)(C_{1-4}$ alkyl), and $-(CH_2)_{1-3}CH(OH)(C_{1-4}$ alkyl);

$R^9$ is independently selected from: OH, $C_{1-6}$ alkyl, $C_{2-6}$ alkenyl, $NH_2$, $NH(C_{1-6}$ alkyl), $NH(C_{2-6}$ alkenyl), $NH(C_{1-4}$ haloalkyl), NHPh, and phenyl substituted with 0-2 halogens;

$R^a$ is, independently at each occurrence, selected from: halogen, $C_{1-6}$ alkyl substituted with 0-1 $R^f$, $C_{1-4}$ alkoxy substituted with 0-1 $R^f$, $C_{1-6}$ haloalkyl, $C_{1-6}$ haloalkoxy, OH, CN, $NO_2$, $CO_2H$, $CO_2(C_{1-4}$ alkyl), $CO_2Bn$, $NR^gR^h$, $CONR^gR^h$, $CONR^gR^j$, $NHCOR^i$, $NHCO_2R^i$, $SO_2NR^gR^h$, $-(O)_n-(CH_2)_t-R^j$, and $-CO-R^j$;

$R^{a1}$ is, independently selected from: $=O$ and $R^a$;

$R^b$ is, independently at each occurrence, selected from: halogen, $C_{1-4}$ alkyl, $C_{1-4}$ alkoxy, $C_{1-4}$ haloalkyl, $C_{1-4}$ haloalkoxy, OH, CN, $NH_2$, $NO_2$, $NH(C_{1-4}$ alkyl), $N(C_{1-4}$ alkyl$)_2$, $CO_2H$, $CO_2(C_{1-4}$ alkyl), $SO_2(C_{1-4}$ alkyl), $SO_2NH_2$, $CONH_2$, and $CONH(C_{1-4}$ alkyl);

$R^c$ is, independently at each occurrence, selected from: H, $C_{1-6}$ alkyl substituted with 0-1 $R^e$, $CO(C_{1-4}$ alkyl), $CO_2(C_{1-4}$ alkyl), COBn, $CO_2Bn$, $-(CH_2)_t$-piperidinyl, $-(CH_2)_t$-morpholinyl, $-(CH_2)_t$-piperazinyl, pyrimidinyl and $-(CH_2)_t-(C_{3-6}$ carbocycle substituted with 0-2 $R^e$);

$R^d$ is, independently at each occurrence, selected from: $C_{1-6}$ alkyl and $-(CH_2)_t$-(phenyl substituted with 0-2 $R^e$);

$R^e$ is, independently at each occurrence, selected from: OH, halogen, $C_{1-4}$ alkyl, $C_{1-4}$ alkoxy, $C_{1-4}$ haloalkyl, and $C_{1-4}$ haloalkoxy;

$R^f$ is, independently at each occurrence, selected from: OH, CN, halogen, $C_{1-4}$ alkyl, $C_{1-4}$ alkoxy, $C_{1-4}$ haloalkyl, and $C_{1-4}$ haloalkoxy;

$R^g$ is, independently at each occurrence, selected from: H and $C_{1-4}$ alkyl;

$R^h$ is, independently at each occurrence, selected from: H, $C_{1-6}$ haloalkyl and $C_{1-6}$ alkyl substituted with 0-1 $R^f$;

$R^i$ is, independently at each occurrence, selected from: $C_{1-4}$ haloalkyl and $C_{1-4}$ alkyl substituted with 0-1 $R^f$;

$R^j$ is, independently at each occurrence: $C_{3-6}$ carbocycle or a 4- to 6-membered heterocycle comprising carbon atoms and 1-4 heteroatoms selected from N, $NR^g$, O, and $S(O)_p$; wherein said carbocycle and heterocycle are substituted with 0-2 $R^f$;

m and t are, independently at each occurrence, selected from 0, 1, 2, and 3;

n is, independently at each occurrence, selected from 0 and 1;

p is, independently at each occurrence, selected from 0, 1, and 2; and s is, independently at each occurrence, selected from 1, 2, and 3.

In another aspect, the present invention provides a compound of Formula (I), or a stereoisomer, a tautomer, a pharmaceutically acceptable salt, or a solvate thereof, wherein:

$R^1$ is independently selected from: phenyl and a 5- to 6-membered heterocycle comprising carbon atoms and 1-4 heteroatoms selected from N, $NR^c$, O, and $S(O)_p$; wherein each phenyl and heterocycle are substituted with 0-3 $R^a$;

$R^2$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CN, $NH_2$, $NO_2$, $NH(C_{1-4}$ alkyl), $N(C_{1-4}$ alkyl$)_2$, $CO_2H$, $CO_2(C_{1-4}$ alkyl), and $CONH_2$;

$R^3$ is independently selected from: $C_{1-6}$ alkyl, $C_{2-6}$ alkenyl, $-(CH_2)_mCHF_2$, $-(CH_2)_mCF_3$, $-(CH_2)_m-(O)_p-(C_{3-6}$ carbocycle substituted with 0-3 $R^b$), $-(CH_2)_m-(O)_n$-(pyridyl substituted with 0-2 $R^b$), $-(CH_2)_sNHCONHR^d$, $-(CH_2)_sNHCO_2R^d$,

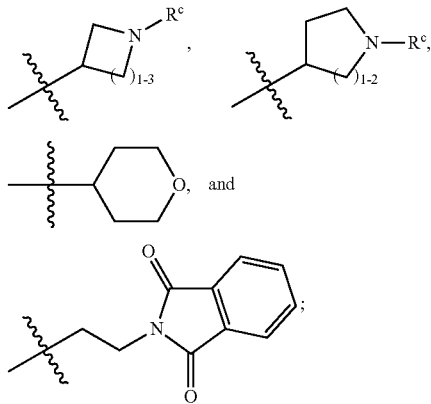

$R^4$ independently selected from:

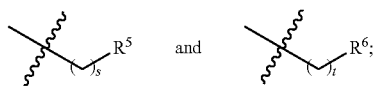

$R^5$ is independently selected from: $NH_2$, $NH(C_{1-4}$ alkyl), $N(C_{1-4}$ alkyl$)_2$, $CONH_2$, $CONH(C_{1-4}$ alkyl), $CON(C_{1-4}$ alkyl$)_2$, $NHCO(C_{1-4}$ alkyl), $NHCO_2(C_{1-4}$ alkyl), $NHCONH(C_{1-4}$ alkyl), $SO_2OH$, $SO_2$(4-halo-Ph), $SO_2NH_2$, $SO_2NHCH_2CF_3$, $SO_2NHPh$, $NHSO_2NH_2$, $NHSO_2(C_{1-4}$ alkyl), $SO_2NHSO_2(CH_2)_{2-3}CF_3$, $N(C_{1-4}$ alkyl)$SO_2NH_2$, $N(CO_2C_{1-4}$ alkyl)$SO_2(C_{1-4}$ alkyl), and

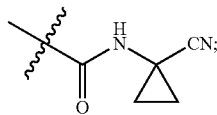 [SMILES: *C(=O)NC1(C#N)CC1]

$R^6$ is independently selected from:

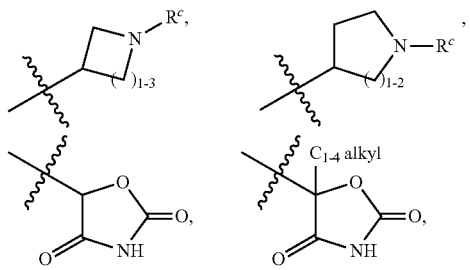

-continued

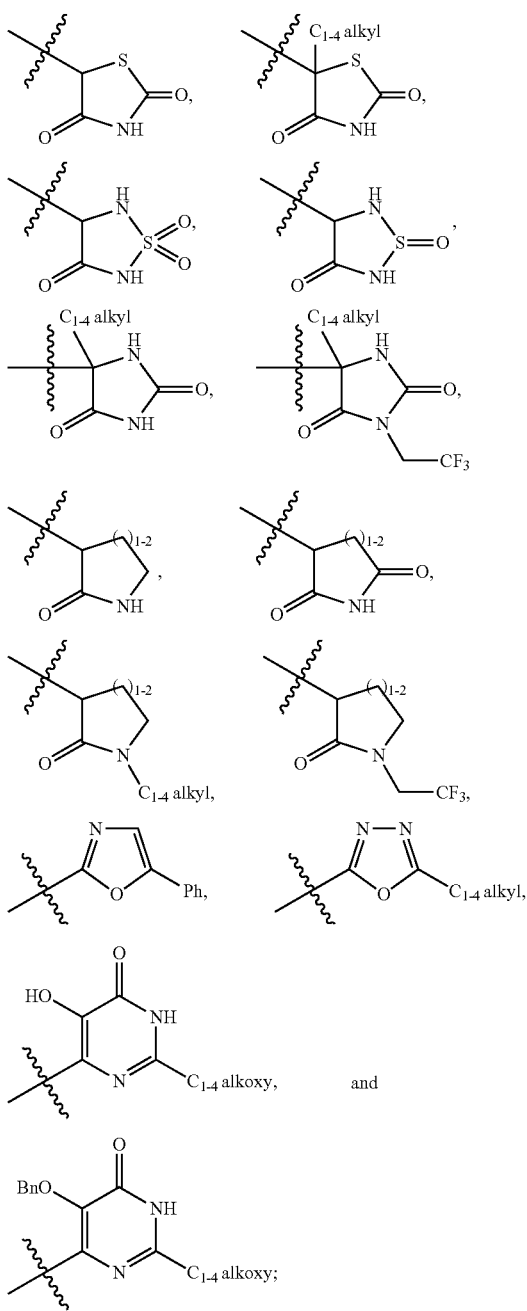

$R^a$ is, independently at each occurrence, selected from: halogen, $C_{1-6}$ alkyl substituted with 0-1 OH, $C_{1-4}$ alkoxy, $C_{1-6}$ haloalkyl, $C_{1-6}$ haloalkoxy, OH, CN, $NO_2$, $NH_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $SO_2NH_2$, $SO_2N(C_{1-4}$ alkyl)$_2$, $CONH(CH_2)_{1-3}CF_3$, pyrazolyl,

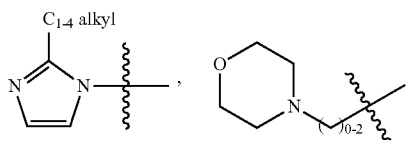

-continued

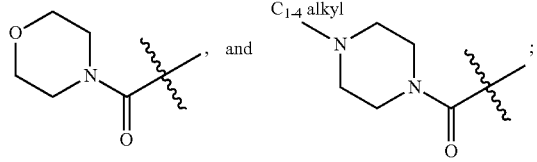

$R^b$ is, independently at each occurrence, selected from: halogen, $C_{1-4}$ alkyl, $C_{1-4}$ alkoxy, $C_{1-4}$ haloalkyl, $C_{1-4}$ haloalkoxy, OH, CN, $NH_2$, $NO_2$, $NH(C_{1-4}$ alkyl), $N(C_{1-4}$ alkyl)$_2$, $CO_2H$, $CO_2(C_{1-4}$ alkyl), $SO_2(C_{1-4}$ alkyl), $SO_2NH_2$, $CONH_2$, and $CONH(C_{1-4}$ alkyl);

$R^c$ is, independently at each occurrence, selected from: H, $C_{1-6}$ alkyl, $CO(C_{1-4}$ alkyl), $CO_2(C_{1-4}$ alkyl), COBn, $CO_2Bn$,

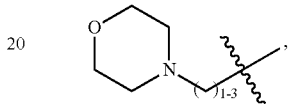

pyrimidinyl and —$(CH_2)_t$—($C_{3-6}$ carbocycle substituted with 0-2 $R^e$);

$R^d$ is, independently at each occurrence, selected from: $C_{1-6}$ alkyl and —$(CH_2)_t$-(phenyl substituted with 0-2 $R^e$);

$R^e$ is, independently at each occurrence, selected from: halogen, $C_{1-4}$ alkyl, $C_{1-4}$ alkoxy, $C_{1-4}$ haloalkyl, and $C_{1-4}$ haloalkoxy;

m and t are, independently at each occurrence, selected from 0, 1, 2, and 3;

n is, independently at each occurrence, selected from 0 and 1;

p is, independently at each occurrence, selected from 0, 1, and 2; and s is, independently at each occurrence, selected from 1, 2, and 3.

In another aspect, the present invention includes a compound of Formula (I), or a stereoisomer, a tautomer, a pharmaceutically acceptable salt, or a solvate thereof, within the scope of the first aspect, wherein:

$R^6$ is independently selected from:

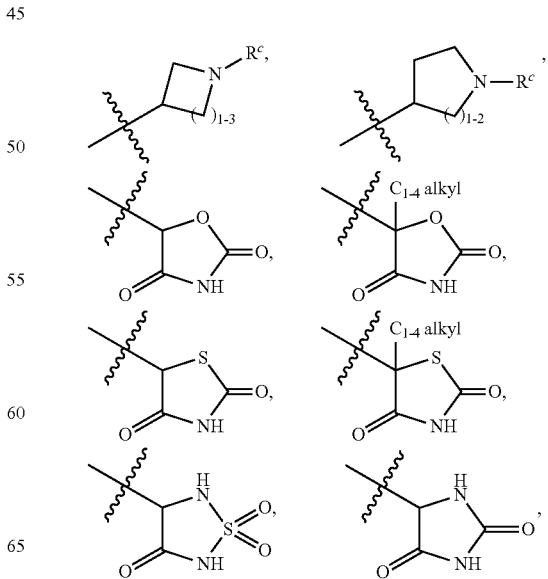

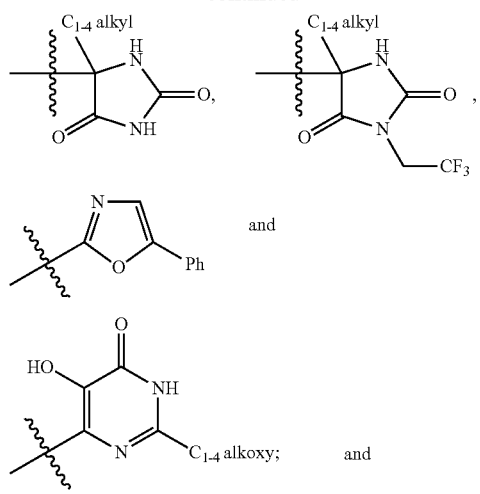

t is, independently at each occurrence, selected from 0, 1, and 2.

In another aspect, the present invention includes a compound of Formula (IIa), or a stereoisomer, a tautomer, a pharmaceutically acceptable salt, or a solvate thereof, within the scope of the first or second aspect; wherein:

$R^2$ is independently selected from: halogen and $C_{1-4}$ alkyl.

In another aspect, the present invention includes a compound of Formula (I), (IIa) or (IIIa), or a stereoisomer, a tautomer, a pharmaceutically acceptable salt, or a solvate thereof, wherein:

$R^1$ is independently selected from: Ph, 4-halo-Ph, 4-OBn-Ph, 2-halo-pyrid-4-yl, 6-halo-pyrid-3-yl,

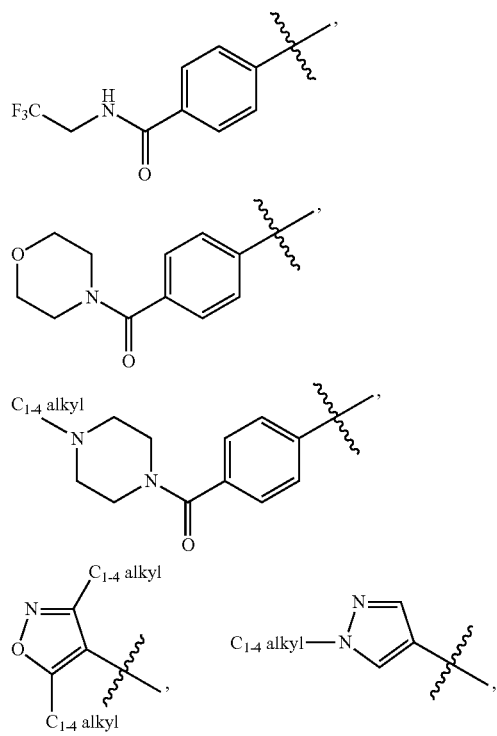

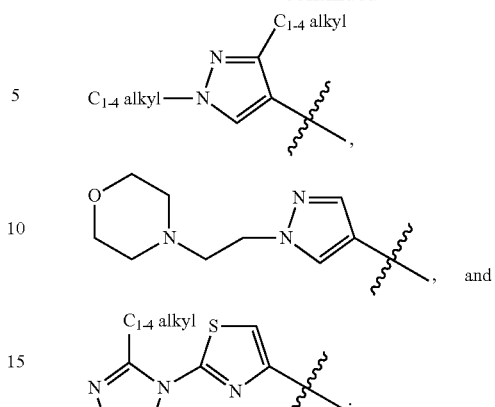

$R^3$ is independently selected from: $C_{1-4}$ alkyl, —$(CH_2)_{1-3}CF_3$, —$(CH_2)_{0-1}$—$(C_{3-6}$ cycloalkyl), Bn, 2-$C_{1-4}$ alkyl-Bn, 3-$C_{1-4}$ alkyl-Bn, 2-halo-Bn, 3-halo-Bn, 4-halo-Bn, 3-$CF_3$-Bn, 4-$CF_3$-Bn, 3-halo-4-halo-Bn, 3-halo-5-halo-Bn, 3-$CF_3$-5-$CF_3$-Bn, —$CH_2CH_2CH_2Ph$, —$(CH_2)_{1-3}$NHCONHBn, (6-halo-pyrid-3-yl)methyl, (6-$CF_3$-pyrid-3-yl)methyl,

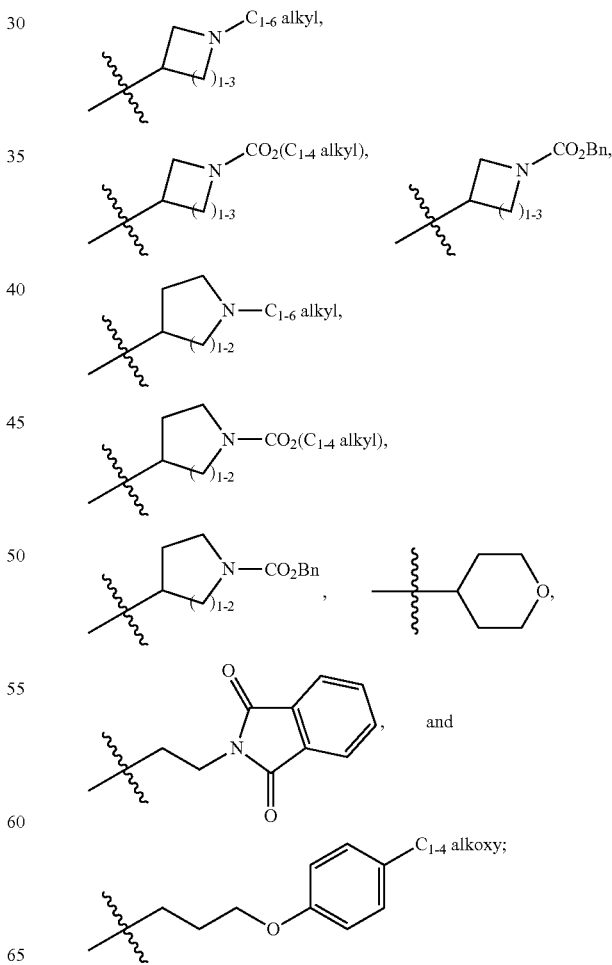

and

R⁴ independently selected from:

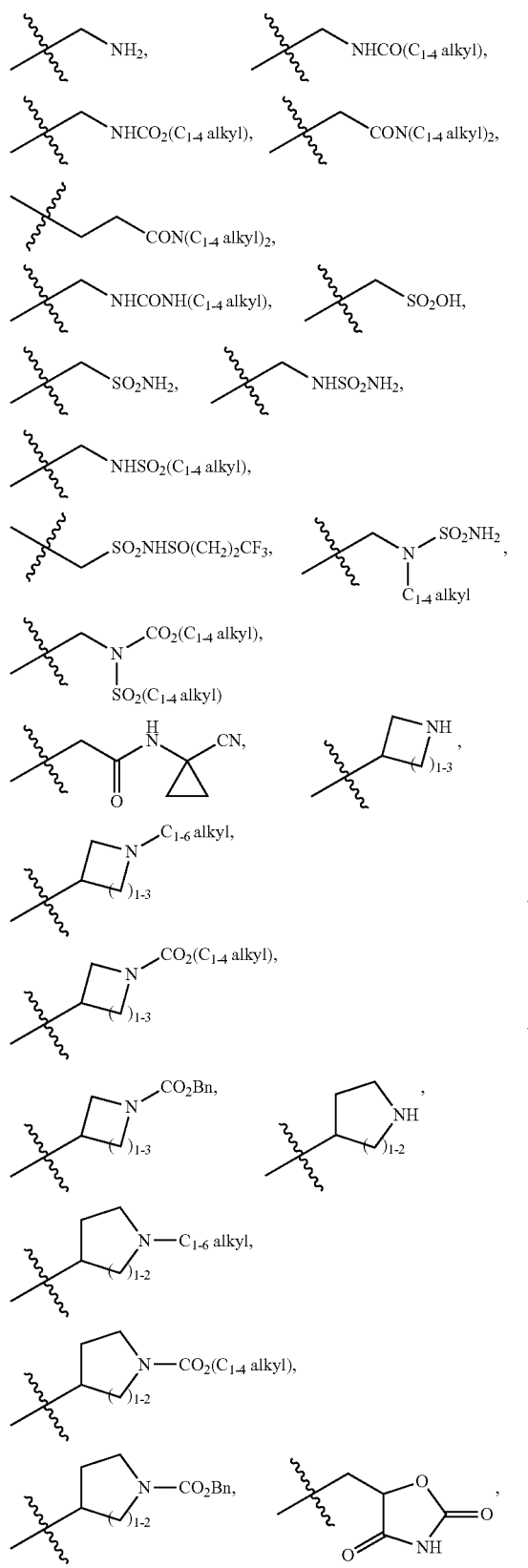
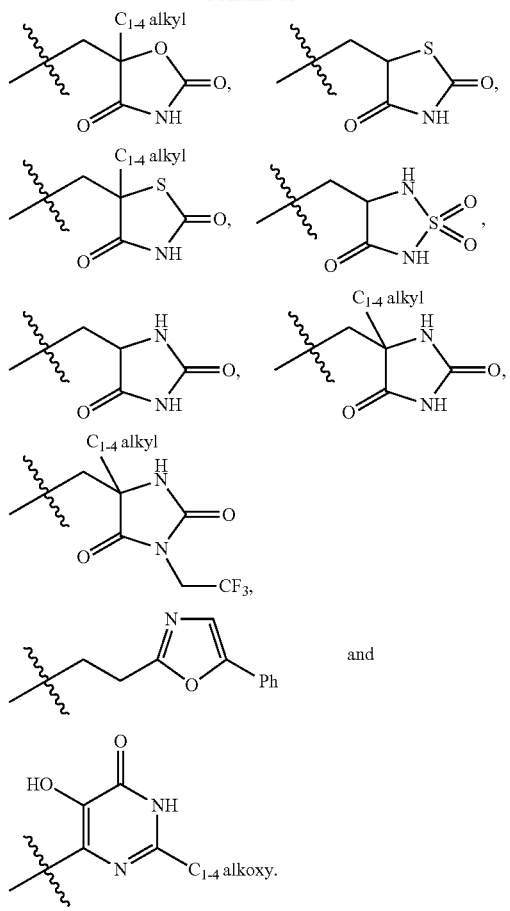

In another aspect, the present invention includes a compound of Formula (I), (IIa) or (IIIa), or a stereoisomer, a tautomer, a pharmaceutically acceptable salt, or a solvate thereof, wherein:

R¹ is Ph;

R³ is independently selected from: $C_{1-4}$ alkyl, —(CH₂)$_{1-3}$CF₃, —(CH₂)$_{0-1}$—(C$_{3-6}$ cycloalkyl), Bn, 2-C$_{1-4}$ alkyl-Bn, 3-C$_{1-4}$ alkyl-Bn, 2-halo-Bn, 3-halo-Bn, 4-halo-Bn, 3-CF₃-Bn, 4-CF₃-Bn, 3-halo-4-halo-Bn, 3-halo-5-halo-Bn, 3-CF₃-5-CF₃-Bn, —CH₂CH₂CH₂Ph,

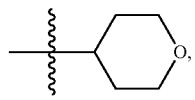
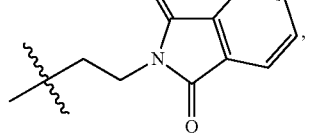
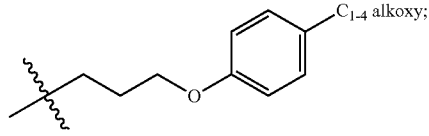

and $R^4$ independently selected from:

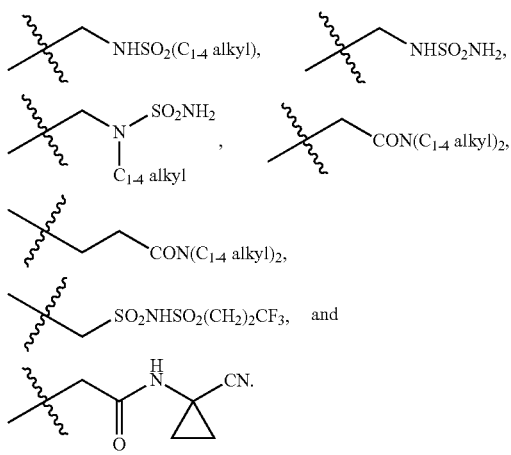

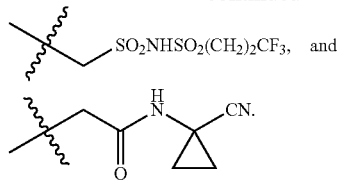

In another aspect, the present invention includes a compound of Formula (I), (IIa) or (IIIa), or a stereoisomer, a tautomer, a pharmaceutically acceptable salt, or a solvate thereof, wherein:

$R^3$ is independently selected from: Me, Et, Pr, i-Pr, i-Bu, —$(CH_2)_{2-3}CF_3$, cyclopropyl, cyclopropylmethyl, cyclopentyl, cyclohexylmethyl, Bn, 2-Me-Bn, 3-Me-Bn, 2-F-Bn, 3-F-Bn, 4-F-Bn, 3-Cl-Bn, 4-Cl-Bn, 3-Br-Bn, 3-$CF_3$-Bn, 4-$CF_3$-Bn, 3,4-diCl-Bn, 3,5-diCl-Bn, 3-$CF_3$-5-$CF_3$-Bn, —$CH_2CH_2CH_2Ph$,

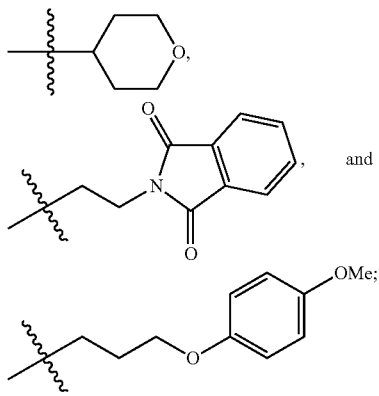

and $R^4$ independently selected from:

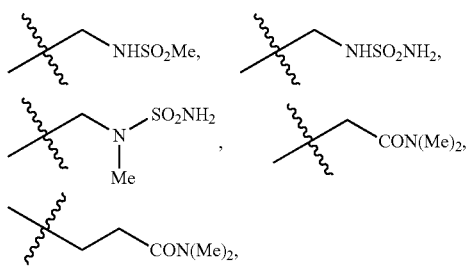

In another aspect, the present invention includes a compound of Formula (I), (IIa) or (IIIa), or a stereoisomer, a tautomer, a pharmaceutically acceptable salt, or a solvate thereof, wherein:

$R^1$ is independently selected from: 6-halo-pyrid-3-yl,

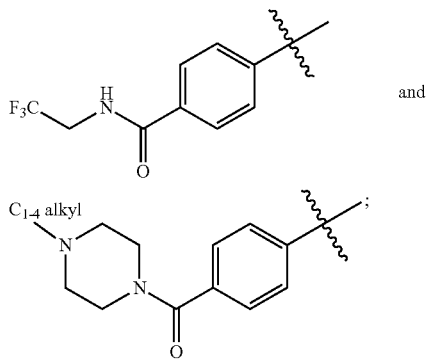

$R^3$ is independently selected from: $C_{1-4}$ alkyl, Bn, (6-halo-pyrid-3-yl)methyl, and (6-$CF_3$-pyrid-3-yl)methyl; and

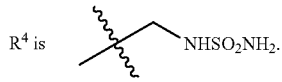

In another aspect, the present invention includes a compound of Formula (I), (IIa) or (IIIa), or a stereoisomer, a tautomer, a pharmaceutically acceptable salt, or a solvate thereof, wherein:

$R^1$ is independently selected from: 6-F-pyrid-3-yl.

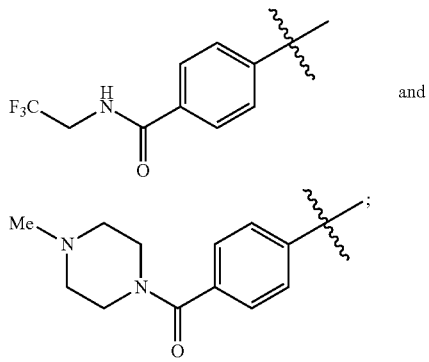

and $R^3$ is independently selected from: Me, Bn, (6-F-pyrid-3-yl)methyl, and (6-$CF_3$-pyrid-3-yl)methyl.

In another aspect, the present invention includes a compound of Formula (I), (IIa) or (IIIa), or a stereoisomer, a tautomer, a pharmaceutically acceptable salt, or a solvate thereof, wherein:

$R^1$ independently selected from: Ph, 4-halo-Ph,

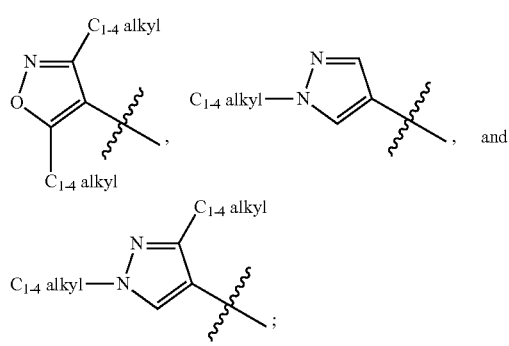

$R^3$ independently selected from: $C_{1-4}$ alkyl, $-(CH_2)_{1-3}CF_3$, Bn, 4-halo-Bn, 4-$CF_3$-Bn, $-(CH_2)_{1-3}NHCO_2Bn$,

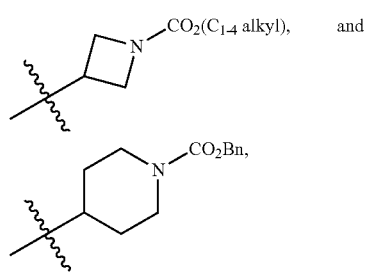

and $R^4$ is independently selected from:

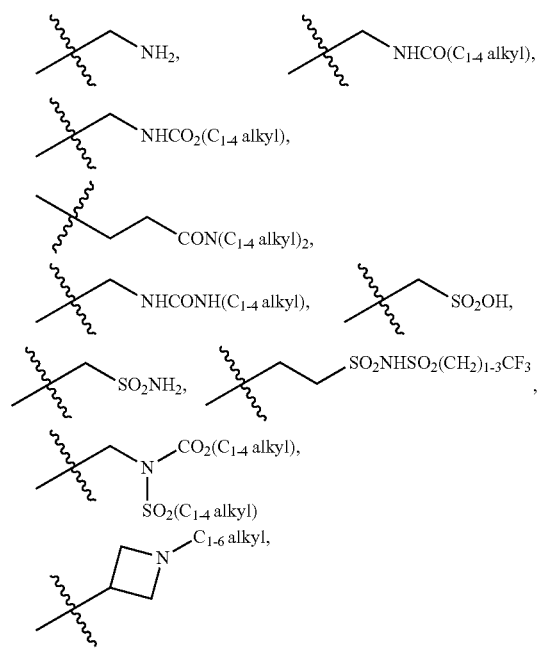

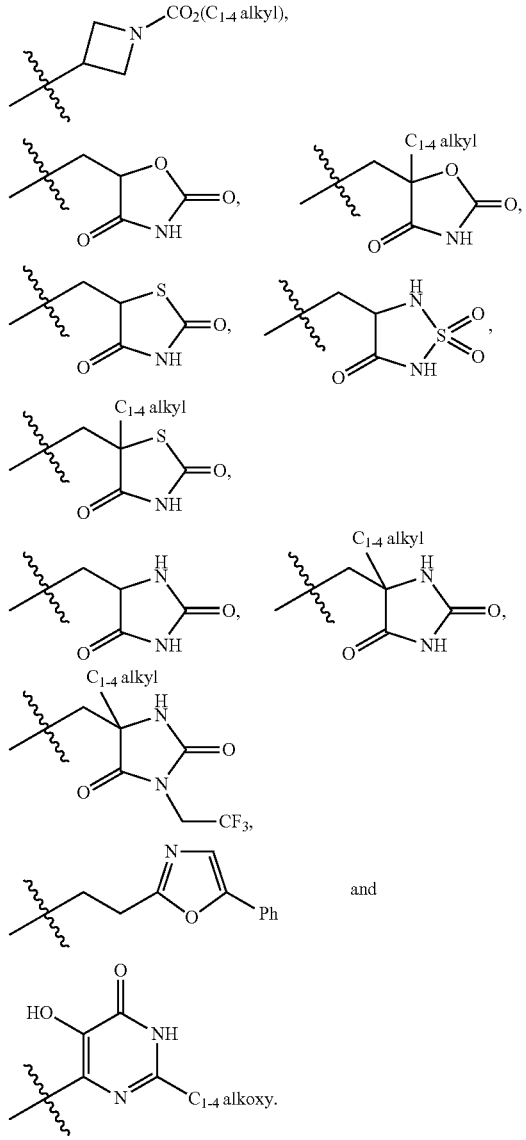

In another aspect, the present invention includes a compound of Formula (I), (IIa) or (IIIa), or a stereoisomer, a tautomer, a pharmaceutically acceptable salt, or a solvate thereof, wherein:

$R^1$ independently selected from: Ph, 4-F-Ph,

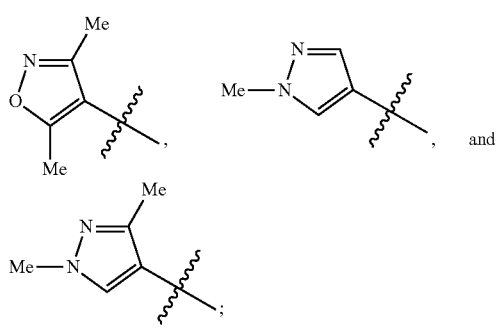

$R^3$ is independently selected from: Me, i-Pr, —$(CH_2)_2CF_3$, Bn, 4-F-Bn, 4-$CF_3$-Bn, —$(CH_2)_2NHCO_2Bn$, and

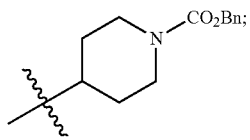 [SMILES: *C1CCN(C(=O)OCc2ccccc2)CC1]

and $R^4$ is independently selected from:

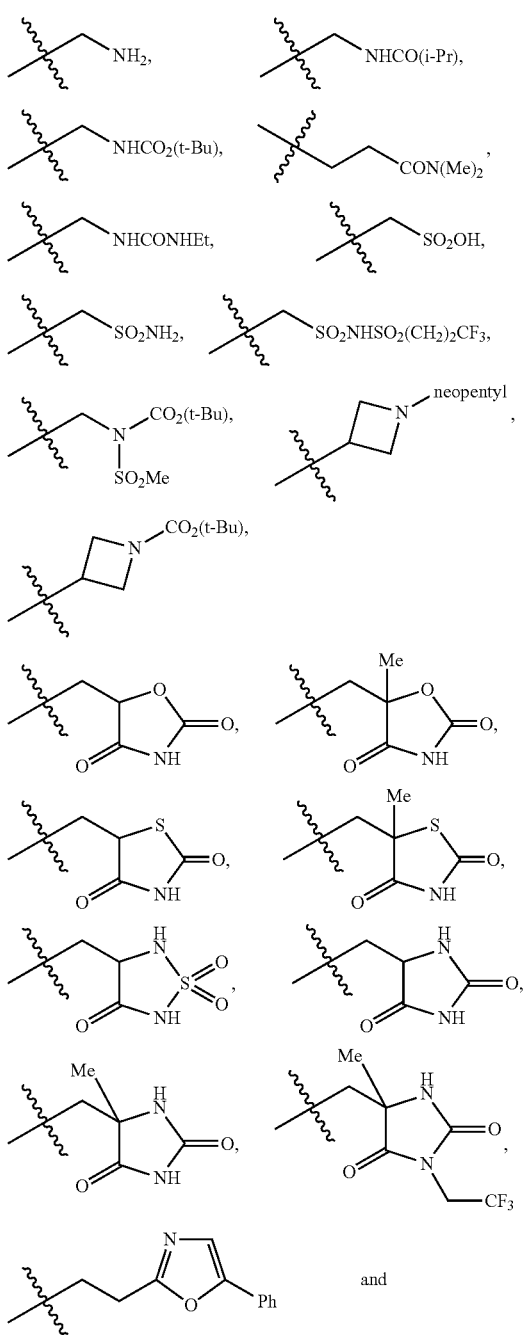

In another aspect, the present invention includes a compound of Formula (I), (IIa) or (IIIa), or a stereoisomer, a tautomer, a pharmaceutically acceptable salt, or a solvate thereof, wherein:

$R^1$ is independently selected from: 4-OBn-Ph, 2-halo-pyrid-4-yl, 6-halo-pyrid-3-yl,

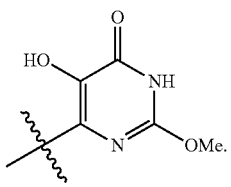

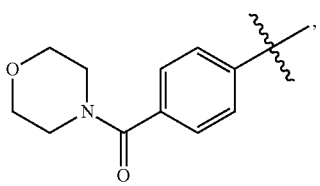

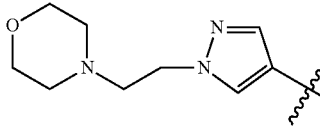

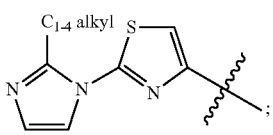

$R^3$ is independently selected from: $C_{1-4}$ alkyl, Bn and —$(CH_2)_{1-3}CF_3$; and $R^4$ is independently selected from:

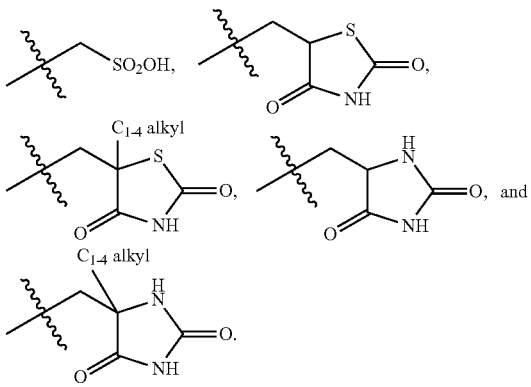

In another aspect, the present invention includes a compound of Formula (I), (IIa) or (IIIa), or a stereoisomer, a tautomer, a pharmaceutically acceptable salt, or a solvate thereof, wherein:

$R^1$ is independently selected from: 4-OBn-Ph, 2-F-pyrid-4-yl, 6-F-pyrid-3-yl,

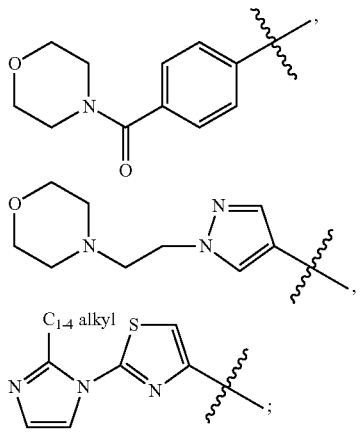

and

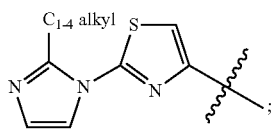

;

$R^3$ is independently selected from: Me, Bn and —(CH$_2$)$_2$CF$_3$; and $R^4$ is independently selected from:

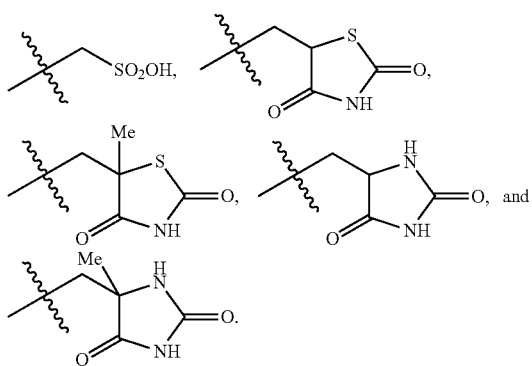

In another aspect, the present invention includes a compound of Formula (I), (IIa), (IIb), (IIIa) or (IIIb), or a stereoisomer, a tautomer, a pharmaceutically acceptable salt, or a solvate thereof, wherein:

$R^1$ is independently selected from: —CO-morpholinyl, 3-CO$_2$H-Ph, 3-CONH(CH$_2$)$_2$O(C$_{1-4}$ alkyl)-Ph,

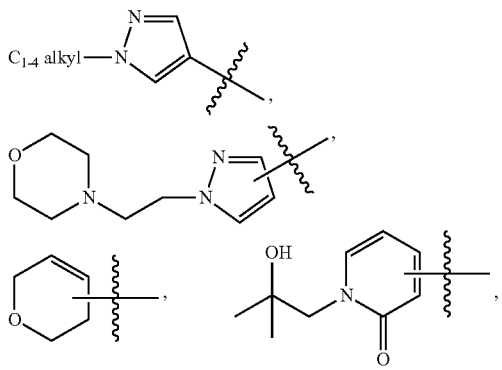

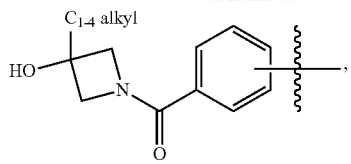

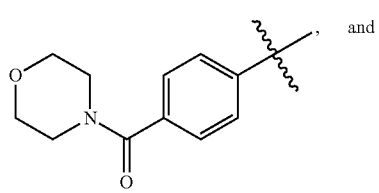

and

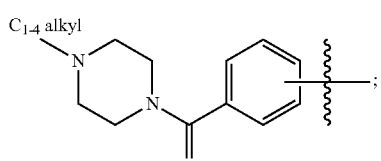

;

$R^3$ is independently selected from: C$_{1-4}$ alkyl substituted with 0-1 C$_{1-4}$ alkoxy, C$_{2-4}$ alkenyl, —(CH$_2$)$_2$CF$_3$, Bn, —CH$_2$—C$_{3-6}$ cycloalkyl,

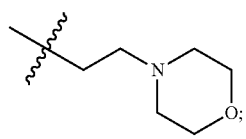 [SMILES: *CCN1CCOCC1]

;

and $R^4$ is independently selected from:

CONHCH$_2$CH(OH)C$_{1-4}$ alkyl),

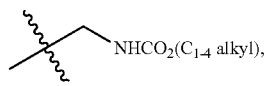 NHCO$_2$(C$_{1-4}$ alkyl), 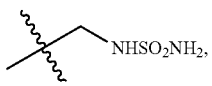 NHSO$_2$NH$_2$,

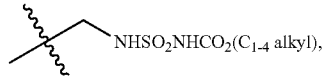 NHSO$_2$NHCO$_2$(C$_{1-4}$ alkyl),

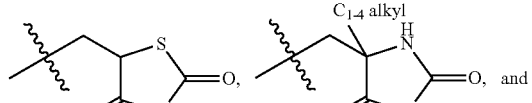

, and

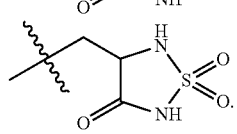

In another aspect, the present invention includes a compound of Formula (I), (IIa), (IIb), (IIIa) or (IIIb), or a stereoisomer, a tautomer, a pharmaceutically acceptable salt, or a solvate thereof, wherein:

$R^1$ is independently selected from: —CO-morpholinyl, 3-CO$_2$H-Ph, 3-CONH(CH$_2$)$_2$O(Me)-Ph,

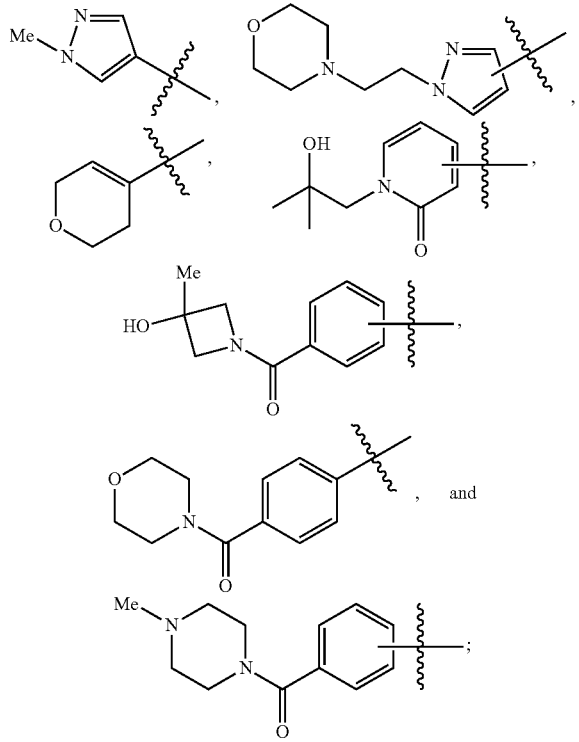

$R^3$ is independently selected from: C$_{1-4}$ alkyl substituted with 0-1 C$_{1-4}$ alkoxy, C$_{2-4}$ alkenyl, —(CH$_2$)$_2$CF$_3$, Bn, —CH$_2$—C$_{3-6}$ cycloalkyl,

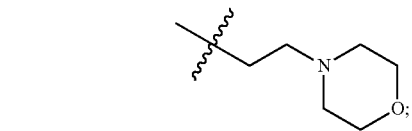 [SMILES: *CCN1CCOCC1]

and $R^4$ is independently selected from:

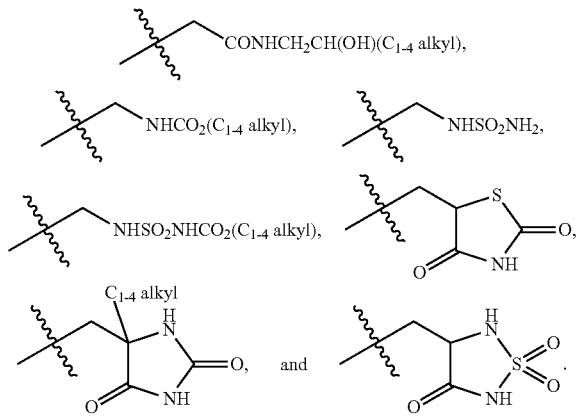

In an eleventh aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the fourteenth aspect.

In another embodiment, the compounds of the present invention have EL IC$_{50}$ values ≤300 nM.

In another embodiment, the compounds of the present invention have EL IC$_{50}$ values ≤100 nM.

In another embodiment, the compounds of the present invention have EL IC$_{50}$ values ≤50 nM.

In another embodiment, the compounds of the present invention have EL IC$_{50}$ values ≤25 nM.

In another embodiment, the compounds of the present invention have EL IC$_{50}$ values ≤10 nM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the treatment and/or prophylaxis of dyslipidemias and the sequelae thereof comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment and/or prophylaxis of atherosclerosis, coronary heart disease, cerebrovascular disorders and dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of dyslipidemias and the sequelae thereof.

In another embodiment, the present invention also provides the use of a compound of the present invention for the manufacture of a medicament for the treatment and/or prophylaxis of dyslipidemias and the sequelae thereof.

In another embodiment, the present invention provides a method for the treatment and/or prophylaxis of dyslipidemias and the sequelae thereof, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, antioxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(═O)CH$_3$, SCH$_3$, S(═O)CH$_3$, S(═O)$_2$CH$_3$, CH$_3$, CH$_2$CH$_3$, CO$_2$H, and CO$_2$CH$_3$.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand, an imine (—C—C=N) group in a molecule may tautomerize to its enol form (—C=C—N) and the double bond can exist as geometrical (E and Z) isomers as shown, wherein $R^1$, $R^2$, $R^3$, and $R^4$ are as defined above:

and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

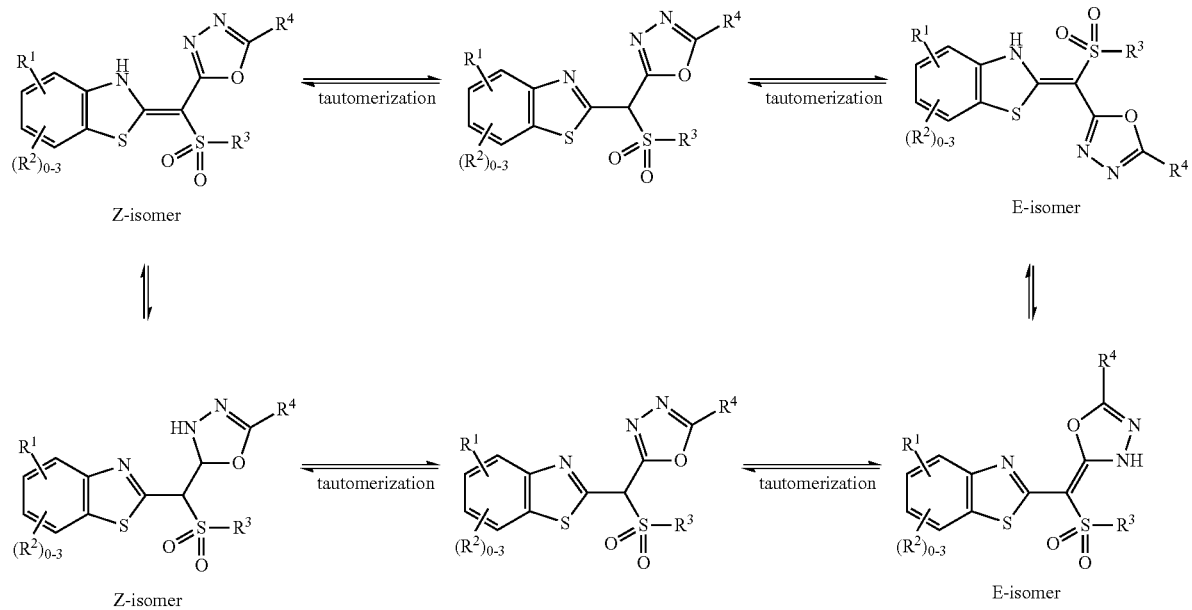

Thus, this disclosure is intended to cover all possible tautomers even when a structure depicts only one of them.

The phrase "pharmaceutically acceptable" is employed herein to refer to those compounds, materials, compositions, In addition, compounds of Formula (I), Formula (II), or Formula (III) may have prodrug forms. Any compound that will be converted in vivo to provide the bioactive agent (i.e., a compound of Formula (I), Formula (II) or Formula (III)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112: 309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984);
f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield Formula (I), (IIa), (IIb), (IIIa) or (IIIb) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, $3^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| AcOH or HOAc | acetic acid |
| $AlCl_3$ | aluminum chloride |
| Alk | alkyl |
| $BBr_3$ | boron tribromide |
| $BCl_3$ | boron trichloride |
| Bn | benzyl |
| Boc | tert-butyloxycarbonyl |
| BOP reagent | benzotriazol-1-yloxytris(dimethylamino)phosphonium hexafluorophosphate |
| Bu | butyl |
| i-Bu | isobutyl |
| t-Bu | tert-butyl |
| t-BuOH | tert-butanol |
| Cbz | carbobenzyloxy |
| $CDCl_3$ | deutero-chloroform |
| $CD_3OD$ | deutero-methanol |
| $CH_2Cl_2$ | dichloromethane |
| $CH_3CN$ or ACN | acetonitrile |
| $CHCl_3$ | chloroform |
| $CO_2$ | carbon dioxide |
| mCPBA or m-CPBA | meta-chloroperbenzoic acid |
| $Cs_2CO_3$ | cesium carbonate |
| $Cu(OAc)_2$ | copper (II) acetate |
| DBU | 1,8-diazabicyclo[5.4.0]undec-7-ene |
| DCE | 1,2-dichloroethane |
| DCM | dichloromethane |
| DEA | diethylamine |
| DIC or DIPCDI | diisopropylcarbodiimide |
| DIEA, DIPEA or Hunig's base | diisopropylethylamine |

-continued

| | |
|---|---|
| DMAP | 4-dimethylaminopyridine |
| DME | 1,2-dimethoxyethane |
| DMF | dimethyl formamide |
| DMSO | dimethyl sulfoxide |
| cDNA | complimentary DNA |
| Dppp | (R)-(+)-1,2-bis(diphenylphosphino)propane |
| EDC | N-(3-dimthylaminopropyl)-N'-ethylcarbodiimide |
| EDTA | ethylenediaminetetraacetic acid |
| Et | ethyl |
| $Et_3N$ or TEA | triethylamine |
| $Et_2O$ | diethyl ether |
| EtOAc | ethyl acetate |
| EtOH | ethanol |
| HATU | (2-(7-aza-1H-benzotriazole-1-yl)-1,1,3,3-tetramethyluronium hexafluorophosphate) |
| HCl | hydrochloric acid |
| HOBt or HOBT | 1-hydroxybenzotriazole |
| HPLC | high-performance liquid chromatography |
| $H_3PO_4$ | phosphoric acid |
| $H_2SO_4$ | sulfuric acid |
| $K_2CO_3$ | potassium carbonate |
| KOAc | potassium acetate |
| $K_3PO_4$ | potassium phosphate |
| LAH | lithium aluminum hydride |
| LDA | lithium diisopropylamide |
| LG | leaving group |
| LiOH | lithium hydroxide |
| Me | methyl |
| MeOH | methanol |
| $MgSO_4$ | magnesium sulfate |
| MsOH or MSA | methylsulfonic acid |
| NaCl | sodium chloride |
| $Na_2CO_3$ | sodium carbonate |
| NaH | sodium hydride |
| $NaHB(OAc)_3$ | sodium triacetoxyborohydride |
| $NaHCO_3$ | sodium bicarbonate |
| NaHMDS | sodium hexamethyldisilazane |
| NaOH | sodium hydroxide |
| NaOMe | sodium methoxide |
| $Na_2SO_3$ | sodium sulfite |
| $Na_2SO_4$ | sodium sulfate |
| NBS | N-bromosuccinimide |
| $NH_3$ | ammonia |
| $NH_4Cl$ | ammonium chloride |
| $NH_4OAc$ | ammonium acetate |
| $NH_4OH$ | ammonium hydroxide |
| OTf | triflate or trifluoromethanesulfonate |
| $Pd_2(dba)_3$ | tris(dibenzylideneacetone)dipalladium(0) |
| $Pd(OAc)_2$ | palladium(II) acetate |
| Pd/C | palladium on carbon |
| $Pd(dppf)Cl_2$ | [1,1'-bis(diphenylphosphino)-ferrocene]dichloropalladium(II) |
| $Ph_3PCl_2$ | triphenylphosphine dichloride |
| PG | protecting group |
| Ph | phenyl |
| PMB | p-methoxybenzyl |
| $POCl_3$ | phosphorus oxychloride |
| Pr | propyl |
| i-Pr | isopropyl |
| i-PrOH or IPA | isopropanol |
| PS | polystyrene |
| $PS-Pd(Ph_3)_4$ | tetrakis(triphenylphosphine)palladium (0) on polystyrene support |
| PyBOP | (benzotriazol-1-yloxy)tripyrrolidinophosphonium hexafluorophosphate |
| $SiO_2$ | silica oxide |
| $SnCl_2$ | tin(II) chloride |
| TBAF | tetra-n-butylammonium fluoride |
| TBAI | tetra-n-butylammonium iodide |
| TEA | triethylamine |
| TFA | trifluoroacetic acid |
| THF | tetrahydrofuran |
| $TMSCHN_2$ | trimethylsilyldiazomethane |
| T3P | 1-propanephosphonic acid cyclic anhydride |
| Xantphos or X-Phos | 4,5-bis(diphenylphosphino)-9,9-dimethylxanthene |

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH Publishers, Inc., New York (1999). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts, P. G. M. and Greene, T. W. (*Protective Groups in Organic Synthesis*, Wiley and Sons (1991)).

Generic Schemes

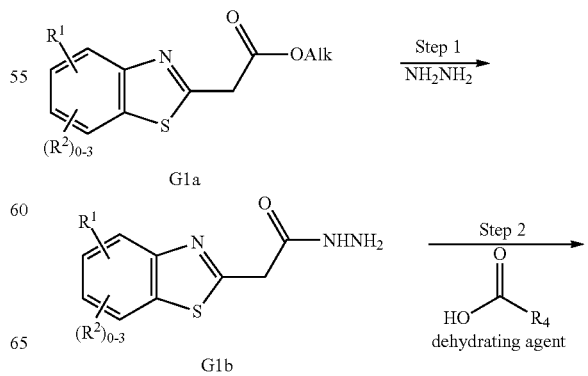

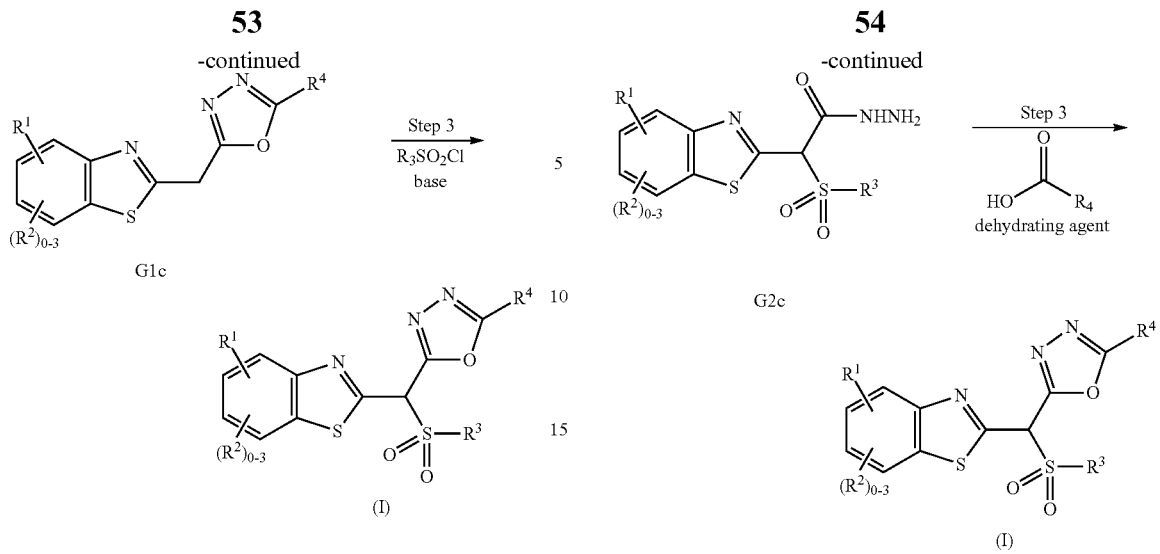

Step 1

Step 1 describes the preparation of compounds of Formula (G1b) by reacting the ester of Formula (G1a) with hydrazine. The preferred solvent includes alcohols (such as MeOH, EtOH and the like).

Step 2

Step 2 describes the preparation of oxadiazoles of Formula (G1c) by reacting the hydrazide of Formula (G1b) with an acid of formula $R_4$—$CO_2H$ in the presence of a coupling agent/dehydrating agent. Preferred reagents for the dehydration are anhydrides (such as T3P and the like). Preferred reaction solvents are ethers (such as dioxane, THF and the like), esters (such as EtOAc and the like) and halogenated hydrocarbons (such as DCM, chloroform, 1,2-DCE and the like). Bases such as an organic amine (such as TEA, DIEA, DBU, 2,6-lutidine and the like) can be used.

Step 3

Step 3 describes the preparation of compounds of Formula (I) by reacting a compound of Formula (G1c) with a sulfonylating reagent $R_3$—$SO_2Cl$. Preferred solvents are polar aprotic solvents (such as DMF and the like) and ethers (such as THF, dioxane and the like). Preferred bases include metal hydrides (such as NaH and the like), metal amides (such as NaHMDS, LDA and the like) and organic amines (such as DBU, TEA and the like).

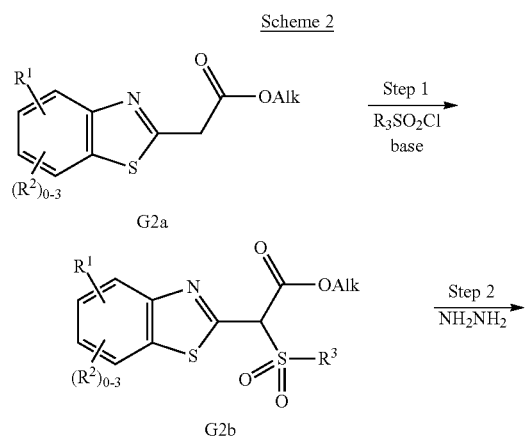

Step 1

Step 1 describes the preparation of a compound of Formula (G2b) from a compound of Formula (G2a) and is analogous to Step 3 in Scheme 1.

Step 2

Step 2 describes the preparation of a compound of Formula (G2c) from a compound of Formula (G2b) and is analogous to Step 1 in Scheme 1.

Step 3

Step 3 describes the preparation of a compound of Formula (I) from a compound of Formula (G2c) and is analogous to Step 2 in Scheme 1.

General Methods

The following methods were used in the exemplified Examples, except where noted otherwise.

Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% MeOH, 89.9% water, 0.1% TFA; B: 10% water, 89.9% MeOH, 0.1% TFA, UV 220 nm), or Method B: PHENOMENEX® Luna C18 column (4.6×50 mm) eluted at 4 mL/min with a 4 min gradient from 100% A to 100% B (A: 10% ACN, 89.9% water, 0.1% TFA; B: 10% water, 89.9% ACN, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% MeOH, 89.9% water, 0.1% $H_3PO_4$; B: 10% water, 89.9% MeOH, 0.1% $H_3PO_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% MeOH, 89.9% water, 0.1% $NH_4OAc$; B: 10% water, 89.9% MeOH, 0.1% $NH_4OAc$, UV 220 nm).

Purification of intermediates and final products was carried out via either normal or reverse phase chromatography. Normal phase chromatography was carried out using prepacked $SiO_2$ cartridges eluted with gradients of hexanes and ethyl acetate or methylene chloride and methanol unless specified otherwise. Reverse phase preparative HPLC was carried out using a Shimadzu Preparative HPLC system running Discovery VP software using:

Method A: YMC Sunfire 5 μm C18 30×100 mm column with a 10 min gradient at 40 mL/min from 100% A to 100%

B (A: 10% MeOH, 89.9% water, 0.1% TFA; B: 10% water, 89.9% MeOH, 0.1% TFA, UV 220 nm);

Method B: PHENOMENEX® Axia Luna 5 μm C18 30×100 mm column with a 10 min gradient at 40 mL/min from 100% A to 100% B (A: 10% ACN, 89.9% water, 0.1% TFA; B: 10% water, 89.9% ACN, 0.1% TFA, UV 220 nm);

Method C: PHENOMENEX® Luna 5 μm C18 30×100 mm column with a 10 min gradient at 40 mL/min from 100% A to 100% B (A: 10% ACN, 89.9% water, 0.1% TFA; B: 10% water, 89.9% ACN, 0.1% TFA, UV 220 nm);

Method D: PHENOMENEX® Luna 5 μm C18 30×100 mm column with a 10 min gradient at 40 mL/min from 100% A to 100% B (A: 10% MeOH, 89.9% water, 0.1% TFA; B: 10% water, 89.9% MeOH, 0.1% TFA, UV 220 nm);

Method E: Waters XBridge C18, 19×250 mm, 5 μm column; Mobile Phase A: 5:95 acetonitrile:water with 10 mM ammonium acetate; Mobile Phase B: 95:5 acetonitrile:water with 10-mM ammonium acetate; Flow: 20 mL/min; or Method F: Waters XBridge C18, 19×250 mm, 5 μm column; Mobile Phase A: 5:95 acetonitrile:water with 0.1% TFA; Mobile Phase B: 95:5 acetonitrile:water with 0.1% TFA; Flow: 20 mL/min.

Alternatively, reverse phase preparative HPLC was carried out using a VARIAN® ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% ACN, 0.05% TFA; B: 98% ACN, 2% water, 0.05% TFA, UV 254 nm).

LCMS chromatograms were obtained on a Shimadzu HPLC system running Discovery VP software, coupled with a Waters ZQ mass spectrometer running MassLynx version 3.5 software and using the following respective methods. Unless specified otherwise, for each method, the LC column was maintained at room temperature and UV detection was set to 220 nm.

Method A: A linear gradient using solvent A (10% MeOH, 90% water, 0.1% of TFA) and solvent B (90% MeOH, 10% water, 0.1% of TFA); 0-100% of solvent B over 4 min and then 100% of solvent B over 1 min. Column: PHENOMENEX® Luna 5 μm C18 (4.5×50 mm). Flow rate was 4 mL/min.

Method B: A linear gradient using solvent A (10% MeOH, 90% water, 0.1% of TFA) and solvent B (90% MeOH, 10% water, 0.1% of TFA); 0-100% of solvent B over 2 min and then 100% of solvent B over 1 min. Column: PHENOMENEX® Luna 5 μm C18 (2.0×30 mm). Flow rate was 1 mL/min.

Method C: A linear gradient using solvent A (10% ACN, 90% water, 10 mM NH$_4$OAc) and solvent B (90% ACN, 10% water, 10 mM NH$_4$OAc); 0-100% of solvent B over 4 min and then 100% of solvent B over 1 min. Column: PHENOMENEX® Luna 5 μm C18 (4.5×50 mm). Flow rate was 4 mL/min.

Method D: A linear gradient using solvent A (10% ACN, 90% water, 0.05% of TFA) and solvent B (90% ACN, 10% water, 0.05% of TFA); 0-100% of solvent B over 2 min and then 100% of solvent B over 1 min. Column: PHENOMENEX® Luna 5 μm C18 (4.5×30 mm). Flow rate was 1 mL/min.

Method E: A linear gradient using solvent A (10% MeOH, 90% water, 10 mM NH$_4$OAc) and solvent B (90% MeOH, 10% water, 10 mM NH$_4$OAc); 0-100% of solvent B over 4 min and then 100% of solvent B over 1 min. Column: PHENOMENEX® Luna 5 μm C18 (4.5×50 mm). Flow rate was 4 mL/min.

Method F: A linear gradient using solvent A (10 mM NH$_4$OAc, 95% water, 5% ACN) and solvent B (10 mM NH$_4$OAc, 95% ACN, 5% water); 0-100% of solvent B over 4 min and then 100% of solvent B over 1 min. Column: MacMod Halo (C18, 4.6×50 mm). Flow rate was 4 mL/min.

Method G: A linear gradient using solvent A (10% ACN, 90% water, 0.1% TFA) and solvent B (90% ACN, 10% water, 0.1% TFA); 0-100% of solvent B over 4 min and then 100% of solvent B over 1 min. Column: PHENOMENEX® Luna 3 μm C18 (2.0×50 mm). Flow rate was 4 mL/min.

Method H: A linear gradient using solvent A (10% MeOH, 90% water, 0.1% of formic acid) and solvent B (90% MeOH, 10% water, 0.1% of formic acid); 0-100% of solvent B over 2 min and then 100% of solvent B over 1 min. Column: PHENOMENEX® Luna 3 μm C18 (2.0×30 mm). Flow rate was 1 mL/min.

Method I: A linear gradient using solvent A (10% MeOH, 90% water, 10 mM NH$_4$OAc) and solvent B (90% MeOH, 10% water, 10 mM NH$_4$OAc); 0-100% of solvent B over 2 min and then 100% of solvent B over 1 min. Column: PHENOMENEX® Luna 3 μm C18 (2.0×30 mm). Flow rate was 1 mL/min.

Method J: A linear gradient using solvent A (10% MeOH, 90% water, 0.1% of formic acid) and solvent B (90% MeOH, 10% water, 0.1% of TFA); 0-100% of solvent B over 4 min and then 100% of solvent B over 1 min. Column: PHENOMENEX® Luna 5 μm C18 (4.5×50 mm). Flow rate was 4 mL/min.

Method K: A linear gradient using solvent A (10 mM NH$_4$OAc, 95% water, 5% ACN) and solvent B (10 mM NH$_4$OAc, 95% ACN, 5% water); 0-100% of solvent B over 5.5 min and then 100% of solvent B over 1.5 min. Column: SUPELCO® Ascentis 4.6×50 mm 2.7 μm C18. Flow rate was 4 mL/min.

Method L: A linear gradient using solvent A (5% MeOH, 95% water, 0.05% of TFA) and solvent B (95% MeOH, 5% water, 0.05% of TFA); 0-100% of solvent B over 4 min and then 100% of solvent B over 1 min. Column: WATERS® XBridge C18 (4.6×50 mm, 5 μm). Flow rate was 4 mL/min. The LC column was maintained at 35° C.

Method M: A linear gradient using of Solvent A (0.05% TFA, 100% water) and Solvent B (0.05% TFA, 100% ACN); 2 to 98% B over 1 min, with 0.5 min hold time at 98% B. Column: WATERS® BEH C18 (2.1×50 mm). Flow rate: 0.8 mL/min.

Method N: A linear gradient using solvent A (5% ACN, 95% water, 10 mM NH$_4$OAc) and solvent B (95% ACN, 5% water, 10 mM NH$_4$OAc); 0-100% of solvent B over 3 min and then 100% of solvent B over 1 min. Column: WATERS® BEH C18 (2.1×50 mm). Flow rate: 1.1 mL/min.

Method O: A linear gradient using solvent A (5% ACN, 95% water, 0.05% of TFA) and solvent B (95% ACN, 5% water, 0.05% of TFA); 0-100% of solvent B over 3 min and then 100% of solvent B over 1 min. Column: WATERS® BEH C18 (2.1×50 mm). Flow rate: 1.1 mL/min.

Method P: A linear gradient using solvent A (5% ACN, 95% water, 10 mM NH$_4$OAc) and solvent B (95% ACN, 5% water, 10 mM NH$_4$OAc); 0-100% of solvent B over 4 min and then 100% of solvent B over 1 min. Column: WATERS® XBridge C18 (4.6×50 mm, 5 μm). Flow rate was 4 mL/min.

Method Q: A linear gradient using solvent A (10% MeOH, 90% water, 0.1% TFA) and solvent B (90% MeOH, 10% water, 0.1% TFA); 0-100% of solvent B over 2 min and then 100% of solvent B over 1 min. Column: PHENOMENEX® Luna 3 μm C18 (2.0×50 mm). Flow rate was 1 mL/min.

Method R: A linear gradient using solvent A (10% MeOH, 90% water, 0.1% TFA) and solvent B (90% MeOH, 10% water, 0.1% TFA); 0-100% of solvent B over 4 min and then 100% of solvent B over 1 min. Column: PHENOMENEX® Luna 3 µm C18 (2.0×50 mm). Flow rate was 0.8 mL/min.

Method S: A linear gradient using solvent A (5% ACN, 95% water, 10 mM $NH_4OAc$) and solvent B (95% ACN, 5% water, 10 mM $NH_4OAc$); 0% solvent B for 0.5 min, 0-100% of solvent B over 4 min and then 100% of solvent B for 0.5 min. Column: WATERS® BEH C18 (2.0×50 mm). Flow rate: 1.0 mL/min.

Preparative HPLC methods employed in the purification of products:

Method A: Linear gradient of 0 to 100% B over 10 min, with 5 min hold time at 100% B; Shimadzu LC-8A binary pumps Waters ZQ mass spectrometer using Waters MassLynx 4.0 SP4 MS software
    UV visualization at 220 nm
    Column: WATERS® XBridge 19×150 mm 5 µm C18
    Flow rate: 20 mL/min
    Peak collection triggered by mass spectrometry
    Solvent A: 0.1% TFA, 10% ACN, 90% water
    Solvent B: 0.1% TFA, 90% ACN, 10% water NMR Employed in Characterization of Examples $^1$H NMR spectra were obtained with Bruker or JEOL® Fourier transform spectrometers operating at frequencies as follows: $^1$H NMR: 400 MHz (Bruker or JEOL®) or 500 MHz (JEOL®). $^{13}$C NMR: 100 MHz (Bruker or JEOL®) Spectra data are reported in the format: chemical shift (multiplicity, coupling constants, number of hydrogens). Chemical shifts are specified in ppm downfield of a tetramethylsilane internal standard (δ units, tetramethylsilane =0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

IV. Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman, J. et al., *Science*, 235:442-447 (1987); Yanagisawa, M. et al., *Nature*, 332(6163):411-415 (1988); Folkman, J. et al., *J. Biol. Chem.*, 267(16):10931-10934 (1992); Janssens, S. P. et al., *J. Biol. Chem.*, 267(21):14519-14522 (1992); Lamas, S. et al., *Proc. Natl. Acad. Sci. U.S.A.*, 89(14):6348-6352 (1992); Luscher, T. F. et al., *Hypertension*, 19(2):117-130 (1992); Williams et al., *Am. Rev. Respir. Dis.*, 146:S45-S50 (1992); and Bevilacqua, M. P. et al., *J. Clin. Invest.*, 91(2):379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S. In 2008, cardiovascular disease accounted for 33% of all deaths in the U.S., and ~1 of every 6 deaths were specifically caused by atherosclerotic coronary heart disease (*Circulation* 125:e2-e220 (2012)).

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. A low level of high density lipoprotein-cholesterol (HDL-C) is also a known risk factor for CHD (Gordon, D. J. et al., *Circulation*, 79(1):8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos, A. S. et al., *Circulation*, 106(11):1321-1326 (2002)). Notably, the endothelial lipase-mediated binding and uptake of HDL particles and the selective uptake of HDL-derived cholesteryl esters have been reported to be independent of its enzymatic lipolytic activity (Strauss, J. G. et al., *Biochem. J.*, 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA1 lipoprotein concentrations; (d) high LDL cholesterol concentrations; (e) high levels of small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase (EL) and hepatic lipase (HL) activities were measured using a fluorescent substrate, A10070, (Invitrogen, CA) doped into an artificial vesicle containing DMPG (Avanti Polar Lipids) as the excipient. Vesicles were prepared by combining 571 µL of 29 mM DMPG in a 1:1 mixture of MeOH and CHCl$_3$ with 2000 µL of 1 mM A10070 in a 1:1 mixture of MeOH and CHCl$_3$. The mixture was dried under nitrogen in multiple vials then resuspended in 20 mL total volume of 50 mM HEPES pH 8.0 buffer containing 50 mM NaCl and 0.2 mM EDTA. The sample was allowed to sit at room temperature for 15 min and then was sonicated 3×4 mins on ice with a Branson Sonicator using duty cycle 1. This preparation provides vesicles with a mole fraction of 0.11 for the FRET substrate.

The enzymatic assay was measured using 384-well white Optiplates. Each well contained 20 µL of assay buffer (50 mM HEPES pH 8.0, 50 mM NaCl and 1 mM CaCl$_2$) and 0.25 µL of a DMSO solution containing a compound of interest. EL or HL (10 µL) was added and allowed to incubate with the compound for 30 min at 37° C. The source of EL was conditioned media obtained from HT-1080 cells that were transformed using RAGE technology (Athersys) to overexpress endogenous EL, and HL was partially purified from conditioned media obtained from COS cells overexpressing HL. The reaction was started by the addition of 10 µL of a 1:10 dilution of vesicles. The final total reaction volume was 20.25 µL. The reaction rates were measured on a Gemini plate reader with an excitation wavelength of 490 nm and an emission wavelength of 530 nm. Readings were taken over a period of 60 minutes, and the slope between 300 and 900 secs of the readout was used to calculate the rate of the reaction.

Comparator and Reference Compounds

The following comparator compounds, their preparations and EL IC$_{50}$ values are disclosed in WO 2011074560.

| Example No. in WO 2011/074560 | Structure | EL IC$_{50}$ (nM) |
|---|---|---|
| I-1-85 | 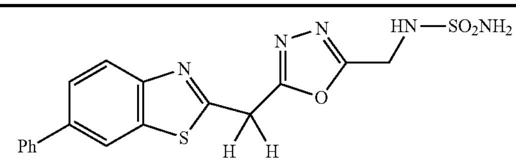 | 6 reported in WO 2011074560 |
| I-3-21 | 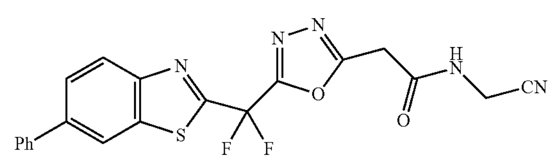 [SMILES: N#CCNC(=O)Cc1nnc(C(F)(F)c2nc3ccc(-c4ccccc4)cc3s2)o1] | 250 reported in WO 2011074560 |

The following reference compounds and their preparations are described below. The EL IC$_{50}$ values were measured using the EL assay described above.

| Compound No. | Structure | EL IC$_{50}$ (nM) |
|---|---|---|
| Reference 1 | 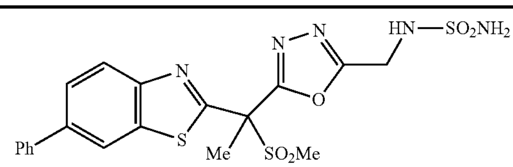 | Isomer A, 3751 Isomer B, 5202 |

-continued

| Compound No. | Structure | EL IC$_{50}$ (nM) |
|---|---|---|
| Reference 2 | [structure: 6-Ph-benzothiazole linked to 1,3,4-oxadiazole bearing CH$_2$-NH-SO$_2$NH$_2$, with quaternary carbon substituted by Me and SO$_2$Bn] | Isomer A, >25000<br>Isomer B, 713 |
| Reference 3 | [structure: 6-(6-fluoropyridin-3-yl)-benzothiazole linked to 1,3,4-oxadiazole bearing CH$_2$-NH-SO$_2$NH$_2$, with CH(Me) linker] | 6518 |
| Reference 4 | [structure: 6-(6-fluoropyridin-3-yl)-benzothiazole linked to 1,3,4-oxadiazole bearing CH$_2$-NH-SO$_2$NH$_2$, with C(OH)(Me) linker] | 14880 |

The exemplified compounds, Example 1 to Example 267, disclosed in the present invention were tested in the EL assay described above. Surprisingly, Example 1 to Example 267 were found having a range of EL IC$_{50}$ values of ≤0.3 μM (300 nM), as shown below.

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, pheniramine, β₃-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following Examples demonstrate a partial scope of the invention and are not meant to be limiting of the scope of the invention.

Example 1
5-((5-((Benzylsulfonyl)(6-(6-fluoropyridin-3-yl)benzo[d]thiazol-2-yl)methyl)-1,3,4-oxadiazol-2-yl)methyl)-5-methylthiazolidine-2,4-dione (Isomer A)
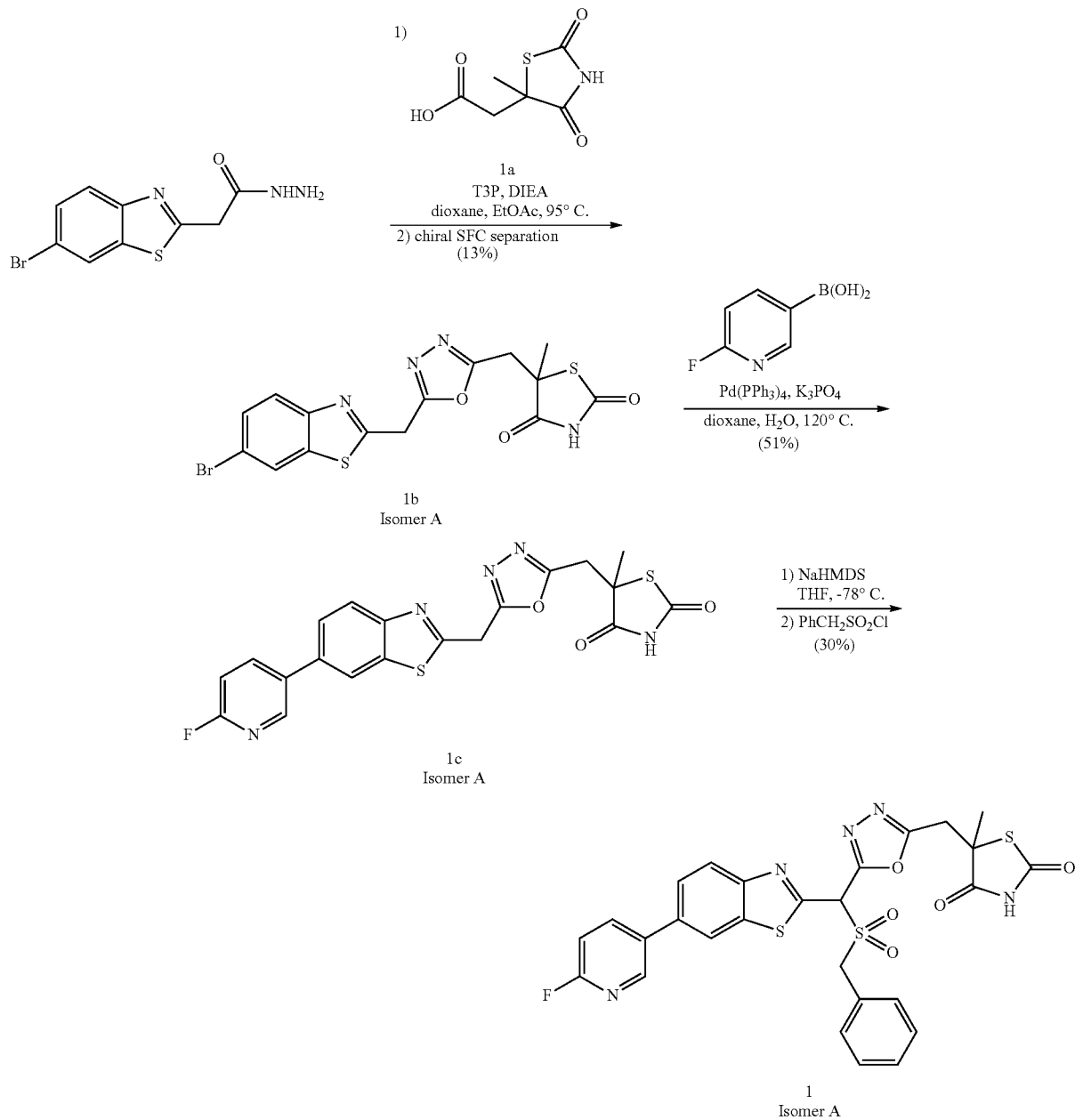
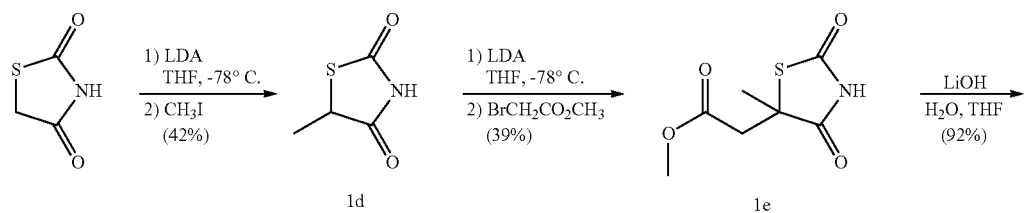

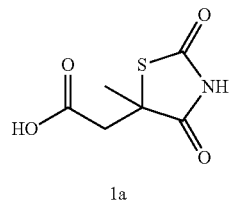

1a

Compound 1b. 5-((5-((6-Bromobenzo[d]thiazol-2-yl)methyl)-1,3,4-oxadiazol-2-yl)methyl)-5-methylthiazolidine-2,4-dione (Isomer A)

To a solution of Compound 1a (150 mg, 0.77 mmol) (described below in this Example) and 2-(6-bromobenzo[d]thiazol-2-yl)acetohydrazide (220 mg, 0.77 mmol) (described in WO 2011/074560) in dioxane (3 mL) was added 50% T3P in EtOAc (1.1 mL, 1.9 mmol) followed by DIEA (0.36 mL, 1.9 mmol) and the reaction mixture heated at 70° C. for 1 h. Additional 50% T3P in EtOAc (0.36 mL, 1.9 mmol) and DIEA (0.36 mL, 1.9 mmol) was added and the reaction mixture was heated at 95° C. for 16 h. The reaction mixture was allowed to cool to rt, evaporated under reduced pressure, and the residue purified by silica gel chromatography eluting with 0-100% EtOAc/hexanes to afford the racemic product (180 mg, 54% combined yield) as a light brown solid. LCMS=1.79 min using analytical method (B), 440.9 (M+H). The enantiomers were separated by preparative chiral SFC(CHIRALPAK® AS-H, 30×250 mm ID, 5 µm, 85 mL/min, 150 bar BP, 40° C. 30% EtOH/70% CO$_2$/0.1% DEA) to afford isomer A as Compound 1b (RT=7.8 min, 45 mg, 13% yield), LCMS=1.79 min using analytical method (B), 440.9 (M+H). $^1$H NMR (400 MHz, CDCl$_3$) δ 8.01 (d, J=1.8 Hz, 1H), 7.88 (d, J=8.6 Hz, 1H), 7.60 (dd, J=8.7, 1.9 Hz, 1H), 4.72 (d, J=1.1 Hz, 2H), 3.65-3.45 (m, 2H), 1.89 (s, 3H); and isomer B (RT=12.8 min, 45 mg, 13% yield), LCMS=1.77 min using analytical method (B), 440.9 (M+H).

Compound 1c. 5-((5-((6-(6-Fluoropyridin-3-yl)benzo[d]thiazol-2-yl)methyl)-1,3,4-oxadiazol-2-yl)methyl)-5-methylthiazolidine-2,4-dione (Isomer A)

Compound 1b (45 mg, 0.10 mmol), (6-fluoropyridin-3-yl)boronic acid (22 mg, 0.15 mmol), potassium phosphate (54 mg, 0.26 mmol) and tetrakis(triphenylphosphine)palladium (0) (5.9 mg, 5.1 µmol) were combined in a microwave tube and sealed. The mixture was degassed with argon (3×), treated with dioxane (1.0 mL) and water (0.3 mL) then heated by microwave irradiation at 120° C. for 0.5 h. After allowing to cool to rt, the solvent was evaporated under reduced pressure. The residue was dissolved in DMF and purified by preparative HPLC (Method B, gradient elution of 20-100% solvent B). Fractions containing product were made basic by the addition of 1.5 M phosphate buffer, evaporated under reduced pressure to remove most of the ACN, acidified by the addition of satd. NH$_4$Cl and extracted with DCM (3×), dried (Na$_2$SO$_4$), filtered and concentrated under reduced pressure to afford Compound 1c (25 mg, 51%) as a white solid. LCMS=1.68 min using analytical method (B), 456.0 (M+H). $^1$H NMR (400 MHz, CDCl$_3$) δ 8.51-8.42 (m, 1H), 8.17-8.08 (m, 1H), 8.03 (d, J=1.3 Hz, 2H), 7.69-7.60 (m, 1H), 7.10-7.00 (m, 1H), 4.78 (s, 2H), 3.51 (m, 2H), 1.90 (s, 3H).

Example 1

To a solution of Compound 1c (10 mg, 0.020 mmol) in THF (1 mL) at −78° C. was added 1M NaHMDS in THF (55 µL, 0.055 mmol) and the reaction mixture stirred for 15 min. Phenylmethanesulfonyl chloride (5.0 mg, 0.026 mmol) was added and the reaction mixture stirred for 15 min then quenched by the addition of AcOH (5 µL), diluted with MeOH and purified by preparative HPLC (Method B, gradient elution of 20-100% solvent B). Fractions containing product were made basic by the addition of 1.5 M phosphate buffer, evaporated under reduced pressure to remove most of the ACN, acidified by the addition of satd. NH$_4$Cl then extracted with DCM (3×), dried (Na$_2$SO$_4$), filtered and concentrated under reduced pressure to afford Example 1 (4.0 mg, 30%) as white powder. LCMS=1.96 min using analytical method (B), 610.1 (M+H). $^1$H NMR (400 MHz, CDCl$_3$) δ 8.44-8.37 (m, 1H), 8.06-7.95 (m, 1H), 7.69 (m, 1H), 7.56 (m 2H), 7.26 (m 5H), 7.07 (dd, J=8.4, 2.4 Hz, 1H), 4.48 (s, 2H), 3.70-3.47 (m, 2H), 1.93 (s, 3H). EL IC$_{50}$<10 nM.

Compound 1d. 5-Methylthiazolidine-2,4-dione

To a stirred solution of thiazolidine-2,4-dione (1.50 g, 13 mmol) in THF (50 mL) at −78° C. was added 2 M LDA in heptane/THF/benzene (14 mL, 27 mmol) dropwise over 10 minutes. The reaction mixture was stirred for 15 minutes then treated with iodomethane (0.88 mL, 14 mmol). The reaction mixture was stirred at −78° C. for 2 h then quenched by dropwise addition of AcOH (2 mL), diluted with EtOAc and the organic portion washed with water (2×), brine (2×), dried (Na$_2$SO$_4$), filtered and concentrated under reduced pressure. The residue was purified by silica gel chromatography eluting with 0-100% EtOAc/hexanes to afford Compound 1d (700 mg, 42%) as a clear oil. LCMS=0.47 min using analytical method (B), 131.8 (M+H). $^1$H NMR (400 MHz, CDCl$_3$) δ 4.35-4.25 (m, 1H), 1.72 (d, J=7.3 Hz, 3H).

Compound 1e. Methyl 2-(5-methyl-2,4-dioxothiazolidin-5-yl)acetate

To a stirred solution of Compound 1d (300 mg, 2.3 mmol) in THF (20 mL) at −40° C. was added 2 M LDA in heptane/THF/benzene (2.4 mL, 4.8 mmol) dropwise. After 15 minutes, methyl 2-bromoacetate (0.30 mL, 3.2 mmol) was added and the reaction mixture stirred at −40° C. for 2 h then quenched by dropwise addition of AcOH (0.8 mL). The reaction mixture was diluted with EtOAc, and the organic portion washed with water (2×), brine (2×), dried (Na$_2$SO$_4$), filtered and concentrated under reduced pressure. The product was purified by silica gel chromatography eluting with 0-100% EtOAc/hexanes to afford Compound 1e (180 mg, 39%) as a clear oil. LCMS=1.06 min using analytical method (B), 225.9 (M+Na). $^1$H NMR (400 MHz, CDCl$_3$) δ 3.75 (s, 3H), 3.24-2.84 (m, 2H), 1.81 (s, 3H).

Compound 1a. 2-(5-Methyl-2,4-dioxothiazolidin-5-yl)acetic acid

To a solution of Compound 1e (0.18 g, 0.86 mmol) in THF (8 mL) was added 1 M LiOH (2.6 mL, 2.6 mmol) at rt. After 5 h, the organic solvent was evaporated under reduced pressure and the resultant aqueous layer was diluted with water and acidified by the addition of 1 N HCl solution to pH ~2. The solution was extracted with EtOAc (2×) and the combined extracts were dried (Na$_2$SO$_4$), filtered and concentrated under reduced pressure to afford Compound 1a (150 mg, 92%) as a white solid. LCMS=0.67 min using analytical method (B), 189.9 (M+H). $^1$H NMR (400 MHz, CD$_3$OD) δ 3.15-2.89 (m, 2H), 1.72 (s, 3H).

Example 2 to Example 25 were prepared by the general procedures described for Example 1.

| Ex. No. | Structure | Name | $^1$H NMR | LC/MS RT (min) Method M + H | EL IC$_{50}$ (nM) |
|---|---|---|---|---|---|
| 2 | 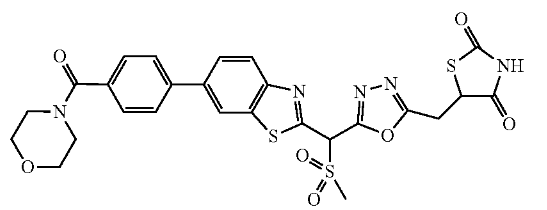 | 5-((5-((methylsulfonyl)(6-(4-(4-morpholinylcarbonyl)phenyl)-1,3-benzothiazol-2-yl)methyl)-1,3,4-oxadiazol-2-yl)methyl)-1,3-thiazolidine-2,4-dione | $^1$H NMR (500 MHz, DMSO-d$_6$) δ 8.22-8.17 (m, 1H), 7.94-7.81 (m, 2H), 7.79-7.73 (m, 2H), 7.55-7.47 (m, 2H), 5.05-4.99 (m, 1H), 3.71-3.49 (m, 8H), 3.23 (m, 2H), 3.22 (s, 3H) | 1.66 B 614.0 | <10 |
| 3 | 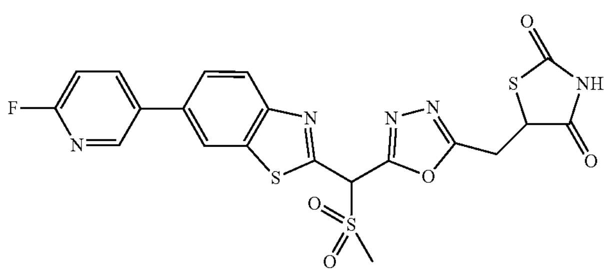 | 5-((5-((6-(6-fluoro-3-pyridinyl)-1,3-benzothiazol-2-yl)(methylsulfonyl)methyl)-1,3,4-oxadiazol-2-yl)methyl)-1,3-thiazolidine-2,4-dione | $^1$H NMR (500 MHz, DMSO-d$_6$) δ 8.68-8.60 (m, 1H), 8.59 (d, J = 2.5 Hz, 1H), 8.31 (m, 1H), 8.27 (d, J = 1.7 Hz, 1H), 7.97 (m, 1H), 7.79 (m, 1H), 7.33 (m, 1H), 5.10-5.04 (m, 1H), 3.81-3.69 (m, 2H), 3.29 (s, 3H) | 1.67 B 519.8 | <10 |
| 4 | 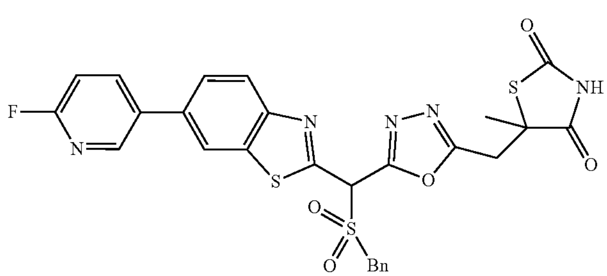 | 5-((5-((benzylsulfonyl)(6-(6-fluoropyridin-3-yl)benzo[d]thiazol-2-yl)methyl)-1,3,4-oxadiazol-2-yl)methyl)-5-methylthiazolidine-2,4-dione (Isomer B) | $^1$H NMR (400 MHz, CDCl$_3$) δ 8.35 (d, J = 2.0 Hz, 1H), 7.94 (m, 1H), 7.63 (s, 1H), 7.50 (m, 2H), 7.20 (br. s., 5H), 7.01 (m, 1H), 4.43 (br. s., 2H), 3.65-3.41 (m, 2H), 1.87 (s, 3H) | 1.97 B 610.0 | <10 |
| 5 | 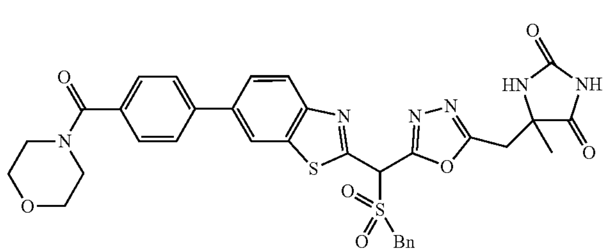 | 5-((5-((benzylsulfonyl)(6-(4-(morpholine-4-carbonyl)phenyl)benzo[d]thiazol-2-yl)methyl)-1,3,4-oxadiazol-2-yl)methyl)-5-methylimidazolidine-2,4-dione | $^1$H NMR (400 MHz, DMSO-d$_6$) δ 12.56 (br. s., 1H), 10.76 (s, 1H), 8.13 (s, 2H), 7.78-7.65 (m, 3H), 7.51 (d, J = 8.3 Hz, 2H), 7.34-7.18 (m, 5H), 4.94-4.41 (m, 2H), 3.85-3.41 (m, 8H), 3.43-3.18 (m, 2H), 1.49 (s, 3H) | 1.72 B 686.9 | 30 |

| Ex. No. | Structure | Name | $^1$H NMR | LC/MS RT (min) Method M + H | EL IC$_{50}$ (nM) |
|---|---|---|---|---|---|
| 6 | 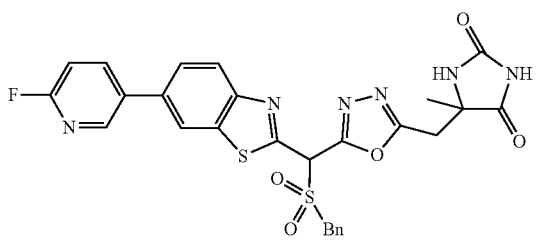 | 5-((5-((benzylsulfonyl)(6-(6-fluoropyridin-3-yl)benzo[d]thiazol-2-yl)methyl)-1,3,4-oxadiazol-2-yl)methyl)-5-methylimidazolidine-2,4-dione (Isomer A) | $^1$H NMR (400 MHz, DMSO-d$_6$) δ 10.76 (s, 1H), 8.54 (d, J = 2.5 Hz, 1H), 8.36-8.22 (m, 1H), 8.13 (s, 2H), 7.92 (d, J = 8.5 Hz, 1H), 7.73 (dd, J = 8.5, 1.8 Hz, 1H) 7.37-6.99 (m, 6H), 4.79-4.50 (m, 2H), 3.45-3.16 (m, 3H), 1.48 (s, 3H) | 1.78 B 592.9 | 11 |
| 7 | 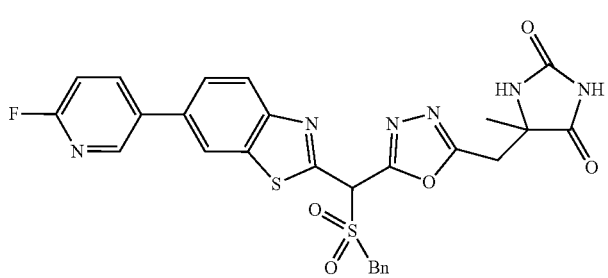 | 5-((5-((benzylsulfonyl)(6-(6-fluoropyridin-3-yl)benzo[d]thiazol-2-yl)methyl)-1,3,4-oxadiazol-2-yl)methyl)-5-methylimidazolidine-2,4-dione (Isomer B) | $^1$H NMR (400 MHz, DMSO-d$_6$) δ 10.76 (s, 1H), 8.54 (d, J = 2.5 Hz, 1H), 8.36-8.22 (m, 1H), 8.13 (s, 2H), 7.92 (d, J = 8.5 Hz, 1H), 7.73 (dd, J = 8.5, 1.8 Hz, 1H) 7.37-6.99 (m, 6H), 4.79-4.50 (m, 2H), 3.45-3.16 (m, 3H), 1.48 (s, 3H) | 1.78 B 592.9 | 188 |
| 8 | 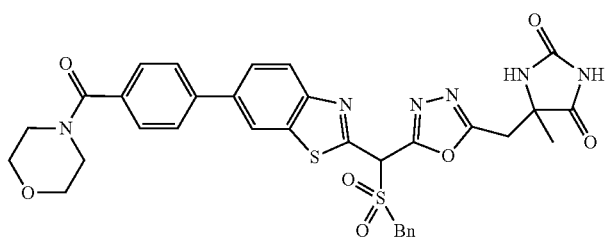 | 5-((5-((benzylsulfonyl)(6-(4-(morpholine-4-carbonyl)phenyl)benzo[d]thiazol-2-yl)methyl)-1,3,4-oxadiazol-2-yl)methyl)-5-methylimidazolidine-2,4-dione | $^1$H NMR (400 MHz, DMSO-d$_6$) δ 12.56 (br. s., 1H), 10.76 (s, 1H), 8.13 (s, 2H), 7.78-7.65 (m, 3H), 7.51 (d, J = 8.3 Hz, 2H), 7.34-7.18 (m, 5H), 4.94-4.41 (m, 2H), 3.85-3.41 (m, 8H), 3.43-3.18 (m, 2H), 1.49 (s, 3H) | 1.72 B 687.1 | 62 |
| 9 | 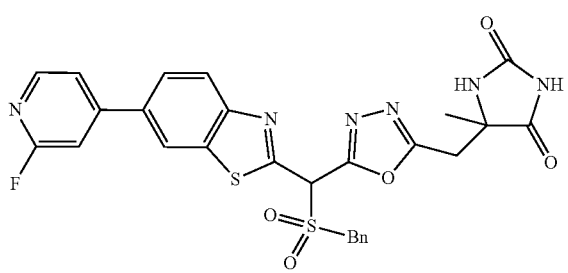 | 5-((5-((benzylsulfonyl)(6-(2-fluoropyridin-4-yl)benzo[d]thiazol-2-yl)methyl)-1,3,4-oxadiazol-2-yl)methyl)-5-methylimidazolidine-2,4-dione (Isomer A) | $^1$H NMR (400 MHz, DMSO-d$_6$) δ 10.76 (s, 1H), 8.33-8.23 (m, 2H), 8.13 (br. s., 1H), 7.88 (d, J = 8.0 Hz, 1H), 7.69 (d, J = 5.3 Hz, 1H), 7.52 (s, 1H), 7.36-7.14 (m, 5H), 4.95-4.25 (m, 2H), 3.48-3.16 (m, 3H), 1.48 (s, 3H) | 1.78 B 593.0 | 122 |

| Ex. No. | Structure | Name | ¹H NMR | LC/MS RT (min) Method M + H | EL IC$_{50}$ (nM) |
|---|---|---|---|---|---|
| 10 | 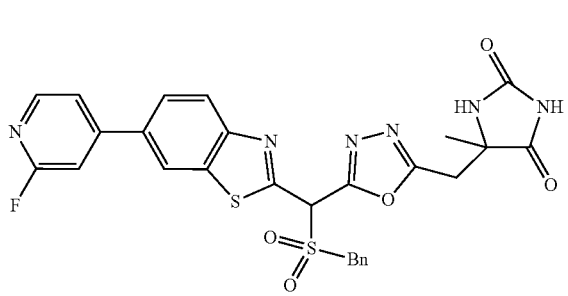 | 5-((5-((benzylsulfonyl)(6-(2-fluoropyridin-4-yl)benzo[d]thiazol-2-yl)methyl)-1,3,4-oxadiazol-2-yl)methyl)-5-methylimidazolidine-2,4-dione (Isomer B) | ¹H NMR (400 MHz, DMSO-d$_6$) δ 10.76 (s, 1H), 8.33-8.23 (m, 2H), 8.13 (br. s., 1H), 7.88 (d, J = 8.0 Hz, 1H), 7.69 (d, J = 5.3 Hz, 1H), 7.52 (s, 1H), 7.36-7.14 (m, 5H), 4.95-4.25 (m, 2H), 3.48-3.16 (m, 3H), 1.48 (s, 3H) | 1.77 B 593.0 | 19 |
| 11 | 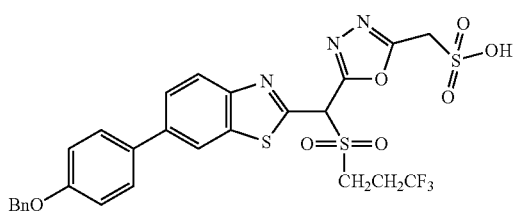 | (5-((6-(4-(benzyloxy)phenyl)benzo[d]thiazol-2-yl)((3,3,3-trifluoropropyl)sulfonyl)methyl)-1,3,4-oxadiazol-2-yl)methanesulfonic acid | ¹H NMR (400 MHz, CD$_3$OD) δ 7.97 (s, 1H), 7.70-7.67 (m, 2H), 7.60 (d, J = 8.8 Hz, 2H),7.49-7.45 (m, 2H),7.39 (t, J = 7.3 Hz, 2H), 7.33 (d, J = 7.1 Hz, 1H), 7.10 (d, J = 8.8 Hz, 2H), 5.15 (s, 2H), 4.43 (s, 2H), 3.73-3.64 (m, 2H), 2.74 (dd, J = 15.9, 10.6 Hz, 2H) | 2.27 B 654.1 | >10 |
| 12 | 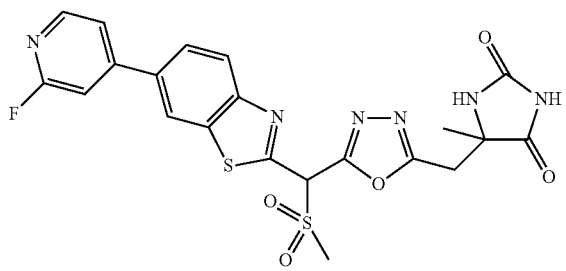 [SMILES: CC1(Cc2nnc(C(c3nc4ccc(-c5ccnc(F)c5)cc4s3)S(C)(=O)=O)o2)NC(=O)NC1=O] | 5-((5-((6-(2-fluoropyridin-4-yl)benzo[d]thiazol-2-yl)(methylsulfonyl)methyl)-1,3,4-oxadiazol-2-yl)methyl)-5-methylimidazolidine-2,4-dione (Isomer B) | ¹H NMR (400 MHz, DMSO-d$_6$) δ 10.74-10.65 (m, 1H), 8.48-8.39 (m, 1H), 8.35-8.30 (m, 1H), 8.09-8.06 (m, 1H), 7.97-7.90 (m, 2H), 7.75-7.69 (m, 1H), 7.56-7.51 (m, 1H), 3.41-3.21 (m, 5H), 1.47-1.44 (m, 3H) | 1.60 B 517.0 | 54 |
| 13 | 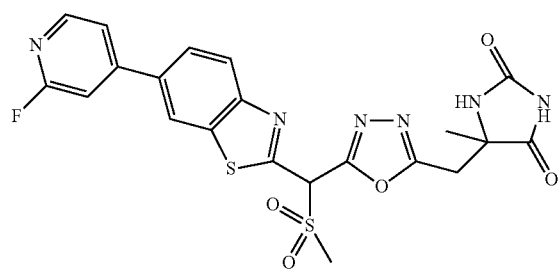 [SMILES: CC1(Cc2nnc(C(c3nc4ccc(-c5ccnc(F)c5)cc4s3)S(C)(=O)=O)o2)NC(=O)NC1=O] | 5-((5-((6-(2-fluoropyridin-4-yl)benzo[d]thiazol-2-yl)(methylsulfonyl)methyl)-1,3,4-oxadiazol-2-yl)methyl)-5-methylimidazolidine-2,4-dione (Isomer A) | ¹H NMR (400 MHz, DMSO-d$_6$) δ 10.74-10.65 (m, 1H), 8.48-8.39 (m, 1H), 8.35-8.30 (m, 1H), 8.09-8.06 (m, 1H), 7.97-7.90 (m, 2H), 7.75-7.69 (m, 1H), 7.56-7.51 (m, 1H), 3.41-3.21 (m, 5H), 1.47-1.44 (m, 3H) | 1.60 B 517.0 | <10 |

-continued

| Ex. No. | Structure | Name | ¹H NMR | LC/MS RT (min) Method M + H | EL IC₅₀ (nM) |
|---|---|---|---|---|---|
| 14 | 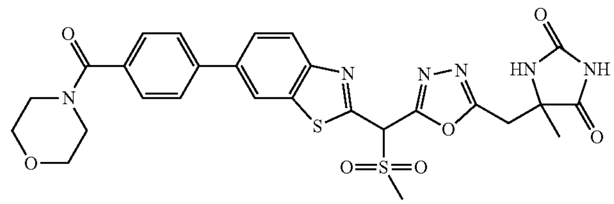 [SMILES: CC1(Cc2nnc(C(c3nc4ccc(-c5ccc(C(=O)N6CCOCC6)cc5)cc4s3)S(C)(=O)=O)o2)NC(=O)NC1=O] | 5-methyl-5-((5-((methylsulfonyl)(6-(4-(morpholine-4-carbonyl)phenyl)benzo[d]thiazol-2-yl)methyl)-1,3,4-oxadiazol-2-yl)methyl)imidazolidine-2,4-dione (Isomer A) | ¹H NMR (400 MHz, DMSO-$d_6$) δ 10.72 (s, 1H), 8.26-8.21 (m, 1H), 8.10-8.05 (m, 1H), 7.97-7.89 (m, 1H), 7.80-7.74 (m, 3H), 7.52 (d, J = 8.3 Hz, 2H), 3.62 (br. s., 8H), 3.38 (d, J = 5.5 Hz, 2H), 3.29-3.18 (m, 3H), 1.47-1.43 (m, 3H) | 1.53 B 611.1 | 12 |
| 15 | 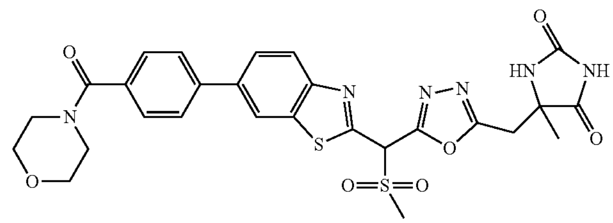 | 5-methyl-5-((5-((methylsulfonyl)(6-(4-(morpholine-4-carbonyl)phenyl)benzo[d]thiazol-2-yl)methyl)-1,3,4-oxadiazol-2-yl)methyl)imidazolidine-2,4-dione (Isomer B) | ¹H NMR (400 MHz, DMSO-$d_6$) δ 10.72 (s, 1H), 8.26-8.21 (m, 1H), 8.10-8.05 (m, 1H), 7.97-7.89 (m, 1H), 7.80-7.74 (m, 3H), 7.52 (d, J = 8.3 Hz, 2H), 3.62 (br. s., 8H), 3.38 (d, J = 5.5 Hz, 2H), 3.29-3.18 (m, 3H), 1.47-1.43 (m, 3H) | 1.53 B 611.1 | 65 |
| 16 | 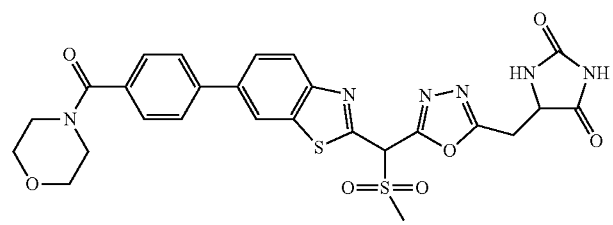 [SMILES: CC1(Cc2nnc(C(c3nc4ccc(-c5ccc(C(=O)N6CCOCC6)cc5)cc4s3)S(C)(=O)=O)o2)NC(=O)NC1=O] | 5-((5-((methylsulfonyl)(6-(4-(morpholine-4-carbonyl)phenyl)benzo[d]thiazol-2-yl)methyl)-1,3,4-oxadiazol-2-yl)methyl)imidazolidine-2,4-dione | ¹H NMR (400 MHz, DMSO-$d_6$) δ 10.78-10.71 (m, 1H), 8.25 (d, J = 1.8 Hz, 1H), 8.06-7.98 (m, 1H), 7.95-7.92 (m, 1H), 7.80-7.73 (m, 3H), 7.52 (d, J = 8.3 Hz, 2H), 4.53 (t, J = 4.9 Hz, 1H), 3.62 (br. s., 8H), 3.41-3.38 (m, 2H), 3.27 (br. s., 3H) | 0.70 M 596.8 | 46 |
| 17 | 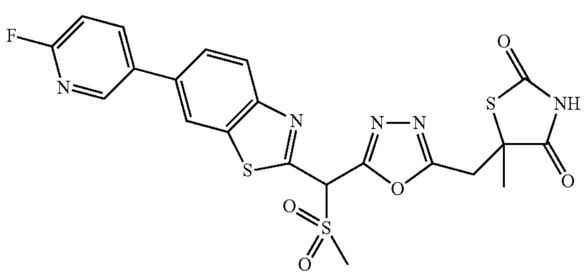 [SMILES: CC1(Cc2nnc(C(c3nc4ccc(-c5ccc(F)nc5)cc4s3)S(C)(=O)=O)o2)SC(=O)NC1=O] | 5-((5-((6-(6-fluoropyridin-3-yl)benzo[d]thiazol-2-yl)(methylsulfonyl)methyl)-1,3,4-oxadiazol-2-yl)methyl)-5-methylthiazolidine-2,4-dione (Isomer A) | ¹H NMR (400 MHz, CDCl₃) δ 8.38 (br. s., 1H), 8.02-7.93 (m, 1H), 7.80-7.73 (m, 1H), 7.58-7.52 (m, 2H), 7.08-6.99 (m, 1H), 3.48-3.64 (m, 2H), 3.15 (s, 3H), 1.86 (s, 3H) | 1.71 B 534.0 | <10 |
| 18 | 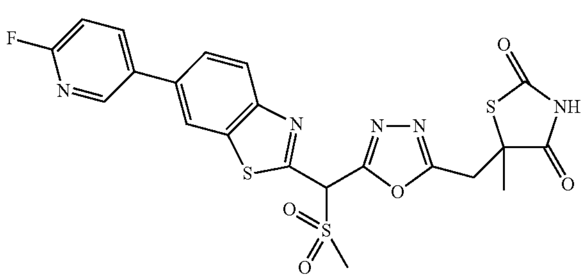 [SMILES: CC1(Cc2nnc(C(c3nc4ccc(-c5ccc(F)nc5)cc4s3)S(C)(=O)=O)o2)SC(=O)NC1=O] | 5-((5-((6-(6-fluoropyridin-3-yl)benzo[d]thiazol-2-yl)(methylsulfonyl)methyl)-1,3,4-oxadiazol-2-yl)methyl)-5-methylthiazolidine-2,4-dione (Isomer B) | ¹H NMR (400 MHz, CDCl₃) δ 8.36 (s, 1H), 7.99-7.91 (m, 1H), 7.72 (s, 1H), 7.52-7.54 (m, 2H), 6.99-7.01 (m, 1H), 3.67-3.45 (m, 2H), 3.15 (s, 3H), 1.84 (s, 2H) | 1.71 B 534.0 | <10 |

-continued

| Ex. No. | Structure | Name | ¹H NMR | LC/MS RT (min) Method M + H | EL IC₅₀ (nM) |
|---|---|---|---|---|---|
| 19 | 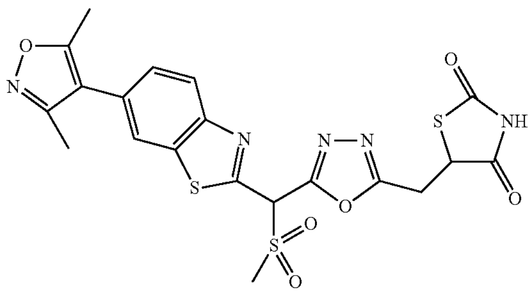 [SMILES: Cc1noc(C)c1-c1ccc2nc(C(c3nnc(CC4SC(=O)NC4=O)o3)S(C)(=O)=O)sc2c1] | 5-((5-((6-(3,5-dimethylisoxazol-4-yl)benzo[d]thiazol-2-yl)(methylsulfonyl)methyl)-1,3,4-oxadiazol-2-yl)methyl)thiazolidine-2,4-dione | ¹H NMR (400 MHz, CDCl₃) δ 8.33 (bs, 1H), 7.55 (d, J = 8.3 Hz, 1H), 7.50 (d, J = 1.0 Hz, 1H), 7.31 (m, 1H), 4.84 (m, 1H), 3.85-3.65 (m, 2H), 3.21 (s, 3H), 2.43 (s, 3H), 2.29 (s, 3H) | 1.61 B 520.0 | <10 |
| 20 | 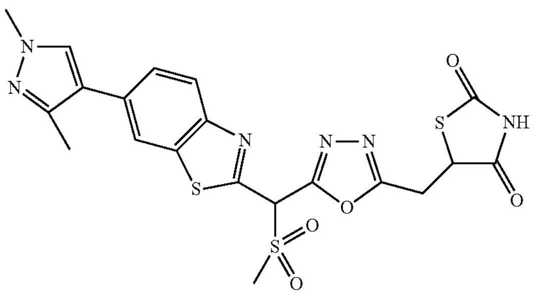 [SMILES: Cc1nn(C)cc1-c1ccc2nc(C(c3nnc(CC4SC(=O)NC4=O)o3)S(C)(=O)=O)sc2c1] | 5-((5-((6-(1,3-dimethyl-1H-pyrazol-4-yl)benzo[d]thiazol-2-yl)(methylsulfonyl)methyl)-1,3,4-oxadiazol-2-yl)methyl)thiazolidine-2,4-dione | ¹H NMR (400 MHz, CDCl₃) δ 7.58 (s, 1H), 7.51 (d, J = 8.5 Hz, 1H), 7.37 (d, J = 8.3 Hz, 1H), 7.27 (m, 1H), 6.06 (s, 1H), 4.73 (m, 1H), 3.78-3.70 (m, 5H), 3.14 (s, 3H), 2.21 (s, 3H) | 1.59 B 519.0 | <10 |
| 21 | 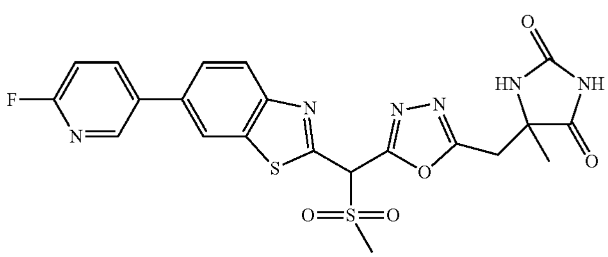 [SMILES: CC1(Cc2nnc(C(c3nc4ccc(-c5ccc(F)nc5)cc4s3)S(C)(=O)=O)o2)NC(=O)NC1=O] | 5-((5-((6-(6-fluoropyridin-3-yl)benzo[d]thiazol-2-yl)(methylsulfonyl)methyl)-1,3,4-oxadiazol-2-yl)methyl)-5-methylimidazolidine-2,4-dione (Isomer A) | ¹H NMR (400 MHz, DMSO-d₆) δ 10.89-10.41 (m, 1H), 8.80-8.52 (m, 1H), 8.44-8.18 (m, 2H), 8.10-7.90 (m, 2H), 7.82-7.51 (m, 1H), 7.40-7.26 (m, 1H), 3.47-3.09 (m, 5H), 1.45 (s, 3H) | 0.77 M 516.8 | 281 |
| 22 | 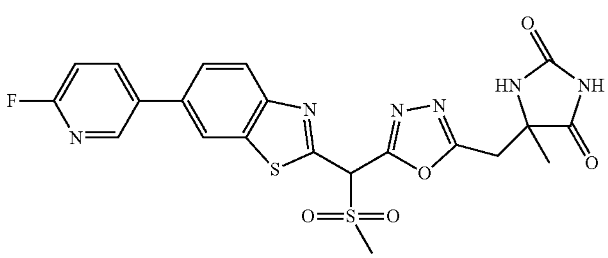 [SMILES: CC1(Cc2nnc(C(c3nc4ccc(-c5ccc(F)nc5)cc4s3)S(C)(=O)=O)o2)NC(=O)NC1=O] | 5-((5-((6-(6-fluoropyridin-3-yl)benzo[d]thiazol-2-yl)(methylsulfonyl)methyl)-1,3,4-oxadiazol-2-yl)methyl)-5-methylimidazolidine-2,4-dione (Isomer B) | ¹H NMR (400 MHz, DMSO-d₆) δ 10.89-10.41 (m, 1H), 8.80-8.52 (m, 1H), 8.44-8.18 (m, 2H), 8.10-7.90 (m, 2H), 7.82-7.51 (m, 1H), 7.40-7.26 (m, 1H), 3.47-3.09 (m, 5H), 1.45 (s, 3H) | 0.77 M 516.8 | 27 |
| 23 | 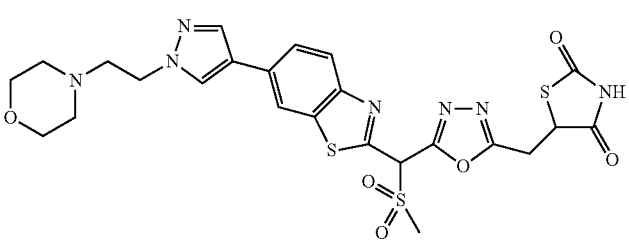 [SMILES: CS(=O)(=O)C(c1nnc(CC2SC(=O)NC2=O)o1)c1nc2ccc(-c3cnn(CCN4CCOCC4)c3)cc2s1] | 5-((5-((methylsulfonyl)(6-(1-(2-morpholinoethyl)-1H-pyrazol-4-yl)benzo[d]thiazol-2-yl)methyl)-1,3,4-oxadiazol-2-yl)methyl)thiazolidine-2,4-dione | ¹H NMR (500 MHz, DMSO-d₆) δ 8.44-8.37 (m, 1H), 8.26 (s, 1H), 8.16-8.10 (m, 1H), 8.08 (d, J = 1.7 Hz, 1H), 7.91-7.80 (m, 1H), 7.65 (dd, J = 8.4, 1.5 Hz, 1H), 5.11-5.00 (m, 1H), 4.60 (m, 2H), 3.86 - 3.57 (m, 6H), 3.39 (m, 2H), 3.27 (br. s., 3H), 3.17 (m, 4H) | 1.24 B 604.2 | <10 |

| Ex. No. | Structure | Name | $^1$H NMR | LC/MS RT (min) Method M + H | EL IC$_{50}$ (nM) |
|---|---|---|---|---|---|
| 24 | 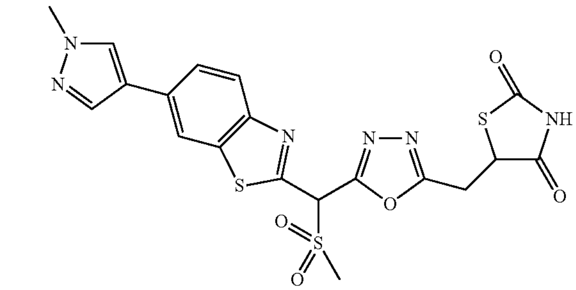 [SMILES: Cn1cc(-c2ccc3nc(C(c4nnc(CC5SC(=O)NC5=O)o4)S(C)(=O)=O)sc3c2)cn1] | 5-((5-((6-(1-methyl-1H-pyrazol-4-yl)benzo[d]thiazol-2-yl)(methylsulfonyl)methyl)-1,3,4-oxadiazol-2-yl)methyl)thiazolidine-2,4-dione | $^1$H NMR (400 MHz, CDCl$_3$) δ 7.69-7.61 (m, 3H), 7.46-7.38 (m, 2H), 4.76-4.68 (m, 1H), 3.85 (s, 3H), 3.58-3.45 (m, 2H), 3.22 (s, 3H) | 1.54 B 505.1 | <10 |
| 25 | 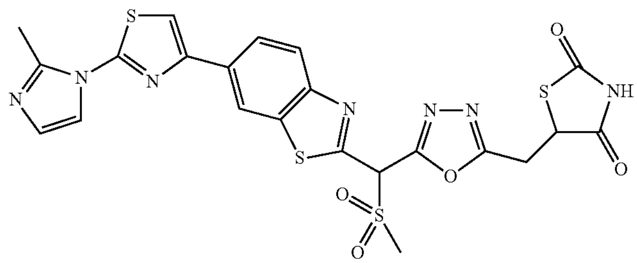 [SMILES: Cc1nccn1-c1nc(-c2ccc3nc(C(c4nnc(CC5SC(=O)NC5=O)o4)S(C)(=O)=O)sc3c2)cs1] | 5-((5-((6-(2-(2-methyl-1H-imidazol-1-yl)thiazol-4-yl)benzo[d]thiazol-2-yl)(methylsulfonyl)methyl)-1,3,4-oxadiazol-2-yl)methyl)thiazolidine-2,4-dione | $^1$H NMR (400 MHz, CDCl$_3$) δ 8.12 (d, J = 1.3 Hz, 1H), 7.88 (dd, J = 8.4, 1.6 Hz, 1H), 7.59 (s, 1H), 7.57 (d, J = 2.0 Hz, 1H), 7.51 (d, J = 8.5 Hz, 1H), 7.31 (d, J = 2.0 Hz, 1H), 4.74 (m, 1H), 3.73 (m, 2H), 3.15 (s, 3H), 2.88 (s, 3H) | 1.33 B 588.1 | <10 |

Example 26

5-Methyl-5-((5-((6-phenylbenzo[d]thiazol-2-yl)methyl)-1,3,4-oxadiazol-2-yl)methyl)-3-(2,2,2-trifluoroethyl)imidazolidine-2,4-dione (Isomer B)

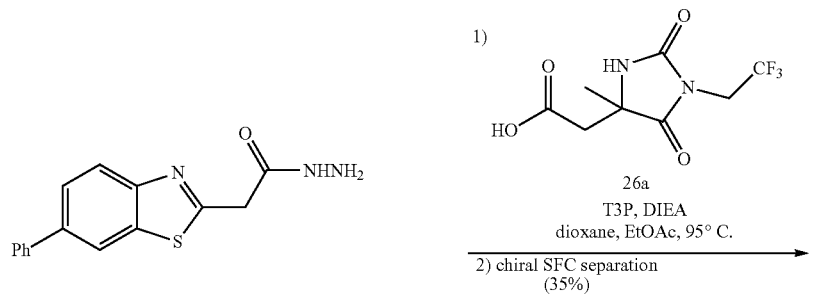

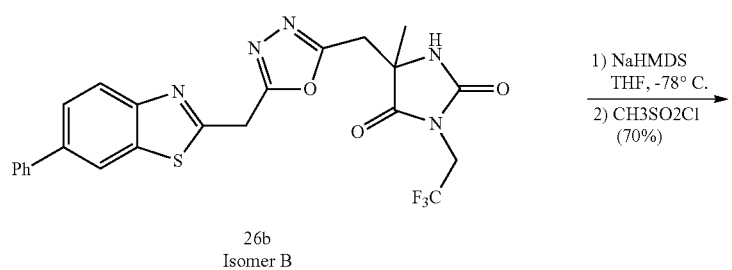

26b
Isomer B

-continued

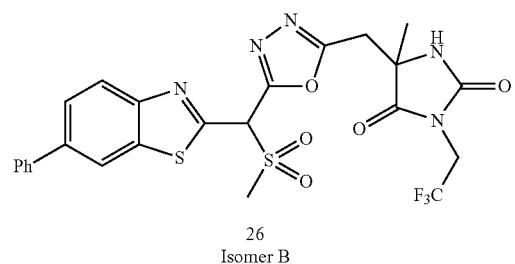

26
Isomer B

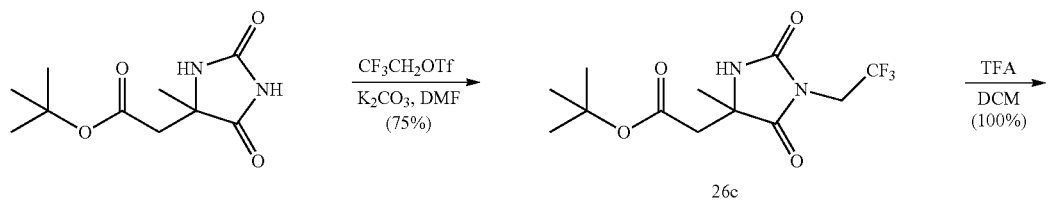

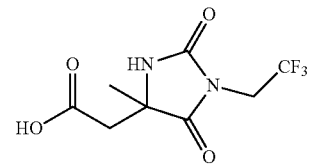

Compound 26b. 5-Methyl-5-((5-((6-phenylbenzo[d]thiazol-2-yl)methyl)-1,3,4-oxadiazol-2-yl)methyl)-3-(2,2,2-trifluoroethyl)imidazolidine-2,4-dione (Isomer B)

Compound 26b was prepared from Compound 26a (described below in this example) and 2-(6-phenylbenzo[d]thiazol-2-yl)acetohydrazide (described in WO 2011/074560) in 85% yield using the general procedure given for Compound 1b. The enantiomers were separated by preparative chiral SFC (Lux Cellulose-4 30×250 mm ID, 5 µm, 100 mL/min, 150 bar BP, 40° C., 25% isopropanol/75% $CO_2$) to afford isomer A (RT=7.8 min, 37% yield), LCMS=2.0 min using analytical method (B), 502.1 (M+H); and isomer B as Compound 26b (RT=9.6 min, 35% yield), LCMS=2.0 min using analytical method (B), 502.1 (M+H). $^1$H NMR (400 MHz, DMSO-$d_6$) δ 8.69 (s, 1H), 8.43 (d, J=1.5 Hz, 1H), 8.05 (d, J=8.5 Hz, 1H), 7.83 (dd, J=8.5, 1.8 Hz, 1H), 7.78-7.68 (m, 2H), 7.54-7.46 (m, 2H), 7.44-7.34 (m, 1H), 4.86 (d, J=1.3 Hz, 2H), 4.10 (q, J=9.2 Hz, 2H), 3.34 (t, J=15.6 Hz, 2H), 1.46 (s, 3H).

Example 26

Example 26 was prepared from Compound 26b in 70% yield as a yellow solid using the general procedure given for Example 1. $^1$H NMR (400 MHz, CDCl$_3$) δ 12.67 (br. s., 1H), 7.72 (d, J=1.5 Hz, 1H), 7.62-7.52 (m, 3H), 7.50-7.43 (m, 3H), 7.42-7.37 (m, 1H), 6.75 (s, 1H), 4.26-4.13 (m, 2H), 3.45 (d, J=2.5 Hz, 2H), 3.19 (s, 3H), 1.68 (s, 3H). LCMS=2.0 min using analytical method (B), 580.0 (M+H). EL $IC_{50}$<10 nM.

Compound 26c. tert-Butyl 2-(4-methyl-2,5-dioxo-1-(2,2,2-trifluoroethyl)imidazolidin-4-yl)acetate To a solution of tert-butyl 2-(4-methyl-2,5-dioxoimidazolidin-4-yl)acetate (100 mg, 0.44 mmol) in DMF (1 mL) was added potassium carbonate (120 mg, 0.88 mmol) followed by 2,2,2-trifluoroethyl trifluoromethanesulfonate (110 mg, 0.48 mmol) and the reaction mixture stirred at rt overnight. The mixture was diluted with EtOAc (30 mL) and washed with brine, dried (Na$_2$SO$_4$), filtered and concentrated under reduced pressure. The residue was purified by silica gel chromatography eluting with 0-100% EtOAc/hexane followed by 10% MeOH/DCM to give Compound 26c (102 mg, 75% yield). $^1$H NMR (400 MHz, CDCl$_3$) δ 6.12 (br. s., 1H), 4.14 (q, J=8.5 Hz, 2H), 2.78-2.62 (m, 2H), 1.52 (s, 3H), 1.45 (s, 9H).

Compound 26a. 2-(4-Methyl-2,5-dioxo-1-(2,2,2-trifluoroethyl)imidazolidin-4-yl)acetic acid To a solution of Compound 26c (100 mg, 0.32 mmol) in DCM (1 mL) was added TFA (1 mL) and the reaction mixture stirred for 1 h. The mixture was concentrated under reduced pressure, co-evaporated with toluene under reduced pressure, then dried under high vacuum to give Compound 26a (89 mg, 100% yield). LCMS=0.9 min using analytical method (B), 255.1 (M+H). $^1$H NMR (400 MHz, DMSO-$d_6$) δ 12.50 (br. s., 1H), 8.45 (s, 1H), 4.37-4.00 (m, 2H), 2.88 (d, J=16.8 Hz, 1H), 2.60 (d, J=17.1 Hz, 1H), 1.31 (s, 3H).

Example 27 to Example 41 were prepared as described in the general procedures given for Example 26.

| Ex. No. | Structure | Name | ¹H NMR | LC/MS RT (min) Method M + H | EL IC₅₀ (nM) |
|---|---|---|---|---|---|
| 27 | 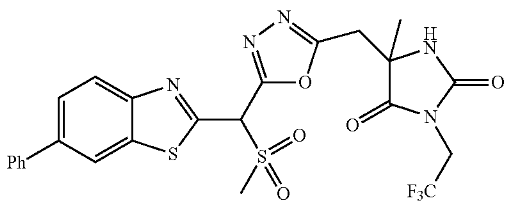 [SMILES: CC1(Cc2nnc(C(c3nc4ccc(-c5ccccc5)cc4s3)S(C)(=O)=O)o2)NC(=O)N(CC(F)(F)F)C1=O] | 5-methyl-5-((5-(methylsulfonyl (6-phenylbenzo[d]thiazol-2-yl)methyl)-1,3,4-oxadiazol-2-yl)methyl)-3-(2,2,2-trifluoroethyl)imidazolidine-2,4-dione (Isomer A) | ¹H NMR (400 MHz, CDCl₃) δ 7.71 (d, J = 1.5 Hz, 1H), 7.61-7.50 (m, 3H), 7.49-7.43 (m, 3H), 7.42-7.35 (m, 1H), 6.74 (s, 1H), 4.33-3.95 (m, 3H), 3.44 (d, J = 2.5 Hz, 2H), 3.18 (s, 3H), 1.67 (s, 3H) | 2.0 B 580.0 | <10 |
| 28 | 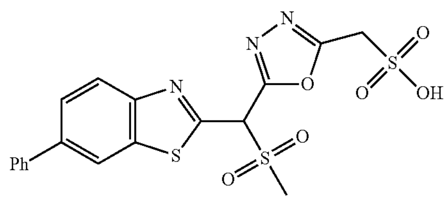 [SMILES: CS(=O)(=O)C(c1nnc(CS(=O)(=O)O)o1)c1nc2ccc(-c3ccccc3)cc2s1] | (5-((methylsulfonyl)(6-phenyl-1,3-benzothiazol-2-yl)methyl)-1,3,4-oxadiazol-2-yl)methanesulfonic acid | ¹H NMR (500 MHz, DMSO-d₆) δ 8.22-8.18 (m, 1H), 7.95-7.88 (m, 1H), 7.80-7.77 (m, 1H), 7.74-7.68 (m, 2H), 7.58-7.46 (m, 3H), 7.45-7.36 (m, 1H), 4.16-4.05 (m, 2H), 3.45-3.29 (m, 3H) | 1.81 Q 466.1 | <10 |
| 29 | 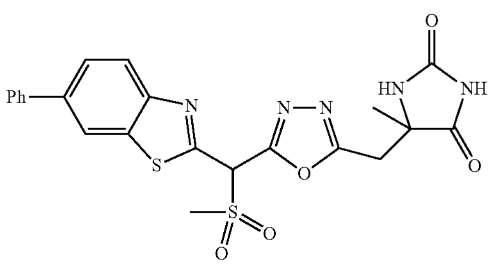 [SMILES: CC1(Cc2nnc(C(c3nc4ccc(-c5ccccc5)cc4s3)S(C)(=O)=O)o2)NC(=O)NC1=O] | 5-methyl-5-((5-((methylsulfonyl)(6-phenyl-1,3-benzothiazol-2-yl)methyl)-1,3,4-oxadiazol-2-yl)methyl)-2,4-imidazolidinedione | ¹H NMR (400 MHz, DMSO-d₆) δ 10.86-10.49 (m, 1H), 8.29-8.16 (m, 1H), 8.09-8.00 (m, 1H), 7.99-7.87 (m, 1H), 7.85-7.64 (m, 3H), 7.58-7.27 (m, 3H), 3.58-3.01 (m, 5H), 1.45 (s, 3H) | 0.90 M 498.0 | <10 |
| 30 | 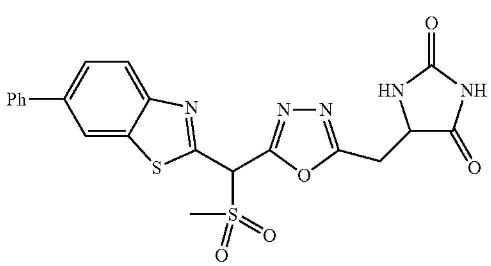 [SMILES: CS(=O)(=O)C(c1nnc(CC2NC(=O)NC2=O)o1)c1nc2ccc(-c3ccccc3)cc2s1] | 5-((5-((methylsulfonyl)(6-phenyl-1,3-benzothiazol-2-yl)methyl)-1,3,4-oxadiazol-2-yl)methyl)-2,4-imidazolidinedione | ¹H NMR (400 MHz, DMSO-d₆) δ 10.77-10.72 (m, 1H), 8.21-8.17 (m, 1H), 7.98 (br. s., 1H), 7.94-7.86 (m, 1H), 7.74-7.65 (m, 2H), 7.55-7.45 (m, 3H), 4.53 (br. s., 2H), 3.40-3.37 (m, 2H), 3.27 (br. s., 3H) | 0.88 M 483.9 | 16 |
| 31 | 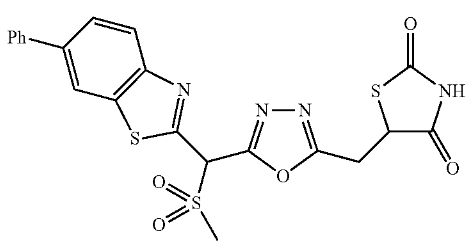 | 5-((5-((methylsulfonyl)(6-phenyl-1,3-benzothiazol-2-yl)methyl)-1,3,4-oxadiazol-2-yl)methyl)-1,3-thiazolidine-2,4-dione | ¹H NMR (400 MHz, CDCl₃) δ 7.78 (s, 1H), 7.61 (m, 1H), 7.57-7.51 (m, 3H), 7.42 (m, 2H), 7.37-7.32 (m, 1H), 4.76 (m, 1H), 3.77 (dd, J = 16.6, 4.8 Hz, 1H), 3.56 (dd, J = 16.7, 8.2 Hz, 1H), 3.17 (s, 2H) | 1.96 B 500.9 | <10 |

| Ex. No. | Structure | Name | ¹H NMR | LC/MS RT (min) Method M + H | EL IC₅₀ (nM) |
|---|---|---|---|---|---|
| 32 | 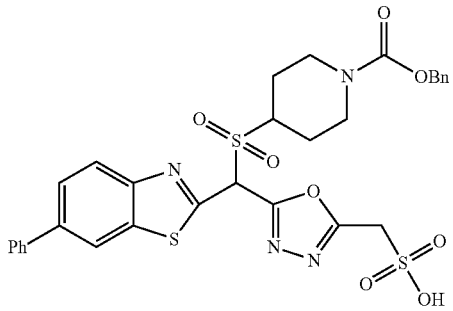 [SMILES: O=C(OCc1ccccc1)N1CCC(S(=O)(=O)C(c2nnc(CS(=O)(=O)O)o2)c2nc3ccc(-c4ccccc4)cc3s2)CC1] | (5-(((1-((benzyloxy)carbonyl)-4-piperidinyl)sulfonyl)(6-phenyl-1,3-benzothiazol-2-yl)methyl)-1,3,4-oxadiazol-2-yl)methanesulfonic acid | ¹H NMR (400 MHz, CD₃OD) δ 8.06 (s, 1H), 7.77 (s, 2H), 7.71 (d, J = 7.3 Hz, 2H), 7.51 (t, J = 7.6 Hz, 2H), 7.44-7.38 (m, 5H), 7.36 (dd, J = 8.0, 4.2 Hz, 1H), 5.17 (s, 2H), 4.47 (s, 2H), 4.28 (d, J = 12.9 Hz, 2H), 4.00-3.89 (m, 1H), 3.01 (br. s., 2H), 2.13 (d, J = 11.6 Hz, 2H), 1.78 (qd, J = 12.3, 4.4 Hz, 2H) | 2.24 Q 668.8 | <10 |
| 33 | 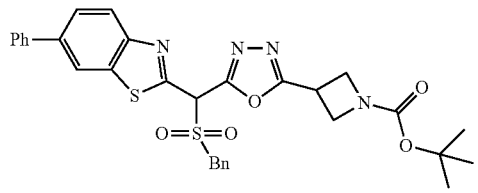 [SMILES: CC(C)(C)OC(=O)N1CC(c2nnc(C(c3nc4ccc(-c5ccccc5)cc4s3)S(=O)(=O)Cc3ccccc3)o2)C1] | tert-butyl 3-(5-((benzylsulfonyl)(6-phenylbenzo[d]thiazol-2-yl)methyl)-1,3,4-oxadiazol-2-yl)azetidine-1-carboxylate | ¹H NMR (400 MHz, CDCl₃) δ 7.73 (d, J = 1.5 Hz, 1H), 7.62 (dd, J = 8.5, 1.6 Hz, 1H), 7.59-7.53 (m, 2H), 7.51-7.43 (m, 3H), 7.43-7.35 (m, 2H), 7.24 (s, 4H), 4.45 (s, 2H), 4.37-4.30 (m, 3H), 4.27-4.20 (m, 2H), 1.49 (s, 9H) | 2.28 Q 603.1 | 14 |
| 34 | 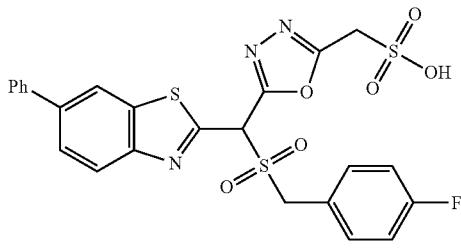 [SMILES: O=S(=O)(O)Cc1nnc(C(c2nc3ccc(-c4ccccc4)cc3s2)S(=O)(=O)Cc2ccc(F)cc2)o1] | (5-(((4-fluorobenzyl)sulfonyl)(6-phenylbenzo[d]thiazol-2-yl)methyl)-1,3,4-oxadiazol-2-yl)methanesulfonic acid | ¹H NMR (500 MHz, (CD₃)₂CO) δ 8.83 (s, 1H), 8.08 (d, J = 1.7 Hz, 1H), 7.97 (d, J = 8.3 Hz, 1H), 7.77 (dd, J = 8.4, 1.8 Hz, 1H), 7.73-7.68 (m, 2H), 7.50 (t, J = 7.7 Hz, 2H), 7.44-7.35 (m, 2H), 7.12 (t, J = 8.8 Hz, 1H), 7.03 (t, J=8.8 Hz, 2H), 4.63 (s, 2H), 4.56 (s, 2H) | 3.95 R 560.0 | 131 |
| 35 | 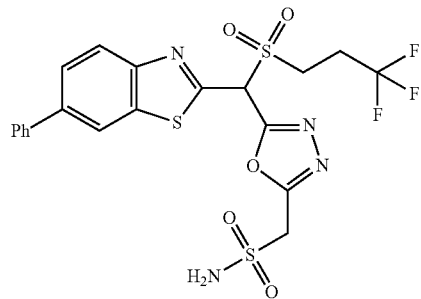 [SMILES: NS(=O)(=O)Cc1nnc(C(c2nc3ccc(-c4ccccc4)cc3s2)S(=O)(=O)CCC(F)(F)F)o1] | (5-((6-phenylbenzo[d]thiazol-2-yl)((3,3,3-trifluoropropyl)sulfonyl)methyl)-1,3,4-oxadiazol-2-yl)methanesulfonamide | ¹H NMR (500 MHz, CDCl₃) δ 7.85-7.77 (m, 1H), 7.67-7.63 (m, 1H), 7.61 (d, J = 5.2 Hz, 2H), 7.58-7.53 (m, 2H), 7.45-7.40 (m, 3H), 4.73-4.69 (m, 3H), 4.10-4.06 (m, 1H), 3.96 (dd, J = 5.6, 3.4 Hz, 2H) | 2.03 Q 547.1 | <10 |

-continued

| Ex. No. | Structure | Name | ¹H NMR | LC/MS RT (min) Method M + H | EL IC$_{50}$ (nM) |
|---|---|---|---|---|---|
| 36 | 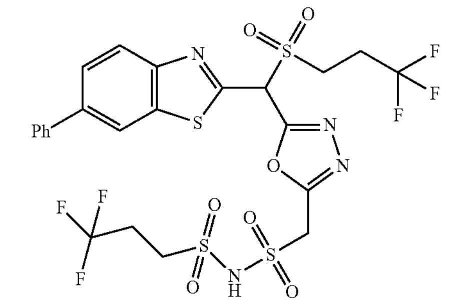 [SMILES: O=S(=O)(CCC(F)(F)F)NS(=O)(=O)Cc1nnc(C(c2nc3ccc(-c4ccccc4)cc3s2)S(=O)(=O)CCC(F)(F)F)o1] | 3,3,3-trifluoro-N-(((5-((6-phenylbenzo[d]thiazol-2-yl)((3,3,3-trifluoropropyl)sulfonyl)methyl)-1,3,4-oxadiazol-2-yl)methyl)sulfonyl)propane-1-sulfonamide | ¹H NMR (500 MHz, CD$_3$OD) δ 8.05 (d, J = 1.1 Hz, 1H), 7.79-7.72 (m, 2H), 7.71-7.66 (m, 2H), 7.48 (t, J = 7.7 Hz, 2H), 7.41-7.35 (m, 1H), 3.77-3.73 (m, 2H), 3.42-3.36 (m, 3H), 3.30-3.27 (m, 1H), 2.82-2.65 (m, 4H) | 2.23 Q 707.8 | <10 |
| 37 | 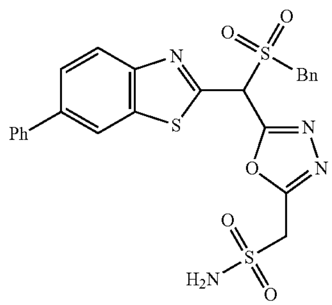 [SMILES: NS(=O)(=O)Cc1nnc(C(c2nc3ccc(-c4ccccc4)cc3s2)S(=O)(=O)Cc2ccccc2)o1] | (5-((benzylsulfonyl)(6-phenylbenzo[d]thiazol-2-yl)methyl)-1,3,4-oxadiazol-2-yl)methanesulfonamide | ¹H NMR (500 MHz, CDCl$_3$) δ 8.22 (d, J = 8.5 Hz, 1H), 8.17 (d, J = 1.4 Hz, 1H), 7.78 (dd, J = 8.5, 1.7 Hz, 1H), 7.73 (s, 1H), 7.68-7.60 (m, 1H), 7.56 (d, J=7.4 Hz, 2H), 7.54-7.44 (m, 3H), 7.43-7.38 (m, 2H), 7.26-7.26 (m, 1H), 5.28 (br. s., 1H), 4.64 (br. s., 2H), 4.50 (s, 2H) | 1.99 Q 541.1 | <10 |
| 38 | 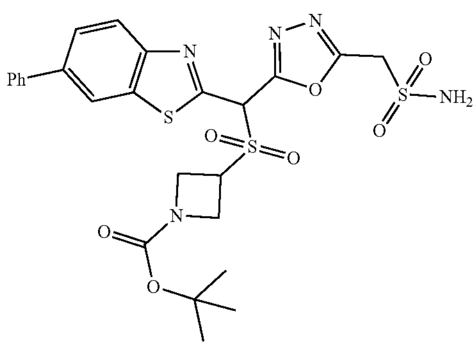 [SMILES: CC(C)(C)OC(=O)N1CC(S(=O)(=O)C(c2nnc(CS(N)(=O)=O)o2)c2nc3ccc(-c4ccccc4)cc3s2)C1] | tert-butyl 3-(((6-phenylbenzo[d]thiazol-2-yl)(5-(sulfamoylmethyl)-1,3,4-oxadiazol-2-yl)methyl)sulfonyl)azetidine-1-carboxylate | ¹H NMR (500 MHz, CD$_3$OD) δ 8.06-8.01 (m, 1H), 7.80-7.71 (m, 2H), 7.69-7.63 (m, 2H), 7.52-7.44 (m, 2H), 7.41-7.34 (m, 1H), 4.81-4.77 (m, 2H), 4.58-4.49 (m, 1H), 4.31-4.15 (m, 4H), 1.50-1.42 (m, 9H) | 1.04 M 605.9 | <10 |
| 39 | 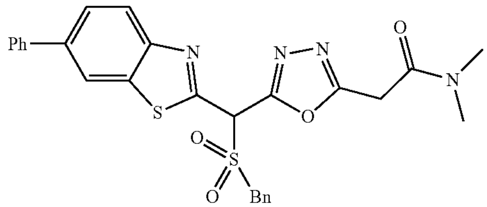 [SMILES: CN(C)C(=O)Cc1nnc(C(c2nc3ccc(-c4ccccc4)cc3s2)S(=O)(=O)Cc2ccccc2)o1] | 2-(5-((benzylsulfonyl)(6-phenylbenzo[d]thiazol-2-yl)methyl)-1,3,4-oxadiazol-2-yl)-N,N-dimethylacetamide | ¹H NMR (400 MHz, CDCl$_3$ containing CD$_3$OD) δ 7.77-7.69 (m, 1H), 7.65-7.54 (m, 3H), 7.50-7.40 (m, 1H), 7.38-7.29 (m, 2H), 7.21 (d, J = 5.8 Hz, 1H), 4.83 (dd, J = 4.1, 2.1 Hz, 1H), 4.14 (s, 1H), 3.19 (s, 2H), 3.11-2.99 (m, 4H) | 2.08 B 533.2 | 190 |
| 40 | 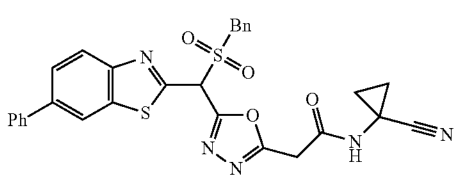 [SMILES: N#CC1(NC(=O)Cc2nnc(C(c3nc4ccc(-c5ccccc5)cc4s3)S(=O)(=O)Cc3ccccc3)o2)CC1] | 2-(5-((benzylsulfonyl)(6-phenylbenzo[d]thiazol-2-yl)methyl)-1,3,4-oxadiazol-2-yl)-N-(1-cyanocyclopropyl)acetamide | ¹H NMR (400 MHz, CDCl$_3$ containing CD$_3$OD) δ 7.77 (s, 1H), 7.59-7.53 (m, 3H), 7.48-7.41 (m, 2H), 7.38-7.28 (m, 3H), 7.21 (d, J = 6.8 Hz, 3H), 4.60-4.54 (m, 2H), 3.93 (s, 2H), 1.57-1.48 (m, 2H), 1.34-1.28 (m, 2H) | 2.32 B 570.2 | <10 |

-continued

| Ex. No. | Structure | Name | ¹H NMR | LC/MS RT (min) Method M + H | EL IC$_{50}$ (nM) |
|---|---|---|---|---|---|
| 41 | 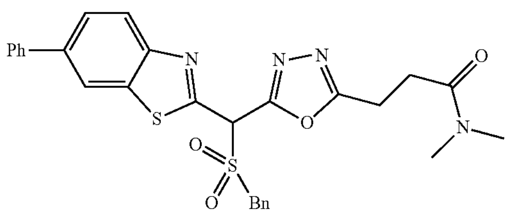 [SMILES: CN(C)C(=O)CCc1nnc(C(c2nc3ccc(-c4ccccc4)cc3s2)S(=O)(=O)Cc2ccccc2)o1] | 3-(5-((benzylsulfonyl)(6-phenylbenzo[d]thiazol-2-yl)methyl)-1,3,4-oxadiazol-2-yl)-N,N-dimethylpropanamide | ¹H NMR (400 MHz, CDCl₃ containing CD₃OD) δ 7.73 (d, J = 1.3 Hz, 1H), 7.59-7.52 (m, 6H), 7.41 (t, J = 7.5 Hz, 3H), 7.28-7.19 (m, 4H), 3.18 (t, J = 6.9 Hz, 2H), 3.10 (s, 2H), 2.95 (s, 6H) | 2.08 B 547.2 | 58 |

Example 42

(5R)-5-Methyl-5-((5-((methylsulfonyl)(6-phenyl-benzo[d]thiazol-2-yl)methyl)-1,3,4-oxadiazol-2-yl)methyl)oxazolidine-2,4-dione

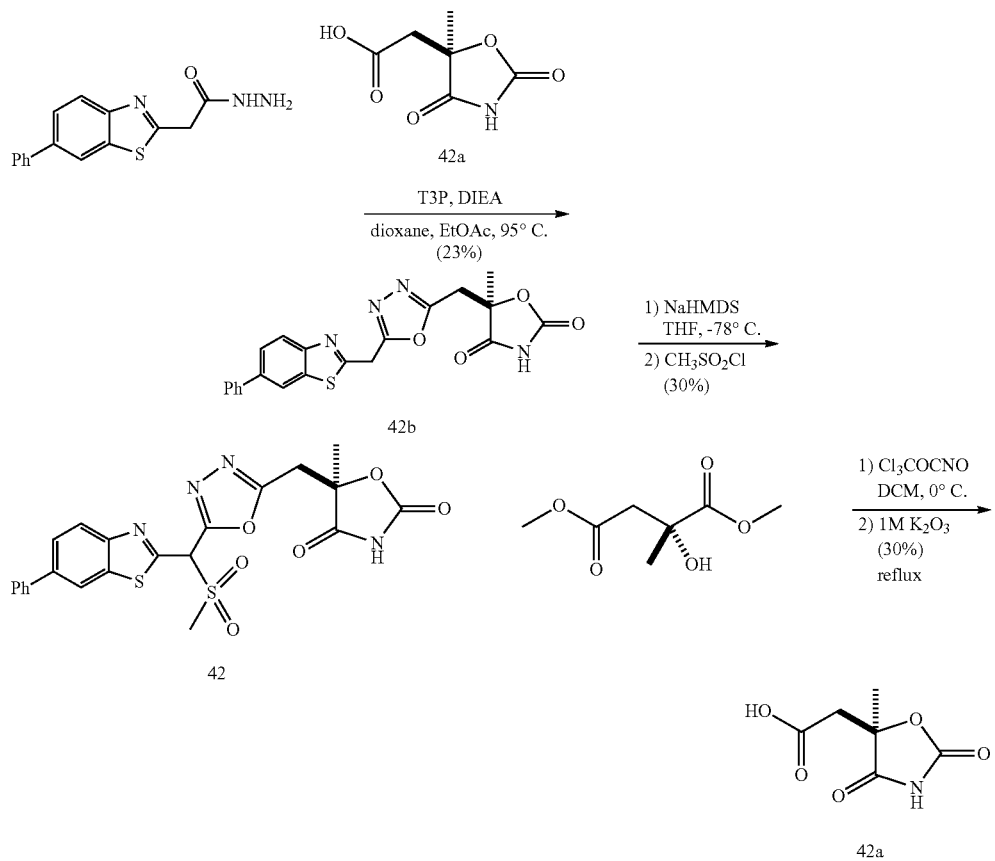

Compound 42b. (R)-5-Methyl-5-((5-((6-phenylbenzo[d]thiazol-2-yl)methyl)-1,3,4-oxadiazol-2-yl)methyl)oxazolidine-2,4-dione Compound 42b was prepared from Compound 42a (described below in this example) and 2-(6-phenylbenzo[d]thiazol-2-yl)acetohydrazide (described in WO 2011/074560) in 23% yield as a pale yellow solid using the general procedure given for Compound 1b. LCMS=1.81 min using analytical method (B), 421.1 (M+H). ¹H NMR (400 MHz, CDCl₃ containing CD₃OD) δ 8.10-8.02 (m, 2H), 7.73 (dd, J=8.5, 1.8 Hz, 1H), 7.63 (dd, J=7.0, 1.3 Hz, 2H), 7.52-7.43 (m, 2H), 7.42-7.35 (m, 1H), 3.63-3.40 (m, 2H), 1.70 (s, 3H).

Example 42

Example 42 was prepared from Compound 42b in 43% yield as a yellow solid using the general procedure given for Example 1. ¹H NMR (400 MHz, CDCl₃ containing CD₃OD) δ 7.64 (s, 1H), 7.48-7.35 (m, 4H), 7.25 (t, J=7.3 Hz, 2H), 7.16 (d, J=7.3 Hz, 1H), 3.43-3.32 (m, 2H), 3.05 (s, 3H), 1.54 (s, 3H). LCMS=1.94 min using analytical method (B), 499.0 (M+H). EL IC$_{50}$<10 nM.

Compound 42a. (R)-2-(5-Methyl-2,4-dioxooxazolidin-5-yl)acetic acid

To a solution of (R)-dimethyl 2-hydroxy-2-methylsuccinate (530 mg, 3.0 mmol) in DCM (10 mL) at 0° C. was added dropwise trichloroacetyl isocyanate (530 mL, 4.5 mmol). The ice bath was removed and the reaction mixture stirred for 2 h then quenched by the addition of MeOH (2 mL) and evaporated under reduced pressure to dryness. To the residue was added 1 M K₂CO₃ (15 mL, 15 mmol) and the reaction mixture heated at reflux for 0.5 h. The reaction mixture was allowed to cool to rt, extracted with Et₂O (2×), then acidified to pH 2 by the addition of 1 N HCl and extracted with EtOAc (3×). The combined extracts were dried (Na₂SO₄) filtered and concentrated under reduced pressure. The residue was triturated with Et₂O, and the triturate evaporated under reduced pressure. The residue was chromatographed by silica gel chromatography eluting with 1 to 10% MeOH/DCM (bromocresol green stain) to give Compound 42a (130 mg, 24% yield) as a clear colorless oil which solidified upon standing. ¹H NMR (400 MHz, CDCl₃) δ 8.95 (br. s., 1H), 3.14 (d, J=17.3 Hz, 1H), 2.97 (d, J=17.3 Hz, 1H), 1.62 (s, 3H). The structure was confirmed by single crystal X-ray diffraction analysis with material crystallized from Et₂O/hexanes.

Example 43

6-(5-((6-(4-Fluorophenyl)benzo[d]thiazol-2-yl)(methylsulfonyl)methyl)-1,3,4-oxadiazol-2-yl)-5-hydroxy-2-methoxypyrimidin-4(3H)-one

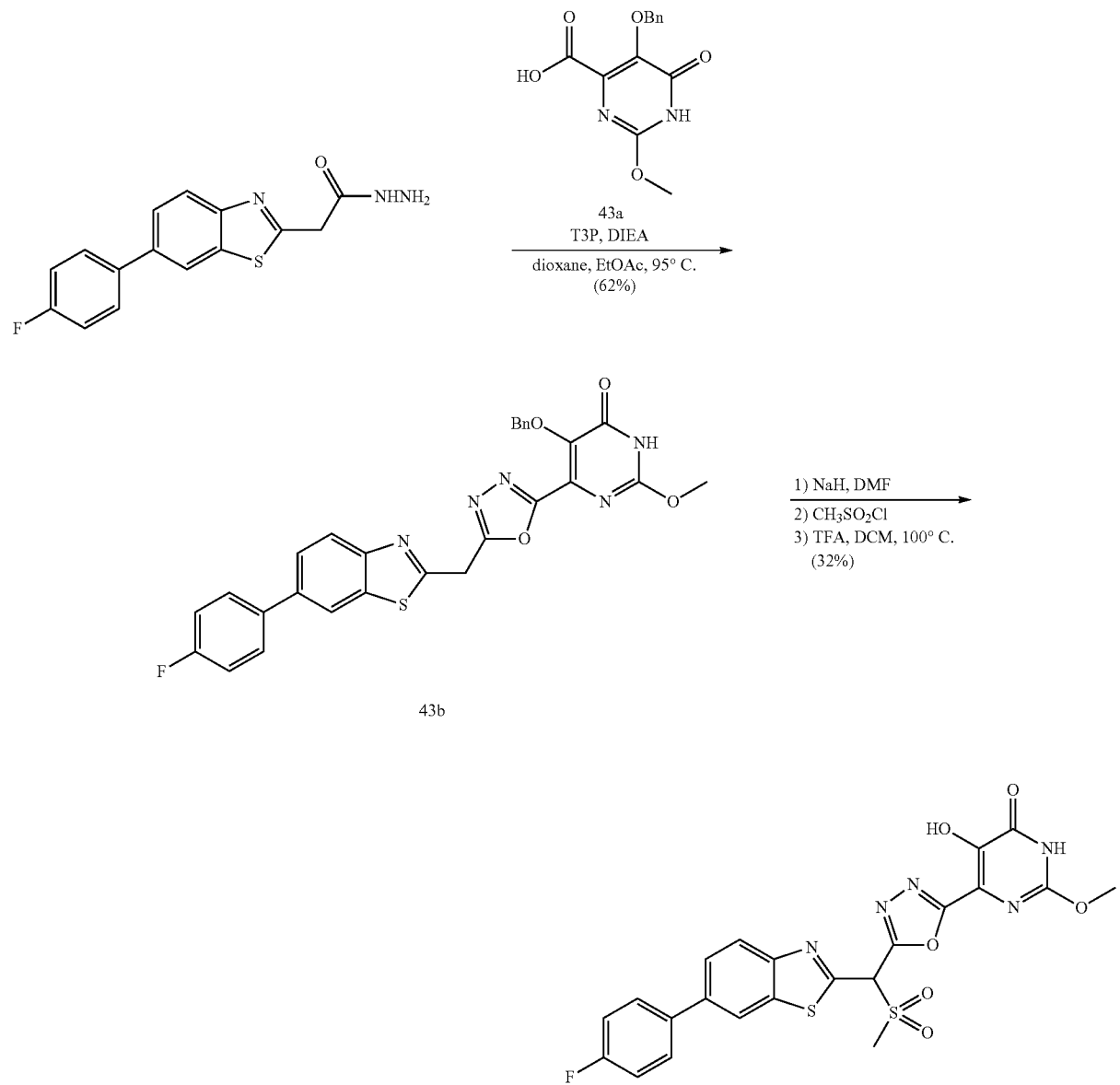

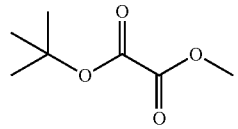 + 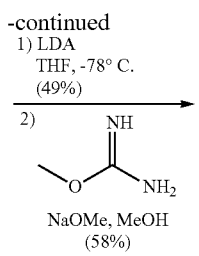

-continued
1) LDA
THF, -78° C.
(49%)
2)

NaOMe, MeOH
(58%)

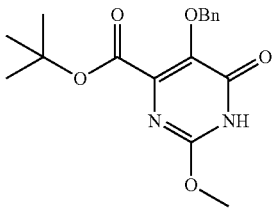

43c

NaOH
THF, MeOH
50° C.
(89%)

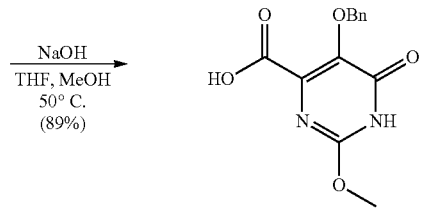

43a

Compound 43b. 5-(Benzyloxy)-6-(5-((6-(4-fluorophenyl)benzo[d]thiazol-2-yl)methyl)-1,3,4-oxadiazol-2-yl)-2-methoxypyrimidin-4(3H)-one Compound 43b was prepared from Compound 43a (described below in this example) and 2-(6-(4-fluorophenyl)benzo[d]thiazol-2-yl)acetohydrazide (described in WO 2011/074560) in 62% yield using the general procedure given for Compound 1b. LCMS=2.22 min using analytical method (Q), 541.9 (M+H). $^1$H NMR (400 MHz, CDCl$_3$) δ 8.56-7.74 (m, 2H), 7.75-6.87 (m, 10H), 5.29 (s, 2H), 4.78 (s, 2H), 4.04 (s, 3H).

Example 43

To a solution of Compound 43b (20 mg, 0.037 mmol) in DMF (1 mL) was added a 60% dispersion of NaH in mineral oil (7.4 mg, 0.18 mmol) and the reaction mixture stirred for 10 min. Methanesulfonyl chloride (14 mg, 0.12 mmol) was added dropwise and the reaction mixture stirred for 1 h then quenched by the addition of satd. NH$_4$Cl. The resulting solution was extracted with CH$_2$Cl$_2$ (2×) and the combined organic extracts washed with H$_2$O, brine, and concentrated under reduced pressure to give the bis-sulfonylated material which was used directly in the next step. LCMS ESI 619.9 (M+H), RT=2.27 min (Method B). 5-(benzyloxy)-6-(5-((6-(4-fluorophenyl)benzo[d]thiazol-2-yl)(methylsulfonyl)methyl)-1,3,4-oxadiazol-2-yl)-2-methoxy-3-(methylsulfonyl) pyrimidin-4(3H)-one (14 mg, 0.020 mmol) was stirred in CH$_2$Cl$_2$ (1 mL) and TFA (1 mL) at 100° C. under microwave irradiation for 10 min. After allowing to cool to rt the mixture was concentrated under reduced pressure and the residue triturated with MeOH/CH$_2$Cl$_2$ to give Example 43 (4.3 mg, 32% yield). LCMS ESI 529.9 (M+H), retention=2.09 min (Method Q). $^1$H NMR (400 MHz, DMSO-d$_6$) δ 8.21 (br. s., 1H), 7.95-7.66 (m, 4H), 7.33 (br. s., 3H), 3.92 (s., 3H), 3.39 (s., 3H). EL IC$_{50}$ 14 nM.

Compound 43c. tert-Butyl 5-(benzyloxy)-2-methoxy-6-oxo-1,6-dihydropyrimidine-4-carboxylate To a solution of tert-butyl methyl oxalate (5.8 g, 36 mmol) and methyl 2-(benzyloxy)acetate (6.5 g, 36 mmol) in THF (80 mL) at −78° C. was added a dropwise a solution of LDA (prepared by dropwise addition of nBuLi (20 mL, 50 mmol) to diisopropylamine (7.1 mL, 50 mmol) in THF (20 mL) at 0° C. then stirring for 10 min). After the addition, the reaction mixture was stirred at −78° C. for 2 h then allowed to warm to rt over the course of 1 h. The reaction mixture was cooled to 0° C. then cold 1 N HCl (ca. 70 mL) was added. The resulting solution was extracted with EtOAc (3×), and the combined organic portions dried (Na$_2$SO$_4$), filtered and concentrated under reduced pressure. The residue was purified by silica gel chromatography eluting with EtOAc/hexanes to give 4-tert-butyl 1-methyl 2-(benzyloxy)-3-hydroxyfumarate (5.4 g, 49% yield) as tan viscous oil. O-Methylisourea hydrogensulfate (2.5 g, 14 mmol) and 4-tert-butyl 1-methyl 2-(benzyloxy)-3-hydroxyfumarate (5.4 g, 17 mmol) were stirred in anhydrous MeOH (15 mL) at 0° C. under argon. Sodium methoxide (10 g, 46 mmol) in MeOH (25% wt) was added and the reaction mixture was stirred at rt for 40 h. MeOH (3 mL) was added and the mixture cooled in an ice bath. 1 N HCl (11 mL) was added to acidify the mixture and the resulting precipitate was collected and rinsed with cold H$_2$O:MeOH (10:1). The filtrate was concentrated under reduced pressure and the residue was extracted with CH$_2$Cl$_2$ (2×). The organic extracts and the precipitate were combined, concentrated under reduced pressure, then purified by silica gel chromatography eluting with EtOAc/hexanes to give Compound 43c (2.8 g, 58% yield) as a white solid. LCMS=2.02 min using analytical method (Q), 333.2 (M+H-tBu). $^1$H NMR (400 MHz, DMSO-d$_6$) δ 13.48-12.16 (m, 1H), 7.91-6.79 (m, 5H), 5.02 (s, 2H), 3.86 (s, 3H), 1.44 (s, 9H).

Compound 43a. 5-(Benzyloxy)-2-methoxy-6-oxo-1, 6-dihydropyrimidine-4-carboxylic acid To a solution of Compound 43c (1.1 g, 3.2 mmol) in MeOH (20 mL) and THF (20 mL) was added 7 N NaOH (4.0 mL, 28 mmol) and the solution stirred at 50° C. for 3 h. The reaction mixture was cooled in an ice bath then acidified by the addition of 1 N HCl (20 mL). The resulting precipitate was filtered, rinsed with water then dried under vacuum to give Compound 43a (790 mg, 89% yield) as a white solid. LCMS=1.41 min using analytical method (Q), 277.0 (M+H).

$^1$H NMR (400 MHz, DMSO-d$_6$) δ 13.49 (br. s., 1H), 12.91 (br. s., 1H), 7.90-6.67 (m, 5H), 5.01 (s, 2H), 3.86 (s, 3H).

Example 44

5-Hydroxy-2-methoxy-6-(5-((6-phenylbenzo[d]thiazol-2-yl)((3,3,3-trifluoropropyl)sulfonyl)methyl)-1,3,4-oxadiazol-2-yl)pyrimidin-4(3H)-one

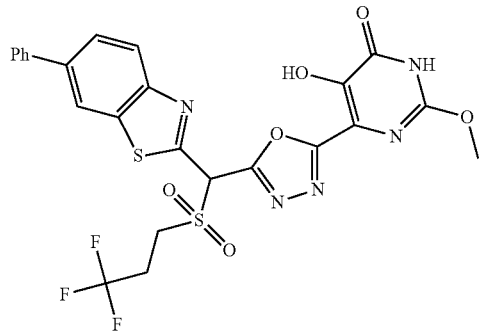 [SMILES: COc1nc(-c2nnc(C(c3nc4ccc(-c5ccccc5)cc4s3)S(=O)(=O)CCC(F)(F)F)o2)c(O)c(=O)[nH]1]

Example 44 was prepared by the general procedures described for Example 43. LCMS=4.16 min using analytical method (R), 594.0 (M+H). EL IC$_{50}$=77 nM.

Example 45

(4S)-4-((5-((Methylsulfonyl)(6-phenylbenzo[d]thiazol-2-yl)methyl)-1,3,4-oxadiazol-2-yl)methyl)-1,2,5-thiadiazolidin-3-one 1,1-dioxide

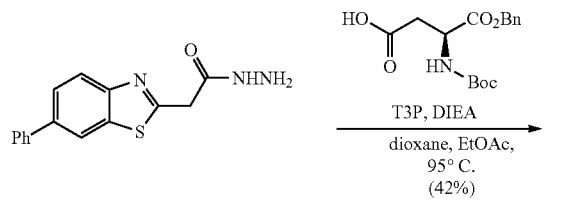

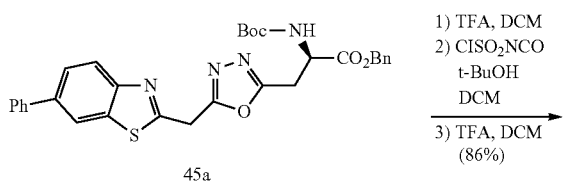

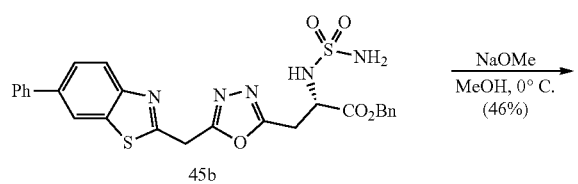

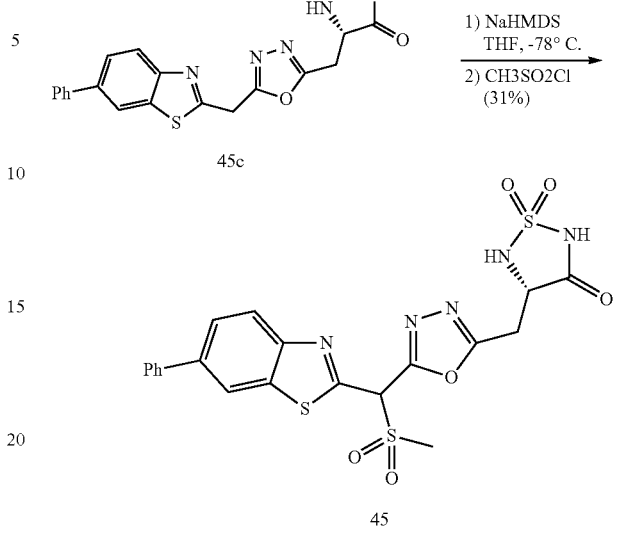

Compound 45a. (S)-Benzyl 2-((tert-butoxycarbonyl)amino)-3-(5-((6-phenylbenzo[d]thiazol-2-yl)methyl)-1,3,4-oxadiazol-2-yl)propanoate Compound 45a was prepared from (S)-4-(benzyloxy)-3-((tert-butoxycarbonyl)amino)-4-oxobutanoic acid and 2-(6-phenylbenzo[d]thiazol-2-yl)acetohydrazide (described in WO 2011/074560) in 42% yield as a yellow solid using the general procedure given for Compound 1b. LCMS=1.13 min using analytical method (M), 571.2 (M+H). $^1$H NMR (400 MHz, CDCl$_3$) δ 8.19-7.95 (m, 2H), 7.79-7.55 (m, 3H), 7.47 (t, J=7.7 Hz, 2H), 7.42-7.27 (m, 6H), 5.56 (d, J=7.0 Hz, 1H), 5.14 (s, 2H), 4.79 (br. s., 1H), 4.65 (s, 2H), 3.52-3.23 (m, 2H), 1.49-1.32 (m, 9H).

Compound 45b. (S)-Benzyl 3-(5-((6-phenylbenzo[d]thiazol-2-yl)methyl)-1,3,4-oxadiazol-2-yl)-2-(sulfamoylamino)propanoate To a solution of Compound 45a (460 mg, 0.81 mmol) in DCM (5 mL) was added TFA (5 mL) and the reaction mixture stirred for 1 h. The reaction mixture was concentrated under reduced pressure, and the residue was co-evaporated with toluene (3×) and DCM, then dried under high vacuum to give (S)-benzyl 2-amino-3-(5-((6-phenylbenzo[d]thiazol-2-yl)methyl)-1,3,4-oxadiazol-2-yl)propanoate (500 mg, 100% yield) as a yellow solid. LCMS=1.90 min using analytical method (B), 471.0 (M+H). In a separate flask, to a solution of sulfurisocyanatidic chloride (170 mg, 1.2 mmol) in DCM (2 mL) was added 2-methylpropan-2-ol (90 mg, 1.2 mmol) in DCM (2 mL) and the reaction mixture stirred for 20 min. The resulting solution was then added to a mixture of (S)-benzyl 2-amino-3-(5-((6-phenylbenzo[d]thiazol-2-yl)methyl)-1,3,4-oxadiazol-2-yl)propanoate (500 mg, 0.81 mmol) and TEA (0.56 mL, 4.0 mmol) in DCM (5 mL) and the reaction mixture stirred for 3 h. The reaction mixture was concentrated under reduced pressure and the residue was dissolved in EtOAc, washed with 1 N HCl solution and brine, dried (Na$_2$SO$_4$), filtered and concentrated under reduced pressure. The residue was dissolved in DCM (6 mL) and treated with TFA (3 mL) then stirred for 1 h. The mixture was concentrated under reduced pressure, co-evaporated under reduced pressure with toluene and DCM, and the residue purified by silica gel chromatography eluting with 0-10% MeOH/DCM to give Compound 45b (380 mg, 86% yield) as a yellow solid. LCMS=2.00 min using analytical method (B), 550.2 (M+H). $^1$H NMR (400 MHz, CDCl$_3$) δ 8.15-8.08 (m, 1H), 8.06-8.00 (m, 1H), 7.76-7.70 (m, 1H), 7.66-7.58 (m, 2H), 7.50-7.44 (m, 2H), 7.42-7.27 (m, 7H), 5.65-5.58 (m, 1H), 5.23-5.19 (m, 1H), 5.16-5.09 (m, 2H), 4.73-4.61 (m, 3H), 3.53-3.30 (m, 2H).

Compound 45c. (S)-4-((5-(((6-Phenylbenzo[d]thiazol-2-yl)methyl)-1,3,4-oxadiazol-2-yl)methyl)-1,2,5-thiadiazolidin-3-one 1,1-dioxide To a solution of Compound 45b (130 mg, 0.24 mmol) in MeOH (3 mL) and THF (3 mL) at 0° C. was added a solution of NaOMe (1.0 M in MeOH, 0.11 mL, 0.48 mmol) and the reaction mixture was stirred for 0.5 h. The reaction mixture was added dropwise to 1 N HCl (5 mL) at 0° C. The solution was extracted with DCM (3×) then the combined extracts dried (Na$_2$SO$_4$), filtered and concentrated under reduced pressure. The residue was purified by silica gel chromatography eluting with 0 to 20% MeOH/DCM to give Compound 45c (51 mg, 46% yield) as a yellow solid. LCMS=1.80 min using analytical method (B), 442.0 (M+H). $^1$H NMR (400 MHz, DMSO-d$_6$) δ 8.44 (d, J=1.8 Hz, 1H), 8.06 (d, J=8.5 Hz, 1H), 7.86-7.81 (m, 1H), 7.79-7.73 (m, 2H), 7.57-7.48 (m, 2H), 7.44-7.37 (m, 1H), 4.92 (s, 2H), 4.63 (dd, J=7.9, 4.6 Hz, 1H), 3.44-3.19 (m, 2H). LC/MS=1.80 min using analytical method (B), 442.0 (M+H).

Example 45

Example 45 was prepared from Compound 45c in 31% yield as a yellow solid using the general procedure given for Example 1. $^1$H NMR shows isomers in 3:2 ratio. $^1$H NMR of major isomer: $^1$H NMR (400 MHz, DMSO-d$_6$) δ 8.20 (s, 1H), 7.90 (dd, J=8.6, 1.8 Hz, 1H), 7.81-7.75 (m, 1H), 7.72-7.66 (m, 2H), 7.48 (t, J=7.5 Hz, 2H), 7.40-7.33 (m, 1H), 4.57-4.49 (m, 1H), 3.32-3.24 (m, 2H). LCMS=0.90 min using analytical method (M), 519.8 (M+H). EL IC$_{50}$<10 nM.

Example 46

N-({5-[(Methylsulfonyl)(6-phenyl-1,3-benzothiazol-2-yl)methyl]-1,3,4-oxadiazol-2-yl}methyl)sulfuric diamide

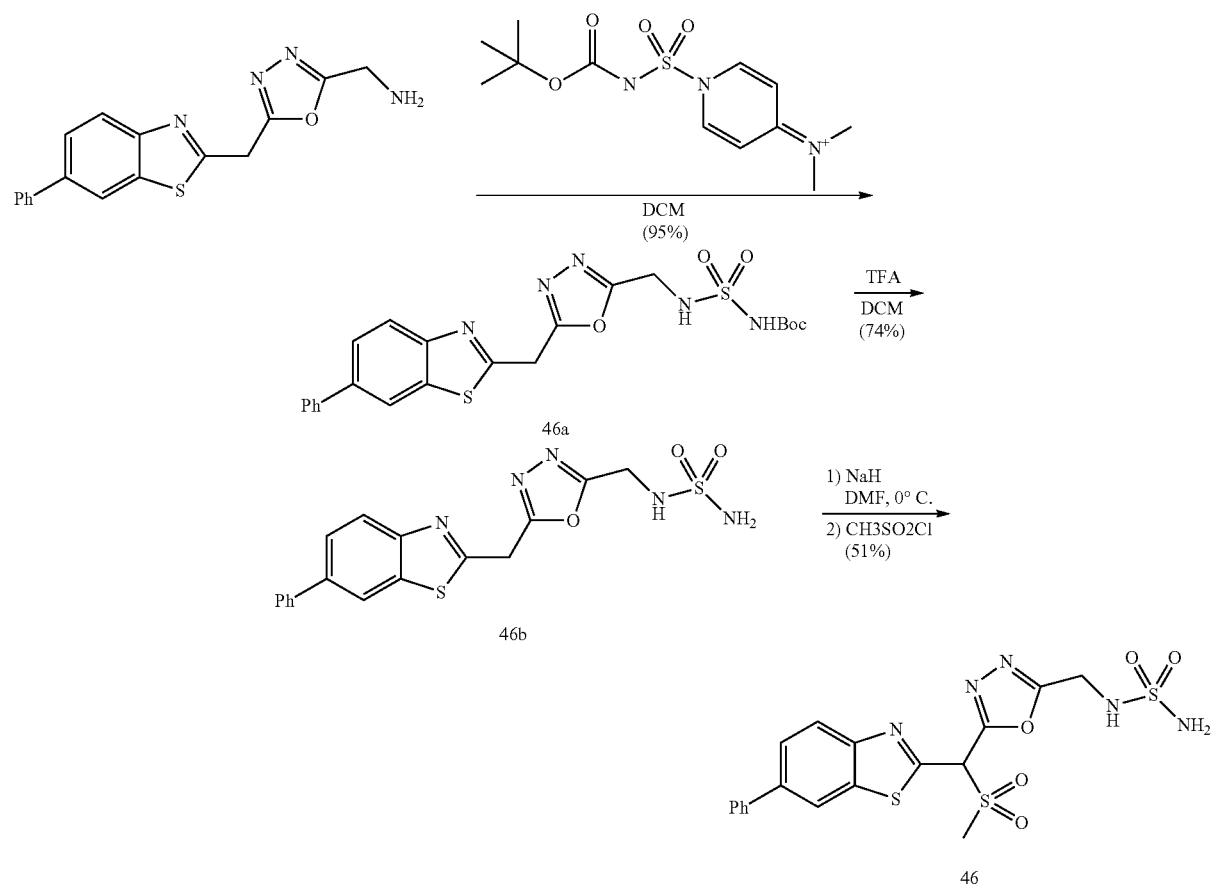

46

Compound 46a. tert-Butyl N-((5-((6-phenylbenzo[d]thiazol-2-yl)methyl)-1,3,4-oxadiazol-2-yl)methyl)sulfamoylcarbamate To a solution of (5-((6-phenylbenzo[d]thiazol-2-yl)methyl)-1,3,4-oxadiazol-2-yl)methanamine (788 mg, 2.44 mmol) (described in WO 2011/074560) in DCM (10 mL) was added N-(tert-butoxycarbonyl)-N-[4-(dimethylazaniumylidene)-1,4-dihydropyridin-1-ylsulfonyl]azanide (737 mg, 2.44 mmol) (Winum, J.-Y. et al., *Org. Lett.*, 3(14):2241-2243 (2001)) and the reaction mixture stirred at rt for 3 days. The mixture was diluted with satd. $NH_4Cl$ and extracted with EtOAc (3×). The combined extracts were washed with brine, dried ($Na_2SO_4$) filtered and concentrated under reduced pressure. The residue was purified by silica gel chromatography eluting with 10-100% EtOAc/DCM to give Compound 46a (1.16 g, 95% yield) as a brown oil. LCMS=0.99 min using analytical method (M), 502.0 (M+H). $^1$H NMR (400 MHz, $CDCl_3$) δ 8.07 (d, J=8.5 Hz, 1H), 8.06 (s, 1H), 7.74 (dd, J=8.4, 1.9 Hz, 1H), 7.68-7.61 (m, 2H), 7.49 (t, J=7.4 Hz, 2H), 7.44-7.36 (m, 1H), 6.96 (br. s., 1H), 5.26 (br. s., 2H), 4.79 (s, 2H), 4.63 (s, 2H), 1.37 (s, 9H).

Compound 46b. N-{[5-(6-Phenyl-1,3-benzothiazol-2-ylmethyl)-1,3,4-oxadiazol-2-yl]methyl}sulfuric diamide To a solution of Compound 46a (1.16 g, 2.3 mmol) in DCM (10 mL) was added TFA (5 mL) and the reaction mixture stirred for 0.5 h. The reaction mixture was concentrated under reduced pressure then evaporated under reduced pressure from toluene (2×). The residue was diluted with 1.5 M $K_3PO_4$ then extracted with DCM (3×). The combined extracts were washed with brine, dried ($Na_2SO_4$), filtered and evaporated under reduced pressure. The residue was purified by silica gel chromatography eluting with 1 to 15% MeOH/DCM to give Compound 46b (68 mg, 74% yield) as a pale brown solid. LCMS=1.71 min using analytical method (B), 402.0 (M+H). $^1$H NMR (400 MHz, $CD_3OD$) δ 8.24 (d, J=1.5 Hz, 1H), 8.01 (d, J=8.8 Hz, 1H), 7.79 (dd, J=8.5, 1.8 Hz, 1H), 7.73-7.65 (m, 2H), 7.47 (t, J=7.7 Hz, 2H), 7.41-7.32 (m, 1H), 4.47 (s, 2H).

Example 46

To a solution of Compound 46b (21 mg, 0.054 mmol) in DMF (0.6 mL) at 0° C. was added 60% NaH in mineral oil (4.3 mg, 0.11 mmol) and the reaction mixture stirred for 0.5 h. Methanesulfonyl chloride (10 μL, 0.13 mmol) was added dropwise and the reaction mixture stirred for 1 h. The reaction mixture was poured into satd. $NH_4Cl$ (5 mL) and the resulting solution extracted with DCM (3×5 mL). The combined organic extracts were dried ($Na_2SO_4$), filtered, and concentrated under reduced pressure. The residue was purified by preparative HPLC (RT=10.0 min using Method A, gradient elution of 30 to 100% solvent B over 14 min) to give Example 46 (13 mg, 51% yield) as a white solid. LCMS=1.77 min using analytical method (B), 479.9 (M+H). $^1$H NMR (400 MHz, pyridine-$d_5$) δ 8.06 (s, 1H), 7.76-7.65 (m, 4H), 7.50 (t, J=7.7 Hz, 2H), 7.44-7.37 (m, 1H), 5.07 (s, 2H), 3.48 (s, 3H). EL $IC_{50}$<10 nM.

Example 47 to Example 79 were prepared by the general procedures described for Example 46 using either 60% NaH in mineral oil or 1 M NaHMDS in THF as the base in the final step.

| Ex. No. | Structure | Name | ¹H NMR | LC/MS RT (min) Method M+H | EL IC₅₀ (nM) |
|---|---|---|---|---|---|
| 47 | 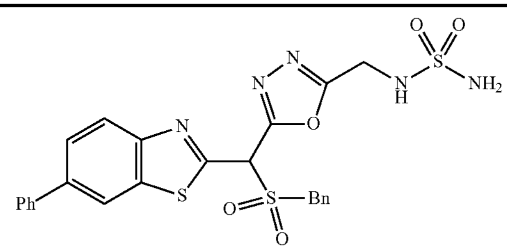 | N-((5-((benzylsulfonyl)(6-phenyl-1,3-benzothiazol-2-yl)(methyl))-1,3,4-oxadiazol-2-yl)methyl)sulfamide | ¹H NMR (400 MHz, CDCl₃ containing CD₃OD) δ 7.78 (d, J = 13 Hz, 1H), 7.67-7.62 (m, 1H), 7.62-7.56 (m, 3H), 7.46 (t, J = 7.5 Hz, 2H), 7.41-7.35 (m, 1H), 7.34-7.28 (m, 2H), 7.27-7.21 (m, 3H), 4.59 (s, 2H), 4.05 (s, 2H) | 1.00 M 55.9 | <10 |
| 48 | 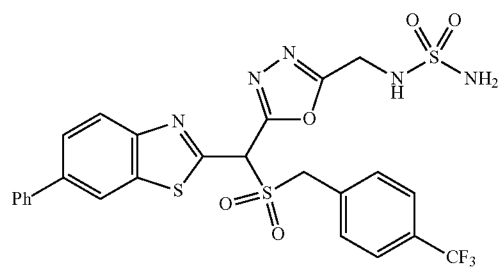 | N-(5-((6-phenyl-1,3-benzothiazol-2-yl)((4-(trifluoromethyl)benzyl)sulfonyl)methyl)-1,3,4-oxadiazol-2-yl)methyl)sulfamide | ¹H NMR (500 MHz, DMSO-d₆) δ 8.08 (br.s., 1H), 7.88 (d, J = 8.9 Hz, 1H), 7.69 (d, J = 7.9 Hz, 1H), 7.66 (d, J = 1.5 Hz, 2H), 7.63 (br. s., 2H), 7.58-7.55 (m, 2H), 7.47 (t, J = 7.7 Hz, 2H), 7.40-7.35 (t, 1H), 6.85 (s, 2H), 4.87 (br. s., 2H), 4.42 (br. s., 2H) | 2.00 M 624.1 | <10 |
| 49 | 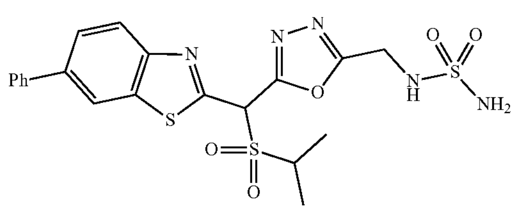 [SMILES: CC(C)S(=O)(=O)C(c1nnc(CNS(N)(=O)=O)o1)c1nc2ccc(-c3ccccc3)cc2s1] | N-({5-[(6-phenyl-1,3-benzothiazol-2-yl)(propan-2-ylsulfonyl)methyl]-1,3,4-oxadiazol-2-yl}methyl)sulfuric diamide | ¹H NMR (500 MHz, CD3OD) δ 7.86 (s, 1H), 7.72-7.62 (m, 2H), 7.59 (s, 1H), 7.44 (t, J = 7.7 Hz, 2H), 7.38-7.32 (m, 1H), 4.51 (s, 2H), 3.64-3.55 (m, 1H), 1.38 (d, J = 6.9 Hz, 6H) | 1.75 N 508.1 | <10 |

-continued

| Ex. No. | Structure | Name | $^1$H NMR | LC/MS RT (min) Method M + H | EL IC$_{50}$ (nM) |
|---|---|---|---|---|---|
| 50 | 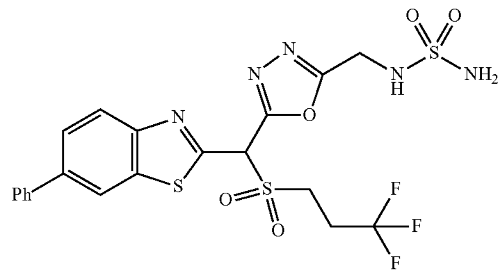 [SMILES: NS(=O)(=O)NCc1nnc(C(c2nc3ccc(-c4ccccc4)cc3s2)S(=O)(=O)CCC(F)(F)F)o1] | N-[(5-{(6-phenyl-1,3-benzothiazol-2-yl)[(3,3,3-trifluoropropyl)sulfonyl]methyl}-1,3,4-oxadiazol-2-yl)methyl]sulfuric diamide | $^1$H NMR (500 MHz, DMSO-d$_6$) δ 8.22 (s, 1H), 7.95 (s, 1H), 7.84 (d, J = 6.9 Hz, 1H), 7.69 (d, J = 7.4 Hz, 2H), 7.50 (d, J = 7.4 Hz, 2H), 7.40-7.36 (m, 1H), 6.80 (s, 2H), 4.38 (d, J = 5.0 Hz, 2H), 3.69 (br. s., 2H), 2.89-2.87 (m, 2H) | 1.90 O 562.1 | <10 |
| 51 | 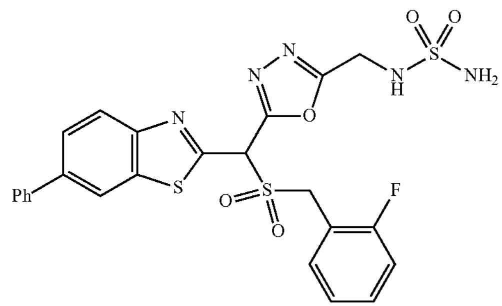 [SMILES: NS(=O)(=O)NCc1nnc(C(c2nc3ccc(-c4ccccc4)cc3s2)S(=O)(=O)Cc2ccccc2F)o1] | N-((5-(((2-fluorobenzyl)sulfonyl)(6-phenyl-1,3-benzothiazol-2-yl)methyl)-1,3,4-oxadiazol-2-yl)methyl)sulfamide | $^1$H NMR (500 MHz, DMSO-d$_6$) δ 7.70-7.63 (m, 3H), 7.57-7.52 (m, 1H), 7.50-7.43 (m, 3H), 7.36 (t, J = 7.2 Hz, 1H), 7.15-7.03 (m, 3H), 6.81 (s, 2H), 4.77 (br. s., 2H), 4.38 (br. s., 2H) | 1.85 N 574.1 | <10 |
| 52 | 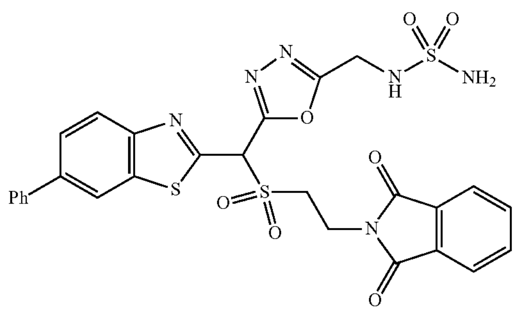 [SMILES: NS(=O)(=O)NCc1nnc(C(c2nc3ccc(-c4ccccc4)cc3s2)S(=O)(=O)CCN2C(=O)c3ccccc3C2=O)o1] | N-[(5-{(6-phenyl-1,3-benzothiazol-2-yl)[2-(1,3-dioxo-1,3-dihydro-2H-isoindol-2-yl)ethyl]sulfonyl]methyl}-1,3,4-oxadiazol-2-yl)methyl]sulfuric diamide | $^1$H NMR (500 MHz, DMSO-d$_6$) δ 8.16 (s, 1H), 7.96 (s, 1H), 7.89-7.82 (m, 2H), 7.75 (br. s., 2H), 7.71 (dd, J = 7.4 Hz, 3H), 7.50 (t, J = 7.7 Hz, 2H), 7.42-7.37 (t, 1H), 6.81 (s, 2H), 4.37 (br. s., 2H), 3.99 (d, J = 5.0 Hz, 2H), 3.92 (d, J = 4.0 Hz, 2H) | 1.73 N 639.2 | <10 |

| Ex. No. | Structure | Name | ¹H NMR | LC/MS RT (min) Method M + H | EL IC$_{50}$ (nM) |
|---|---|---|---|---|---|
| 53 | 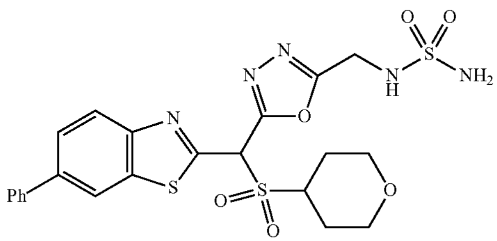 [SMILES: NS(=O)(=O)NCc1nnc(C(c2nc3ccc(-c4ccccc4)cc3s2)S(=O)(=O)C2CCOCC2)o1] | N-({5-[6-phenyl-1,3-benzothiazol-2-yl(tetrahydro-2H-pyran-4-ylsulfonyl)methyl]-1,3,4-oxadiazol-2-yl}methyl) sulfuric diamide | ¹H NMR (500 MHz, CDCl$_3$-containing CD$_3$OD) δ 7.87 (s, 1H), 7.70-7.62 (m, 3H), 7.44 (t, J = 7.7 Hz, 3H), 7.38-7.32 (m, 2H), 4.52 (s, 2H), 4.31 (br. s., 1H), 4.03 (d, J = 10.4 Hz, 2H), 3.45 (d, J = 11.3, 3.2 Hz, 2H), 2.00-1.90 (m, 4H) | 1.69 O 550.0 | <10 |
| 54 | 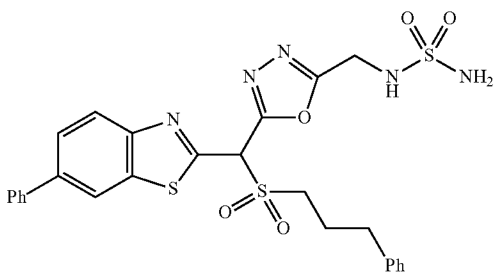 [SMILES: NS(=O)(=O)NCc1nnc(C(c2nc3ccc(-c4ccccc4)cc3s2)S(=O)(=O)CCCc2ccccc2)o1] | N-((5-((6-phenyl-1,3-benzothiazol-2-yl)(3-phenylpropyl)sulfonyl(methyl)-1,3,4-oxadiazol-2-yl)methyl) sulfamide | ¹H NMR (500 MHz, DMSO-d$_6$) δ 8.18 (br. s., 1H), 7.90 (dd, J = 8.4, 2.0 Hz, 1H), 7.71 (d, J = 8.4 Hz, 1H), 7.68 (d, J = 6.9 Hz, 2H), 7.48 (t, J = 7.7 Hz, 2H), 7.40-7.35 (m, 1H), 7.26-7.21 (m, 2H),7.16 (d, J = 7.4 Hz, 3H), 4.37 (br. s., 2H), 3.42 (d, J = 7.4 Hz, 2H), 2.69 (t, J = 7.4 Hz, 2H), 1.95 (br. s., 2H) | 2.04 N 584.1 | ~10 |
| 55 | 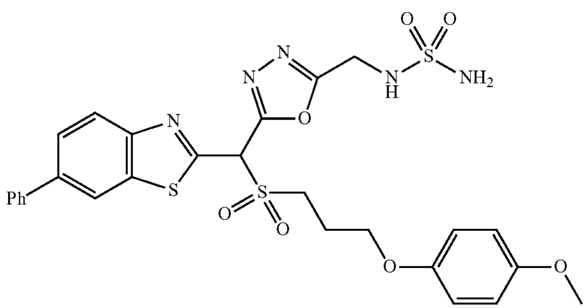 [SMILES: COc1ccc(OCCCS(=O)(=O)C(c2nnc(CNS(N)(=O)=O)o2)c2nc3ccc(-c4ccccc4)cc3s2)cc1] | N-(5-((3-(4-methoxyphenoxy)propyl)sulfonyl)(6-phenyl-1,3-benzothiazol-2-yl)methyl)-1,3,4-oxadiazol-2-yl)methyl)sulfamide | ¹H NMR (500 MHz, DMSO-d$_6$) δ 8.20 (d, J = 6.9 Hz, 1H), 7.69 (d, J = 6.9 Hz, 3H), 7.54-7.46 (m, 3H), 6.86-6.75 (m, 6H), 4.43-4.32 (m, 2H), 4.04-3.95 (m, 2H), 3.65 (s, 3H), 3.57 (br. s., 2H), 3.37 (s, 2H) | 1.99 O 630.0 | <10 |

-continued

| Ex. No. | Structure | Name | ¹H NMR | LC/MS RT (min) Method M+H | EL IC₅₀ (nM) |
|---|---|---|---|---|---|
| 56 | 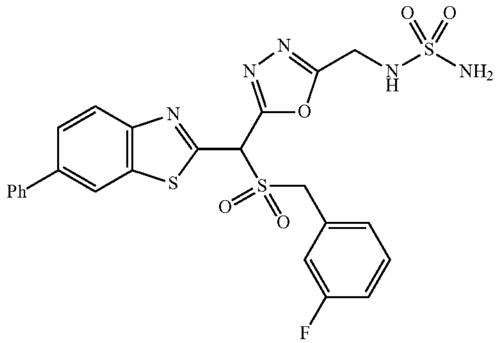 [SMILES: NS(=O)(=O)NCc1nnc(C(c2nc3ccc(-c4ccccc4)cc3s2)S(=O)(=O)Cc2cccc(F)c2)o1] | N-((5-(((3-fluorobenzyl) sulfonyl)(6-phenyl-1,3-benzothiazol-2-yl)methyl)-1,3,4-oxadiazol-2-yl)methyl)sulfamide | ¹H NMR (500 MHz, DMSO-d₆) δ 7.66 (d, J = 7.4 Hz, 3H), 7.46 (t, J = 7.4 Hz, 2H), 7.39-7.32 (m, 1H), 7.32-7.25 (m, 1H), 7.19-7.11 (m, 2H), 6.86 (s, 2H), 4.39 (br. s., 2H) | 1.89 N 574.1 | <10 |
| 57 | 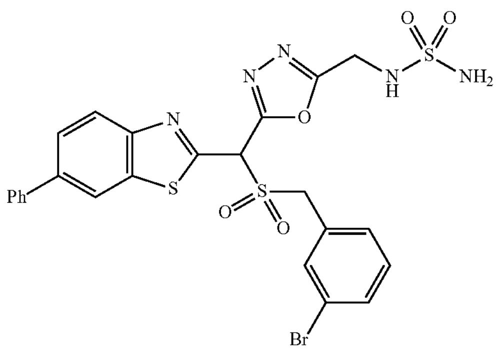 [SMILES: NS(=O)(=O)NCc1nnc(C(c2nc3ccc(-c4ccccc4)cc3s2)S(=O)(=O)Cc2cccc(Br)c2)o1] | N-((5-(((3-bromobenzyl) sulfonyl)(6-phenyl-1,3-benzothiazol-2-yl)methyl)-1,3,4-oxadiazol-2-yl)methyl)sulfamide | ¹H NMR (500 MHz, DMSO-d₆) δ 8.12 (br. s., 1H), 7.95 (s, 1H), 7.97-7.94 (m, 1H), 7.72-7.64 (m, 3H), 7.60-7.53 (m, 1H), 7.50-7.42 (m, 3H), 7.39-7.35 (m, 1H), 7.25-7.25 (m, 2H), 7.25-7.19 (m, 1H), 6.85 (s, 2H), 4.75 (br. s., 2H), 4.42 (br. s., 2H) | 1.97 N 635.8 | <10 |

| Ex. No. | Structure | Name | ¹H NMR | LC/MS RT (min) Method M + H | EL IC₅₀ (nM) |
|---|---|---|---|---|---|
| 58 | 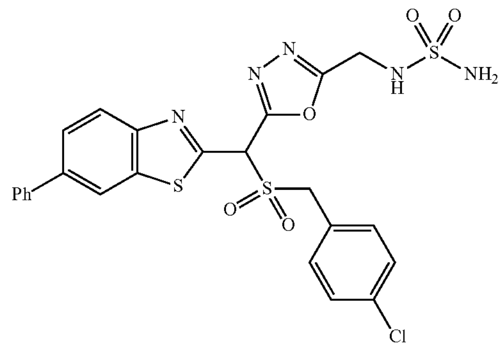 [SMILES: NS(=O)(=O)NCc1nnc(C(c2nc3ccc(-c4ccccc4)cc3s2)S(=O)(=O)Cc2ccc(Cl)cc2)o1] | N-((5-(((4-chlorobenzyl)sulfonyl)(6-phenyl-1,3-benzothiazol-2-yl)methyl)-1,3,4-oxadiazol-2-yl)methyl)sulfamide | ¹H NMR (500 MHz, DMSO-d₆) δ 8.12 (br. s., 1H), 7.68 (d, J = 7.4 Hz, 3H), 7.48 (t, J = 7.9 Hz, 3H), 7.35 (s, 5H), 4.76 (br. s., 2H), 4.43 (br. s., 2H) | 1.96 N 590.0 | <10 |
| 59 | 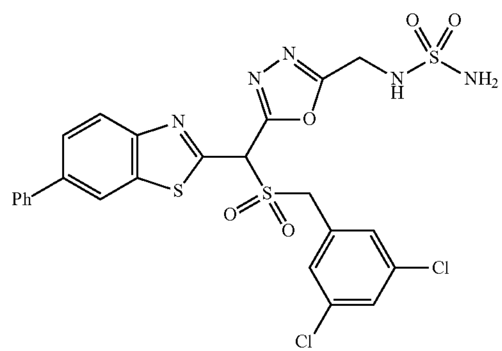 [SMILES: NS(=O)(=O)NCc1nnc(C(c2nc3ccc(-c4ccccc4)cc3s2)S(=O)(=O)Cc2cc(Cl)cc(Cl)c2)o1] | N-((5-(((3,5-dichlorobenzyl)sulfonyl)(6-phenyl-1,3-benzothiazol-2-yl)methyl)-1,3,4-oxadiazol-2-yl)methyl)sulfamide | ¹H NMR (500 MHz, DMSO-d₆) δ 8.14 (br. s., 1H), 7.89 (m, 1H), 7.67 (dd, J = 5.9 Hz, 1H), 7.68 (br. s., 1H), 7.57 (br. s., 2H), 7.52 (br. s., 1H), 7.48 (t, J = 7.7 Hz, 2H), 7.41-7.35 (m, 3H), 6.85 (s, 2H), (br. s., 2H), 4.42 (br. s., 2H) | 2.14 O 624.0 | <10 |

| Ex. No. | Structure | Name | ¹H NMR | LC/MS RT (min) Method M+H | EL IC₅₀ (nM) |
|---|---|---|---|---|---|
| 60 | 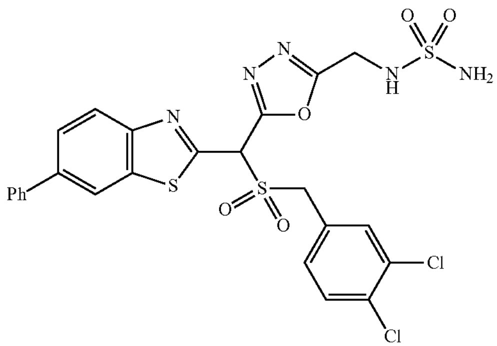 [SMILES: NS(=O)(=O)NCc1nnc(C(c2nc3ccc(-c4ccccc4)cc3s2)S(=O)(=O)Cc2ccc(Cl)c(Cl)c2)o1] | N-((5-(((3,4-chlorobenzyl) sulfonyl)(6-phenyl-1,3-benzothiazol-2-yl)methyl)-1,3,4-oxadiazol-2-yl)methyl)sulfamide | ¹H NMR (500 MHz, DMSO-d₆) δ 8.12 (br. s., 1H), 7.95 (s, 1H), 7.67 (d, J = 7.4 Hz, 2H), 7.60 (br. s., 1H), 7.57 (d, J = 5.9 Hz, 1H), 7.54 (d, J = 7.9 Hz, 1H), 7.47 (t, J = 7.7 Hz, 2H), 7.39-7.35 (m, 1H), 7.30 (d, J = 7.9 Hz, 1H), 6.85 (s, 2H), 4.78 (br. s., 2H), 4.41 (br. s., 2H) | 2.10 O 624.1 | <10 |
| 61 | 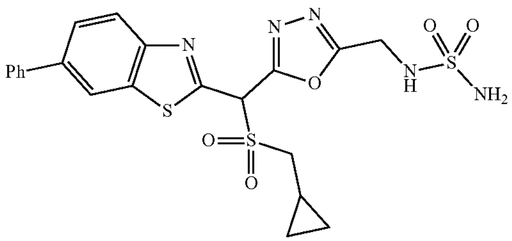 [SMILES: NS(=O)(=O)NCc1nnc(C(c2nc3ccc(-c4ccccc4)cc3s2)S(=O)(=O)CC2CC2)o1] | N-[(5-{(6-phenyl-1,3-benzothiazol-2-yl](cyclopropylmethyl)sulfonyl]methyl]-1,3,4-oxadiazol-2-yl)methyl]sulfuric diamide | ¹H NMR (500 MHz, DMSO-d₆) δ 8.21 (s, 1H), 7.96 (d, 1H), 7.73 (d, J = 8.4, 1.5 Hz, 1H), 7.70 (d, J = 7.4 Hz, 2H), 7.52-7.46 (m, 2H), 7.41-7.37 (m, 1H), 6.78 (s, 2H), 4.37 (d, J = 5.4 Hz, 2H), 3.37 (s, 2H), 1.00 (br. s., 1H), 0.44 (d, J = 7.4 Hz, 2H), 0.23 (d, J = 4.0 Hz, 2H) | 1.81 O 520.2 | <10 |
| 62 | 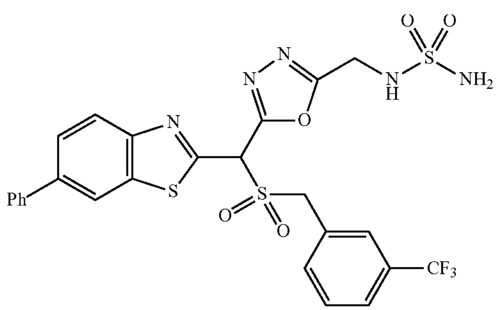 [SMILES: NS(=O)(=O)NCc1nnc(C(c2nc3ccc(-c4ccccc4)cc3s2)S(=O)(=O)Cc2cccc(C(F)(F)F)c2)o1] | N-((5-((3-(trifluoromethyl) benzyl)sulfonyl)(6-phenyl-1,3-benzothiazol-2-yl)methyl)-1,3,4-oxadiazol-2-yl)methyl)sulfamide | ¹H NMR (500 MHz, DMSO-d₆) δ 8.07 (br. s., 1H), 7.95 (s, 1H), 7.67 (br.s., 2H), 7.65 (s, 1H), 7.63-7.57 (m, 3H), 7.51 (d, J = 7.9 Hz, 1H), 7.48 (s, 1H), 7.47-7.45 (m, 1H), 7.39-7.34 (m, 1H), 7.34-7.34 (m, 1H), 6.85 (s, 2H), 4.86 (br. s., 2H), 4.42 (br. s., 2H) | 2.05 O 624.1 | <10 |

-continued

| Ex. No. | Structure | Name | ¹H NMR | LC/MS RT (min) Method M+H | EL IC₅₀ (nM) |
|---|---|---|---|---|---|
| 63 | 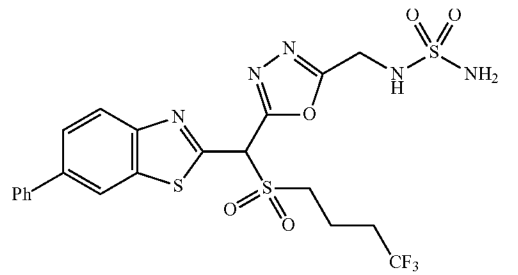 | N-[(5-{(6-phenyl-1,3-benzothiazol-2-yl)[(4,4,4-trifluorobutyl)sulfonyl]methyl}-1,3,4-oxadiazol-2-yl)methyl]sulfuric diamide | ¹H NMR (500 MHz, CDCl₃ containing CD₃OD) δ 7.86 (s, 1H), 7.68-7.65 (m, 1H), 7.64-7.62 (m, 1H), 7.58 (d, J = 7.4 Hz, 2H), 7.56 (s, 2H), 7.44 (t, J = 7.7 Hz, 2H), 7.37-7.33 (t, 1H), 4.51 (s, 2H), 3.47 (t, J = 7.4 Hz, 2H), 2.39-2.28 (m, 2H), 2.05 (quin, J = 7.8 Hz, 2H) | 1.95 O 576.0 | <10 |
| 64 | 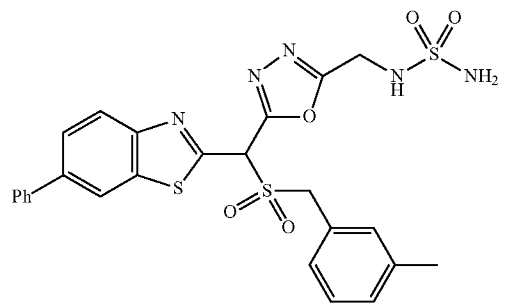 | N-((5-(((3-methylbenzyl)sulfonyl)(6-phenyl-1,3-benzothiazol-2-yl)methyl)-1,3,4-oxadiazol-2-yl)methyl)sulfamide | ¹H NMR (500 MHz, CDCl₃ containing CD₃OD) δ 7.78 (s, 1H), 7.65-7.61 (m, 1H), 7.58 (s, 1H), 7.56 (s, 3H), 7.43 (t, J = 7.7 Hz, 2H), 7.36-7.32 (t, 1H), 7.12-7.04 (m, 3H), 4.52 (s, 2H), 4.47 (s, 2H), 2.20 (s, 3H) | 1.99 O 570.1 | <10 |
| 65 | 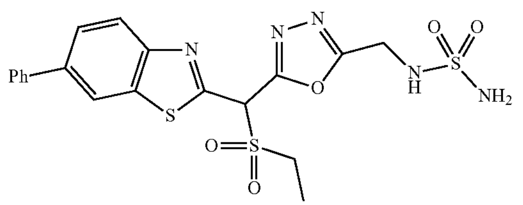 [SMILES: CCS(=O)(=O)C(c1nnc(CNS(N)(=O)=O)o1)c1nc2ccc(-c3ccccc3)cc2s1] | N-({5-[(ethylsulfonyl)(6-phenyl-1,3-benzothiazol-2-yl)methyl]-1,3,4-oxadiazol-2-yl}methyl)sulfuric diamide | ¹H NMR (500 MHz, DMSO-d₆) δ 8.19 (br. s, 1H), 7.92 (d, J = 8.4 Hz, 1H), 7.74-7.71 (m, 1H), 7.69 (d, J = 7.4 Hz, 2H), 7.49-7.46 (m, 2H), 7.40-7.36 (m, 1H), 6.80 (s, 2H), 4.38 (d, J = 4.5 Hz, 2H), 3.47-3.40 (m, 2H), 1.21 (br. s., 3H) | 1.66 N 494.1 | <10 |

| Ex. No. | Structure | Name | ¹H NMR | LC/MS RT (min) Method M + H | EL IC₅₀ (nM) |
|---|---|---|---|---|---|
| 66 | 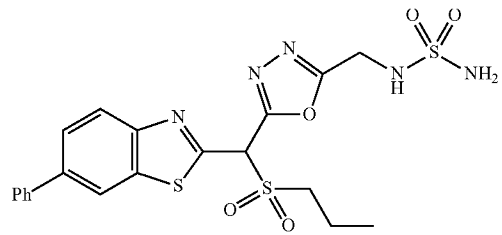 [SMILES: CCCS(=O)(=O)C(c1nnc(CNS(N)(=O)=O)o1)c1nc2ccc(-c3ccccc3)cc2s1] | N-({5-[(propylsulfonyl)(6-phenyl-1,3-benzothiazol-2-yl)methyl]-1,3,4-oxadiazol-2-yl}methyl)sulfuric diamide | ¹H NMR (500 MHz, DMSO-d₆) δ 8.19 (s, 1H), 7.97-7.91 (m, 1H), 7.72 (dd, J = 8.7, 1.7 Hz, 1H), 7.70-7.68 (dd, 2H), 7.49-7.46 (t, 2H), 7.40-7.35 (t, 1H), 6.83-6.78 (m, 2H), 4.39 (d, J = 5.4 Hz, 2H), 3.44-3.38 (m, 2H), 1.69 (d, J = 6.9 Hz, 2H), 1.00-0.94 (m, 3H) | 1.78 N 508.1 | <10 |
| 67 | 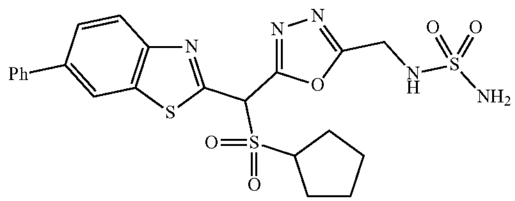 [SMILES: NS(=O)(=O)NCc1nnc(C(c2nc3ccc(-c4ccccc4)cc3s2)S(=O)(=O)C2CCCC2)o1] | N-({5-[(cyclopentylsulfonyl)(6-phenyl-1,3-benzothiazol-2-yl)methyl]-1,3,4-oxadiazol-2-yl}methyl)sulfuric diamide | ¹H NMR (500 MHz, DMSO-d₆) δ 8.19-8.16 (m, 1H), 7.72-7.69 (m, 1H), 7.68 (s, 1H), 7.53-7.49 (m, 2H), 7.49-7.46 (m, 2H), 7.40-7.35 (t, 1H), 6.80 (br. s., 2H), 1.98-1.92 (m, 2H), 1.90 (d, J = 9.4 Hz, 2H), 1.72 (br. s., 2H), 1.62-1.56 (m, 2H) | 1.90 N 534.2 | <10 |
| 68 | 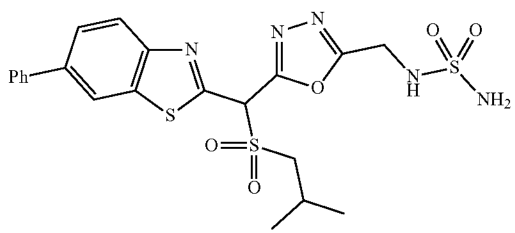 [SMILES: CC(C)CS(=O)(=O)C(c1nnc(CNS(N)(=O)=O)o1)c1nc2ccc(-c3ccccc3)cc2s1] | N-{[5-(6-phenyl-1,3-benzothiazol-2-yl)[(2-methylpropyl)sulfonyl]methyl]-1,3,4-oxadiazol-2-yl)methyl]sulfuric diamide | ¹H NMR (500 MHz, CD₃OD) δ 7.86 (s, 1H), 7.67-7.64 (m, 1H), 7.63-7.60 (m, 1H), 7.59 (dd, 2H), 7.43 (t, J = 7.4 Hz, 2H), 7.37-7.32 (t, 1H), 4.52 (s, 2H), 3.28 (d, J = 5.9 Hz, 2H), 2.29-2.23 (m, 1H), 1.09 (d, J = 6.9 Hz, 6H) | 1.87 N 522.2 | <10 |
| 69 | 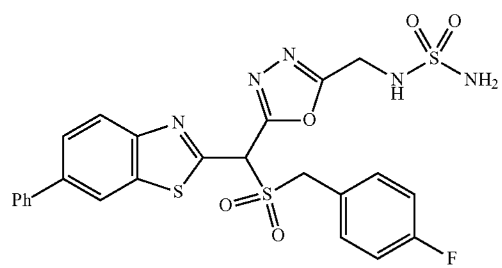 [SMILES: NS(=O)(=O)NCc1nnc(C(c2nc3ccc(-c4ccccc4)cc3s2)S(=O)(=O)Cc2ccc(F)cc2)o1] | N-(5-((4-fluorobenzyl)sulfonyl)(6-phenyl-1,3-benzothiazol-2-yl)methyl)-1,3,4-oxadiazol-2-yl)methyl)sulfamide | ¹H NMR (500 MHz, CD₃OD containing CDCl₃) δ 7.78 (s, 1H), 7.64-7.61 (m, 1H), 7.57 (s, 3H), 7.43 (t, J = 7.4 Hz, 2H), 7.37-7.29 (m, 3H), 6.93 (t, J = 8.4 Hz, 2H), 4.57 (s, 2H), 4.51 (s, 2H) | 1.94 O 574.1 | <10 |

-continued

| Ex. No. | Structure | Name | $^1$H NMR | LC/MS RT (min) Method M+H | EL IC$_{50}$ (nM) |
|---|---|---|---|---|---|
| 70 | 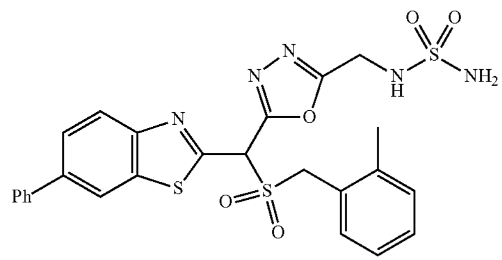 [SMILES: Cc1ccccc1CS(=O)(=O)C(c1nnc(CNS(N)(=O)=O)o1)c1nc2ccc(-c3ccccc3)cc2s1] | N-((5-(((2-methylbenzyl)sulfonyl)(6-phenyl-1,3-benzothiazol-2-yl)methyl)-1,3,4-oxadiazol-2-yl)methyl)sulfamide | $^1$H NMR (500 MHz, DMSO-d$_6$) δ 8.13 (s, 1H), 7.71-7.63 (m, 3H), 7.55-7.43 (m, 3H), 7.39-7.32 (m, 1H), 7.20-7.13 (m, 2H), 7.08-7.01 (m, 1H), 6.84-6.79 (m, 2H), 4.43-4.33 (m, 2H), 2.46-2.40 (m, 3H) | 2.65 P 570.0 | <10 |
| 71 | 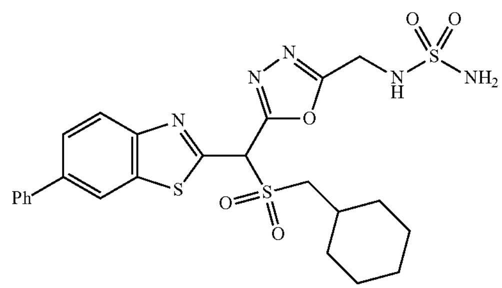 [SMILES: NS(=O)(=O)NCc1nnc(C(c2nc3ccc(-c4ccccc4)cc3s2)S(=O)(=O)CC2CCCCC2)o1] | N-((5-(((cyclohexylmethyl)sulfonyl)(6-phenyl-1,3-benzothiazol-2-yl)methyl)-1,3,4-oxadiazol-2-yl)methyl)sulfamide | $^1$H NMR (500 MHz, CD$_3$OD) δ 7.88 (d, J = 1.5 Hz, 1H), 7.69-7.65 (m, 1H), 7.65-7.62 (m, 1H), 7.62-7.59 (dd, J = 1.5 Hz, 2H), 7.46 (t, J = 7.7 Hz, 2H), 7.40-7.34 (t, 1H), 4.54 (s, 2H), 3.29 (d, J = 5.9 Hz, 2H), 2.06-1.99 (m, 1H), 1.98-1.92 (m, 2H), 1.73-1.66 (m, 2H), 1.65-1.59 (m, 1H), 1.33-1.23 (m, 1H), 1.22-1.09 (m, 1H) | 2.84 P 562.0 | <10 |
| 72 | 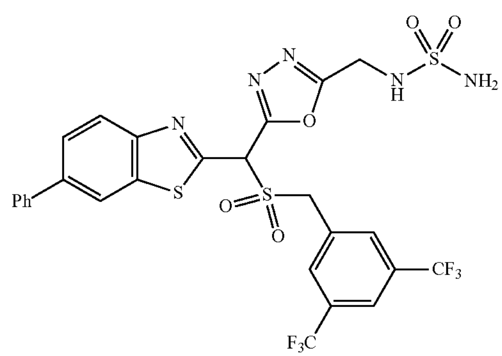 [SMILES: NS(=O)(=O)NCc1nnc(C(c2nc3ccc(-c4ccccc4)cc3s2)S(=O)(=O)Cc2cc(C(F)(F)F)cc(C(F)(F)F)c2)o1] | N-((5-(((3,5-bis(trifluoromethyl)benzyl)sulfonyl)(6-phenyl-1,3-benzothiazol-2-yl)methyl)-1,3,4-oxadiazol-2-yl)methyl)sulfamide | $^1$H NMR (500 MHz, CDCl$_3$ containing CD$_3$OD) δ 7.90 (br. s., 1H), 7.75 (d, J = 5.9 Hz, 1H), 7.66-7.61 (m, 1H), 7.58 (m, 3H), 7.56 (dd, 2H), 7.43 (t, J = 7.7 Hz, 2H), 7.37-7.32 (t, 1H), 4.77 (br. s., 2H), 4.56 (s, 2H) | 2.94 P 692.1 | <10 |

| Ex. No. | Structure | Name | ¹H NMR | LC/MS RT (min) Method M + H | EL IC₅₀ (nM) |
|---|---|---|---|---|---|
| 73 | 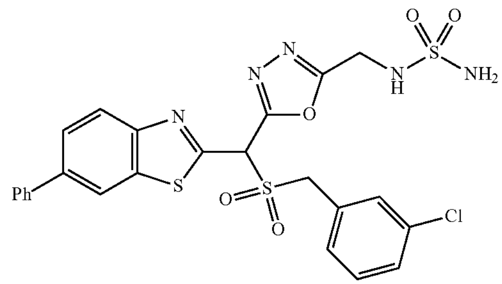 [SMILES: NS(=O)(=O)NCc1nnc(C(c2nc3ccc(-c4ccccc4)cc3s2)S(=O)(=O)Cc2cccc(Cl)c2)o1] | N-((5-(((3-chlorobenzyl)sulfonyl)(6-phenyl-1,3-benzothiazol-2-yl)methyl)-1,3,4-oxadiazol-2-yl)methyl)sulfamide | ¹H NMR (500 MHz, CDCl₃ containing CD₃OD) δ 7.80 (s, 1H), 7.65-7.64 (m, 1H), 7.62 (br. s., 1H), 7.61 (m, 1H), 7.58 (d, J = 6.9 Hz, 2H), 7.43 (t, J = 7.7 Hz, 2H), 7.37 (s, 1H), 7.36-7.32 (m, 1H), 7.19 (d, J = 5.0 Hz, 2H), 4.58 (s, 2H), 4.52 (s, 2H) | 1.64 N 590.0 | <10 |
| 74 | 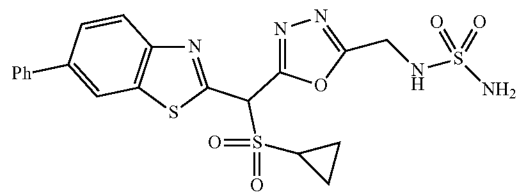 [SMILES: NS(=O)(=O)NCc1nnc(C(c2nc3ccc(-c4ccccc4)cc3s2)S(=O)(=O)C2CC2)o1] | N-({5-[(cyclopropylsulfonyl)(6-phenyl-1,3-benzothiazol-2-yl)methyl]-1,3,4-oxadiazol-2-yl}methyl)sulfamide | ¹H NMR (400 MHz, CDCl₃ containing CD₃OD) δ 7.97-7.76 (m, 1H), 7.66-7.53 (m, 1H), 7.44 (d, J = 7.0 Hz, 1H), 7.38-7.30 (m, 1H), 4.52 (s, 1H), 4.22 (m, 2), 1.39-1.32 (m, 1H), 1.22 (s, 1H), 1.12-0.94 (m, 3H) | 1.88 B 505.9 | <10 |
| 75 | 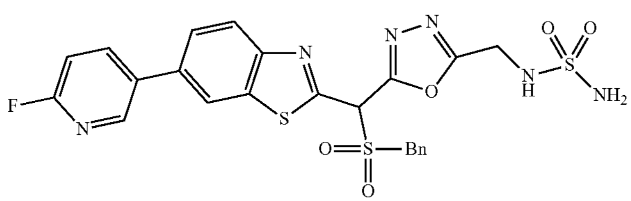 [SMILES: NS(=O)(=O)NCc1nnc(C(c2nc3ccc(-c4ccc(F)nc4)cc3s2)S(=O)(=O)Cc2ccccc2)o1] | N-((5-((benzylsulfonyl)(6-(6-fluoro-3-pyridinyl)-1,3-benzothiazol-2-yl)methyl)-1,3,4-oxadiazol-2-yl)methyl)sulfamide | ¹H NMR (400 MHz, CDCl₃ containing CD₃OD) δ 8.37 (d, J = 2.8 Hz, 1H), 8.04 (dd, J = 8.0, 2.6 Hz, 1H),7.72 (s, 1H),7.56 (s, 2H), 7.30-7.17 (m, 5H), 7.07 (dd, J = 8.5, 2.8 Hz, 1H), 4.55 (s, 2H), 4.47 (s, 2H) | 1.80 B 575.0 | <10 |
| 76 | 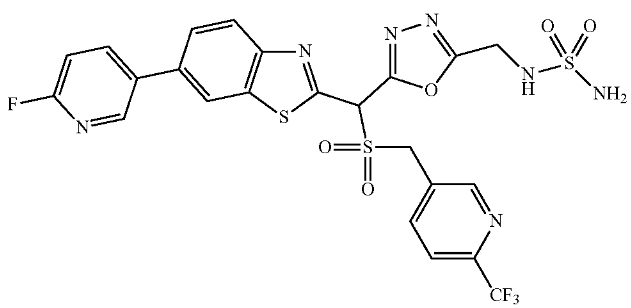 [SMILES: NS(=O)(=O)NCc1nnc(C(c2nc3ccc(-c4ccc(F)nc4)cc3s2)S(=O)(=O)Cc2ccc(C(F)(F)F)nc2)o1] | N-({5-[6-(6-fluoro-3-pyridinyl)-1,3-benzothiazol-2-yl]-[{6-(trifluoromethyl)pyridin-3-yl]methyl}sulfonyl)methyl]-1,3,4-oxadiazol-2-yl}methyl)sulfuric diamide | ¹H NMR (400 MHz, CDCl₃ containing CD₃OD) δ 8.78-8.67 (m, 1H), 8.53 (br. s., 1H), 8.45 (s, 1H), 8.32-8.04 (m, 3H), 7.86 (d, J = 8.0 Hz, 1H), 7.71 (br. s., 1H), 7.16 (d, J = 8.8 Hz, 1H), 4.72 (s, 2H), 4.32 (q, J = 7.0 Hz, 2H) | 1.74 B 644.0 | 11 |

-continued

| Ex. No. | Structure | Name | ¹H NMR | LC/MS RT (min) Method M + H | EL IC₅₀ (nM) |
|---|---|---|---|---|---|
| 77 | 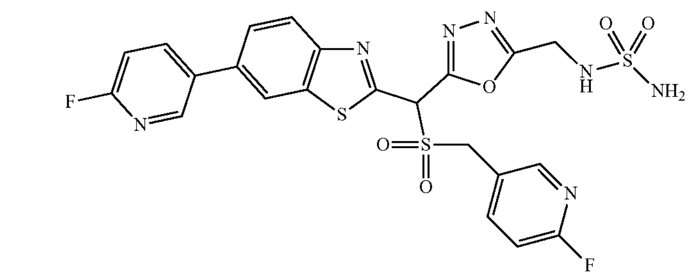 [SMILES: NS(=O)(=O)NCc1nnc(C(c2nc3ccc(-c4ccc(F)nc4)cc3s2)S(=O)(=O)Cc2ccc(F)nc2)o1] | N-({5-[6-(6-fluoro-3-pyridinyl)-1,3-benzothiazol-2-yl({[6-fluoropyridin-3-yl]methyl}sulfonyl)methyl]-1,3,4-oxadiazol-2-yl}methyl)sulfuric diamide | ¹H NMR (500 MHz, DMSO-d₆) δ 8.56 (d, J = 2.4 Hz, 1H), 8.28 (td, J = 8.3, 2.6 Hz, 1H), 8.17 (br. s., 1H), 7.93 (d, J = 7.3 Hz, 1H), 7.76 (dd, J = 8.6, 1.5 Hz, 1H), 7.59 (br. s., 1H), 7.31 (dd, J = 8.6, 2.6 Hz, 1H), 7.14 (dd, J = 8.5, 2.5 Hz, 1H), 6.85 (s, 2H), 4.84 (br. s., 2H), 4.44 (d, J = 5.3 Hz, 2H) | 1.63 B 594.1 | 18 |
| 78 | 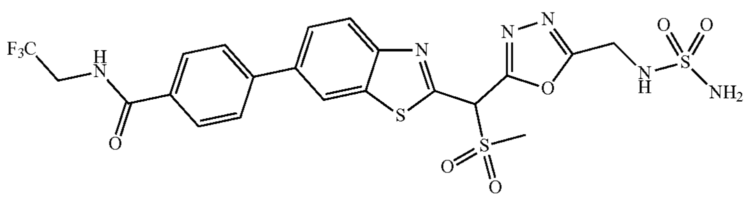 [SMILES: CS(=O)(=O)C(c1nnc(CNS(N)(=O)=O)o1)c1nc2ccc(-c3ccc(C(=O)NCC(F)(F)F)cc3)cc2s1] | 4-(2-((methylsulfonyl)(5-((sulfamoylamino)methyl)-1,3,4-oxadiazol-2-yl)methyl)benzo[d]thiazol-6-yl)-N-(2,2,2-trifluoroethyl)benzamide | ¹H NMR (500 MHz, DMSO-d₆) δ 9.33-8.97 (m, 1H), 8.12-7.75 (m, 5H), 7.57-7.36 (m, 1H), 6.93-6.72 (m, 2H), 4.55-4.30 (m, 2H), 4.21-4.03 (m, 2H), 3.53-3.33 (m, 3H) | 0.81 M 604.7 | <10 |
| 79 | 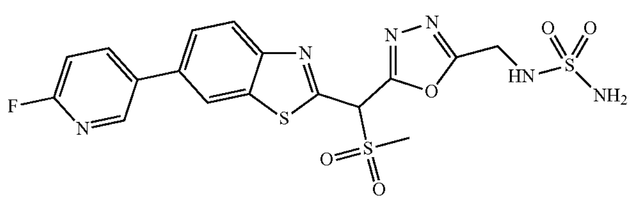 [SMILES: CS(=O)(=O)C(c1nnc(CNS(N)(=O)=O)o1)c1nc2ccc(-c3ccc(F)nc3)cc2s1] | N-((5-((6-(6-fluoro-3-pyridinyl)-1,3-benzothiazol-2-yl)(methylsulfonyl)methyl)-1,3,4-oxadiazol-2-yl)methyl) sulfamide | ¹H NMR (500 MHz, DMSO-d₆) δ 8.36-8.20 (m, 2H), 8.04-7.92 (m, 1H), 7.85-7.57 (m, 1H), 7.56-7.46 (m, 1H), 7.40-7.30 (m, 1H), 6.80 (d, J = 5.8 Hz, 2H), 4.42 (dd, J = 11.1, 5.9 Hz, 3H), 3.42 (s, 3H) | 0.78 M 498.8 | <10 |
| 80 | 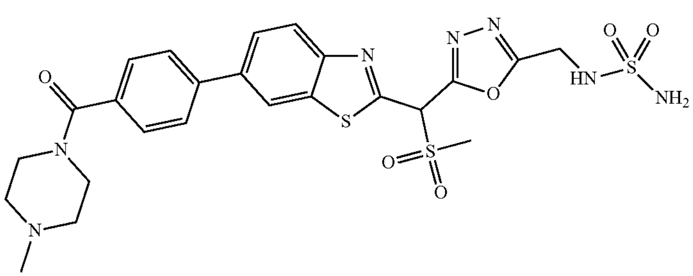 [SMILES: CN1CCN(C(=O)c2ccc(-c3ccc4nc(C(c5nnc(CNS(N)(=O)=O)o5)S(C)(=O)=O)sc4c3)cc2)CC1] | N-((5-((6-(4-(4-methyl-1-piperazinyl)carbonyl)phenyl)-1,3-benzothiazol-2-yl)(methylsulfonyl)methyl)-1,3,4-oxadiazol-2-yl)methyl) sulfamide | ¹H NMR (500 MHz, DMSO-d6) δ 9.96-9.64 (m, 1H), 8.33-8.15 (m, 1H), 8.04-7.94 (m, 1H), 7.96-7.85 (m, 1H), 7.81 (d, J = 8.3 Hz, 2H), 7.67-7.47 (m, 3H), 6.81 (d, J = 5.5 Hz, 2H), 4.48-4.33 (m, 2H), 4.11-3.04 (m, 11H), 2.84 (br. s., 3H) | 0.58 M 605.8 | 57 |

Example 81

N-Methyl-N-({5-[(methylsulfonyl)(6-phenyl-1,3-benzothiazol-2-yl)methyl]-1,3,4-oxadiazol-2-yl}methyl)sulfuric diamide

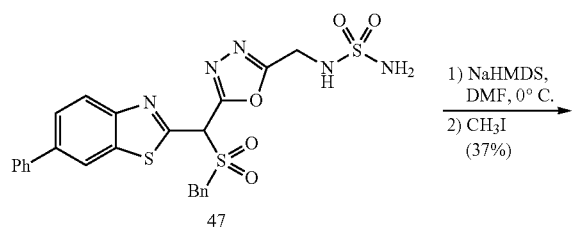

Example 82

2-((Benzylsulfonyl)(6-phenylbenzo[d]thiazol-2-yl)methyl)-5-(1-neopentylazetidin-3-yl)-1,3,4-oxadiazole

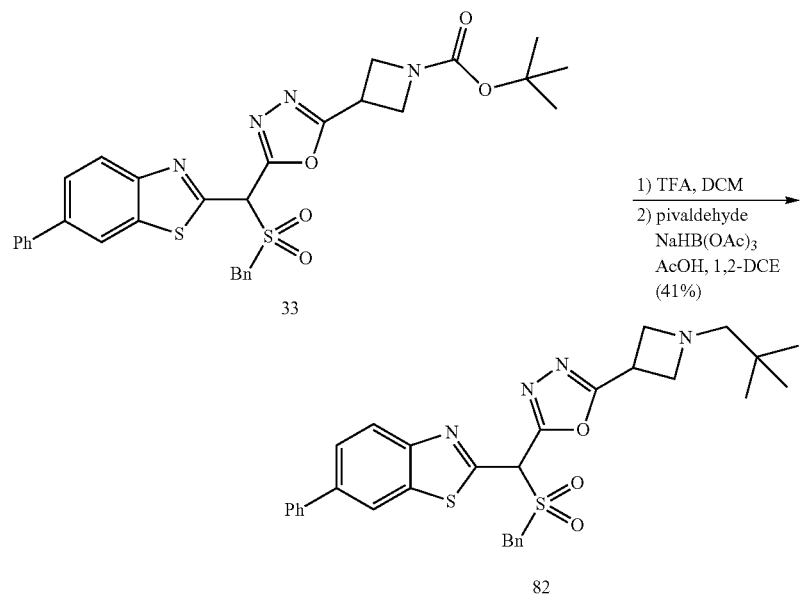

To a solution of Example 47 (11 mg, 0.020 mmol) in DMF (0.4 mL) at 0° C. was added 1 M NaHMDS in THF (0.024 mL, 0.024 mmol) and the reaction mixture stirred for 10 min. 2 M iodomethane in tert-butyl methyl ether (0.012 mL, 0.024 mmol) was added and the reaction mixture stirred for 15 min. Additional 1 M NaHMDS in THF (0.016 mL, 0.016 mmol) was added and the reaction mixture stirred 15 min then quenched by the addition of a drop of AcOH. The material was purified by preparative HPLC (RT=9.09 min using Method B). The fraction containing product was made basic by the addition of satd. NaHCO$_3$, evaporated under reduced pressure to remove the ACN, acidified by the addition of satd. NH$_4$Cl and extracted with DCM (3×). The combined extracts were dried (Na$_2$SO$_4$) filtered and concentrated under reduced pressure to give Example 81 (4.3 mg, 37% yield) as a white solid. RT=1.04 min using analytical method (M), 569.9 (M+H). $^1$H NMR (400 MHz, DMSO-d$_6$) δ 8.10 (s, 1H), 7.63-7.76 (m, 3H), 7.58-7.15 (m, 9H), 7.02 (s, 2H), 5.75 (s, 1H), 4.69 (br. s., 2H), 4.51 (s, 2H), 2.83 (s, 3H). HMBC correlation between $^1$H NMR of the methyl group at 2.83 ppm with $^{13}$C NMR signal at 44 ppm. $^{13}$C NMR signal of methyl group at 35 ppm. EL IC$_{50}$ 32 nM.

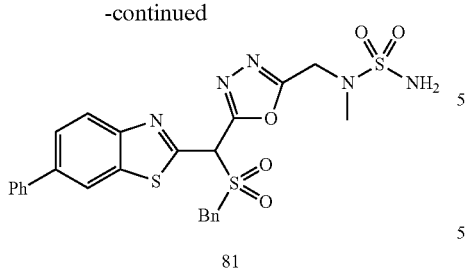

To a solution of Example 33 (50 mg, 0.083 mmol) in CH$_2$Cl$_2$ (4 mL) was added TFA (1.5 mL) and the mixture stirred for 1 h. The solvent was evaporated under reduced pressure and the residue dissolved in DCE (2 mL) then pivalaldehyde (14 mg, 0.17 mmol), NaHB(OAc)$_3$ (27 mg, 0.13 mmol), and AcOH (0.12 μL, 2.2 μmol) added and the reaction mixture stirred for 20 h. H$_2$O was added, followed by CH$_2$Cl$_2$. The layers were separated and the organic portion concentrated under reduced pressure and purified by HPLC (Method B) to give Example 82 (20 mg, 41% yield) as an off-white solid. LCMS ESI 573.2 (M+H), RT=3.68 min (Method R). $^1$H NMR (400 MHz, CDCl$_3$) δ 7.78 (br. s., 1H), 7.65 (d, J=8.34 Hz, 1H), 7.58 (d, J=7.07 Hz, 2H), 7.44-7.55 (m, 3H), 7.37-7.44 (m, 1H), 7.16-7.31 (m, 6H), 5.01 (br. s., 2H), 4.46 (br. s., 2H), 4.35 (br. s., 2H), 3.99 (s, 1H), 3.16 (s, 2H), 1.11 (s, 9H). EL IC$_{50}$=26 nM.

Example 83 tert-Butyl ((5-((methylsulfonyl)(6-phenylbenzo[d]thiazol-2-yl)methyl)-1,3,4-oxadiazol-2-yl)methyl)carbamate and

Example 84 tert-Butyl methylsulfonyl((5-((methylsulfonyl)(6-phenylbenzo[d]thiazol-2-yl)methyl)-1,3,4-oxadiazol-2-yl)methyl)carbamate

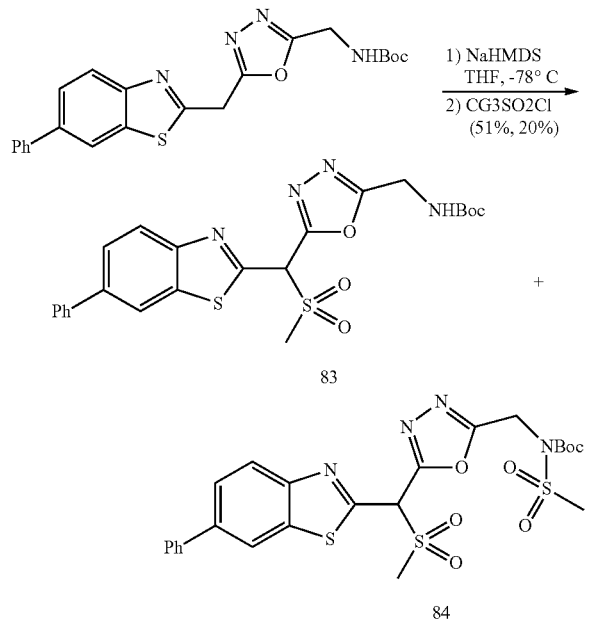

Example 83 and Example 84 were prepared from tert-butyl ((5-((6-phenylbenzo[d]thiazol-2-yl)methyl)-1,3,4-oxadiazol-2-yl)methyl)carbamate (described in WO 2011/074560) in 51% and 20% yield respectively as pale yellow solids using the general procedure given for Example 1. Example 83 $^1$H NMR (400 MHz, CDCl$_3$) δ 12.88 (br. s., 1H), 7.80 (d, J=1.5 Hz, 1H), 7.67-7.61 (m, 1H), 7.60-7.55 (m, 2H), 7.52 (d, J=8.6 Hz, 1H), 7.47 (t, J=7.6 Hz, 2H), 7.43-7.34 (m, 1H), 5.18 (br. s., 1H), 4.62 (d, J=6.1 Hz, 2H), 3.23 (s, 3H), 1.48 (s, 9H). LCMS=2.16 min using analytical method (B), 501.1 (M+H). EL IC$_{50}$<10 nM. Example 84 $^1$H NMR (400 MHz, CDCl$_3$) δ 12.84 (br. s., 1H), 7.81 (d, J=1.5 Hz, 1H), 7.63 (d, J=1.5 Hz, 1H), 7.58 (d, J=7.3 Hz, 2H), 7.52 (d, J=8.3 Hz, 1H), 7.47 (t, J=7.5 Hz, 2H), 7.41-7.35 (m, 1H), 5.20 (s, 2H), 3.54 (s, 3H), 3.22 (s, 3H), 1.55 (s, 9H). LCMS=2.18 min using analytical method (B), 579.2 (M+H). EL IC$_{50}$<10 nM.

Example 85

(5-((Methylsulfonyl)(6-phenylbenzo[d]thiazol-2-yl)methyl)-1,3,4-oxadiazol-2-yl)methanamine

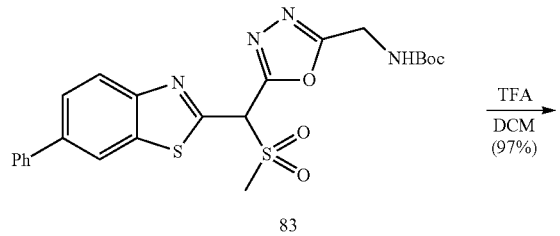

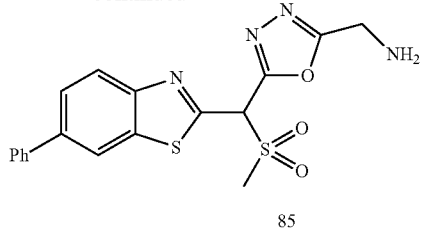

Example 85 was prepared from Example 83 in 97% yield using the general procedure given for Compound 26a. $^1$H NMR (400 MHz, CDCl$_3$) δ 7.81 (d, J=1.3 Hz, 1H), 7.64 (dd, J=8.3, 1.5 Hz, 1H), 7.59 (d, J=7.3 Hz, 2H), 7.53 (d, J=8.8 Hz, 1H), 7.47 (t, J=7.5 Hz, 2H), 7.42-7.36 (m, 1H), 4.16 (s, 2H), 3.23 (s, 3H). LCMS=0.79 min using analytical method (M), 401.1 (M+H). EL IC$_{50}$=48 nM.

Example 86

N-((5-((Methylsulfonyl)(6-phenylbenzo[d]thiazol-2-yl)methyl)-1,3,4-oxadiazol-2-yl)methyl)methanesulfonamide

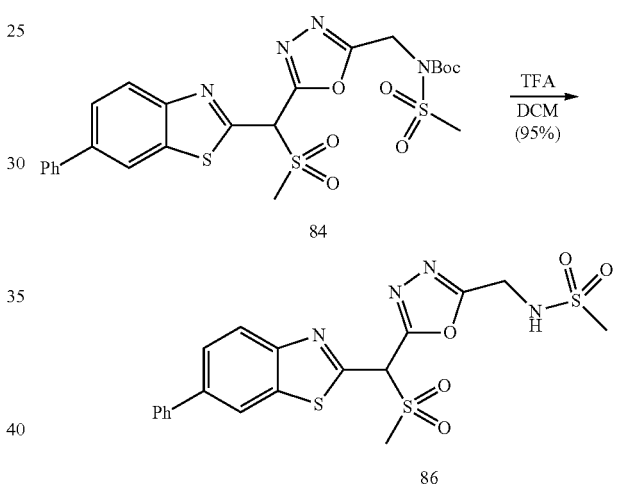

Example 86 was prepared from Example 84 in 95% yield using the general procedure given for Compound 26a. $^1$H NMR shows isomers in 3:2 ratio. $^1$H NMR of major isomer: (400 MHz, DMSO-d$_6$ containing D$_2$O) δ 8.18 (s, 1H), 7.77 (d, J=7.5 Hz, 1H), 7.70 (d, J=7.5 Hz, 2H), 7.52-7.50 (m, 1H), 7.50-7.45 (m, 2H), 7.40-7.34 (m, 1H), 4.53 (s, 2H), 3.30 (s, 3H), 3.03 (s, 3H). LCMS=0.93 min using analytical method (M), 479.1 (M+H). EL IC$_{50}$=47 nM.

Example 87

1-Ethyl-3-((5-((methylsulfonyl)(6-phenylbenzo[d]thiazol-2-yl)methyl)-1,3,4-oxadiazol-2-yl)methyl)urea

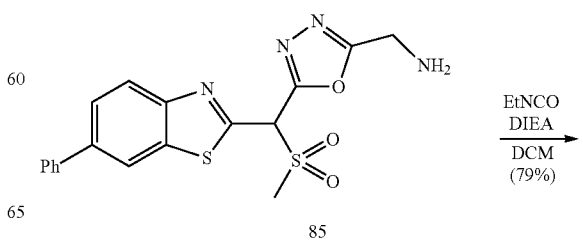

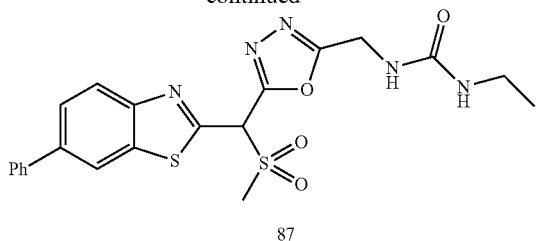

To a solution of Example 85 (7.0 mg, 0.016 mmol) in DCM (0.4 mL) was added DIEA (5.7 μL, 0.032 mmol) followed by ethyl isocyanate (2.5 μL, 0.032 mmol) and the reaction mixture stirred for 0.5 h then purified by silica gel chromatography eluting with 0 to 8% MeOH/DCM to give Example 87 (6.4 mg, 79% yield). $^1$H NMR (400 MHz, CDCl$_3$ containing CD$_3$OD) δ 7.83 (s, 1H), 7.69-7.63 (m, 1H), 7.62-7.54 (m, 3H), 7.47 (t, J=7.5 Hz, 2H), 7.39 (t, J=7.5 Hz, 1H), 4.64 (s, 2H), 3.26 (br. s., 3H), 3.21 (q, J=7.3 Hz, 2H), 1.14 (t, J=7.3 Hz, 3H). LCMS=1.86 min using analytical method (B), 472.1 (M+H). EL IC$_{50}$=46 nM.

Example 88

N-((5-((Methylsulfonyl)(6-phenylbenzo[d]thiazol-2-yl)methyl)-1,3,4-oxadiazol-2-yl)methyl)isobutyramide

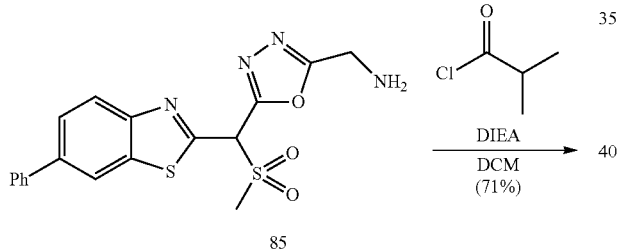

To a solution of Example 85 (7.0 mg, 0.016 mmol) in DCM (0.4 mL) was added DIEA (5.7 μL, 0.032 mmol) followed by isobutyryl chloride (2.0 μL, 0.019 mmol) and the reaction mixture stirred for 15 min then purified by silica gel chromatography eluting with 0 to 100% EtOAc/DCM to give Example 88 (5.8 mg, 71% yield). $^1$H NMR (400 MHz, CDCl$_3$) δ 12.81 (br. s., 1H), 7.79 (d, J=1.5 Hz, 1H), 7.63 (dd, J=8.4, 1.6 Hz, 1H), 7.60-7.55 (m, 2H), 7.50 (d, J=8.5 Hz, 1H), 7.49-7.44 (m, 2H), 7.42-7.36 (m, 1H), 6.24 (t, J=5.5 Hz, 1H), 4.76 (d, J=5.8 Hz, 2H), 3.22 (s, 3H), 2.50 (dt, J=13.8, 6.9 Hz, 1H), 1.24 (d, J=7.0 Hz, 6H). LCMS=1.93 min using analytical method (B), 471.1 (M+H). EL IC$_{50}$=195 nM.

Example 89

(5-((Methylsulfonyl)(6-phenylbenzo[d]thiazol-2-yl)methyl)-1,3,4-oxadiazol-2-yl)methanesulfonamide

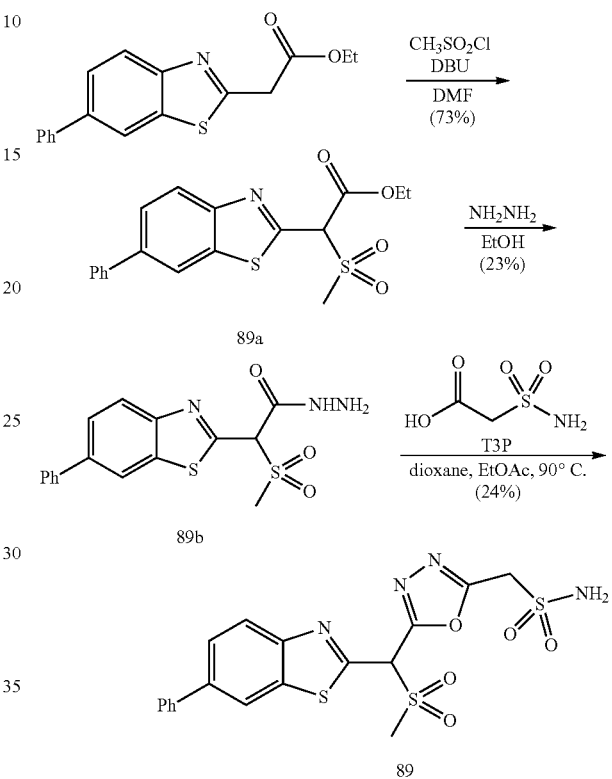

Compound 89a. Ethyl 2-(methylsulfonyl)-2-(6-phenylbenzo[d]thiazol-2-yl)acetate

To a solution of ethyl 2-(6-phenylbenzo[d]thiazol-2-yl)acetate (390 mg, 1.3 mmol) (described in WO 2011/074560) in DMF (4 mL) at 0° C. was added DBU (0.49 mL, 3.3 mmol) and the reaction mixture was stirred at rt for 10 min. Methanesulfonyl chloride (0.12 mL, 1.6 mmol) was added dropwise and the mixture stirred for 0.5 h. Additional methanesulfonyl chloride (0.030 mL, 0.40 mmol) was added and the reaction mixture stirred for 10 min. The reaction mixture was diluted with H$_2$O then extracted with EtOAc (3×), dried (Na$_2$SO$_4$), filtered and concentrated under reduced pressure. The residue was purified by silica gel chromatography eluting with 0 to 100% EtOAc/hexane to give Compound 89a (360 mg, 73% yield) as yellow powder. RT=2.06 min using analytical method (Q), 376.9 (M+H). $^1$H NMR (500 MHz, CDCl$_3$) δ 7.88-7.75 (m, 1H), 7.68-7.53 (m, 3H), 7.53-7.34 (m, 5H), 4.42 (qd, J=7.2, 3.0 Hz, 2H), 3.39-3.21 (m, 3H).

Compound 89b. 2-((Methylsulfonyl)methyl)-6-phenylbenzo[d]thiazole

To a solution of Compound 89a (100 mg, 0.27 mmol) in EtOH (8 mL) was added hydrazine (0.13 mL, 4.0 mmol) and the reaction mixture stirred at rt for 1 h, then at 50° C. for 1 h. The reaction mixture was allowed to cool, concentrated under reduced pressure and the residue suspended in DCM, filtered and dried under vacuum to give Compound 89b (22 mg, 23% yield). RT=1.65 min using analytical method (Q), 361.9 (M+H). $^1$H NMR (500 MHz, DMSO-$d_6$) δ 8.51-8.45 (m, 1H), 8.15 (d, J=8.5 Hz, 1H), 7.87 (dd, J=8.5, 1.9 Hz, 1H), 7.77 (d, J=7.4 Hz, 2H), 7.53-7.49 (m, 2H), 7.44-7.38 (m, 1H), 5.80 (s, 1H), 3.24 (s, 3H).

Example 89

To a solution of Compound 89b (23 mg, 0.064 mmol) in dioxane (1 mL) was added 2-sulfamoylacetic acid (8.9 mg, 0.064 mmol), 50% T3P in EtOAc (0.095 mL, 0.16 mmol), followed by DIEA (0.022 mL, 0.13 mmol) and the reaction mixture was stirred at 70° C. for 2 h. Additional 50% T3P in EtOAc (0.095 mL, 0.16 mmol) and DIEA (0.022 mL, 0.13 mmol) were added and the reaction mixture stirred at 90° C. for 16 h. The reaction mixture was allowed to cool to rt and concentrated under reduced pressure. The residue was purified by preparative HPLC (RT=7.31 min using Method B). Fractions containing product were evaporated under reduced pressure to remove the ACN then lyophilized to give Example 89 (7.0 mg, 24% yield). RT=1.81 minutes using analytical method (Q), (M+H)=464.9; $^1$H NMR (500 MHz, DMSO-$d_6$) δ 7.78 (d, J=7.4 Hz, 1H), 7.70 (d, J=7.4 Hz, 4H), 7.55-7.50 (m, 1H), 7.47 (br. s., 2H), 7.49-7.46 (m, 1H), 7.38 (br. s., 2H), 4.88 (s, 1H), 3.42 (s, 1H). EL IC$_{50}$<10 nM.

Example 90

(5-((4-Fluoro-6-phenylbenzo[d]thiazol-2-yl)((4-(trifluoromethyl)benzyl)sulfonyl)methyl)-1,3,4-oxadiazol-2-yl)methanesulfonamide

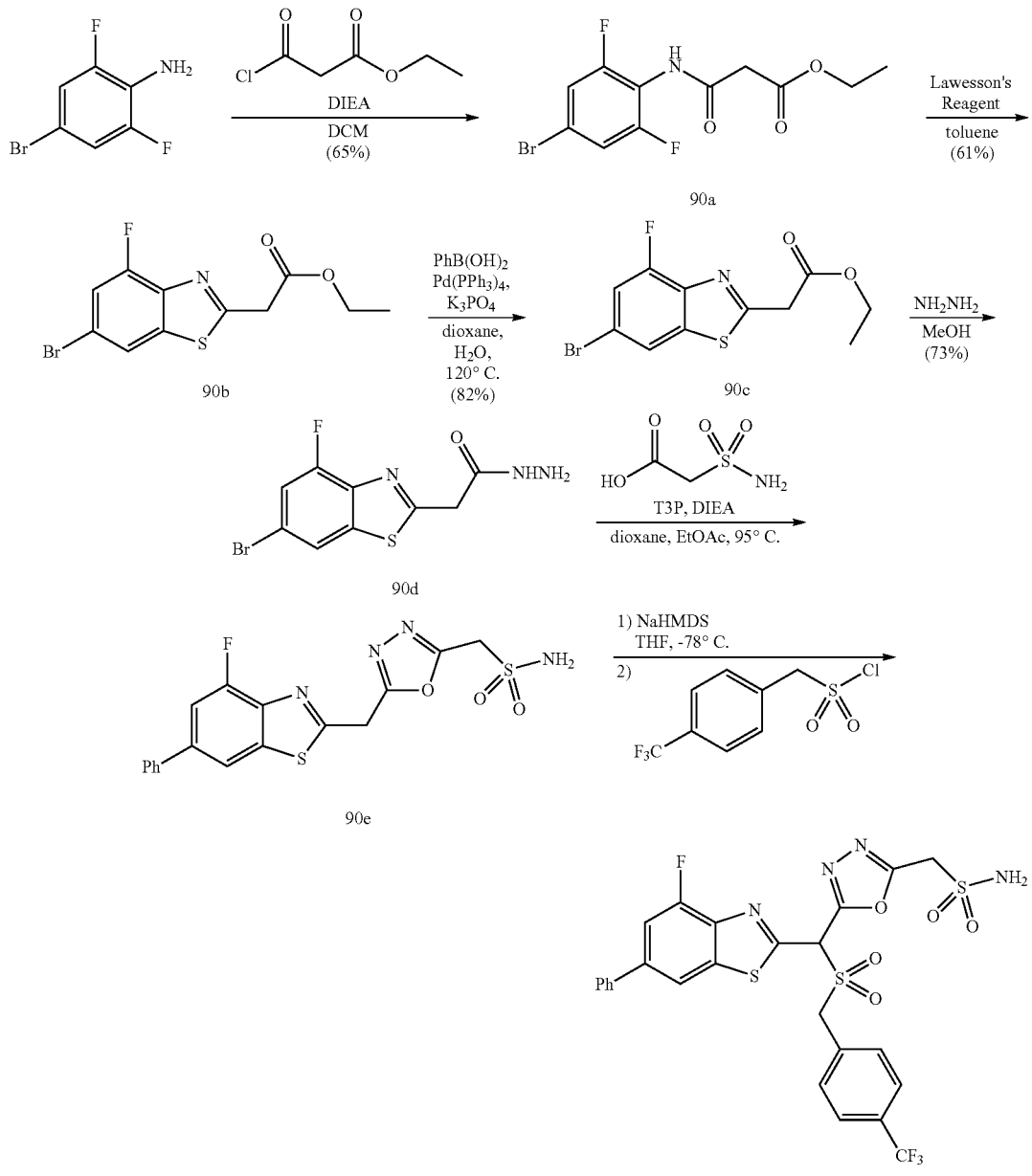

Compound 90a. Ethyl 3-((4-bromo-2,6-difluorophenyl)amino)-3-oxopropanoate

To a solution of 4-bromo-2,6-difluoroaniline (10 g, 48 mmol) in DCM (15 mL) was added ethyl 3-chloro-3-oxopropanoate (6.8 mL, 53 mmol) and DIEA (9.2 mL, 53 mmol) and the reaction mixture stirred for 1 h. The reaction mixture was partitioned between $H_2O$ and DCM and the layers separated. The DCM portion was washed with satd. $NH_4Cl$ and $H_2O$ then dried ($Na_2SO_4$) and filtered. The filtrate was concentrated under reduced pressure to give Compound 90a (10 g, 65% yield). LCMS=1.60 min using analytical method (Q), 321.9 (M+H). $^1$H NMR (500 MHz, $CDCl_3$) δ 8.89 (br. s., 1H), 7.20-7.15 (m, 2H), 4.29 (q, J=7.2 Hz, 2H), 3.54 (s, 2H), 1.36-1.31 (m, 3H).

Compound 89b. Ethyl 2-(6-bromo-4-fluorobenzo[d]thiazol-2-yl)acetate

To a solution of Compound 90a (2.0 g, 6.2 mmol) in toluene (20 mL) was added Lawesson's reagent (1.5 g, 3.7 mmol) and the reaction mixture refluxed for 3 h. $Cs_2CO_3$ (5.1 mg, 16 mmol) was added and the reaction mixture stirred for 16 h. The reaction mixture was filtered, concentrated under reduced pressure, and the residue purified by silica gel chromatography eluting with 0 to 100% EtOAc in hexane to give Compound 90b (1.2 g, 61% yield). LCMS=2.02 min using analytical method (Q), 319.9 (M+H). $^1$H NMR (500 MHz, $CDCl_3$) δ ppm 7.93 (1H, d), 7.66 (1H, d, J=1.7 Hz), 4.28 (2H, q, J=7.2 Hz), 4.22-4.24 (2H, m), 1.33 (3H, t, J=7.2 Hz).

Compound 90c. Ethyl 2-(4-fluoro-6-phenylbenzo[d]thiazol-2-yl)acetate

To a solution of Compound 90b (1.00 g, 3.1 mmol) in dioxane (20 mL) was added phenylboronic acid (460 mg, 3.8 mmol), phosphoric acid, potassium salt (1.67 g, 7.9 mmol), and tetrakis(triphenylphosphine)palladium(0) (730 mg, 0.63 mmol). The reaction mixture was degassed with argon and heated at 105° C. for 16 h. The reaction mixture was allowed to cool to rt and filtered. The filtrate was concentrated under reduced pressure then purified by silica gel chromatography eluting with 0 to 100% EtOAc in DCM to give Compound 90c (810 mg, 82% yield). LCMS=2.20 min using analytical method (Q), 315.9 (M+H). $^1$H NMR (400 MHz, $CDCl_3$) δ ppm 8.02-8.10 (2H, m), 7.71 (1H, dd, J=8.53, 2.01 Hz), 7.64 (2H, dd, J=8.28, 1.25 Hz), 7.43-7.51 (2H, m), 7.34-7.42 (1H, m), 4.27 (2H, q, J=7.03 Hz), 4.19 (2H, s), 1.31 (3H, t, J=7.03 Hz).

Compound 90d. 2-(4-Fluoro-6-phenylbenzo[d]thiazol-2-yl)acetohydrazide

To a solution of Compound 89c (200 mg, 0.63 mmol) in EtOH (1 mL) was added hydrazine (0.30 mL, 9.5 mmol) and the reaction mixture stirred for 3 h then filtered, the solid washed with ether and dried under vacuum to give Compound 90d (140 mg, 73% yield). LCMS=1.72 min using analytical method (Q), 302.0 (M+H). $^1$H NMR (500 MHz, DMSO-$d_6$) δ 9.49 (s, 1H), 8.26 (d, J=1.7 Hz, 1H), 7.81-7.77 (m, 2H), 7.69 (dd, J=12.1, 1.7 Hz, 1H), 7.52-7.48 (m, 2H), 7.44-7.38 (m, 1H), 4.39 (d, J=2.8 Hz, 2H), 4.05 (s, 2H).

Compound 90e. (5-((4-Fluoro-6-phenylbenzo[d]thiazol-2-yl)methyl)-1,3,4-oxadiazol-2-yl)methanesulfonamide Compound 90e was prepared from Compound 90d and 2-sulfamoylacetic acid using the procedure given for Compound 1b. LCMS=1.78 min using analytical method (Q), 405.1 (M+H). $^1$H NMR (500 MHz, $CD_3OD$) δ 8.07 (d, J=1.7 Hz, 1H), 7.74-7.67 (m, 2H), 7.56 (dd, J=12.0, 1.5 Hz, 1H), 7.52-7.43 (m, 2H), 7.43-7.36 (m, 1H), 4.94-4.88 (m, 2H), 4.78-4.74 (m, 2H).

Example 90

Example 90 was prepared from Compound 90e and (4-(trifluoromethyl)phenyl)methanesulfonyl chloride using the procedure given for Example 1. $^1$H NMR (500 MHz, DMSO-$d_6$) δ 7.82-7.77 (m, 2H), 7.73-7.68 (m, 3H), 7.64 (dd, J=16.8, 8.3 Hz, 2H), 7.57 (d, J=8.3 Hz, 1H), 7.55-7.46 (m, 3H), 7.45-7.37 (m, 2H), 5.14 (s, 1H), 4.90 (s, 1H), 4.84 (d, J=10.7 Hz, 2H). LCMS ESI 627.1 (M+H), RT=2.15 min (Method Q). EL $IC_{50}$<10 nM.

Examples 91-97 were prepared by the general procedures given for Example 90. Examples 98-111 were prepared by the general procedures given for Example 1. Examples 112-153 were prepared by the general procedures given for Example 46. Examples 154-157 were prepared by the general procedures given for Example 88. Examples 158-168 were prepared by the general procedures given for Example 90.

| Ex. No. | Structure | Name | $^1$H NMR | LC/MS RT (min) Method M + H | EL $IC_{50}$ (nM) |
|---|---|---|---|---|---|
| 91 | (structure: 5-fluoro-6-phenylbenzo[d]thiazole linked via CH(SO$_2$Bn) to 1,3,4-oxadiazole linked to CH$_2$-thiazolidine-2,4-dione) | 5-((5-((benzylsulfonyl)(5-fluoro-6-phenylbenzo[d]thiazol-2-yl)methyl)-1,3,4-oxadiazol-2-yl)methyl)thiazolidine-2,4-dione | $^1$H NMR (400 MHz, $CDCl_3$) δ 8.20 (s, 1H), 7.60-7.36 (m, 11H), 4.77 (dd, J = 7.6, 4.8 Hz, 1H), 4.44 (s, 2H), 3.68 (dd, J = 16.5, 4.7 Hz, 1H), 3.58-3.47 (m, 1H) | 2.15 Q 595.0 | <10 |

| Ex. No. | Structure | Name | ¹H NMR | LC/MS RT (min) Method M + H | EL IC$_{50}$ (nM) |
|---|---|---|---|---|---|
| 92 | 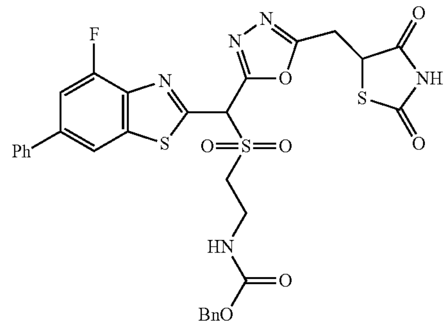 [SMILES: O=C(NCCS(=O)(=O)C(c1nnc(CC2SC(=O)NC2=O)o1)c1nc2c(F)cc(-c3ccccc3)cc2s1)OCc1ccccc1] | benzyl (2-(((5-((2,4-dioxothiazolidin-5-yl)methyl)-1,3,4-oxadiazol-2-yl)(4-fluoro-6-phenylbenzo[d]thiazol-2-yl)methyl)sulfonyl)ethyl)-carbamate | ¹H NMR (400 MHz, (CD$_3$)$_2$CO) δ 8.03 (s, 1H), 7.82 (d, J = 7.1 Hz, 1H), 7.76 (d, J = 8.1 Hz, 2H), 7.65 (d, J = 12.1 Hz, 1H), 7.53 (t, J = 7.6 Hz, 2H), 7.45 (d, J = 7.3 Hz, 1H), 7.37 (d, J = 2.3 Hz, 1H), 7.32 (br. s., 3H), 5.13-5.05 (m, 2H), 4.97 (s, 1H), 3.90-3.85 (m, 1H), 3.77 (d, J = 7.1 Hz, 1H), 3.73-3.61 (m, 4H) | 2.15 Q 682.1 | <10 |
| 93 | 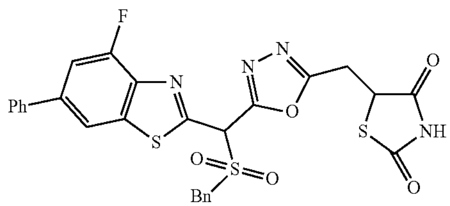 [SMILES: O=C1NC(=O)C(Cc2nnc(C(c3nc4c(F)cc(-c5ccccc5)cc4s3)S(=O)(=O)Cc3ccccc3)o2)S1] | 5-((5-((benzylsulfonyl)(4-fluoro-6-phenylbenzo[d]thiazol-2-yl)methyl)-1,3,4-oxadiazol-2-yl)methyl)thiazolidine-2,4-dione | ¹H NMR (400 MHz, CDCl$_3$) δ 7.68-7.58 (m, 2H), 7.57-7.38 (m, 7H), 7.36-7.32 (m, 2H), 7.22 (s, 1H), 4.79 (d, J = 2.8 Hz, 1H), 4.46 (s, 1H), 3.68 (d, J = 4.8 Hz, 2H), 3.53-3.47 (m, 2H) | 2.14 Q 595.1 | <10 |
| 94 | 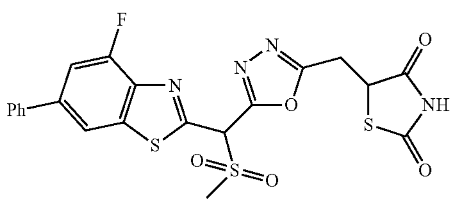 [SMILES: CS(=O)(=O)C(c1nnc(CC2SC(=O)NC2=O)o1)c1nc2c(F)cc(-c3ccccc3)cc2s1] | 5-((5-((4-fluoro-6-phenylbenzo-[d]thiazol-2-yl)(methyl-sulfonyl)methyl)-1,3,4-oxadiazol-2-yl)methyl)thiazol-idine-2,4-dione | ¹H NMR (400 MHz, CDCl$_3$) δ 7.68-7.58 (m, 2H), 7.57-7.38 (m, 7H), 7.36-7.32 (m, 2H), 7.22 (s, 1H), 4.79 (d, J = 2.8 Hz, 1H), 4.46 (s, 1H), 3.68 (d, J = 4.8 Hz, 2H), 3.53-3.47 (m, 2H) | 1.93 Q 519.0 | <10 |
| 95 | 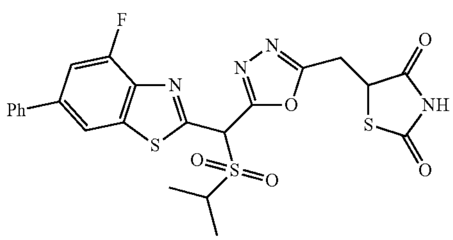 [SMILES: CC(C)S(=O)(=O)C(c1nnc(CC2SC(=O)NC2=O)o1)c1nc2c(F)cc(-c3ccccc3)cc2s1] | 5-((5-((4-fluoro-6-phenylbenzo-[d]thiazol-2-yl)(isopropyl-sulfonyl)methyl)-1,3,4-oxadiazol-2-yl)methyl)thiazol-idine-2,4-dione | ¹H NMR (500 MHz, (CD$_3$)$_2$CO) δ 8.18 (d, J = 1.7 Hz, 1H), 7.80-7.77 (m, 2H), 7.76-7.73 (m, 1H), 7.65-7.61 (m, 1H), 7.53-7.48 (m, 3H), 7.44-7.41 (m, 1H), 5.08-5.01 (m, 1H), 3.88-3.61 (m, 3H), 2.27 (d, J = 17.9 Hz, 6H) | 2.06 Q 547.1 | <10 |
| 96 | 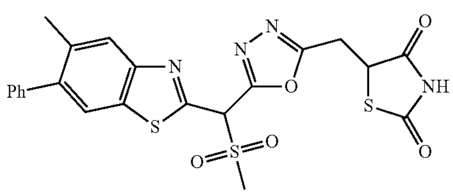 [SMILES: Cc1cc2nc(C(c3nnc(CC4SC(=O)NC4=O)o3)S(C)(=O)=O)sc2cc1-c1ccccc1] | 5-((5-((5-methyl-6-phenyl-benzo[d]thiazol-2-yl)(methyl-sulfonyl)methyl)-1,3,4-oxadiazol-2-yl)methyl)thiazol-idine-2,4-dione | ¹H NMR (500 MHz, CDCl$_3$) δ 7.48-7.43 (m, 3H), 7.41-7.39 (m, 2H), 7.34-7.30 (m, 2H), 4.82 (dd, J = 7.4, 4.7 Hz, 1H), 3.80 (dd, J = 16.8, 4.7 Hz, 1H), 3.68 (dd, J = 16.5, 7.2 Hz, 1H), 3.21 (s, 3H), 2.35 (s, 3H) | 2.01 Q 515.2 | <10 |
| 97 | 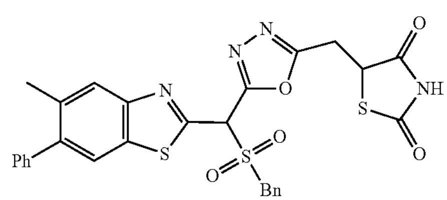 [SMILES: Cc1cc2nc(C(c3nnc(CC4SC(=O)NC4=O)o3)S(=O)(=O)Cc3ccccc3)sc2cc1-c1ccccc1] | 5-((5-((benzylsulfonyl)(5-methyl-6-phenylbenzo[d]-thiazol-2-yl)methyl)-1,3,4-oxadiazol-2-yl)methyl)thiazol-idine-2,4-dione | ¹H NMR (500 MHz, CD$_3$OD) δ 7.43-7.39 (m, 3H), 7.35 (d, J = 7.7 Hz, 1H), 7.30-7.26 (m, 5H), 7.25-7.19 (m, 4H), 4.93 (dd, J = 7.7, 5.2 Hz, 1H), 4.54 (s, 2H), 3.73-3.66 (m, 1H), 3.63-3.56 (m, 1H), 2.29 (s, 3H) | 2.15 Q 591.2 | <10 |

| Ex. No. | Structure | Name | $^1$H NMR | LC/MS RT (min) Method M+H | EL IC$_{50}$ (nM) | HL IC$_{50}$ (nM) |
|---|---|---|---|---|---|---|
| 98 | 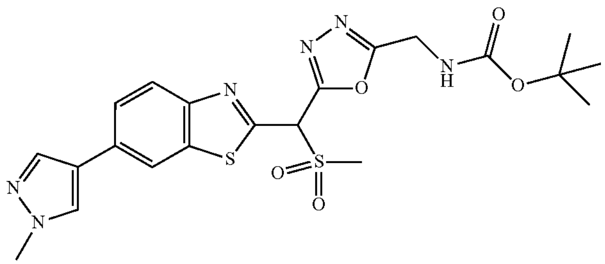 [SMILES: Cn1cc(-c2ccc3nc(C(c4nnc(CNC(=O)OC(C)(C)C)o4)S(C)(=O)=O)sc3c2)cn1] | tert-butyl ((5-((6-(1-methyl-1H-pyrazol-4-yl)-1,3-benzothiazol-2-yl)(methylsulfonyl)methyl)-1,3,4-oxadiazol-2-yl)methyl)carbamate | $^1$H NMR (400 MHz, CDCl$_3$) δ 12.83 (br. s., 1H), 7.76 (d, J = 0.7 Hz, 1H), 7.67 (d, J = 1.1 Hz, 1H), 7.63 (s, 1H), 7.53-7.47 (m, 1H), 7.46-7.40 (m, 1H), 5.19 (br. s., 1H), 4.62 (d, J = 5.9 Hz, 2H), 3.97 (s, 3H), 3.22 (s, 3H), 1.48 (s, 9H) | 1.73 B 505.1 | 168 | >25000 |
| 99 | 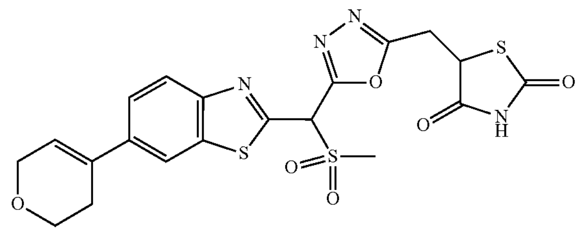 [SMILES: CS(=O)(=O)C(c1nnc(CC2SC(=O)NC2=O)o1)c1nc2ccc(C3=CCOCC3)cc2s1] | 5-((5-((6-(3,6-dihydro-2H-pyran-4-yl)-1,3-benzothiazol-2-yl)(methylsulfonyl)methyl)-1,3,4-oxadiazol-2-yl)methyl)-1,3-thiazolidine-2,4-dione | $^1$H NMR (400 MHz, CDCl$_3$ containing CD$_3$OD) δ 7.50 (s, 1H), 7.33 (s, 2H), 6.03 (s, 1H), 4.68 (dd, J = 8.3, 4.7 Hz, 1H), 4.27-4.15 (m, 2H), 3.81 (t, J = 5.5 Hz, 2H), 3.65 (dd, J = 16.7, 4.6 Hz, 1H), 3.44 (dd, J = 16.7, 8.4 Hz, 1H), 3.06 (s, 3H), 2.40 (d, J = 1.8 Hz, 2H) | 0.87 M 507.1 | <10 | 142 |
| 100 | 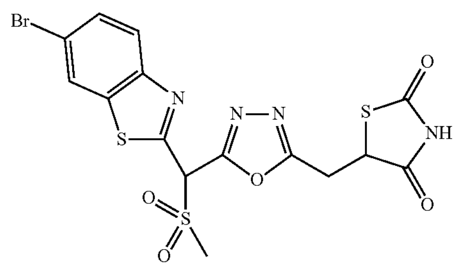 [SMILES: CS(=O)(=O)C(c1nnc(CC2SC(=O)NC2=O)o1)c1nc2ccc(Br)cc2s1] | 5-((5-((6-bromo-1,3-benzothiazol-2-yl)(methylsulfonyl)methyl)-1,3,4-oxadiazol-2-yl)methyl)-1,3-thiazolidine-2,4-dione | $^1$H NMR (500 MHz, DMSO-d$_6$) δ 8.13 (d, J = 1.9 Hz, 1H), 7.81-.72 (m, 1H), 7.60-7.53 (m, 1H), 5.08-5.00 (m, 1H), 3.80-3.65 (m, 2H), 3.26 (br. s., 3H) | 1.46 B 504.9 | 77 | 291 |

-continued

| Ex. No. | Structure | Name | $^1$H NMR | LC/MS RT (min) Method M + H | EL IC$_{50}$ (nM) | HL IC$_{50}$ (nM) |
|---|---|---|---|---|---|---|
| 101 | 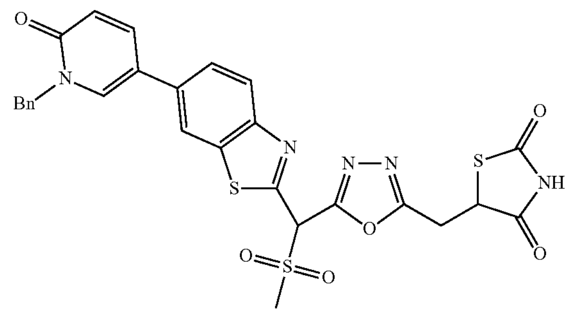 [SMILES: CS(=O)(=O)C(c1nnc(CC2SC(=O)NC2=O)o1)c1nc2ccc(-c3ccc(=O)n(Cc4ccccc4)c3)cc2s1] | 5-((5-((6-(1-benzyl-6-oxo-1,6-dihydro-3-pyridinyl)-1,3-benzothiazol-2-yl)(methylsulfonyl)methyl)-1,3,4-oxadiazol-2-yl)methyl)-1,3-thiazolidine-2,4-dione | $^1$H NMR (500 MHz, DMSO-d$_6$) δ 8.42-8.31 (m, 1H), 8.01 (d, J = 1.3 Hz, 1H), 7.95-7.75 (m, 2H), 7.63-7.51 (m, 1H), 7.35 (d, J = 14.5 Hz, 5H), 6.65-6.48 (m, 1H), 5.28-5.13 (m, 2H), 5.01 (dd, J = 7.5, 4.6 Hz, 1H), 3.92-3.52 (m, 2H), 3.43-3.18 (m, 4H) | 1.0 B 608.1 | <10 | 160 |
| 102 | 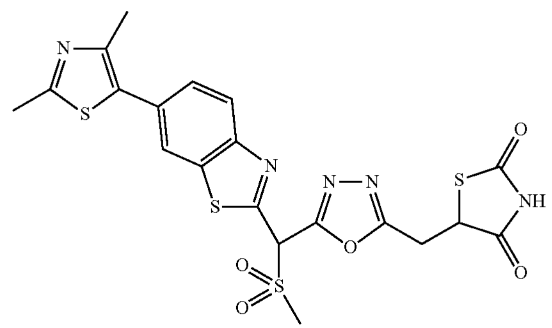 [SMILES: Cc1nc(C)c(-c2ccc3nc(C(c4nnc(CC5SC(=O)NC5=O)o4)S(C)(=O)=O)sc3c2)s1] | 5-((5-((6-(2,4-dimethyl-1,3-thiazol-5-yl)-1,3-benzothiazol-2-yl)(methylsulfonyl)methyl)-1,3,4-oxadiazol-2-yl)methyl)-1,3-thiazolidine-2,4-dione | $^1$H NMR (400 MHz, CDCl$_3$) δ 7.63 (s, 1H), 7.54-7.42 (m, 2H), 4.83 (m, 1H), 3.85-3.76 (m, 1H), 3.68 (m, 1H), 3.21 (s, 3H), 2.71 (s, 3H), 2.46 (s, 3H) | 1.64 B 536.1 | <10 | <10 |
| 103 | 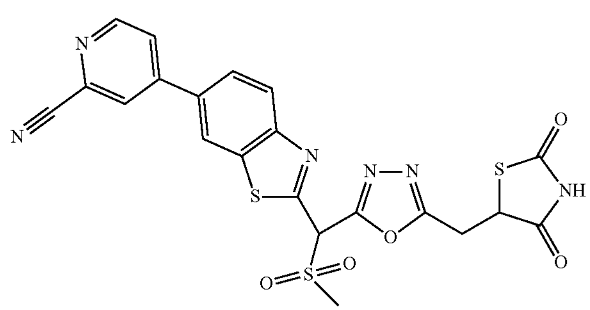 [SMILES: CS(=O)(=O)C(c1nnc(CC2SC(=O)NC2=O)o1)c1nc2ccc(-c3ccnc(C#N)c3)cc2s1] | 4-(2-(5-((2,4-dioxo-1,3-thiazolidin-5-yl)methyl)-1,3,4-oxadiazol-2-yl)(methylsulfonyl)methyl)-1,3-benzothiazol-6-yl)-2-pyridinecarbonitrile | $^1$H NMR (400 MHz, CDCl$_3$) δ 8.78 (dd, J = 5.1, 0.7 Hz, 1H), 7.98 (m, 1H), 7.93 (d, J = 1.3 Hz, 1H), 7.77 (m, 1H), 7.74-7.70 (m, 1H), 7.68-7.64 (m, 1H), 4.81 (m, 1H), 3.82 (dd, J = 16.7, 4.6 Hz, 1H), 3.64 (dd, J = 16.7, 7.9 Hz, 1H), 3.24 (s, 3H) | 1.66 B 527.1 | <10 | <10/36 |

| Ex. No. | Structure | Name | 1H NMR | LC/MS RT (min) Method M + H | EL IC50 (nM) | HL IC50 (nM) |
|---|---|---|---|---|---|---|
| 104 | 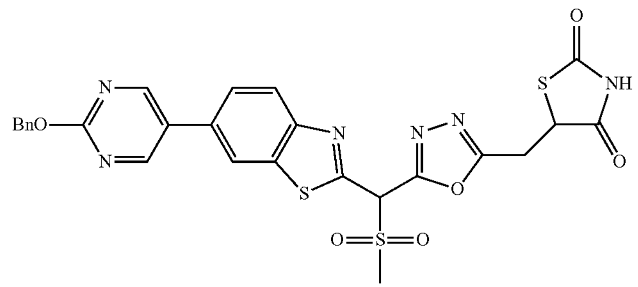 [SMILES: CS(=O)(=O)C(c1nnc(CC2SC(=O)NC2=O)o1)c1nc2ccc(-c3cnc(OCc4ccccc4)nc3)cc2s1] | 5-((5-((6-(2-(benzyloxy)-5-pyrimidinyl)-1,3-benzothiazol-2-yl)(methylsulfonyl)methyl)-1,3,4-oxadiazol-2-yl)methyl)-1,3-thiazolidine-2,4-dione | 1H NMR (400 MHz, DMSO-d6) δ 8.97 (s, 2H), 8.27-8.18 (m, 1H), 7.58-7.28 (m, 7H), 5.57-5.42 (m, 2H), 5.04 (dd, J = 7.5, 4.6 Hz, 1H), 3.83-3.55 (m, 2H), 3.27 (s, 3H), 3.16-3.10 (m, 2H) | 2.0 B 609.2 | <10 | <10/11 |
| 105 | 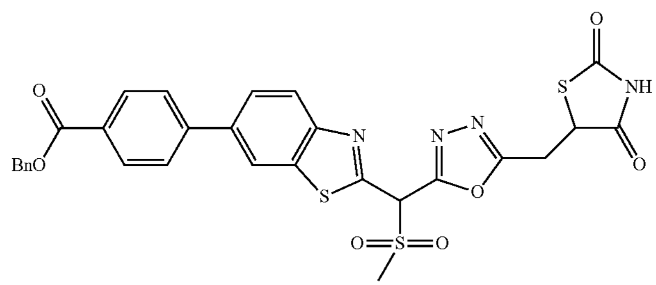 [SMILES: CS(=O)(=O)C(c1nnc(CC2SC(=O)NC2=O)o1)c1nc2ccc(-c3ccc(C(=O)OCc4ccccc4)cc3)cc2s1] | benzyl 4-(2-((5-((2,4-dioxo-1,3-thiazolidin-5-yl)methyl)-1,3,4-oxadiazol-2-yl)(methylsulfonyl)methyl)-1,3-benzothiazol-6-yl )benzoate | 1H NMR (400 MHz, DMSO-d6) δ 8.36-8.20 (m, 2H), 8.09 (d, J = 8.4 Hz, 2H), 7.88 (d, J = 8.4 Hz, 2H), 7.55-7.48 (m, 3H), 7.47-7.35 (m, 3H), 5.45-5.34 (m, 2H), 5.09-4.99 (m, 1H), 3.85-3.56 (m, 2H), 3.46-3.18 (m, 3H), 1.81-1.73 (m, 1H) | 2.2 M 635.2 | <10 | <10 |
| 106 | 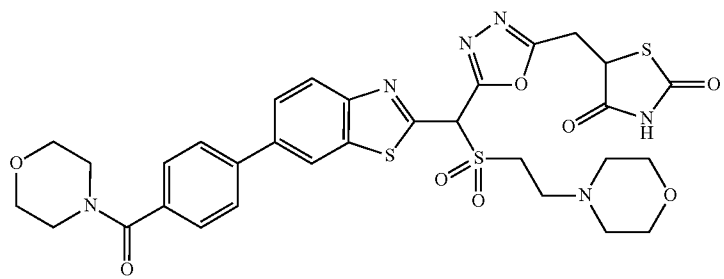 [SMILES: O=C1NC(=O)C(Cc2nnc(C(c3nc4ccc(-c5ccc(C(=O)N6CCOCC6)cc5)cc4s3)S(=O)(=O)CCN3CCOCC3)o2)S1] | 5-((5-((6-(4-(4-morpholinylcarbonyl)phenyl)-1,3-benzothiazol-2-yl)(2-(4-morpholinyl)ethyl)sulfonyl)methyl)-1,3,4-oxadiazol-2-yl)methyl)-1,3-thiazolidine-2,4-dione | 1H NMR (400 MHz, CDCl3 containing CD3OD) δ 7.88 (br. s., 1H), 7.75-7.61 (m, 4H), 7.53 (d, J = 8.4 Hz, 2H), 4.85-4.77 (m, 1H), 3.87-3.47 (m, 20H), 2.93-2.84 (m, 2H), 2.47 (br. s., 3H) | 1.49 B 713.2 | <10 | 1340 |

| Ex. No. | Structure | Name | ¹H NMR | LC/MS RT (min) Method M + H | EL IC₅₀ (nM) | HL IC₅₀ (nM) |
|---|---|---|---|---|---|---|
| 107 | 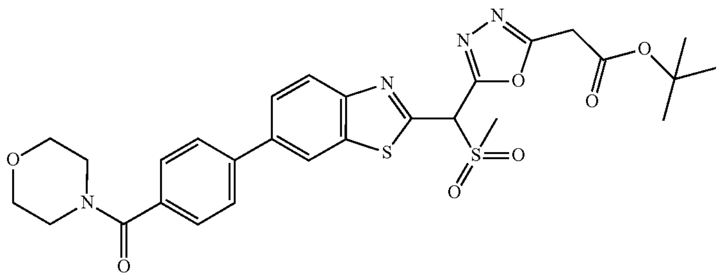 [SMILES: CC(C)(C)OC(=O)Cc1nnc(C(c2nc3ccc(-c4ccc(C(=O)N5CCOCC5)cc4)cc3s2)S(C)(=O)=O)o1] | tert-butyl (5-((methylsulfonyl)(6-(4-(4-morpholinylcarbonyl)phenyl)-1,3-benzothiazol-2-yl)methyl)-1,3,4-oxadiazol-2-yl)acetate | ¹H NMR (400 MHz, CDCl₃) δ 7.81 (d, J = 1.3 Hz, 1H), 7.69-7.59 (m, 3H), 7.57-7.48 (m, 3H), 3.97 (s, 2H), 3.74 (br. s., 8H), 3.25 (s, 3H), 1.55 (s, 9H), 1.51-1.48 (m, 3H) | 1.99 B 599.3 | 28 | 13 |
| 108 | 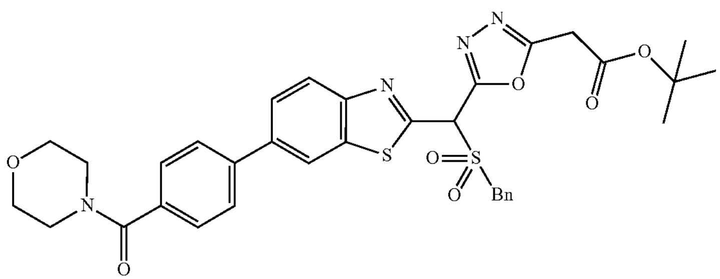 [SMILES: CC(C)(C)OC(=O)Cc1nnc(C(c2nc3ccc(-c4ccc(C(=O)N5CCOCC5)cc4)cc3s2)S(=O)(=O)Cc2ccccc2)o1] | tert-butyl (5-((bnzylsulfonyl)(6-(4-(4-morpholinylcarbonyl)phenyl)-1,3-benzothiazol-2-yl)methyl)-1,3,4-oxadiazol-2-yl)acetate | ¹H NMR (400 MHz, CDCl₃) δ 7.81 (d, J = 1.3 Hz, 1H), 7.69-7.59 (m, 3H), 7.57-7.48 (m, 3H), 3.97 (s, 2H), 3.74 (br. s., 8H), 3.25 (s, 3H), 1.55 (s, 9H), 1.51-1.48 (m, 3H) | 2.08 B 675.2 | 24 | 14 |
| 109 | 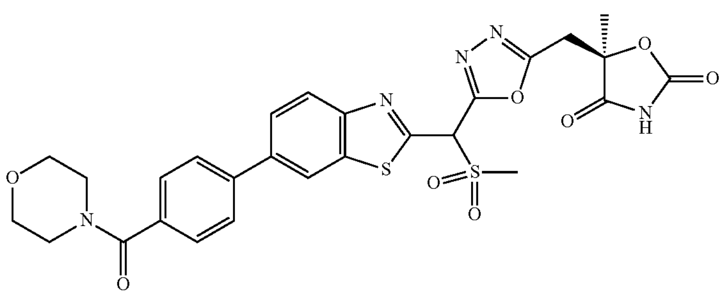 [SMILES: C[C@]1(Cc2nnc(C(c3nc4ccc(-c5ccc(C(=O)N6CCOCC6)cc5)cc4s3)S(C)(=O)=O)o2)OC(=O)NC1=O] | (5R)-5-methyl-5-((5-((methylsulfonyl)(6-(4-(4-morpholinylcarbonyl)phenyl)-1,3-benzothiazol-2-yl)methyl)-1,3,4-oxadiazol-2-yl)methyl)-1,3-oxazolidine-2,4-dione | ¹H NMR (400 MHz, DMSO-d₆ containing D₂O) δ 8.56 (br. s, 1H), 8.24 (s, 1H), 7.94 (dd, J = 8.8, 1.8 Hz, 1H), 7.78 (m, 3H), 7.52 (d, J = 8.4 Hz, 2H), 3.62 (m, 10H), 3.26 (br. s, 3H), 1.67 (s, 3H) | 0.88 M 612.3 | <10 | 764 |

| Ex. No. | Structure | Name | ¹H NMR | LC/MS RT (min) Method M + H | EL IC₅₀ (nM) | HL IC₅₀ (nM) |
|---|---|---|---|---|---|---|
| 110 | 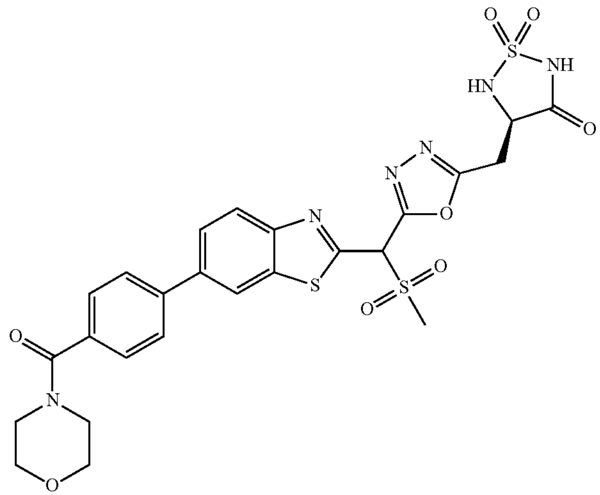 [SMILES: CS(=O)(=O)C(c1nnc(C[C@H]2NS(=O)(=O)NC2=O)o1)c1nc2ccc(-c3ccc(C(=O)N4CCOCC4)cc3)cc2s1] | (4R)-4-((5-((methylsulfonyl) (6-(4-(4-morpholinylcarbonyl) phenyl 3-benzothiazol-2-yl)methyl)-1,3,4-oxadiazol-2-yl)methyl)-1,2,5-thiadiazolidin-3-one 1,1-dioxide | ¹H NMR (400 MHz, CD₃OD) δ 8.61 (s, 2H), 7.92 (s, 1H), 7.81-7.67 (m, 1H), 7.65-7.57 (m, 1H), 4.94 (dd, J = 7.5, 4.8 Hz, 1H), 3.85-3.76 (m, 1H), 3.72-3.63 (m, 2H), 3.50 (s, 1H), 3.26 (br. s., 3H), 3.18-3.11 (m, 1H) | 1.5 M 633.1 | 19 | 3244 |
| 111 | 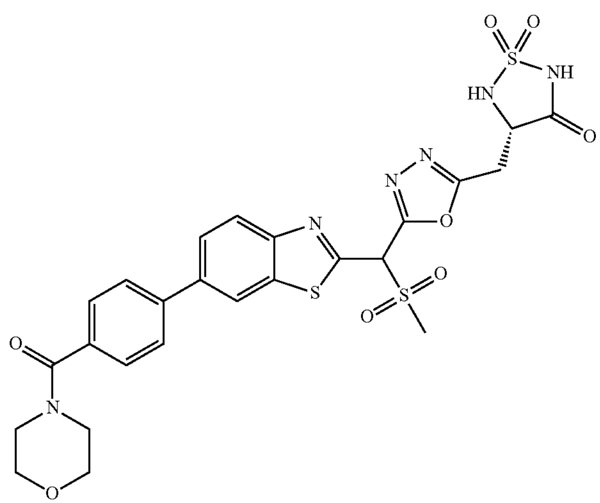 [SMILES: CS(=O)(=O)C(c1nnc(C[C@@H]2NS(=O)(=O)NC2=O)o1)c1nc2ccc(-c3ccc(C(=O)N4CCOCC4)cc3)cc2s1] | (4S)-4-((5-((methylsulfonyl) (6-(4-(4-morpholinylcarbonyl) phenyl)-1,3-benzothiazol-2-yl)methyl)-1,3,4-oxadiazol-2-yl)methyl)-1,2,5-thiadiazolidin-3-one 1,1-dioxide | ¹H NMR (400 MHz, CD₃OD) δ 7.83 (s, 1H), 7.68-7.56 (m, 4H), 7.48 (d, J = 8.4 Hz, 2H), 4.62 (t, J = 5.7 Hz, 1H), 3.89-3.59 (m, 8H), 3.55-3.37 (m, 2H), 3.25 (s, 3H) | 1.6 M 633.2 | <10 | 629 |

| Ex. No. | Structure | Name | ¹H NMR | LC/MS RT (min) Method M+H | EL IC₅₀ (nM) | HL IC₅₀ (nM) |
|---|---|---|---|---|---|---|
| 112 | 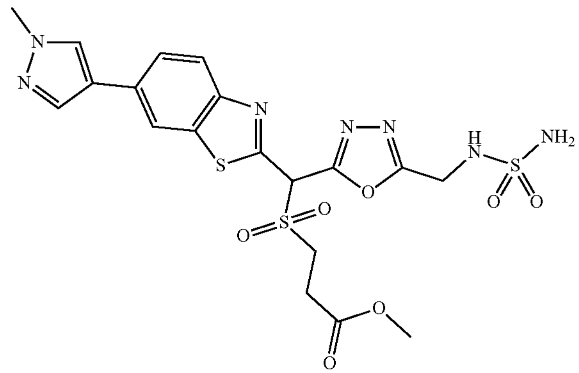 [SMILES: COC(=O)CCS(=O)(=O)C(c1nnc(CNS(N)(=O)=O)o1)c1nc2ccc(-c3cnn(C)c3)cc2s1] | methyl 3-(((6-(1-methyl-1H-pyrazol-4-yl)-1,3-benzothiazol-2-yl)(5-((sulfamoylamino)methyl)-1,3,4-oxadiazol-2-yl)methyl)sulfonyl)propanoate | ¹H NMR (400 MHz, CD₃OD) δ 7.95 (s, 1H), 7.89 (s, 1H), 7.83 (s, 1H), 7.62 (d, J = 0.9 Hz, 2H), 4.53 (s, 2H), 3.94 (s, 3H), 3.80-3.66 (m, 2H), 3.57 (s, 2H), 2.84 (q, J = 6.7 Hz, 2H) | 1.46 B 556.1 | <10 | <10 |
| 113 | 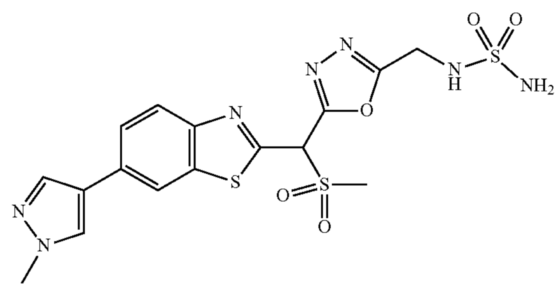 [SMILES: Cn1cc(-c2ccc3nc(C(c4nnc(CNS(N)(=O)=O)o4)S(C)(=O)=O)sc3c2)cn1] | N-((5-((6-(1-methyl-1H-pyrazol-4-yl)-1,3-benzothiazol-2-yl)(methylsulfonyl)methyl)-1,3,4-oxadiazol-2-yl)methyl)sulfamide | ¹H NMR (400 MHz, DMSO-d₆) δ 8.47-7.32 (m, 6H), 6.79 (s, 2H), 4.57-4.24 (d, J = 6.16, 2H), 3.89 (s, 3H), 3.41 (s, 3H) | 0.85 M 484.1 | <10 | 220 |
| 114 | 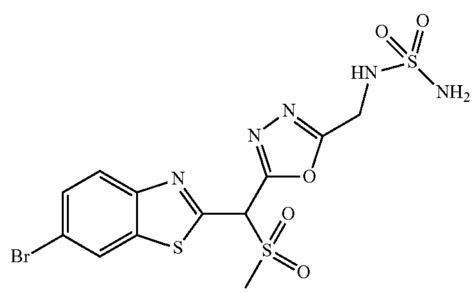 [SMILES: CS(=O)(=O)C(c1nnc(CNS(N)(=O)=O)o1)c1nc2ccc(Br)cc2s1] | N-((5-((6-bromo-1,3-benzothiazol-2-yl)(methylsulfonyl)methyl)-1,3,4-oxadiazol-2-yl)methyl)sulfamide | ¹H NMR (400 MHz, DMSO-d₆) δ 8.34 (s, 1H), 7.87 (d, J = 8.8 Hz, 1H), 7.56 (m, 1H), 4.22 (d, J = 6.2 Hz, 2H), 3.20 (s, 3H) | 1.61 B 483.8 | <10 | 220 |

| Ex. No. | Structure | Name | $^1$H NMR | LC/MS RT (min) Method M + H | EL IC$_{50}$ (nM) | HL IC$_{50}$ (nM) |
|---|---|---|---|---|---|---|
| 115 | 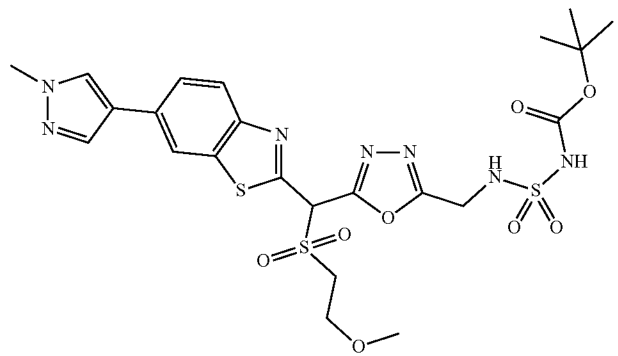 [SMILES: COCCS(=O)(=O)C(c1nnc(CNS(=O)(=O)NC(=O)OC(C)(C)C)o1)c1nc2ccc(-c3cnn(C)c3)cc2s1] | tert-butyl (((5-(((2-methoxyethyl)sulfonyl)(6-(1-methyl-1H-pyrazol-4-yl)-1,3-benzothiazol-2-yl)methyl)-1,3,4-oxadiazol-2-yl)methyl)sulfamoyl)carbamate | $^1$H NMR (400 MHz, CD$_3$OD) δ 7.82-7.73 (m, 3H), 7.27 (dd, J = 8.5, 1.7 Hz, 1H), 7.01 (d, J = 8.4 Hz, 1H), 4.59-4.51 (m, 2H), 4.50-4.42 (m, 2H), 3.88-3.81 (m, 3H), 3.72 (t, J = 5.6 Hz, 2H), 3.27 (s, 3H), 3.25-3.20 (m, 3H), 1.44 (s, 9H) | 0.90 B 628.2 | 117 | >25000 |
| 116 | 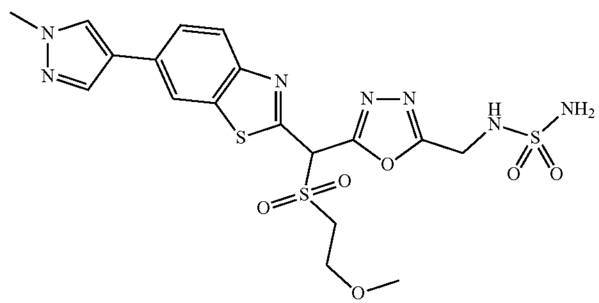 [SMILES: COCCS(=O)(=O)C(c1nnc(CNS(N)(=O)=O)o1)c1nc2ccc(-c3cnn(C)c3)cc2s1] | N-((5-(((2-methoxyethyl)sulfonyl)(6-(1-methyl-1H-pyrazol-4-yl)-1,3-benzothiazol-2-yl)methyl)-1,3,4-oxadiazol-2-yl)methyl)sulfamide | $^1$H NMR (400 MHz, DMSO-d$_6$) δ 8.14 (s, 1H), 7.88 (s, 1H), 7.51 (t, J = 5.6 Hz, 1H), 6.86- 6.69 (m,2H), 4.50-4.23 (m, 2H), 3.96-3.83 (m, 4H), 3.83-3.63 (m, 4H), 3.28 (s, 1H), 3.11 (s, 3H) | 1.5 M 528.0 | <10 | 143 |
| 117 | 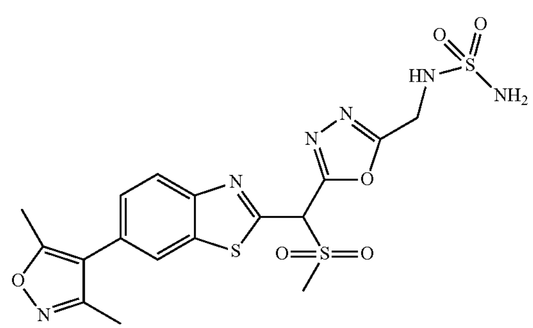 [SMILES: Cc1noc(C)c1-c1ccc2nc(C(c3nnc(CNS(N)(=O)=O)o3)S(C)(=O)=O)sc2c1] | N-[(5-{[6-(3,5-dimethyl-1,2-oxazol-4-yl)-1,3-benzothiazol-2-yl][(methylsulfonyl)methyl]}-1,3,4-oxadiazol-2-yl)methyl] sulfuric diamide | $^1$H NMR (400 MHz, CDCl$_3$) δ 7.56 (d, J = 7.9 Hz, 1H), 7.48 (s, 1H), 7.28 (m, 1H), 4.54 (s, 2H), 3.23 (s, 3H), 2.39 (s, 3H), 2.24 (s, 3H) | 1.46 B 499.0 | 24 | 230 |

| Ex. No. | Structure | Name | $^1$H NMR | LC/MS RT (min) Method M + H | EL IC$_{50}$ (nM) | HL IC$_{50}$ (nM) |
|---|---|---|---|---|---|---|
| 118 | 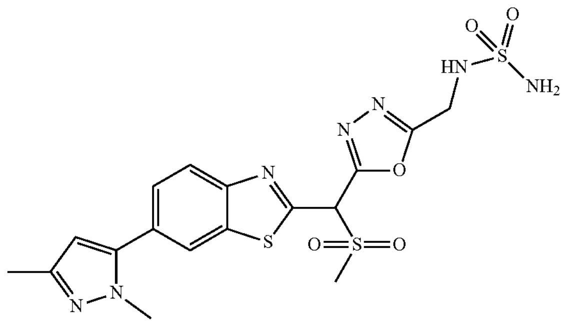 [SMILES: Cc1cc(-c2ccc3nc(C(c4nnc(CNS(N)(=O)=O)o4)S(C)(=O)=O)sc3c2)n(C)n1] | N-[(5-{[6-(1,3-dimethyl-1H-pyrazol-5-yl)-1,3-benzothiazol-2-yl](methylsulfonyl)methyl}-1,3,4-oxadiazol-2-yl)methyl] sulfuric diamide | $^1$H NMR (400 MHz, CDCl$_3$) δ 7.60 (s, 1H), 7.55 (d, J = 8.4 Hz, 1H), 7.42-7.37 (m, 1H), 6.09 (s, 1H), 4.50 (s, 2H), 3.76 (s, 3H), 3.21 (s, 3H), 2.24 (s, 3H) | 1.41 B 498.0 | 18 | 396 |
| 119 | 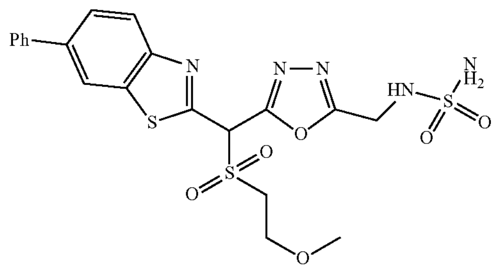 [SMILES: COCCS(=O)(=O)C(c1nnc(CNS(N)(=O)=O)o1)c1nc2ccc(-c3ccccc3)cc2s1] | N-[(5-{[(2-methoxyethyl)sulfonyl](6-phenyl-1,3-benzothiazol-2-yl)methyl}-1,3,4-oxadiazol-2-yl)methylsulfuric diamide | 8.21 (s, 1H), 7.71 (d, J = 7.4 Hz, 2H), 7.56-7.46 (m, 3H), 6.78 (s, 2H), 4.47-4.35 (m, 2H), 3.93-3.79 (m, 1H), 3.70 (br. s.,3H), 3.49-3.25 (m, 3H), 3.12 (s, 2H) | 1.5 B 524.1 | <10 | <10 |
| 120 | 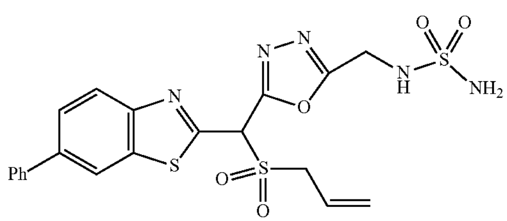 [SMILES: C=CCS(=O)(=O)C(c1nnc(CNS(N)(=O)=O)o1)c1nc2ccc(-c3ccccc3)cc2s1] | N-((5-((allylsulfonyl)(6-phenyl-1,3-benzothiazol-2-yl)methyl)-1,3,4-oxadiazol-2-yl)methyl)sulfamide | $^1$H NMR (400 MHz, CDCl$_3$ containing CD$_3$OD) δ 7.84 (s, 1H), 7.70-7.65 (m, 1H), 7.64-7.56 (m, 3H), 7.48 (t, J = 7.5 Hz, 2H), 7.43-7.39 (m, 1H), 6.02-5.77 (m, 1H), 5.46-5.24 (m, 2H), 4.57 (s, 2H), 4.08 (d, J = 7.3 Hz, 2H) | 1.89 B 506.0 | <10 | <10 |

| Ex. No. | Structure | Name | ¹H NMR | LC/MS RT (min) Method M + H | EL IC₅₀ (nM) | HL IC₅₀ (nM) |
|---|---|---|---|---|---|---|
| 121 | 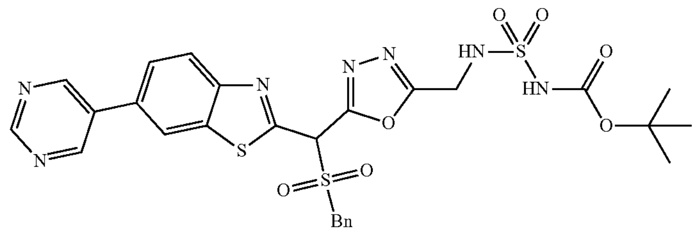 [SMILES: CC(C)(C)OC(=O)NS(=O)(=O)NCc1nnc(C(c2nc3ccc(-c4cncnc4)cc3s2)S(=O)(=O)Cc2ccccc2)o1] | tert-butyl (((5-((benzylsulfonyl)6-(5-pyrimidinyl)-1,3-benzothiazol-2-yl)methyl)-1,3,4-oxadiazol-2-yl)methyl)sulfamoyl)carbamate | ¹H NMR (400 MHz, DMSO-d₆) δ 9.23-9.18 (m, 1H), 9.15 (s, 2H), 8.24 (br. s., 1H), 7.91-7.75 (m, 1H), 7.37-7.17 (m, 5H), 4.77 (br. s., 2H), 4.51 (d, J = 4.8 Hz, 2H), 3.48 (br. s., 2H), 1.43 (s, 9H) | 1.9 M 658.0 | 147 | 6553 |
| 122 | 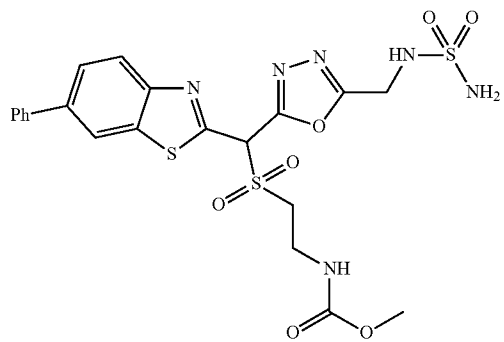 [SMILES: COC(=O)NCCS(=O)(=O)C(c1nnc(CNS(N)(=O)=O)o1)c1nc2ccc(-c3ccccc3)cc2s1] | methyl (2-(((6-phenyl-1,3-benzothiazol-2-yl)(5-((sulfamoylamino)methyl)-1,3,4-oxadiazol-2-yl)methyl)sulfonyl)ethyl)carbamate | ¹H NMR (400 MHz, DMSO-d₆) δ 8.29-8.09 (m, 1H), 7.71 (d, J = 7.4 Hz, 2H), 7.55-7.45 (m, 3H), 6.78 (br. s., 2H), 4.46-4.30 (m, 2H), 3.59 (br. s., 2H), 3.49-3.37 (m, 5H), 2.55 (s, 2H) | 1.7 B 567.1 | <10 | <10 |
| 123 | 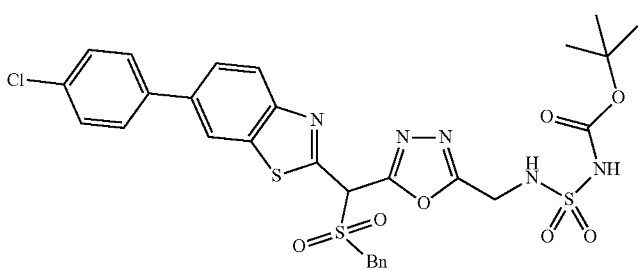 [SMILES: CC(C)(C)OC(=O)NS(=O)(=O)NCc1nnc(C(c2nc3ccc(-c4ccc(Cl)cc4)cc3s2)S(=O)(=O)Cc2ccccc2)o1] | tert-butyl (((5-((benzylsulfonyl)(6-(4-chlorophenyl)-1,3-benzothiazol-2-yl)methyl)-1,3,4-oxadiazol-2-yl)methyl)sulfamoyl)carbamate | ¹H NMR (500 MHz, DMSO-d₆) δ 8.00-7.79 (m, 2H), 7.74-7.65 (m, 3H), 7.57-7.47 (m, 2H), 7.36-7.19 (m, 5H), 4.73 (br. s., 2H), 4.55-4.36 (m, 2H), 1.47-1.34 (m, 7H). | 2.24 N 690.0 | <10 | |

| Ex. No. | Structure | Name | ¹H NMR | LC/MS RT (min) Method M + H | EL IC₅₀ (nM) | HL IC₅₀ (nM) |
|---|---|---|---|---|---|---|
| 124 | 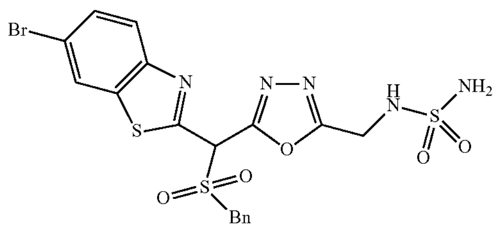 [SMILES: NS(=O)(=O)NCc1nnc(C(c2nc3ccc(Br)cc3s2)S(=O)(=O)Cc2ccccc2)o1] | N-((5-((benzylsulfonyl)(6-bromo-1,3-benzothiazol-2-yl)methyl)-1,3,4-oxadiazol-2-yl)methyl)sulfamide | ¹H NMR (400 MHz, DMSO-d₆) δ 8.01 (s, 1H), 7.73 (d, J = 8.8 Hz, 1H), 7.66-7.49 (m, 2H), 7.30-7.21 (m, 4H), 6.84 (s, 2H), 4.70 (s, 2H), 4.40 (d, J = 5.5 Hz, 2H) | 1.83 B 559.9 | 48 | 37 |
| 125 | 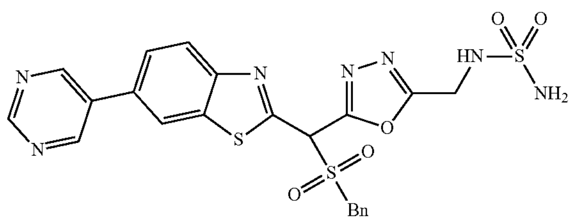 [SMILES: NS(=O)(=O)NCc1nnc(C(c2nc3ccc(-c4cncnc4)cc3s2)S(=O)(=O)Cc2ccccc2)o1] | N-((5-((benzylsulfonyl)(6-(5-pyrimidinyl)-1,3-benzothiazol-2-yl)methyl)-1,3,4-oxadiazol-2-yl)methyl)sulfamide | ¹H NMR (500 MHz, DMSO-d₆) δ 9.22-9.05 (m, 2H), 7.83 (d, J = 8.5 Hz, 1H), 7.35-7.21 (m, 5H), 6.83 (s, 2H), 4.86-4.66 (m, 3H), 4.44 (d, J = 5.5 Hz, 2H), 3.47-3.10 (m, 2H) | 1.3 B 558.1 | <10 | 103 |
| 126 | 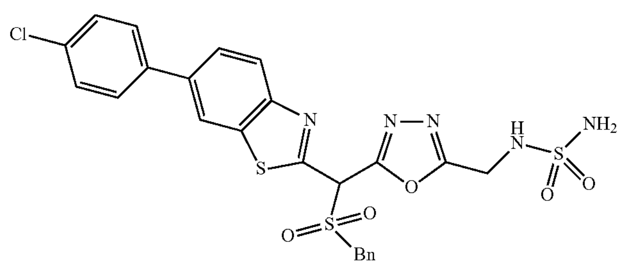 [SMILES: NS(=O)(=O)NCc1nnc(C(c2nc3ccc(-c4ccc(Cl)cc4)cc3s2)S(=O)(=O)Cc2ccccc2)o1] | N-((5-((benzylsulfonyl)(6-(4-chlorophenyl)-1,3-benzothiazol-2-yl)methyl)-1,3,4-oxadiazol-2-yl)methyl)sulfamide | ¹H NMR (500 MHz, DMSO-d₆) δ 8.07 (br. s., 1H), 7.70 (dd, J = 8.5, 5.5 Hz, 3H), 7.35-7.17 (m, 6H), 6.91-6.67 (m, 2H), 4.73 (br. s., 2H), 4.43 (d, J = 4.1 Hz, 2H), 3.91 (s, 1H) | 1.3 B 558.1 | <10 | <10 |
| 128 | 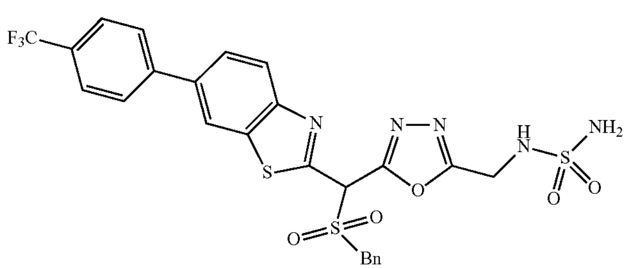 [SMILES: NS(=O)(=O)NCc1nnc(C(c2nc3ccc(-c4ccc(C(F)(F)F)cc4)cc3s2)S(=O)(=O)Cc2ccccc2)o1] | N-((5-((benzylsulfonyl)(6-(4-(trifluoromethyl)phenyl)-1,3-benzothiazol-2-yl)methyl)-1,3,4-oxadiazol-2-yl)methyl)sulfamide | ¹H NMR (500 MHz, DMSO-d₆) δ 7.98-7.88 (m, 3H), 7.85-7.81 (m, 2H), 7.57 (d, J = 6.3 Hz, 1H), 7.43-7.22 (m, 5H), 6.85-6.79 (m, 2H), 4.73 (br. s., 2H), 4.44 (br. s., 2H). | 2.15 B 624.0 | <10 | <10 |

| Ex. No. | Structure | Name | ¹H NMR | LC/MS RT (min) Method M + H | EL IC₅₀ (nM) | HL IC₅₀ (nM) |
|---|---|---|---|---|---|---|
| 129 | 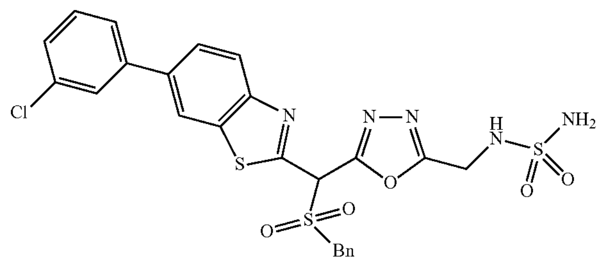 [SMILES: NS(=O)(=O)NCc1nnc(C(c2nc3ccc(-c4cccc(Cl)c4)cc3s2)S(=O)(=O)Cc2ccccc2)o1] | N-((5-((benzylsulfonyl)(6-(3-chlorophenyl)-1,3-benzothiazol-2-yl)methyl)-1,3,4-oxadiazol-2-yl)methyl)sulfamide | ¹H NMR (400 MHz, DMSO-d₆) δ 7.74-7.68 (m, 2H), 7.66-7.39 (m, 5H), 7.35-7.20 (m, 4H), 6.83 (br. s., 2H), 4.73 (br. s., 2H), 4.43 (br. s., 2H) | 2.15 B 589.9 | <10 | <10 |
| 130 | 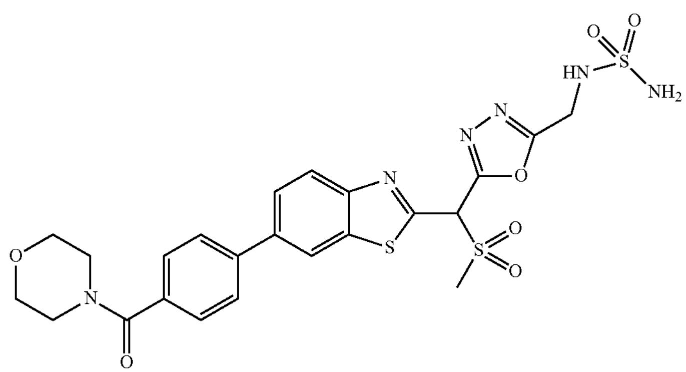 [SMILES: CS(=O)(=O)C(c1nnc(CNS(N)(=O)=O)o1)c1nc2ccc(-c3ccc(C(=O)N4CCOCC4)cc3)cc2s1] | N-((5-((methylsulfonyl)(6-(4-(4-morpholinylcarbonyl)phenyl)-1,3-benzothiazol-2-yl)methyl)-1,3,4-oxadiazol-2-yl)methyl)sulfamide | ¹H NMR (400 MHz, CDCl₃) δ 7.79-7.64 (m, 1H), 7.53-7.38 (m, 1H), 7.19 (d, J = 7.3 Hz, 2H), 7.16-7.05 (m, 3H), 4.60 (m, 2H), 3.87 (m, 4H), 3.60 (m, 2H), 3.37-3.29 (m, 2H), 2.30 (s, 3H) | 1.52 B 593.1 | <10 | 22 |
| 131 | 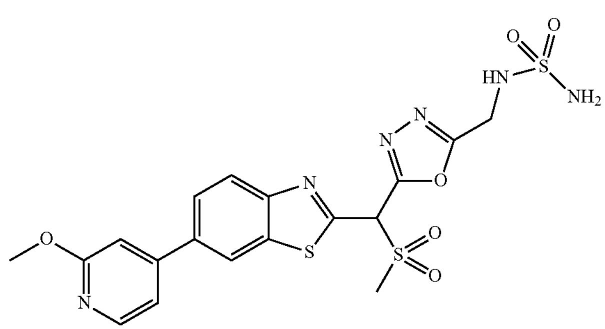 [SMILES: COc1cc(-c2ccc3nc(C(c4nnc(CNS(N)(=O)=O)o4)S(C)(=O)=O)sc3c2)ccn1] | N-((5-((6-(2-methoxy-4-pyridinyl)-1,3-benzothiazol-2-yl)(methylsulfonyl)methyl)-1,3,4-oxadiazol-2-yl)methyl)sulfamide | ¹H NMR (400 MHz, CDCl₃) δ 8.19 (d, J = 5.5 Hz, 1H), 7.84 (s, 1H), 7.68-7.63 (m, 1H), 7.60-7.54 (m, 1H), 7.09 (m, 1H), 6.93 (d, J = 0.9 Hz, 1H), 4.55 (s, 2H), 3.96 (s, 3H), 3.23 (s, 3H) | 1.46 B 511.0 | <10 | 102 |

| Ex. No. | Structure | Name | ¹H NMR | LC/MS RT (min) Method M + H | EL IC₅₀ (nM) | HL IC₅₀ (nM) |
|---|---|---|---|---|---|---|
| 132 | 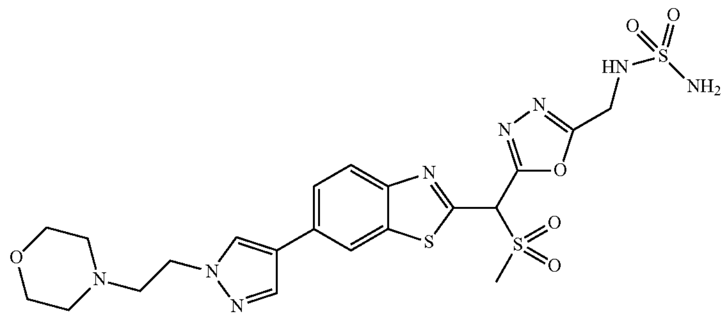 [SMILES: CS(=O)(=O)C(c1nnc(CNS(N)(=O)=O)o1)c1nc2ccc(-c3cnn(CCN4CCOCC4)c3)cc2s1] | N-((5-((methylsulfonyl)(6-(1-(2-(4-morpholinyl)ethyl)-1H-pyrazol-4-yl)-1,3-benzothiazol-2-yl)methyl)-1,3,4-oxadiazol-2-yl)methyl)sulfamide | ¹H NMR (400 MHz, CDCl₃) δ 7.81 (s, 1H), 7.63 (m, 2H), 7.50 (m, 2H), 4.06-3.91 (m, 4H), 3.72 (m, 10H), 3.39 (s, 3H) | 1.18 B 583.1 | 32 | 22270 |
| 133 | 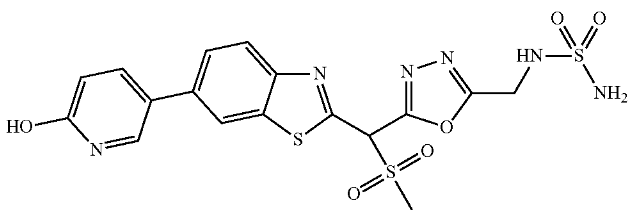 [SMILES: CS(=O)(=O)C(c1nnc(CNS(N)(=O)=O)o1)c1nc2ccc(-c3ccc(O)nc3)cc2s1] | N-((5-((methylsulfonyl)(6-(6-oxo-1,6-dihydro-3-pyridinyl)-1,3-benzothiazol-2-yl)methyl)-1,3,4-oxadiazol-2-yl)methyl)sulfamide | ¹H NMR (400 MHz, DMSO-d₆) δ 8.36-8.20 (m, 2H), 8.09 (d, J = 8.4 Hz, 2H), 7.88 (d, J = 8.4 Hz, 2H), 7.55-7.48 (m, 3H), 7.47-7.35 (m, 3H), 5.45-5.34 (m, 2H), 5.09-4.99 (m, 1H), 3.85-3.56 (m, 2H), 3.46-3.18 (m,3H), 1.81-1.73 (m, 1H) | 1.3 M 497.0 | 16 | 467 |
| 134 | 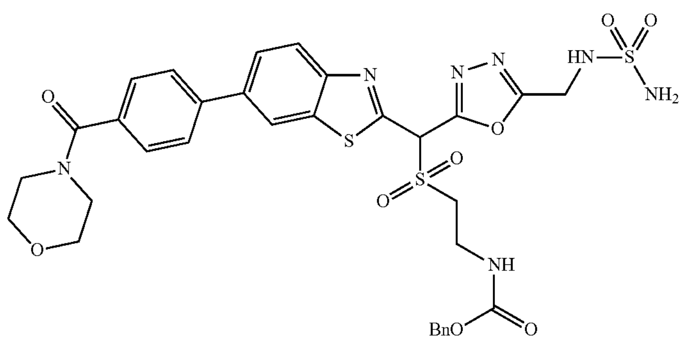 [SMILES: NS(=O)(=O)NCc1nnc(C(c2nc3ccc(-c4ccc(C(=O)N5CCOCC5)cc4)cc3s2)S(=O)(=O)CCNC(=O)OCc2ccccc2)o1] | benzyl{2-[({6-[4-(4-morpholinylcarbonyl)phenyl]-1,3-benzothiazol-2-yl}{5-[(sulfamoylamino)methyl]-1,3,4-oxadiazol-2-yl}methyl)sulfonyl]ethyl}carbamate | ¹H NMR (500 MHz, DMSO-d₆) δ 8.24 (br. s., 1H), 7.77 (d, J = 8.3 Hz, 2H), 7.53 (d, J = 8.3 Hz, 2H), 7.38-7.19 (m, 5H), 6.85-6.64 (m, 2H), 4.90 (s, 2H), 4.48-4.26 (m, 2H), 3.62 (br. s., 12H), 3.44 (br. s., 3H) | 1.4 B 756.1 | 20 | 307 |

| Ex. No. | Structure | Name | ¹H NMR | LC/MS RT (min) Method M + H | EL IC₅₀ (nM) | HL IC₅₀ (nM) |
|---|---|---|---|---|---|---|
| 135 | 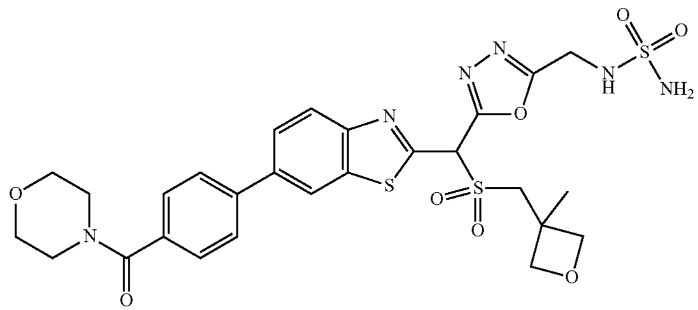 [SMILES: CC1(CS(=O)(=O)C(c2nnc(CNS(N)(=O)=O)o2)c2nc3ccc(-c4ccc(C(=O)N5CCOCC5)cc4)cc3s2)COC1] | N-((5-((((3-methyl-3-oxetanyl)methyl)sulfonyl)(6-(4-(4-morpholinylcarbonyl)phenyl)-1,3-benzothiazol-2-yl)methyl)-1,3,4-oxadiazol-2-yl)methyl)sulfamide | ¹H NMR (400 MHz, CDCl₃ containing CD₃OD) δ 7.89 (s, 1H), 7.73-7.67 (m, 4H), 7.54 (d, J = 8.4 Hz, 2H), 4.85 (d, J = 6.4 Hz, 2H), 4.58 (s, 2H), 4.48 (d, J = 6.4 Hz, 2H), 3.88-3.79 (m, 4H), 3.76-3.51 (m, 6H), 1.72 (s, 3H) | 1.00 M 663.1 | <10 | 91 |
| 136 | 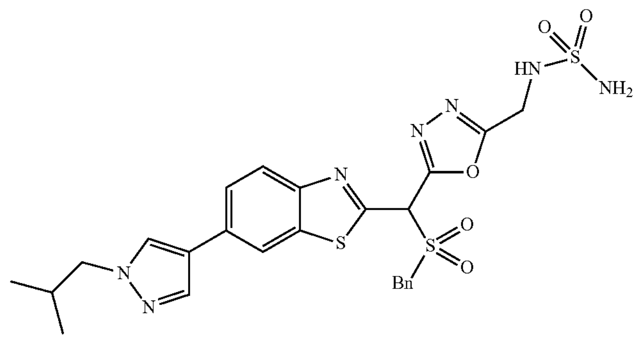 [SMILES: CC(C)Cn1cc(-c2ccc3nc(C(c4nnc(CNS(N)(=O)=O)o4)S(=O)(=O)Cc4ccccc4)sc3c2)cn1] | N-((5-(((benzylsulfonyl)(6-(1-isobutyl-1H-pyrazol-4-yl)-1,3-benzothiazol-2-yl)methyl)-1,3,4-oxadiazol-2-yl)methyl)sulfamide | ¹H NMR (400 MHz, CDCl₃) δ 7.72 (s, 1H), 7.64-7.55 (m, 2H), 7.44 (m, 2H), 7.21 (m, 5H), 4.46 (s, 2H), 4.43 (s, 2H), 3.90 (m, 2H), 3.37-3.31 (m, 1H), 0.90 (d, J = 6.6 Hz, 6H) | 1.85 B 602.1 | <10 | <10 |
| 137 | 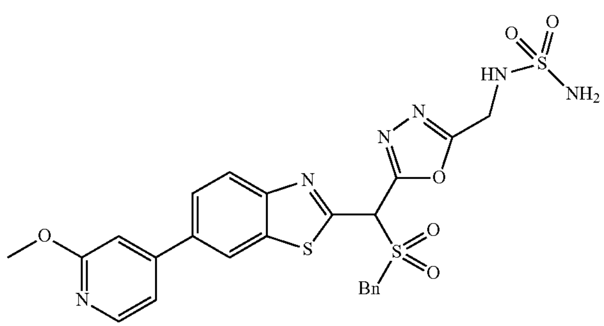 [SMILES: COc1cc(-c2ccc3nc(C(c4nnc(CNS(N)(=O)=O)o4)S(=O)(=O)Cc4ccccc4)sc3c2)ccn1] | N-((5-(((benzylsulfonyl)(6-(2-methoxy-4-pyridinyl)-1,3-benzothiazol-2-yl)methyl)-1,3,4-oxadiazol-2-yl)methyl)sulfamide | ¹H NMR (400 MHz, CDCl₃) δ 8.15 (d, J = 5.5 Hz, 1H), 7.71 (s, 1H), 7.60 (d, J = 8.4 Hz, 1H), 7.54-7.47 (m, 1H), 7.20 (m, 5H), 7.06 (d, J = 5.3 Hz, 1H), 6.89 (s, 1H), 4.48 (s, 2H), 4.44 (s, 2H), 3.93 (s, 3H) | 1.76 B 587.1 | <10 | <10 |

-continued

| Ex. No. | Structure | Name | ¹H NMR | LC/MS RT (min) Method M + H | EL IC₅₀ (nM) | HL IC₅₀ (nM) |
|---|---|---|---|---|---|---|
| 138 | 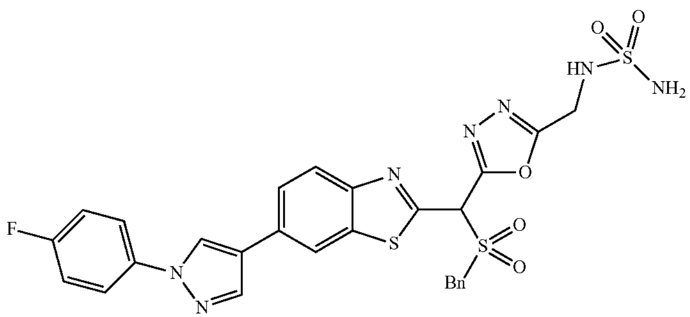 [SMILES: NS(=O)(=O)NCc1nnc(C(c2nc3ccc(-c4cnn(-c5ccc(F)cc5)c4)cc3s2)S(=O)(=O)Cc2ccccc2)o1] | N-((5-((benzylsulfonyl)(6-(1-(4-fluorophenyl)-1H-pyrazol-4-yl))methyl)-1,3-benzothiazol-2-yl)methyl)-1,3,4-oxadiazol-2-yl)methyl)sulfamidt | ¹H NMR (400 MHz, CD₃OD) δ 8.52 (s, 1H), 8.05 (s, 1H), 7.86 (s, 1H), 7.80-7.71 (m, 3H), 7.67 (d, J = 9.0 Hz, 1H), 7.30 (m2H), 7.21 (m, 5H), 4.61 (s, 2H), 4.50 (s, 2H) | 2.03 B 640.1 | <10 | <10 |
| 139 | 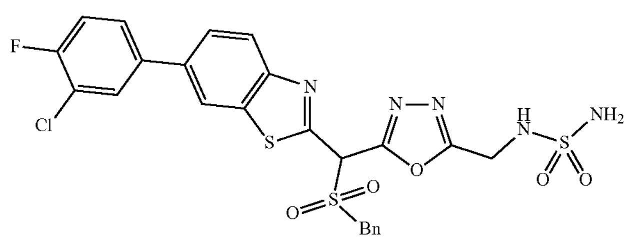 [SMILES: NS(=O)(=O)NCc1nnc(C(c2nc3ccc(-c4ccc(F)c(Cl)c4)cc3s2)S(=O)(=O)Cc2ccccc2)o1] | N-((5-((benzylsulfonyl)(6-(3-chloro-4-fluorophenyl)-1,3-benzothiazol-2-yl)methyl)-1,3,4-oxadiazol-2-yl)methyl)sulfamide | ¹H NMR (500 MHz, DMSO-d₆) δ 8.11 (br. s., 1H), 7.92-7.85 (m, 1H), 7.76-7.67 (m, 2H), 7.60-7.50 (m, 2H), 7.43-7.22 (m, 5H), 6.85-6.77 (m, 2H), 4.73 (br. s., 2H), 4.43 (br. s., 2H) | 2.16 B 608.0 | <10 | <10 |
| 140 | 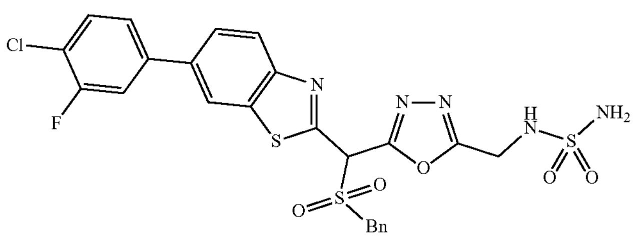 [SMILES: NS(=O)(=O)NCc1nnc(C(c2nc3ccc(-c4ccc(Cl)c(F)c4)cc3s2)S(=O)(=O)Cc2ccccc2)o1] | N-((5-((benzylsulfonyl)(6-(4-chloro-3-fluorophenyl)-K3-benzothiazol-2-yl)methyl)-1,3,4-oxadiazol-2-yl)methyl)sulfamide | ¹H NMR (400 MHz, CD₃OD) δ 8.47 (s, 1H), 8.24 (s, 2H), 8.17-7.99 (m, 5H), 7.89-7.79 (m, 3H), 6.01 (s, 2H), 5.13 (s, 2H), 5.02 (br. s., 2H) | 2.16 B 608.0 | <10 | <10 |

| Ex. No. | Structure | Name | ¹H NMR | LC/MS RT (min) Method M+H | EL IC₅₀ (nM) | HL IC₅₀ (nM) |
|---|---|---|---|---|---|---|
| 141 | 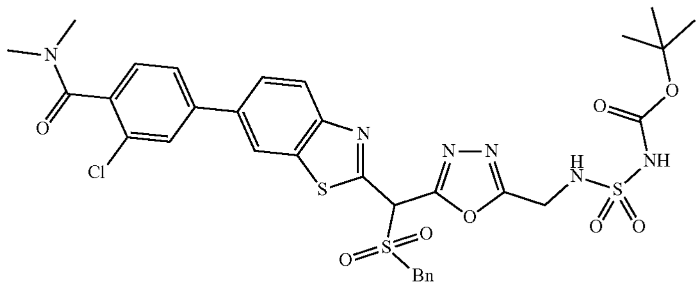 [SMILES: CN(C)C(=O)c1ccc(-c2ccc3nc(C(c4nnc(CNS(=O)(=O)NC(=O)OC(C)(C)C)o4)S(=O)(=O)Cc4ccccc4)sc3c2)cc1Cl] | tert-butyl (((5-((benzylsulfonyl)(6-(3-chloro-4-(dimethylcarbamoyl)phenyl)-1,3-benzothiazol-2-yl)methyl)-1,3,4-oxadiazol-2-yl)methyl)sulfamoyl)carbamate | ¹H NMR (400 MHz, CD₃OD) δ 7.93 (br. s., 1H), 7.82-7.63 (m, 4H), 7.47-7.17 (m, 7H), 4.67 (s, 2H), 4.55 (s, 2H), 3.15 (s, 3H), 2.93 (s, 3H), 1.51-1.38 (m, 9H) | 2.07 B 761.0 | <10 | 50 |
| 142 | 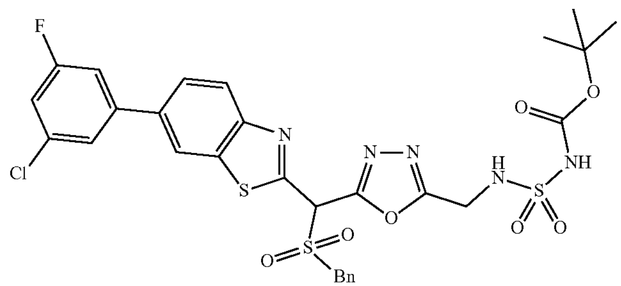 [SMILES: CC(C)(C)OC(=O)NS(=O)(=O)NCc1nnc(C(c2nc3ccc(-c4cc(F)cc(Cl)c4)cc3s2)S(=O)(=O)Cc2ccccc2)o1] | tert-butyl (((5-((benzylsulfonyl)(6-(3-chloro-5-fluorophenyl)-1,3-benzothiazol-2-yl)methyl)-1,3,4-oxadiazol-2-yl)methyl)sulfamoyl)carbamate | ¹H NMR (400 MHz, CD₃OD) δ 7.88 (s, 1H), 7.70-7.57 (m, 2H), 7.51 (br. s., 2H), 7.42-7.31 (m, 5H), 7.27-7.16 (m, 4H), 4.67 (s, 2H), 4.46 (s, 2H), 1.48-1.35 (m, 9H). | 2.30 B 707.9 | <10 | <10 |
| 143 | 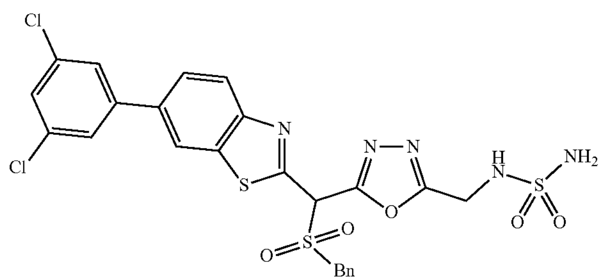 [SMILES: NS(=O)(=O)NCc1nnc(C(c2nc3ccc(-c4cc(Cl)cc(Cl)c4)cc3s2)S(=O)(=O)Cc2ccccc2)o1] | N-((5-((benzylsulfonyl)(6-(3,5-dichlorophenyl)-1,3-benzothiazol-2-yl)methyl)-1,3,4-oxadiazol-2-yl)methyl)sulfamide | ¹H NMR (400 MHz, DMSO-d₆) δ 7.95-7.86 (m, 1H), 7.81-7.72 (m, 2H), 7.62 (d, J = 1.5 Hz, 2H), 7.44-7.21 (m, 5H), 6.86 (br. s., 2H), 4.74 (br. s., 2H), 4.44 (d, J = 5.1 Hz, 2H) | 2.29 B 623.9 | <10 | <10 |

| Ex. No. | Structure | Name | ¹H NMR | LC/MS RT (min) Method M+H | EL IC₅₀ (nM) | HL IC₅₀ (nM) |
|---|---|---|---|---|---|---|
| 144 | 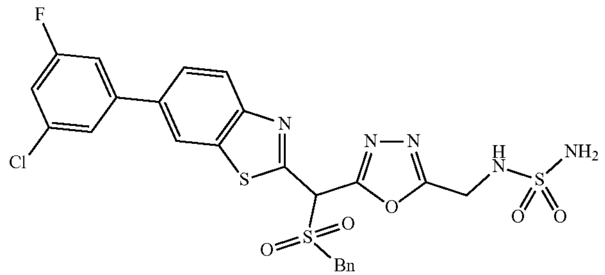 [SMILES: NS(=O)(=O)NCc1nnc(C(c2nc3ccc(-c4cc(F)cc(Cl)c4)cc3s2)S(=O)(=O)Cc2ccccc2)o1] | N-((5-((benzylsulfonyl)(6-(3-chloro-5-fluorophenyl)-1,3-benzothiazol-2-yl)methyl)-1,3,4-oxadiazol-2-yl)methyl)sulfamide | ¹H NMR (400 MHz, CD₃CN) δ 7.91 (s, 1H), 7.68 (s, 2H), 7.52 (s, 2H), 7.39-7.19 (m, 8H), 5.45 (s, 2H), 4.57 (s, 2H), 4.47 (br. s., 2H). | 2.20 B 602.9 | <10 | <10 |
| 145 | 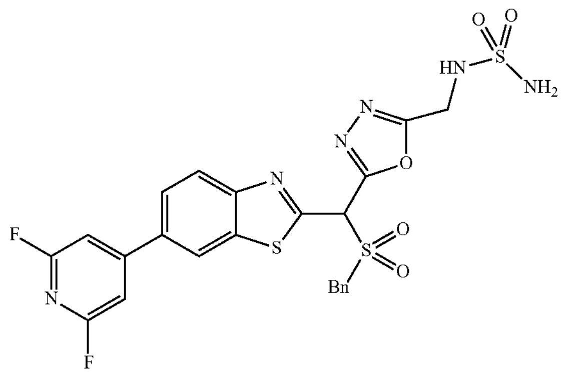 [SMILES: NS(=O)(=O)NCc1nnc(C(c2nc3ccc(-c4cc(F)nc(F)c4)cc3s2)S(=O)(=O)Cc2ccccc2)o1] | N-((5-((benzylsulfonyl)(6-(2,6-difluoro-4-pyridinyl)-1,3-benzothiazol-2-yl)methyl)-1,3,4-oxadiazol-2-yl)methyl)sulfamide | ¹H NMR (400 MHz, CDCl₃) δ 7.78 (s, 1H), 7.63 (m, 1H), 7.58 (m, 1H), 7.34 (m, 2H), 7.23 (m, 2H), 7.03 (m, 3H), 4.51 (s, 2H), 4.46 (s, 2H) | 1.91 B 592.9 | <10 | 77 |
| 146 | 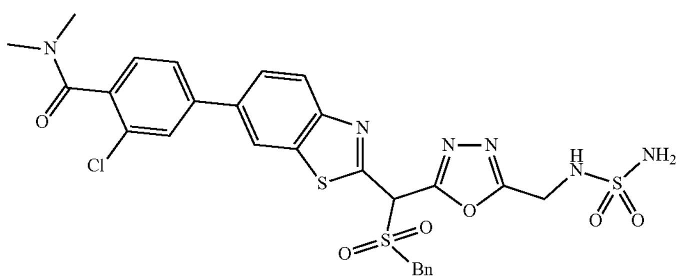 [SMILES: CN(C)C(=O)c1ccc(-c2ccc3nc(C(c4nnc(CNS(N)(=O)=O)o4)S(=O)(=O)Cc4ccccc4)sc3c2)cc1Cl] | 4-(2-((benzylsulfonyl)(5-((sulfamoylamino)methyl)-1,3,4-oxadiazol-2-yl)methyl(-1,3-benzothiazol-6-yl)-2-chloro-N,N-dimethylbenzamide | ¹H NMR (400 MHz, CD₃OD) δ 7.87 (br. s., 1H), 7.65 (d, J = 8.4 Hz, 3H), 7.43-7.18 (m, 6H), 4.63 (br. s., 3H), 4.52 (s, 2H), 3.17 (m, 6H) | 1.82 B 661.0 | <10 | 391 |

| Ex. No. | Structure | Name | ¹H NMR | LC/MS RT (min) Method M + H | EL IC₅₀ (nM) | HL IC₅₀ (nM) |
|---|---|---|---|---|---|---|
| 147 | 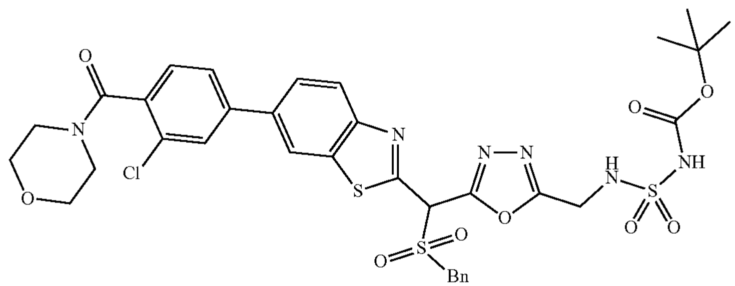 [SMILES: CC(C)(C)OC(=O)NS(=O)(=O)NCc1nnc(C(c2nc3ccc(-c4ccc(C(=O)N5CCOCC5)c(Cl)c4)cc3s2)S(=O)(=O)Cc2ccccc2)o1] | 2-methyl-2-propanyl[({5-[(benzylsulfonyl){6-[3-chloro-4-(4-morpholinyl)carbonyl]phenyl]-1,3-benzothiazol-2-yl}methyl]-1,3,4-oxadiazol-2-yl}methyl)sulfamoyl]carbamate | ¹H NMR (500 MHz, DMSO-d₆) δ 7.95 (s, 1H), 7.82 (d, J = 1.1 Hz, 2H), 7.75-7.69 (m, 2H), 7.47 (d, J = 8.0 Hz, 1H), 7.41-7.19 (m, 6H), 4.73 (br. s., 2H), 4.47 (br. s., 2H), 3.67 (d, J = 5.5 Hz, 4H), 3.56 (t, J = 4.7 Hz, 2H), 3.21-3.15 (m, 2H), 2.89 (s, 3H), 2.73 (s, 3H), 1.46-1.36 (m, 9H) | 2.00 B 803.0 | 17 | 626 |
| 148 | 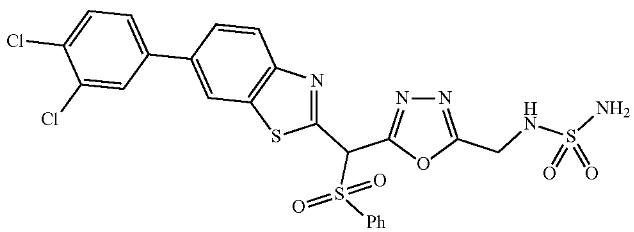 | N-((5-((benzylsulfonyl)(6-(3,4-dichlorophenyl)-1,3-benzothiazol-2-yl)methyl)-1,3,4-oxadiazol-2-yl(methyl)sulfamide | ¹H NMR (500 MHz, DMSO-d₆) δ 8.16 (d, J = 1.9 Hz, 1H), 8.00-7.93 (m, 2H), 7.78-7.66 (m, 3H), 7.37-7.22 (m, 5H), 6.85-6.79 (m, 2H), 4.74 (br. s., 2H), 4.43 (d, J = 5.2 Hz, 2H) | 2.24 B 623.9 | <10 | <10 |
| 149 | 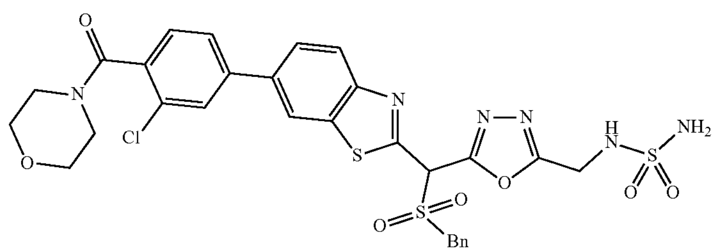 [SMILES: NS(=O)(=O)NCc1nnc(C(c2nc3ccc(-c4ccc(C(=O)N5CCOCC5)c(Cl)c4)cc3s2)S(=O)(=O)Cc2ccccc2)o1] | N-((5-((benzylsulfonyl)(6-(3-chloro-4-(4-morpholinyl)carbonyl)phenyl)-1,3-benzothiazol-2-yl(methyl)-1,3,4-oxadiazol-2-yl)methyl)sulfamide | ¹H NMR (500 MHz, DMSO-d₆) δ 7.80-7.70 (m, 2H), 7.49 (d, J = 8.0 Hz, 1H), 7.45-7.22 (m, 5H), 6.83 (s, 2H), 4.74 (br. s., 2H), 4.44 (d, J = 5.2 Hz, 2H), 3.68 (d, J = 5.8 Hz, 4H), 3.57 (t, J = 4.7 Hz, 2H), 3.20 (t, J = 4.7 Hz, 2H) | 2.23 B 703.0 | <10 | 121 |

| Ex. No. | Structure | Name | ¹H NMR | LC/MS RT (min) Method M + H | EL IC$_{50}$ (nM) | HL IC$_{50}$ (nM) |
|---|---|---|---|---|---|---|
| 150 | 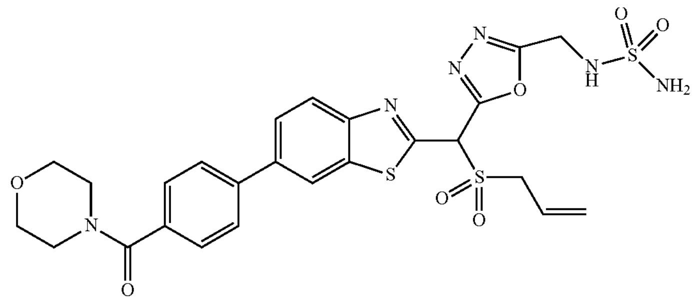 [SMILES: C=CCS(=O)(=O)C(c1nnc(CNS(N)(=O)=O)o1)c1nc2ccc(-c3ccc(C(=O)N4CCOCC4)cc3)cc2s1] | N-((5-((allylsulfonyl)(6-(4-(4-morpholinylcarbonyl)phenyl)-1,3-benzothiazol-2-yl)methyl)-1,3,4-oxadiazol-2-yl)methyl)sulfamide | ¹H NMR (400 MHz, CD$_3$CN) δ 8.03 (s, 1H), 7.77-7.69 (m, 4H), 7.51 (d, J = 8.1 Hz, 2H), 5.96-5.83 (m, 1H), 5.48 (br. s., 1H), 5.39-5.28 (m, 2H), 4.49 (br. s., 2H), 4.08 (d, J = 7.0 Hz, 2H), 3.77-3.55 (m, 7H), 3.45 (br. s., 2H) | 1.62 B 619.1 | <10 | 560 |
| 151 | 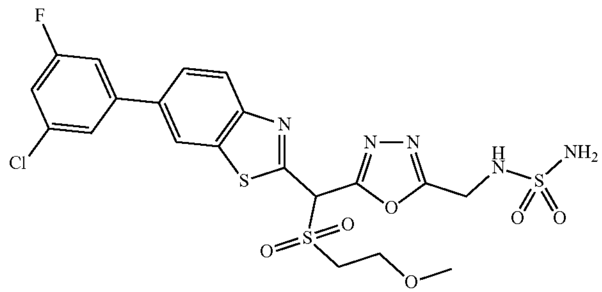 [SMILES: COCCS(=O)(=O)C(c1nnc(CNS(N)(=O)=O)o1)c1nc2ccc(-c3cc(F)cc(Cl)c3)cc2s1] | N-((5-((6-(3-chloro-5-fluorophenyl)-1,3-benzothiazol-2-yl)(2-methoxyethyl)sulfonyl)methyl)-1,3,4-oxadiazol-2-yl)methyl)sulfamide | ¹H NMR (400 MHz, CDCl$_3$) δ containing CD$_3$OD) δ 7.87 (s, 1H), 7.64 (d, J = 1.5 Hz, 2H), 7.41 (t, J = 1.4 Hz, 1H), 7.28-7.22 (m, 1H), 7.10 (dt, J = 8.4, 2.1 Hz, 1H), 4.52 (s, 2H), 3.80 (t, J = 5.4 Hz, 2H), 3.65-3.59 (m, 2H), 3.19 (s, 3H) | 2.20 B 676.0 | <10 | <10 |
| 152 | 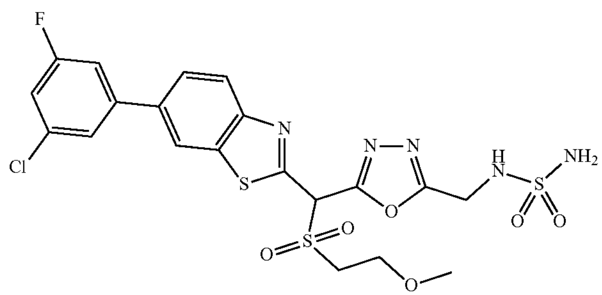 [SMILES: COCCS(=O)(=O)C(c1nnc(CNS(N)(=O)=O)o1)c1nc2ccc(-c3cc(F)cc(Cl)c3)cc2s1] | N-((5-((6-(4-chloro-3-fluorophenyl)-1,3-benzothiazol-2-yl)(2-methoxyethyl)sulfonyl)methyl)-1,3,4-oxadiazol-2-yl)methyl)sulfamide | ¹H NMR (400 MHz, CDCl$_3$ containing CD$_3$OD) δ 7.87 (s, 1H), 7.64 (s, 2H), 7.51-7.31 (m, 4H), 3.81 (t, J = 5.5 Hz, 3H), 3.62 (br. s., 2H), 3.19 (s, 3H). | 2.02 B 576.0 | 2 | 4 |

| Ex. No. | Structure | Name | ¹H NMR | LC/MS RT (min) Method M + H | EL IC₅₀ (nM) | HL IC₅₀ (nM) |
|---|---|---|---|---|---|---|
| 153 | 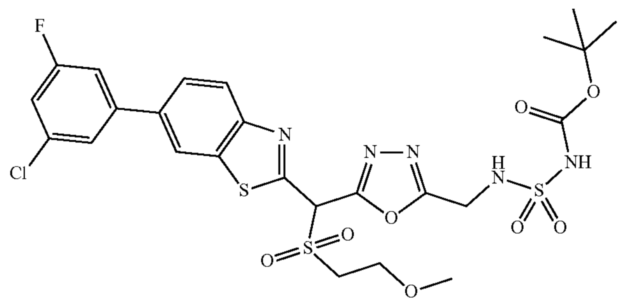 [SMILES: COCCS(=O)(=O)C(c1nnc(CNS(=O)(=O)NC(=O)OC(C)(C)C)o1)c1nc2ccc(-c3cc(F)cc(Cl)c3)cc2s1] | tert-butyl (((5-(6-(3-chloro-5-fluorophenyl)-1,3-benzothiazol-2-yl)(2-methoxyethyl)sulfonyl)methyl)-1,3,4-oxadiazol-2-yl)methyl)sulfamoyl)carbamate | ¹H NMR (400 MHz, CDCl₃ containing CD₃OD) δ 7.91 (s, 1H), 7.66 (s, 2H), 7.50-7.43 (m, 1H), 7.32-7.26 (m, 1H), 7.17-7.11 (m, 1H), 4.56 (s, 2H), 3.82 (t, J = 5.2 Hz, 2H), 3.64 (br.s., 2H), 3.20 (s, 3H), 1.44 (s, 9H) | 2.06 B 676.0 | 19 | 17 |
| 154 | 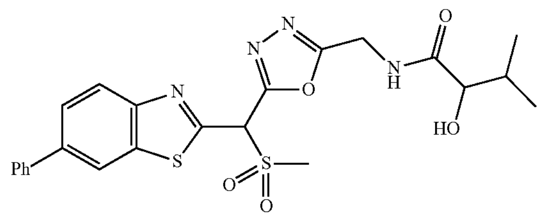 [SMILES: CC(C)C(O)C(=O)NCc1nnc(C(c2nc3ccc(-c4ccccc4)cc3s2)S(C)(=O)=O)o1] | 2-hydroxy-3-methyl-N-(5-((methylsulfonyl)(6-phenyl-1,3-benzothiazol-2-yl)methyl)-1,3,4-oxadiazol-2-yl)methyl)butanamide | ¹H NMR (400 MHz, CDCl₃ containing CD₃OD) δ 7.83 (d, J = 1.3 Hz, 1H), 7.69-7.62 (m, 1H), 7.61-7.54 (m, 3H), 7.47 (t, J = 7.6 Hz, 2H), 7.39 (d, J = 7.3 Hz, 1H), 4.85-4.67 (m, 2H), 4.00 (d, J = 3.3 Hz, 1H), 3.25 (br. s., 3H), 2.16 (ddt, J = 10.2, 6.8, 3.4 Hz, 1H), 1.05 (d, J = 7.0 Hz, 3H), 0.91 (d, J = 6.8 Hz, 3H) | 1.92 B 501.2 | 54 | 25 |
| 155 | 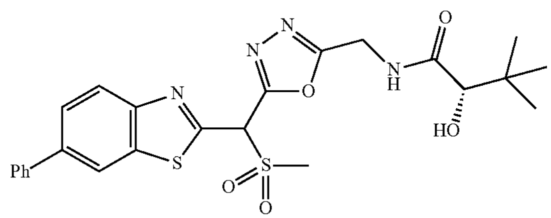 [SMILES: CC(C)(C)[C@H](O)C(=O)NCc1nnc(C(c2nc3ccc(-c4ccccc4)cc3s2)S(C)(=O)=O)o1] | (2S)-2-hydroxy-3,3-dimethyl-N-((5-((methylsulfonyl)(6-phenyl-1,3-benzothiazol-2-yl)methyl)-1,3,4-oxadiazol-2-yl)methyl)butanamide | ¹H NMR (400 MHz, CDCl₃ containing CD₃OD) δ 7.87 (d, J = 1.3 Hz, 1H), 7.71-7.65 (m, 1H), 7.64-7.57 (m, 3H), 7.52-7.45 (m, 2H), 7.42-7.34 (m, 1H), 4.85-4.67 (m, 2H), 3.78 (s, 1H), 3.26 (s, 3H), 1.02 (s, 9H) | 2.11 B 515.2 | 137 | 26 |
| 156 | 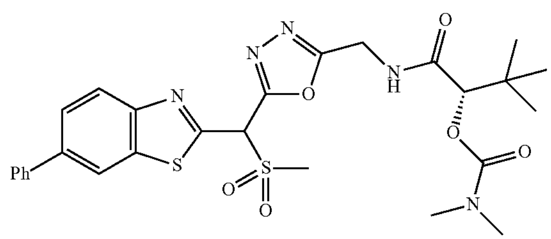 [SMILES: CN(C)C(=O)O[C@H](C(=O)NCc1nnc(C(c2nc3ccc(-c4ccccc4)cc3s2)S(C)(=O)=O)o1)C(C)(C)C] | (1S)-2,2-dimethyl-1-(((5-((methylsulfonyl)(6-phenyl-1,3-benzothiazol-2-yl)methyl)-1,3,4-oxadiazol-2-yl)methyl)carbamoyl)propyl dimethylcarbamate | ¹H NMR (400 MHz, CDCl₃ containing CD₃OD) δ 7.85 (s, 1H), 7.70-7.64 (m, 1H), 7.61 (d, J = 7.9 Hz, 2H), 7.48 (t, J = 7.6 Hz, 2H), 7.41-7.35 (m, 2H), 4.73 (dd, J = 5.7, 2.6 Hz, 2H), 4.61 (s, 1H), 3.26 (s, 3H), 3.04 (s, 3H), 2.92 (s, 3H), 1.08 (s, 9H) | 2.17 B 586.3 | 57 | 71 |

| Ex. No. | Structure | Name | $^1$H NMR | LC/MS RT (min) Method M + H | EL IC$_{50}$ (nM) | HL IC$_{50}$ (nM) |
|---|---|---|---|---|---|---|
| 157 | 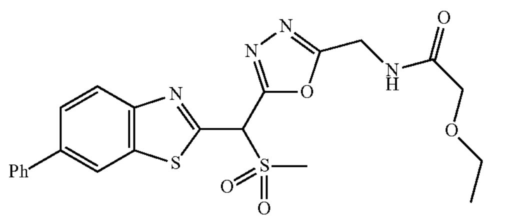 [SMILES: CCOCC(=O)NCc1nnc(C(c2nc3ccc(-c4ccccc4)cc3s2)S(C)(=O)=O)o1] | 2-ethoxy-N-((5-((methylsulfonyl)(6-phenyl-1,3-benzothiazol-2-yl)methyl)-1,3,4-oxadiazol-2-yl)methyl)acetamide | $^1$H NMR (400 MHz, CDCl$_3$) δ 12.84 (br. s., 1H), 7.80 (d, J = 1.3 Hz, 1H), 7.63 (dd, J = 8.4, 1.8 Hz, 1H), 7.60-7.55 (m, 2H), 7.50 (d, J = 8.6 Hz, 1H), 7.49-7.43 (m, 2H), 7.41-7.35 (m, 1H), 7.29 (t, J = 5.9 Hz, 1H), 4.80 (d, J = 6.2 Hz, 2H), 4.04 (s, 2H), 3.63 (q, J = 7.0 Hz, 2H), 3.23 (s, 3H), 1.28 (t, J = 7.0 Hz, 3H) | 1.91 B 487.1 | 223 | 34 |
| 158 | 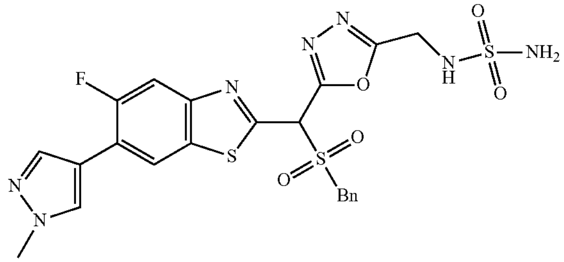 [SMILES: Cn1cc(-c2cc3sc(C(c4nnc(CNS(N)(=O)=O)o4)S(=O)(=O)Cc4ccccc4)nc3cc2F)cn1] | N-((5-((benzylsulfonyl)(5-fluoro-6-(1-methyl-1H-pyrazol-4-yl)-1,3-benzothiazol-2-yl)methyl)-1,3,4-oxadiazol-2-yl)methyl)sulfamide | $^1$H NMR (400 MHz, CD3CN) = 7.93-7.88 (m, 1H), 7.85 (d, J = 7.0 Hz, 1H), 7.80 (s, 1H), 7.53-7.24 (m, 7H), 6.10-5.65 (br. s., 2H), 5.50 (br. s., 2H), 4.62-4.54 (m, 2H), 4.54-4.46 (m, 2H), 3.95 (m, 3H) | 3.15 L 578.1 | <10 | 21 |
| 159 | 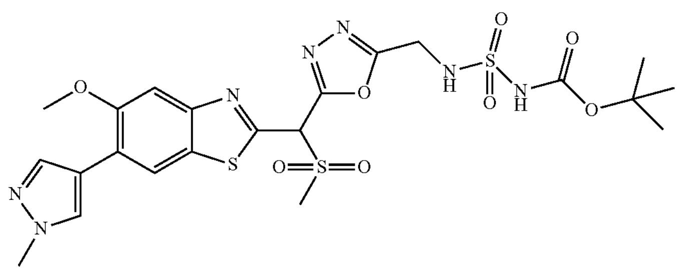 [SMILES: COc1cc2nc(C(c3nnc(CNS(=O)(=O)NC(=O)OC(C)(C)C)o3)S(C)(=O)=O)sc2cc1-c1cnn(C)c1] | 2-methyl-2-propanyl {[(5-{[5-methoxy-6-(1-methyl-1H-pyrazol-4-yl)-1,3-benzothiazol-2-yl](methylsulfonyl)methyl}-1,3,4-oxadiazol-2-yl)methyl]sulfamoyl}carbamate | $^1$H NMR (500 MHz, CDCl3) δ 8.43 (s, 1H), 8.03 (s, 2H), 7.85 (d, J = 9.35 Hz, 2H), 7.10 (s, 1H), 4.64-4.67 (m, 2H), 3.99-4.00 (m, 3H), 3.98 (s, 3H), 3.12 (s, 3H), 1.48 (s, 9H) | 0.84 O 613.8 | 13 | 14 |

| Ex. No. | Structure | Name | ¹H NMR | LC/MS RT (min) Method M + H | EL IC₅₀ (nM) | HL IC₅₀ (nM) |
|---|---|---|---|---|---|---|
| 160 | 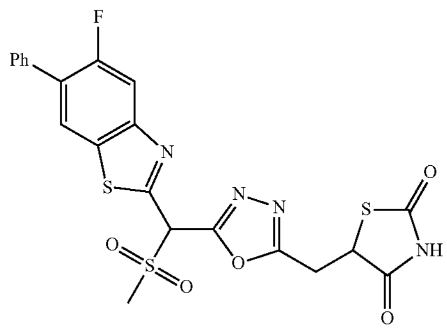 [SMILES: CS(=O)(=O)C(c1nnc(CC2SC(=O)NC2=O)o1)c1nc2cc(F)c(-c3ccccc3)cc2s1] | 5-((5-((5-fluoro-6-phenyl-1,3-benzothiazol-2-yl)(methylsulfonyl)methyl)-1,3,4-oxadiazol-2-yl)methyl)-1,3-thiazolidine-2,4-dione | ¹H NMR (500 MHz, CDCl3) δ 8.23 (br. s., 1H), 7.55 (d, J = 6.8 Hz, 1H), 7.50-7.42 (m, 2H), 7.38 (t, J = 7.4 Hz, 2H), 7.34-7.28 (m, 1H), 7.20 (d, J = 9.7 Hz, 1H), 4.73 (dd, J = 7.3, 4.6 Hz, 1H), 3.77-3.66 (m, 1H), 3.64-3.52 (m, 1H), 3.20-2.99 (m, 3H) | 2.01 Q 529.1 | <10 | 13 |
| 161 | 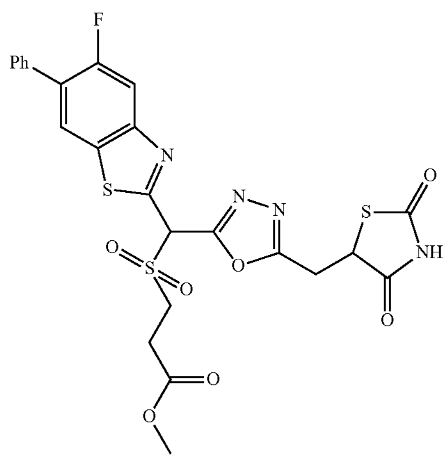 [SMILES: COC(=O)CCS(=O)(=O)C(c1nnc(CC2SC(=O)NC2=O)o1)c1nc2cc(F)c(-c3ccccc3)cc2s1] | methyl 3-(((5-((2,4-dioxo-1,3-thiazolidin-5-yl)methyl)-1,3,4-oxadiazol-2-yl)(5-fluoro-6-phenyl-1,3-benzothiazol-2-yl)methyl)sulfonyl)propanoate | ¹H NMR (400 MHz, DMSO-d6) δ = 12.47-11.36 (m, 1H), 8.54 (d, J = 7.5 Hz, 1H), 8.40-8.23 (m, 1H), 8.13-7.87 (m, 1H), 7.77-7.41 (m, 5H), 5.23-4.94 (m, 1H), 3.95-3.62 (m, 4H), 3.58-3.49 (m, 3H), 2.77-2.60 (m, 2H) | 2.04 Q 591.1 | <10 | <10 |

| Ex. No. | Structure | Name | ¹H NMR | LC/MS RT (min) Method M + H | EL IC₅₀ (nM) | HL IC₅₀ (nM) |
|---|---|---|---|---|---|---|
| 162 | 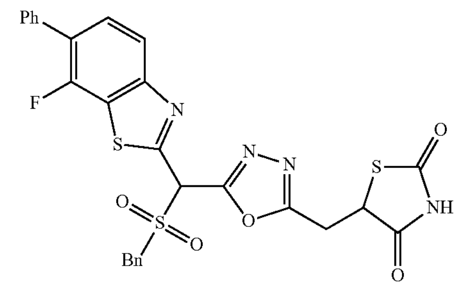 [SMILES: O=C1NC(=O)C(Cc2nnc(C(c3nc4ccc(-c5ccccc5)c(F)c4s3)S(=O)(=O)Cc3ccccc3)o2)S1] | 5-((5-((benzylsulfonyl)(7-fluoro-6-phenyl-1,3-benzothiazol-2-yl)methyl)-1,3,4-oxadiazol-2-yl)methyl)-1,3-thiazolidine-2,4-dione | ¹H NMR (400 MHz, CDCl3) δ 8.25-7.36 (m, 12H), 4.77 (dd, J = 7.6, 4.8 Hz, 1H), 4.44 (s, 2H), 3.68 (dd, J = 16.5, 4.7 Hz, 1H), 3.58-3.47 (m, 1H) | 2.23 Q 595.0 | <10 | <10 |
| 163 | 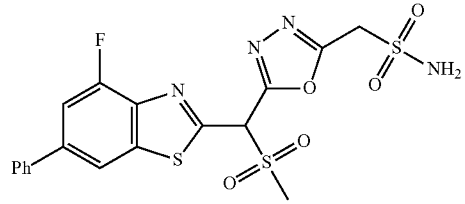 [SMILES: CS(=O)(=O)C(c1nnc(CS(N)(=O)=O)o1)c1nc2c(F)cc(-c3ccccc3)cc2s1] | 1-(5-((4-fluoro-6-phenyl-1,3-benzothiazol-2-yl)(methylsulfonyl)methyl)-1,3,4-oxadiazol-2-yl)methanesulfonamide | ¹H NMR (500 MHz, Acetone-d6) δ 8.03-8.34 (m, 1H), 7.79-7.85 (m, 1H), 7.76 (d = 7.15 Hz, 1H), 7.63-7.73 (m, 1H), 7.50-7.58 (m, 2H), 7.41-7.48 (m, 1H), 6.73 (br. s., 2H), 4.86-4.95 (m, 2H), 3.28-3.49 (m, 3H) | 0.94 O 483.7 | <10 | <10 |
| 164 | 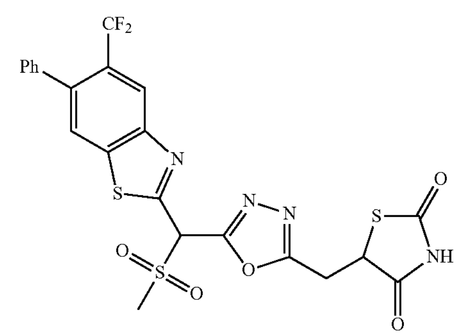 | 5-((5-((methylsulfonyl)(6-phenyl-5-(trifluoromethyl)-1,3-benzothiazol-2-yl)methyl)-1,3,4-oxadiazol-2-yl)methyl)-1,3-thiazolidine-2,4-dione | ¹H NMR (400 MHz, CDCl3) δ 8.58 (br. s., 1H), 8.05-7.80 (m, 1H), 7.66-7.58 (m, 1H), 7.51-7.41 (m, 3H), 7.36 (d, J = 3.5 Hz, 2H), 4.85 (t, J = 5.9 Hz, 1H), 3.89-3.67 (m, 2H), 3.25 (s, 3H) | 2.10 Q 569.1 | <10 | 22 |

| Ex. No. | Structure | Name | ¹H NMR | LC/MS RT (min) Method M + H | EL IC₅₀ (nM) | HL IC₅₀ (nM) |
|---|---|---|---|---|---|---|
| 165 | 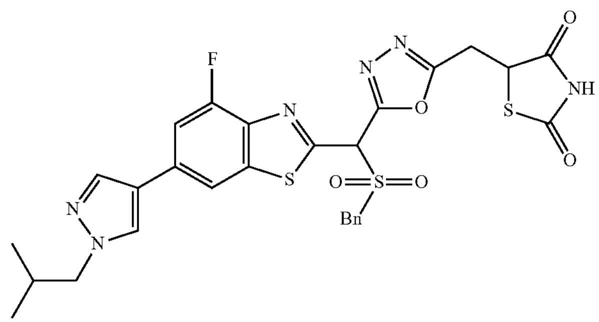 [SMILES: CC(C)Cn1cc(-c2cc(F)c3nc(C(c4nnc(CC5SC(=O)NC5=O)o4)S(=O)(=O)Cc4ccccc4)sc3c2)cn1] | 5-((5-((benzylsulfonyl)(4-fluoro-6-(1-isobutyl-1H-pyrazol-4-yl)-1,3-benzothiazol-2-yl)methyl)-1,3,4-oxadiazol-2-yl)methyl)-1,3-thiazolidine-2,4-dione | ¹H NMR (500 MHz, DMSO-d6) δ 8.33 (s, 1H), 8.24 (s, 1H), 8.21-8.01 (m, 1H), 7.93-7.80 (m, 1H), 7.77-7.58 (m, 1H), 7.54 (d, J = 4.4 Hz, 1H), 7.32-7.22 (m, 3H), 5.05 (dt, J = 7.7, 4.8 Hz, 1H), 4.96 (d, J = 2.2 Hz, 2H), 4.66 (br. s., 1H), 3.94 (dd, J = 13.2, 7.2 Hz, 2H), 3.78-3.72 (m, 1H), 3.72-3.64 (m, 1H), 2.14 (dt, J = 13.1, 6.8 Hz, 1H), 0.87 (dd, J = 9.6, 6.6 Hz, 6H) | 2.01 B 641.1 | <10 | 24 |
| 166 | 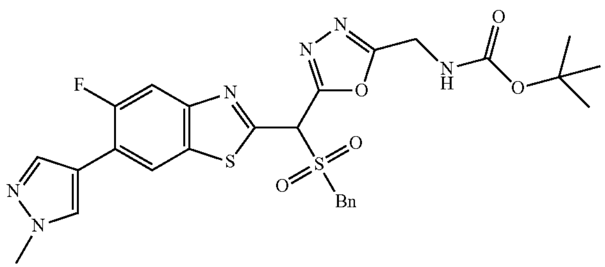 [SMILES: Cn1cc(-c2cc3sc(C(c4nnc(CNC(=O)OC(C)(C)C)o4)S(=O)(=O)Cc4ccccc4)nc3cc2F)cn1] | tert-butyl ((5-((benzylsulfonyl)(5-fluoro-6-(1-methyl-1H-pyrazol-4-yl)-1,3-benzothiazol-2-yl)methyl)-1,3,4-oxadiazol-2-yl)methyl)carbamate | ¹H NMR (400 MHz, CD3CN) δ 7.97-7.87 (m, 2H), 7.84-7.78 (m, 1H), 7.46 (s, 5H), 7.32 (d, J = 16.1 Hz, 1H), 4.61-4.38 (m, 2H), 4.00-3.87 (m, 6H), 2.06 (m, 1H), 1.47-1.42 (m, 9H) | 2.06 Q 599.1 | 23 | 32 |
| 167 | 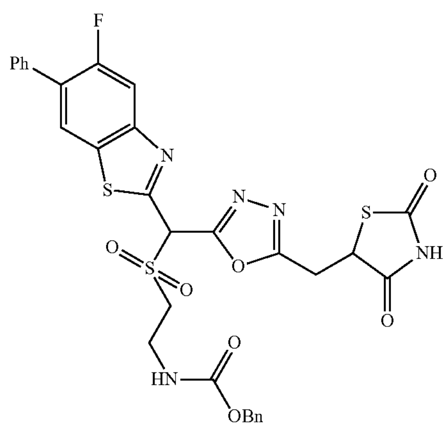 [SMILES: O=C(NCCS(=O)(=O)C(c1nnc(CC2SC(=O)NC2=O)o1)c1nc2cc(F)c(-c3ccccc3)cc2s1)OCc1ccccc1] | benzyl (2-(((5-((1,3-thiazolidin-5-yl)methyl)-1,3,4-oxadiazol-2-yl)(5-fluoro-6-phenyl-1,3-benzothiazol-2-yl)methyl)sulfonyl)ethyl)carbamate | ¹H NMR (400 MHz, CD3OD) δ 7.79 (d, J = 7.3 Hz, 1H), 7.62-7.35 (m, 6H), 7.33-7.12 (m, 5H), 5.29-4.88 (m, 4H), 4.08-3.68 (m, 1H), 3.66-3.43 (m, 4H) | 2.25 Q 682.1 | <10 | <10 |

| Ex. No. | Structure | Name | ¹H NMR | LC/MS RT (min) Method M+H | EL IC₅₀ (nM) | HL IC₅₀ (nM) |
|---|---|---|---|---|---|---|
| 168 | 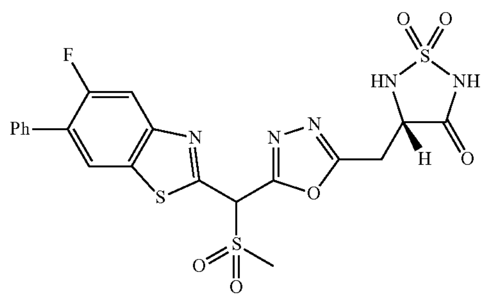 [SMILES: CS(=O)(=O)C(c1nnc(C[C@@H]2NS(=O)(=O)NC2=O)o1)c1nc2cc(F)c(-c3ccccc3)cc2s1] | (4S)-4-((5-((5-fluoro-6-phenyl-1,3-benzothiazol-2-yl)(methylsulfonyl)methyl)-1,3,4-oxadiazol-2-yl)methyl)-1,2,5-thiadiazolidin-3-one 1,1-dioxide | ¹H NMR (400 MHz, CDCl3) δ 8.45-7.82 (m, 2H), 7.69-7.35 (m, 5H), 4.56 (br. s., 1H), 3.50-3.22 (m, 5H). | 1.92 Q 538 | <10 | 19 |

Example 169

N-(((5-((Methylsulfonyl)(6-phenyl-1,3-benzothiazol-2-yl)methyl)-1,3,4-oxadiazol-2-yl)methyl)sulfonyl)acetamide

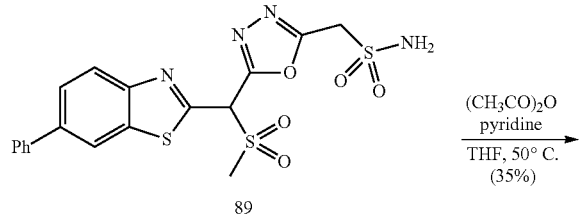

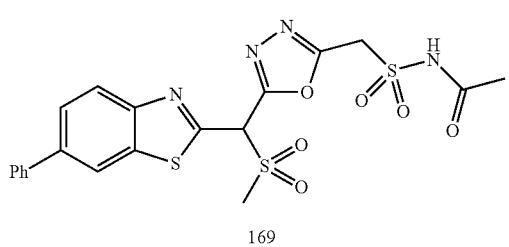

To a solution of Example 89 (10 mg, 0.022 mmol) in THF (1 mL) was added pyridine (5.2 μl, 0.065 mmol) and the mixture stirred at 50° C. for 1 h. Acetic anhydride (2.6 mg, 0.026 mmol) was added and the mixture was stirred at 50° C. for 2 h then allowed to cool to rt. The mixture was diluted with 50% MeOH(aq) (1 mL) then purified by reverse phase preparative HPLC (Method B) to give Example 169 (4.0 mg, 35% yield). $^1$H NMR (400 MHz, DMSO-d$_6$) δ 8.26-8.17 (m, 1H), 8.01-7.89 (m, 1H), 7.80-7.76 (m, 1H), 7.75 (dd, J=8.5, 1.7 Hz, 1H), 7.72-7.68 (m, 2H), 7.52-7.47 (m, 2H), 7.41-7.37 (m, 1H), 5.26 (br. s., 2H), 2.06 (s, 3H). LCMS=1.86 min using analytical method (B), 507.1 (M+H)$^+$. EL IC$_{50}$<10 nM. HL IC$_{50}$=160 nM.

Example 170

N-((5-(((2-Hydroxypropyl)sulfonyl)(6-phenyl-1,3-benzothiazol-2-yl)methyl)-1,3,4-oxadiazol-2-yl)methyl)sulfamide

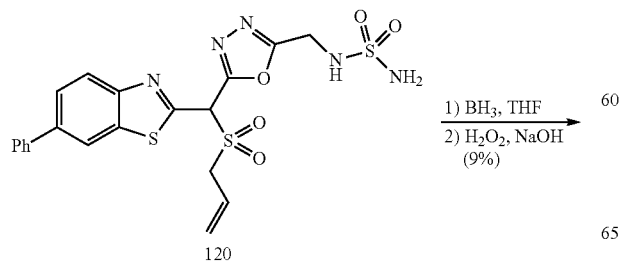

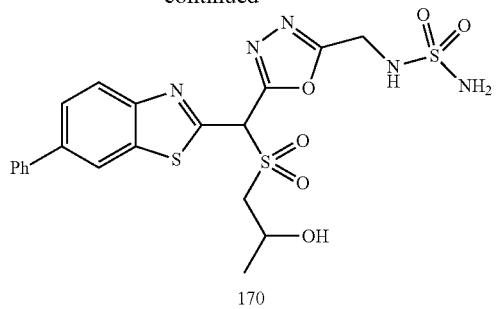

To a suspension of Example 120 (10 mg, 0.020 mmol) in THF (0.4 mL) at 0° C. was added 1.0 M borane tetrahydrofuran complex in tetrahydrofuran (0.040 mL, 0.040 mmol). After 1 h, a solution of 1N NaOH (0.060 mL, 0.060 mmol) was added followed by a solution of 35% H$_2$O$_2$ (65 μL) and the mixture stirred for 2 h. The mixture was poured into brine and extracted with EtOAc (3×). The combined extracts were dried (Na$_2$SO$_4$) filtered and concentrated under reduced pressure. The resulting residue was purified by preparative LC/MS using Method E; Gradient: 20-60% B over 25 min, then a 15-min hold at 100% B; to give Example 170 (0.9 mg, 9% yield) as a white solid. $^1$H NMR (500 MHz, DMSO-d$_6$) δ 8.30-8.06 (m, 1H), 8.01-7.85 (m, 1H), 7.82-7.63 (m, 3H), 7.57-7.26 (m, 4H), 6.79 (br. s., 2H), 4.86 (br. s., 1H), 4.51-4.05 (m, 3H), 3.43 (br. s., 2H), 1.35-1.05 (m, 3H). LCMS=1.61 min using analytical method (N), 524.2 (M+H). EL IC$_{50}$<10 nM. HL IC$_{50}$<10 nM.

Example 171

N-((5-(((2,3-Dihydroxypropyl)sulfonyl)(6-phenyl-1,3-benzothiazol-2-yl)methyl)-1,3,4-oxadiazol-2-yl)methyl)sulfamide

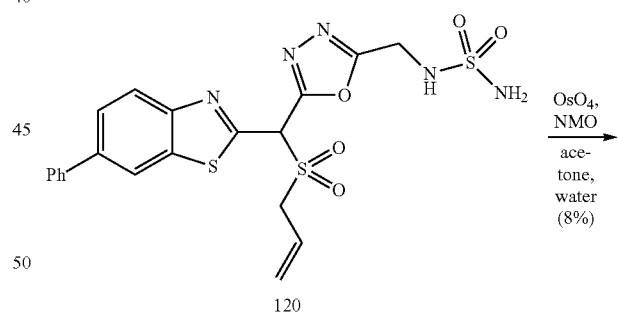

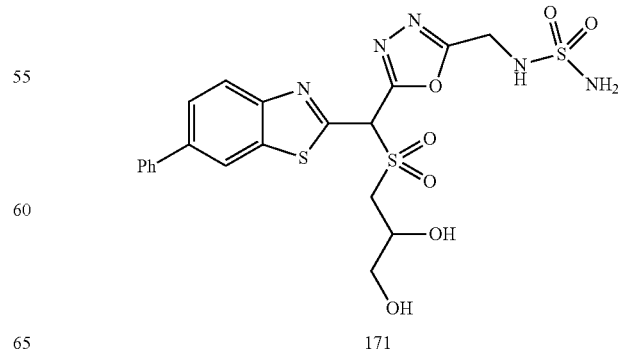

To a mixture of Example 120 (10 mg, 0.020 mmol) and 4-methylmorpholine N-oxide (4.6 mg, 0.040 mmol) in acetone/water (1.2 mL, 4:1) was added 4% aqueous osmium tetroxide (6 μL, 1.0 μmol) and the suspension stirred for 16 h. Additional 4-methylmorpholine N-oxide (4.6 mg, 0.040 mmol) and 4% aqueous osmium tetroxide (60 μL, 10 μmol) were added and the reaction stirred for 24 h. Sodium sulfite (25 mg) was added and the mixture stirred for 1 h then passed through a plug of silica gel. The filtrate was purified by preparative HPLC (RT=7.47 min using Method B) to give Example 171 as a mixture of diastereomers (0.9 mg, 8% yield) as a white solid. $^1$H NMR (400 MHz, CDCl$_3$ containing CD$_3$OD) δ 7.86 (s, 1H), 7.71-7.66 (m, 1H), 7.64-7.58 (m, 3H), 7.48 (t, J=7.5 Hz, 2H), 7.54-7.40 (m, 1H), 4.56 (s, 2H), 4.27-4.20 (m., 1H), 3.69-3.48 (m, 4H). LCMS=1.02 min using analytical method (M), 540.0 (M+H). EL IC$_{50}$<10 nM. HL IC$_{50}$<10 nM.

Example 172

N-((5-((6-(6-Fluoro-3-pyridinyl)-1,3-benzothiazol-2-yl)(methylsulfonyl)methyl)-1,3,4-oxadiazol-2-yl)methyl)methanesulfonamide

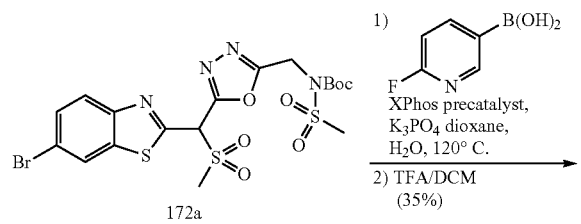

172a

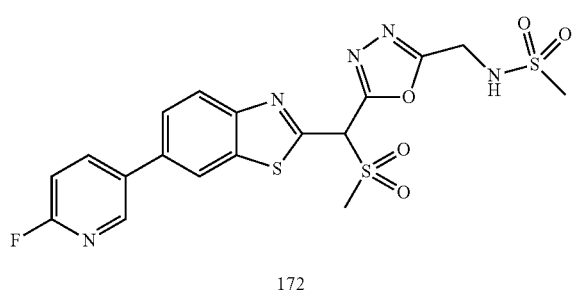

172

To a solution of Compound 172a (33 mg, 0.057 mmol, prepared as described for Example 84) in dioxane (1 mL) was added 2-fluoropyridine-5-boronic acid (12 mg, 0.085 mmol) and 0.5 M potassium phosphate tribasic (0.34 mL, 0.17 mmol). The mixture was degassed under argon (3×) then chloro(2-dicyclohexylphosphino-2',4',6'-triisopropyl-1,1'-biphenyl)[2-(2'-amino-1,1'-biphenyl)]palladium(II) (1.8 mg, 2.3 μmol) was added and the reaction degassed under argon (3×) then heated at 90° C. for 18 h. The mixture was allowed to cool to rt then poured into satd NH$_4$Cl and extracted with DCM (3×). The combined extracts were dried (Na$_2$SO$_4$), filtered and evaporated under reduced pressure. The residue was diluted with DCM (2 mL) then TFA (0.5 mL) added and the mixture stirred for 1 h. The mixture was evaporated under reduced pressure then the residue diluted with DCM and stirred with satd NaHCO$_3$. The layers were separated and the aqueous layer was extracted with DCM (2×). The combined extracts were dried (Na$_2$SO$_4$), filtered and evaporated under reduced pressure, and the residue purified by silica gel chromatography eluting with 0.5 to 5% MeOH/DCM to give Example 172 (11 mg, 35% yield) as a white solid. $^1$H NMR (400 MHz, CDCl$_3$ containing CD$_3$OD) δ 8.32 (d, J=2.4 Hz, 1H), 7.95 (ddd, J=8.5, 7.6, 2.6 Hz, 1H), 7.73 (d, J=0.9 Hz, 1H), 7.57-7.46 (m, 2H), 7.00 (dd, J=8.5, 2.5 Hz, 1H), 4.52 (s, 2H), 3.18 (s, 3H), 2.97 (s, 3H). LCMS=1.57 min using analytical method (B), 498.0 (M+H). EL IC$_{50}$=240 nM. HL IC$_{50}$=32 nM.

Example 173

N-((5-((Methylsulfonyl)(6-(4-(4-morpholinylcarbonyl)phenyl)-1,3-benzothiazol-2-yl)methyl)-1,3,4-oxadiazol-2-yl)methyl)methanesulfonamide

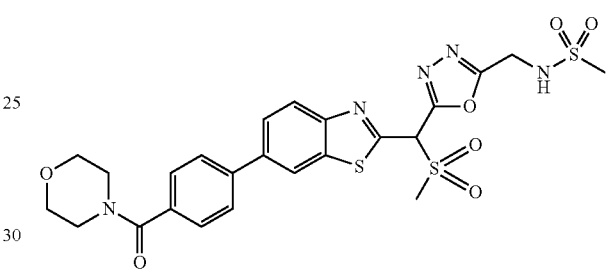

Example 173 was prepared by the general procedure described for Example 172. $^1$H NMR (400 MHz, CDCl$_3$ containing CD$_3$OD) δ 7.90 (s, 1H), 7.74-7.61 (m, 4H), 7.53 (d, J=7.9 Hz, 2H), 4.63 (s, 2H), 3.94-3.50 (m, 8H), 3.36 (s, 3H), 3.29 (s, 3H). LCMS=1.52 min using analytical method (B), 592.1 (M+H). EL IC$_{50}$=35 nM. HL IC$_{50}$=58 nM.

Example 174

3-(((6-(1-Methyl-1H-pyrazol-4-yl)-1,3-benzothiazol-2-yl)(5-((sulfamoylamino)methyl)-1,3,4-oxadiazol-2-yl)methyl)sulfonyl)propanoic acid

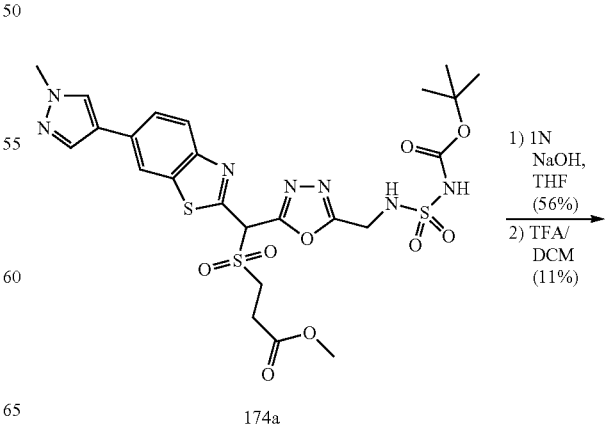

174a

-continued

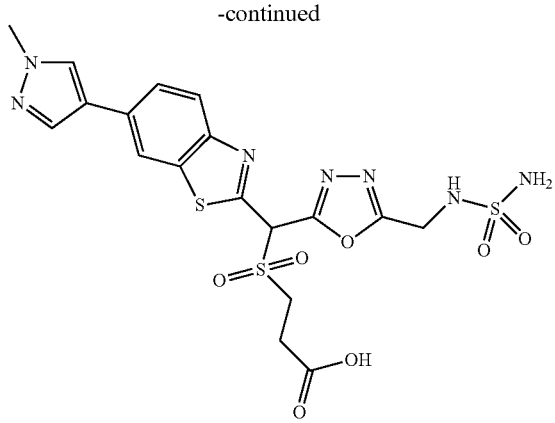

174

To a solution of Compound 174a (44 mg, 0.067 mmol, prepared as described for Example 46) in THF (2 mL) was added 1N NaOH (0.14 mL, 0.14 mmol) and the reaction mixture stirred for 1 h. The reaction mixture was concentrated under reduced pressure then diluted with EtOAc and washed satd NH$_4$Cl and brine. The organic extract was dried (Na$_2$SO$_4$), filtered and concentrated under reduced pressure. The residue was purified by preparative HPLC (Rt=6.70 min using Method B) to give methyl 3-(((5-(((N-(tert-butoxycarbonyl)sulfamoyl)amino)methyl)-1,3,4-oxadiazol-2-yl)(6-(1-methyl-1H-pyrazol-4-yl)benzo[d]thiazol-2-yl)methyl)sulfonyl)propanoate (44 mg, 56% yield) as a white solid. $^1$H NMR (400 MHz, CD$_3$CN) δ 7.92 (s, 1H), 7.90 (s, 1H), 7.83 (s, 1H), 7.72 (s, 1H), 7.62 (s, 2H), 4.55 (s, 2H), 3.94 (s, 3H), 3.70 (t, J=7.3 Hz, 2H), 2.80 (t, J=7.3 Hz, 2H), 1.44 (s, 9H). LCMS=1.66 min using analytical method (B), 642.1 (M+H). 3-(((5-(((N-(tert-Butoxycarbonyl)sulfamoyl)amino)methyl)-1,3,4-oxadiazol-2-yl)(6-(1-methyl-1H-pyrazol-4-yl)benzo[d]thiazol-2-yl)methyl)sulfonyl)propanoic acid (20 mg, 0.031 mmol) was dissolved in DCM (0.8 mL) and TFA (0.8 mL) and the reaction mixture stirred for 45 min. then evaporated under reduced pressure. The residue was diluted with EtOAc and washed 1.5 M phosphate solution and brine. The organic portion was dried (Na$_2$SO$_4$), filtered and concentrated under reduced pressure to give Example 174 (2.0 mg, 11% yield) as a white solid. $^1$H NMR (400 MHz, DMSO-d$_6$) δ 8.14-8.00 (m, 2H), 7.88-7.78 (m, 2H), 7.63 (dd, J=8.5, 1.7 Hz, 1H), 7.43 (d, J=6.4 Hz, 1H), 6.72-6.64 (m, 1H), 4.48-4.37 (m, 2H), 3.95-3.83 (m, 3H), 3.67 (br. s., 2H), 2.85-2.65 (m, 2H). LCMS=1.38 min using analytical method (B), 542.1 (M+H). EL IC$_{50}$=11 nM. HL IC$_{50}$=124 nM.

Example 175

2-(5-((Methylsulfonyl)(6-(4-(4-morpholinylcarbonyl)phenyl)-1,3-benzothiazol-2-yl)methyl)-1,3,4-oxadiazol-2-yl)-N-(3-propoxypropyl)acetamide

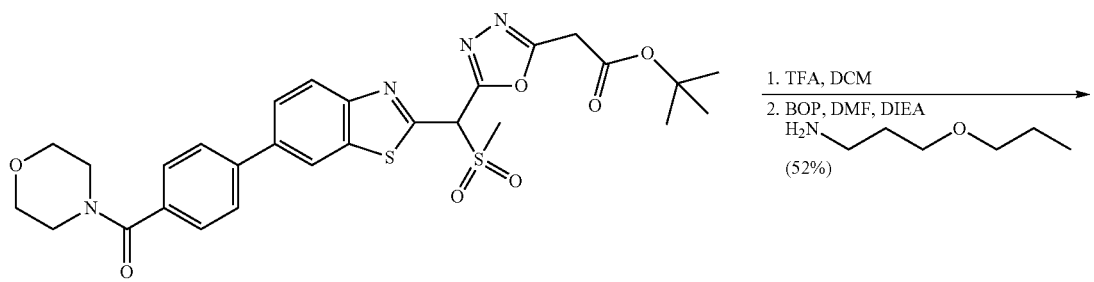

107

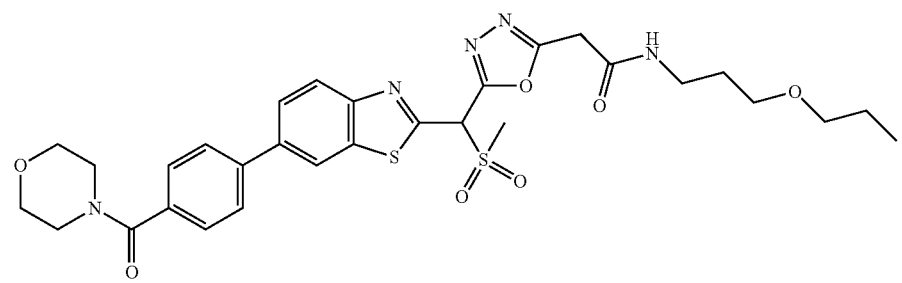

175

To a solution of Example 107 (115 mg, 0.192 mmol) in DCM (1 mL) was added TFA (0.5 mL) and mixture stirred for 30 min. The mixture was evaporated under reduced pressure and the residue was passed through a column of silica gel eluting with 0-10% MeOH in DCM. The effluent containing {5-((methylsulfonyl)(6-(4-(4-morpholinylcarbonyl)phenyl)-1,3-benzothiazol-2-yl)methyl)-1,3,4-oxadiazol-2-yl}acetic acid was concentrated under reduced pressure. A portion of {5-((methylsulfonyl)(6-(4-(4-morpholinylcarbonyl)phenyl)-1,3-benzothiazol-2-yl)methyl)-1,3,4-oxadiazol-2-yl}acetic acid (15 mg, 0.028 mmol) was dissolved in DMF (0.5 mL) then 3-propoxypropan-1-amine (4.6 μL, 0.033 mmol) and TEA (0.019 mL, 0.14 mmol) was added followed by BOP reagent (15 mg, 0.033 mmol). The mixture was stirred for 1 h then diluted with EtOAc and washed with water and brine. The organic portion was dried ($Na_2SO_4$), filtered and evaporated under reduced pressure. The residue was purified by silica gel chromatography eluting with 0-10% MeOH in DCM to give Example 175 (9.8 mg, 0.014 mmol, 52% yield) as a white solid. LCMS=1.58 min using analytical method (B), 614.2 (M+H). $^1$H NMR (400 MHz, $CD_3OD$) δ 7.99 (s, 1H), 7.74 (d, J=0.9 Hz, 3H), 7.69 (br. s., 1H), 7.52 (d, J=8.1 Hz, 1H), 3.93 (s, 1H), 3.76 (br. s., 3H), 3.55 (t, J=5.6 Hz, 1H), 3.48 (dt, J=10.1, 6.2 Hz, 3H), 3.44-3.36 (m, 4H), 3.35 (br. s., 1H), 3.26 (s, 1H), 3.18 (t, J=6.8 Hz, 1H), 3.02 (t, J=7.0 Hz, 1H), 2.67-2.60 (m, 3H), 1.93-1.85 (m, 1H), 1.83-1.77 (m, 1H), 1.73 (quin, J=6.4 Hz, 1H), 1.58 (dt, J=14.0, 7.0 Hz, 3H), 0.92 (td, J=7.5, 3.1 Hz, 3H). LCMS=1.58 min using analytical method (B), 614.2 (M+H). EL $IC_{50}$=12 nM. HL $IC_{50}$=89 nM.

Examples 176-180 were prepared by the general procedures given for Example 175.

Example 181

(4S)-2-Cyclopropyl-4-((5-((methylsulfonyl)(6-phenyl-1,3-benzothiazol-2-yl)methyl)-1,3,4-oxadiazol-2-yl)methyl)-1,2,5-thiadiazolidin-3-one 1,1-dioxide

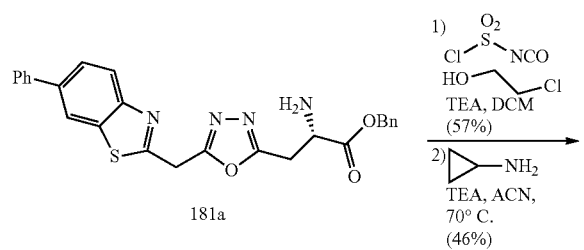

181a

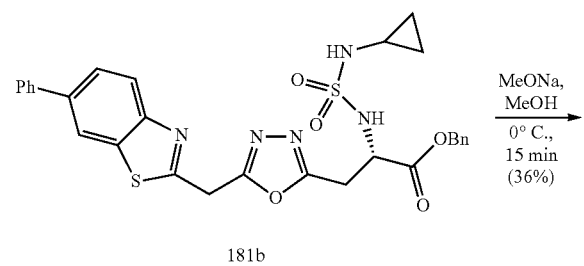

181b

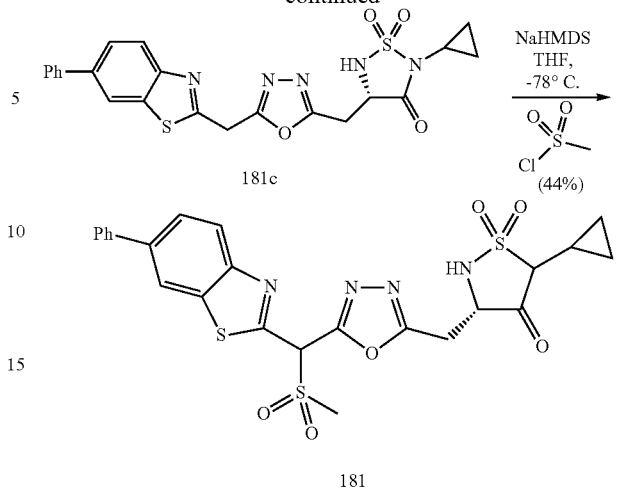

Compound 181b. (S)-Benzyl 2-(N-cyclopropylsulfamoylamino)-3-(5-((6-phenylbenzo[d]thiazol-2-yl)methyl)-1,3,4-oxadiazol-2-yl)propanoate To a solution of 2-chloroethanol (0.10 mL, 1.3 mmol) in DCM (1 mL) at rt was added a solution of sulfurisocyanatidic chloride (180 mg, 1.3 mmol) in DCM (1 mL) and the reaction mixture was stirred for 6 h. The resulting mixture was added to a solution of Compound 181a (300 mg, 0.65 mmol, prepared as described in Example 45) and TEA (0.45 mL, 3.2 mmol) in DCM (4 mL) and the mixture stirred for 30 min then heated at 35° C. for 16 h. The reaction mixture was concentrated under reduced pressure and the residue was purified by silica gel chromatography eluting with 0-100% hexane/EtOAc to afford (S)-benzyl 2-(2-oxooxazolidine-3-sulfonamido)-3-(5-((6-phenylbenzo[d]thiazol-2-yl)methyl)-1,3,4-oxadiazol-2-yl)propanoate (230 mg, 57% yield) as a yellow foam. LCMS=1.2 min using analytical method (B), 620.2 (M+H). A portion of (S)-benzyl 2-(2-oxooxazolidine-3-sulfonamido)-3-(5-((6-phenylbenzo[d]thiazol-2-yl)methyl)-1,3,4-oxadiazol-2-yl)propanoate (93 mg, 0.15 mmol) was dissolved in ACN (3 mL) then TEA (0.031 mL, 0.23 mmol) was added followed by cyclopropanamine (0.053 mL, 0.75 mmol) and the reaction mixture heated at 70° C. for 16 h. The reaction mixture was allowed to cool to rt then concentrated under reduced pressure. The residue was purified by silica gel chromatography eluting with 0-100% hexane/EtOAc to give Compound 181b (41 mg, 46% yield) as a yellow solid. $^1$H NMR (400 MHz, $CDCl_3$) δ 8.13-7.97 (m, 2H), 7.72 (dd, J=8.5, 1.9 Hz, 1H), 7.67-7.59 (m, 2H), 7.51-7.44 (m, 2H), 7.42-7.38 (m, 1H), 7.34-7.31 (m, 3H), 7.30-7.27 (m, 2H), 5.53 (d, J=8.1 Hz, 1H), 5.23 (s, 1H), 5.18 (s, 2H), 4.68 (d, J=4.4 Hz, 2H), 3.43 (dd, J=5.7, 1.8 Hz, 2H), 2.51-2.35 (m, 1H), 0.65-0.43 (m, 4H). LCMS=1.2 min using analytical method (B), 590.2 (M+H)±.

Compound 181c. (4S)-2-Cyclopropyl-4-((5-((6-phenyl-1,3-benzothiazol-2-yl)methyl)-1,3,4-oxadiazol-2-yl)methyl)-1,2,5-thiadiazolidin-3-one 1,1-dioxide To a solution of Compound 181b (41 mg, 0.070 mmol) in THF (3 mL) at 0° C. was slowly added a solution of 25% NaOMe in MeOH (0.035 mL, 0.15 mmol) dissolved in THF (0.5 mL) and the mixture was stirred for 30 min. The reaction was quenched with the addition of cold 1.0 M HCl (0.70 mL, 0.70 mmol) at 0° C., then the mixture was extracted with DCM. The extracts were dried over magnesium sulfate, filtered and concentrated under reduced pressure. The residue was purified by silica gel chromatography eluting with 0-100% EtOAc/hexanes to give Compound 181c (12 mg, 36% yield) as a yellow foam. $^1$H NMR (400 MHz, CDCl$_3$) δ 8.08-8.03 (m, 2H), 7.73 (dd, J=8.6, 1.8 Hz, 1H), 7.66-7.59 (m, 2H), 7.51-7.43 (m, 2H), 7.42-7.35 (m, 1H), 4.73 (s, 2H), 4.69 (dd, J=9.0, 3.5 Hz, 1H), 3.54 (dd, J=16.8, 3.6 Hz, 1H), 3.41-3.30 (m, 1H), 2.70 (dt, J=7.1, 3.4 Hz, 1H), 1.21-1.05 (m, 2H), 1.04-0.86 (m, 2H). LCMS=1.9 min using analytical method (M), 482.0 (M+H)$^+$.

Example 181

Example 181 was prepared from Compound 181c in 44% yield as a white solid using the general procedure given for Example 1. $^1$H NMR (400 MHz, DMF-d$_7$) δ 11.82 (br. s., 1H), 8.32-8.24 (m, 1H), 7.87-7.74 (m, 3H), 7.61-7.36 (m, 5H), 4.94 (dd, J=6.8, 3.5 Hz, 1H), 3.62-3.56 (m, 1H), 3.53 (s, 2H), 3.36 (br. s., 2H), 1.04-0.85 (m, 4H). LCMS=2.1 min using analytical method (M), 560.1 (M+H)$^+$. EL IC$_{50}$=130 nM. HL IC$_{50}$=56 nM.

Example 182

5-((5-((Methylsulfonyl)(6-(2-oxo-1,2-dihydro-5-pyrimidinyl)-1,3-benzothiazol-2-yl)methyl)-1,3,4-oxadiazol-2-yl)methyl)-1,3-thiazolidine-2,4-dione

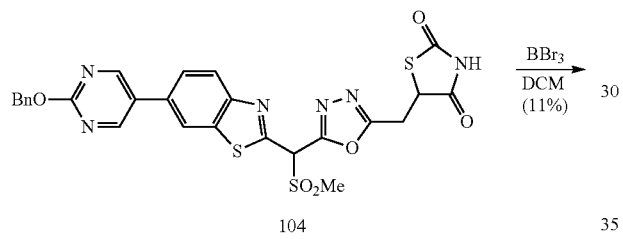

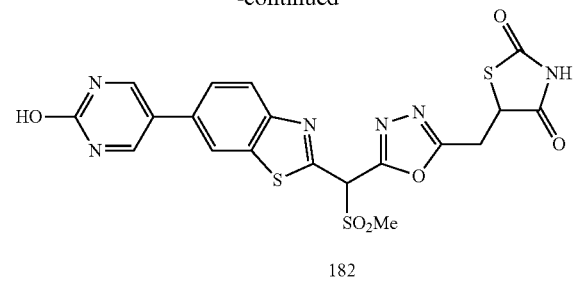

To a suspension of Example 104 (15 mg, 0.025 mmol) in DCM (2 mL) at 0° C. was added a 1.0 M solution of BBr$_3$ in DCM (0.10 mL, 0.10 mmol). The mixture was stirred at 0° C. for 5 min and allowed to warm to rt and stirred for 30 min. The reaction was quenched by the addition of MeOH and concentrated under reduced pressure. The residue was purified by reverse phase preparative HPLC (Method B) to give Example 182 (1.4 mg, 11% yield). $^1$H NMR (400 MHz, CD$_3$OD) δ 8.61 (s, 2H), 7.92 (s, 1H), 7.81-7.67 (m, 1H), 7.65-7.57 (m, 1H), 4.94 (dd, J=7.5, 4.8 Hz, 1H), 3.85-3.76 (m, 1H), 3.72-3.63 (m, 2H), 3.50 (s, 1H), 3.26 (br. s., 3H), 3.18-3.11 (m, 1H). LCMS=1.3 min using analytical method (M), 519.0 (M+H)$^+$. EL IC$_{50}$<10 nM. HL IC$_{50}$=84 nM.

Example 183

N-{[5-([(2-Aminoethyl)sulfonyl]{6-[4-(4-morpholinylcarbonyl)phenyl]-1,3-benzothiazol-2-yl}methyl)-1,3,4-oxadiazol-2-yl]methyl}sulfuric diamide

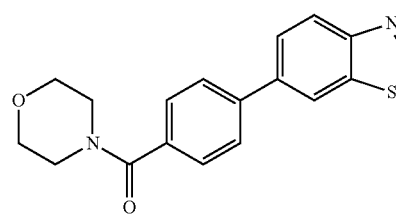

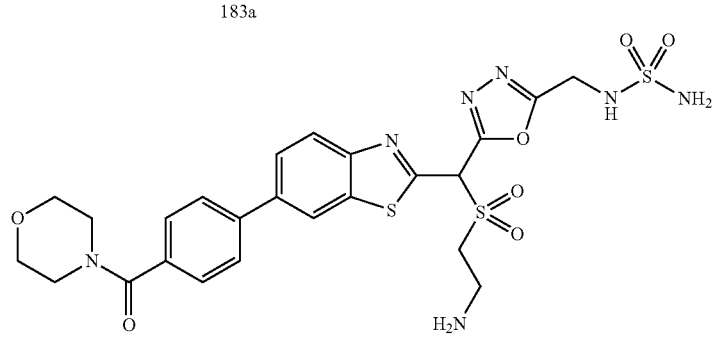

To a solution of Compound 183a (35 mg, 0.041 mmol, prepared as described for Example 46) in acetonitrile (2 mL) was added and TMS-I (50 µl, 0.37 mmol) and the mixture stirred at 50° C. for 4 h. The mixture was allowed to cool to rt and concentrated under reduced pressure. The residue was purified by preparative LC/MS using Method F; Gradient: 5-45% B over 20 minutes, then a 5-minute hold at 100% B; to give Example 183 (12 mg, 43% yield) as a white solid. $^1$H NMR (500 MHz, DMSO-$d_6$) δ 8.28 (br. s., 1H), 8.01-7.86 (m, 4H), 7.78 (d, J=7.7 Hz, 3H), 7.54 (d, J=8.0 Hz, 2H), 7.49 (br. s., 1H), 6.82 (s, 2H), 4.40 (d, J=5.2 Hz, 2H), 3.83-3.44 (m, 10H), 3.30-3.21 (m, 2H). LCMS=1.01 min using analytical method (N), 622.2 (M+H). EL IC$_{50}$=14 nM. HL IC$_{50}$=178 nM.

Examples 184-187 were prepared by the general procedures given for Example 183.

Example 188

5-((5-((Methylsulfonyl)(6-(4-morpholinylcarbonyl)-1,3-benzothiazol-2-yl)methyl)-1,3,4-oxadiazol-2-yl)methyl)-1,3-thiazolidine-2,4-dione

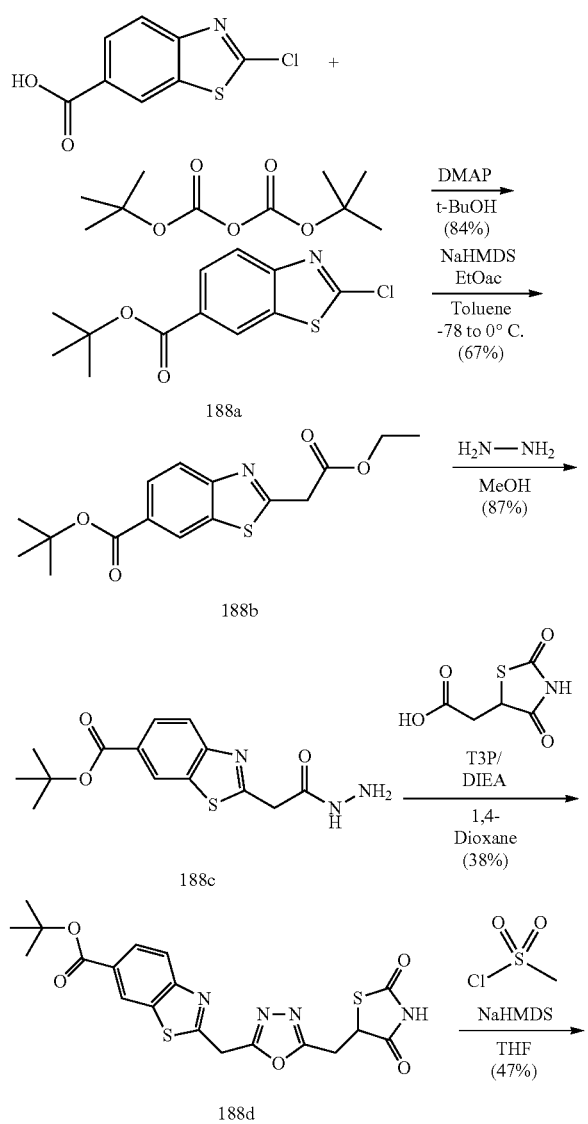

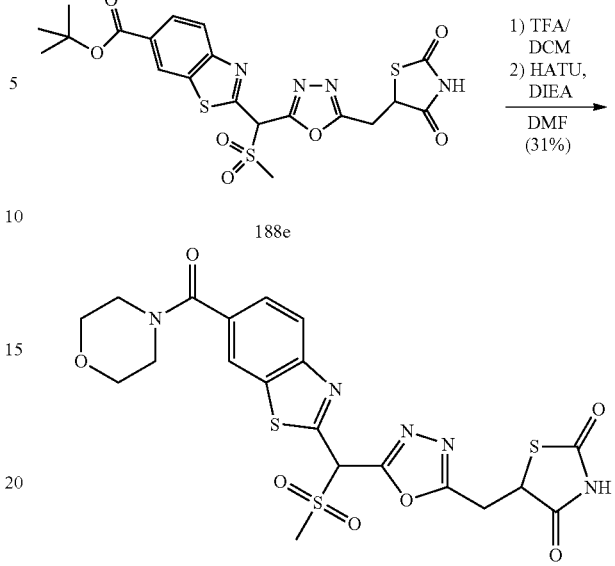

Compound 188a. tert-Butyl 2-chlorobenzo[d]thiazole-6-carboxylate

To a solution of di-tert-butyl dicarbonate (1.2 mL, 5.0 mmol) and 2-chlorobenzo[d]thiazole-6-carboxylic acid (0.53 g, 2.5 mmol) in anhydrous t-butanol (10 mL) was added dimethylaminopyridine (91 mg, 0.74 mmol) and the mixture stirred for 1 h. The reaction was concentrated under reduced pressure and purified by silica gel chromatography eluting with 0-50% EtOAc/hexanes to give Compound 188a (0.56 g, 84% yield) as a clear oil. LCMS=2.22 min using analytical method (B), 270.0 (M+H). $^1$H NMR (400 MHz, CDCl$_3$) δ 8.45 (d, J=1.5 Hz, 1H), 8.12 (dd, J=8.6, 1.8 Hz, 1H), 7.97 (d, J=8.6 Hz, 1H), 1.55-1.42 (m, 9H).

Compound 188b. tert-Butyl 2-(2-ethoxy-2-oxoethyl)benzo[d]thiazole-6-carboxylate

To a solution of sodium bis(trimethylsilyl)amide (4.9 mL of a 1M solution in THF, 4.90 mmol) in toluene (10 mL) at −78° C. was added dropwise ethyl acetate (0.26 mL, 2.7 mmol) and the mixture stirred for 1 h then a solution of Compound 188a (0.60 g, 2.2 mmol) in toluene (5 mL) was added over a 7 minute period. The resulting mixture was maintained at −78° C. for 1 h then slowly warmed to 0° C. over a period of 1.5 h. The reaction mixture was poured into a 1 N HCl solution and extracted with EtOAc. The combined extracts were washed with brine, dried over sodium sulfate, filtered and concentrated under reduced pressure. The residue was purified by silica gel chromatography eluting with 0-50% EtOAc/hexanes to give Compound 188b (480 mg, 67% yield) as a white solid. LCMS=2.13 min using analytical method (B), 322.0 (M+H). $^1$H NMR (400 MHz, CDCl$_3$) δ 8.57-8.52 (m, 1H), 8.11 (dd, J=8.6, 1.5 Hz, 1H), 8.04-7.98 (m, 1H), 4.32-4.25 (m, 2H), 4.20 (s, 2H), 1.63 (s, 9H), 1.32 (t, J=7.2 Hz, 3H).

Compound 188c. tert-Butyl 2-(2-hydrazinyl-2-oxoethyl)benzo[d]thiazole-6-carboxylate To a solution of Compound 188b (480 mg, 1.5 mmol) in methanol (15 mL) was added anhydrous hydrazine (0.19 mL, 6.0 mmol) and the mixture stirred for 16 h. The resulting precipitate was filtered, washed with three volumes of methanol and dried in vacuo to afford Compound 188c (400 mg, 87%) as white powder. LCMS=1.64 min using analytical method (B), 308.0 (M+H). $^1$H NMR (400 MHz, CD$_3$OD) δ 8.59 (d, J=1.1 Hz, 1H), 8.08 (dd, J=8.6, 1.8 Hz, 1H), 8.02-7.97 (m, 1H), 1.63 (s, 9H).

Compound 188d. tert-Butyl 2-((5-((2,4-dioxothiazolidin-5-yl)methyl)-1,3,4-oxadiazol-2-yl)methyl)benzo[d]thiazole-6-carboxylate Compound 188d was prepared from Compound 188c in 38% yield as a white solid using the general procedure given for Compound 1a. LCMS=1.88 min using analytical method (B), 447.0 (M+H). $^1$H NMR (400 MHz, CDCl$_3$) δ 8.54 (d, J=1.1 Hz, 1H), 8.14 (dd, J=8.6, 1.5 Hz, 1H), 8.04 (d, J=8.6 Hz, 1H), 4.82 (dd, J=9.2, 4.2 Hz, 1H), 4.76 (s, 2H), 3.82-3.76 (m, 1H), 3.49 (m, 1H), 1.64 (s, 9H).

Compound 188e. tert-Butyl 2-((5-((2,4-dioxothiazolidin-5-yl)methyl)-1,3,4-oxadiazol-2-yl)(methylsulfonyl)methyl)benzo[d]thiazole-6-carboxylate Compound 188e was prepared from Compound 188d in 47% yield as a yellow solid using the general procedure given for Example 1. LCMS=1.96 min using analytical method (B), 525.0 (M+H). $^1$H NMR (400 MHz, CDCl$_3$) δ 8.23 (d, J=1.1 Hz, 1H), 8.04 (dd, J=8.5, 1.4 Hz, 1H), 7.46 (d, J=8.4 Hz, 1H), 4.73 (dd, J=7.0, 4.8 Hz, 1H), 3.78-3.60 (m, 2H), 3.20 (s, 3H), 1.60 (s, 9H).

Example 188

To a solution of Compound 188e (40 mg, 0.076 mmol) in DCM (0.5 mL) was added TFA (0.5 mL) and the mixture stirred for 1 h. The mixture was evaporated under reduced pressure, the residue diluted with toluene and evaporated under reduced pressure (2×). To a solution of the residue in DMF (10 mL), was added morpholine (5.6 mg, 0.064 mmol), DIEA (11 µL, 0.064 mmol) and HATU (12 mg, 0.034 mmol) and the mixture stirred for 3 h. The mixture was poured into water (20 mL) and extracted with DCM (3×10 mL). The combined organic extracts were dried over Na$_2$SO$_4$, filtered and concentrated under reduced pressure. The residue was purified by silica gel chromatography eluting with 0-15% MeOH/DCM to give Example 188 (4.0 mg, 31% yield) as a clear oil. LCMS=1.33 min using analytical method (B), 538.0 (M+H). $^1$H NMR (400 MHz, CDCl$_3$) δ 7.67 (d, J=1.1 Hz, 1H), 7.52-7.48 (m, 1H), 7.42 (dd, J=8.3, 1.4 Hz, 1H), 4.76 (dd, J=7.9, 4.6 Hz, 1H), 3.82-3.52 (m, 10H), 3.20-3.15 (s, 3H). EL IC$_{50}$=212 nM. HL IC$_{50}$=20990 nM.

Example 189

N-((5-((Benzylsulfonyl)(6-(4-morpholinylcarbonyl)-1,3-benzothiazol-2-yl)methyl)-1,3,4-oxadiazol-2-yl)methyl)sulfamide

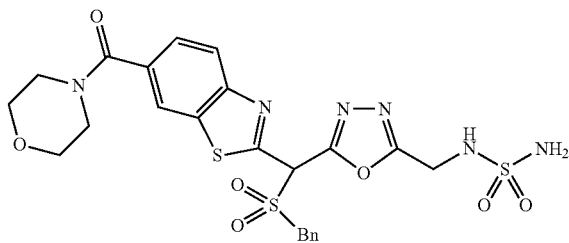 [SMILES: NS(=O)(=O)NCc1nnc(C(c2nc3ccc(C(=O)N4CCOCC4)cc3s2)S(=O)(=O)Cc2ccccc2)o1]

Example 189 was prepared by the general procedures described for Example 188. $^1$H NMR (400 MHz, CDCl$_3$) δ 7.63 (s, 1H), 7.55-7.50 (m, 1H), 7.45 (d, J=8.1 Hz, 1H), 7.29-7.21 (m, 5H), 4.52 (m, 4H), 3.76 (m, 8H). LCMS=1.46 min using analytical method (B), 593.1 (M+H). EL IC$_{50}$=13 nM. HL IC$_{50}$=2367 nM.

Example 190

2-((5-((2,4-Dioxo-1,3-thiazolidin-5-yl)methyl)-1,3,4-oxadiazol-2-yl)(methylsulfonyl)methyl)-1,3-benzothiazole-6-carbonitrile

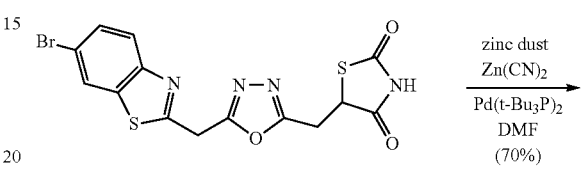

190a

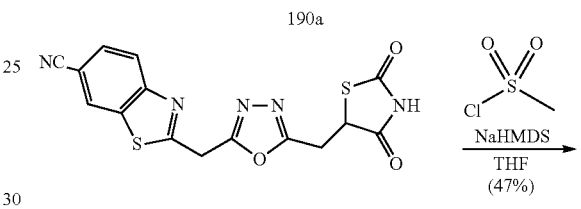

190b

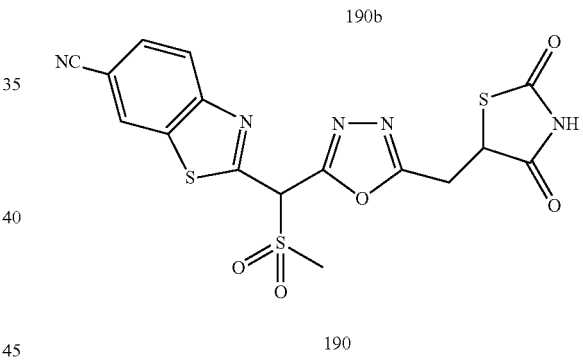

190

Compound 190b. 2-((5-((2,4-Dioxothiazolidin-5-yl)methyl)-1,3,4-oxadiazol-2-yl)methyl)benzo[d]thiazole-6-carbonitrile To a solution of Compound 190a (180 mg, 0.42 mmol, prepared as described for Example 1) in DMF (5.0 mL) was added zinc dust (8.30 mg, 0.13 mmol), zinc cyanide (99.0 mg, 0.85 mmol) and bis(tri-t-butylphosphine)palladium(0) (10.8 mg, 0.021 mmol). Nitrogen was bubbled through the mixture for 15 minutes then the mixture heated at 120° C. via microwave irradiation for 0.5 h. After cooling to rt, the reaction mixture was poured into ice water then extracted with EtOAc (2×). The combined extracts were washed with brine, dried over Na$_2$SO$_4$, filtered and concentrated under reduced pressure. The residue was purified by silica gel chromatography eluting with 0 to 40% EtOAc/hexanes to give Compound 190b (110 mg, 70% yield) as a white solid. LCMS=1.33 min using analytical method (B), 372.0 (M+H). $^1$H NMR (400 MHz, DMSO-d$_6$) δ 8.10 (m, 1H), 7.56-7.50 (m, 1H), 7.46 (m, 1H), 4.99 (m, 1H), 4.92 (s, 2H), 3.71-3.59 (m, 2H).

Example 190

Example 190 was prepared from Compound 190b in 25% yield as a white powder using the general procedure given for Example 1. LCMS=1.33 min using analytical method (B), 450.0 (M+H). $^1$H NMR (500 MHz, DMSO-d$_6$) δ 8.37 (s, 1H), 7.95 (d, J=7.7 Hz, 1H), 7.83 (d, J=8.0 Hz, 1H), 5.08-5.03 (m, 1H), 3.78-3.66 (m, 2H), 3.43-3.35 (m, 2H), 3.27 (s, 3H). EL IC$_{50}$<10 nM. HL IC$_{50}$=418 nM.

Example 191

3-(2-((5-((Sulfamoylamino)methyl)-1,3,4-oxadiazol-2-yl)((3,3,3-trifluoropropyl)sulfonyl)methyl)-1,3-benzothiazol-6-yl)benzoic acid

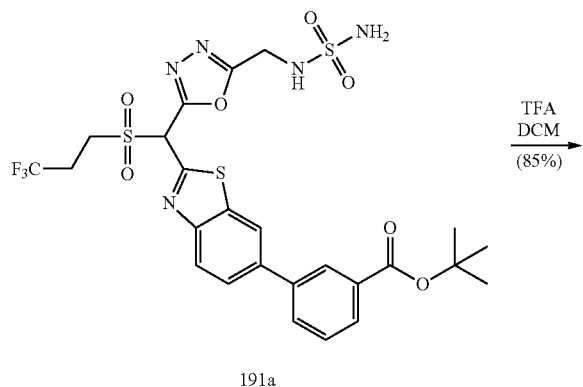

191a

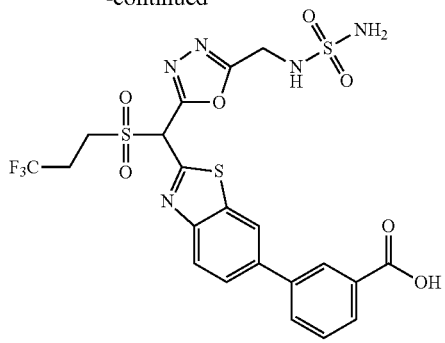

191

Example 191 was prepared from Compound 191a (prepared as described in the general procedure for Example 1) in 85% yield as a white solid using the procedure given for Example 26a. LCMS=2.04 min using analytical method (B), 605.9 (M+H). $^1$H NMR (500 MHz, DMSO-d$_6$) δ 8.29 (s, 1H), 8.22 (s, 1H), 7.95 (dd, J=7.7, 1.5 Hz, 3H), 7.78 (d, J=8.6 Hz, 1H), 7.62 (m, 1H), 7.52 (m, 1H), 6.81 (m, 2H), 4.38 (d, J=4.8 Hz, 2H), 3.69 (m, 2H), 2.85-2.70 (m, 2H). EL IC$_{50}$=15 nM. HL IC$_{50}$=2672 nM.

Example 192

N-((5-((6-(3-((3-Hydroxy-3-methyl-1-azetidinyl)carbonyl)phenyl)-1,3-benzothiazol-2-yl)((3,3,3-trifluoropropyl)sulfonyl)methyl)-1,3,4-oxadiazol-2-yl)methyl)sulfamide

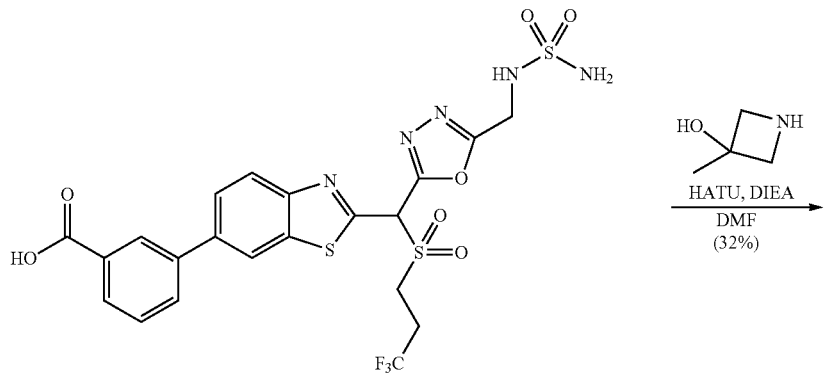

191

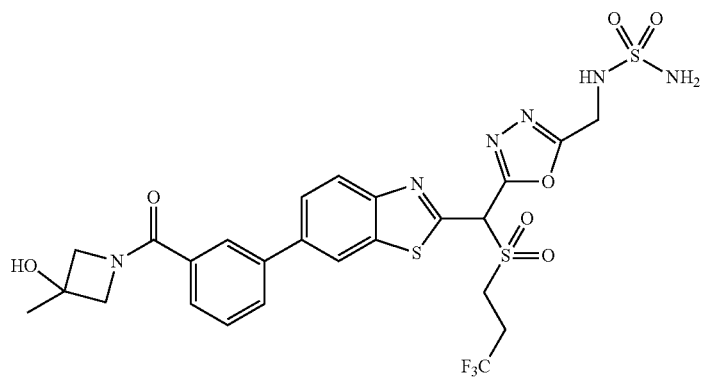

192

Example 192 was prepared from Example 191 in 32% yield as a yellow solid using the general procedure given for Example 188. LCMS=1.96 min using analytical method (O), 675.1 (M+H). $^1$H NMR (500 MHz, DMSO-$d_6$) δ 8.28 (s, 1H), 7.89 (s, 1H), 7.84 (d, J=8.0 Hz, 1H), 7.80-7.74 (m, 1H), 7.66-7.55 (m, 3H), 7.55-7.49 (m, 1H), 6.82 (s, 2H), 4.43-4.36 (m, 2H), 4.27-4.15 (m, 2H), 3.92 (s, 2H), 3.78-3.65 (m, 2H), 2.85-2.76 (m, 2H), 1.42 (s, 3H). EL IC$_{50}$<10 nM. HL IC$_{50}$=81 nM.

Examples 193-202 were prepared by the general procedures given for Example 192.

Example 203 was prepared by the general procedures given for Example 1.

Examples 204-232 were prepared by the general procedures given for Example 1 and Example 192.

Examples 233-249 were prepared by the general procedures given for Example 46.

Example 250 was prepared by the general procedures give for Example 175.

Examples 251-267 were prepared by the general procedures given for Example 192.

Additionally, intermediates Compound 244a and Compound 224b were prepared as shown below:

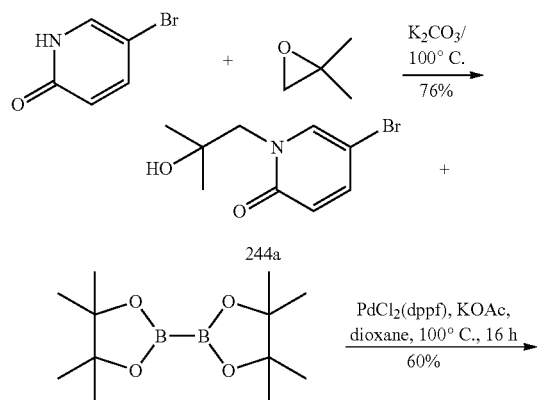

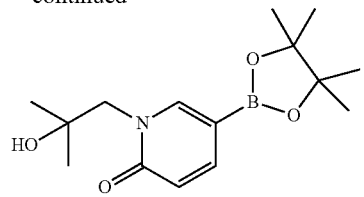

244b

Compound 244a. 5-bromo-1-(2-hydroxy-2-methyl-propyl)pyridin-2(1H)-one

A mixture of 5-bromopyridin-2(1H)-one (600 mg, 3.5 mmol), 2,2-dimethyloxirane (750 mg, 10.4 mmol) and K$_2$CO$_3$ (960 mg, 6.9 mmol) in DMF (3 mL) was heated at 100° C. for 2 hours. The reaction mixture was allowed to cool to room temperature. The reaction mixture was diluted with ethyl acetate (80 mL), washed with water, brine, and dried over MgSO$_4$. The organic layer was filtered and concentrated under reduced pressure. The residue was purified by silica gel chromatography (eluting with 10 to 50% EtOAc/hexane) to give Compound 244a (650 mg, 76% yield). $^1$H NMR (400 MHz, CDCl$_3$) δ 7.50 (d, J=2.6 Hz, 1H), 7.40 (dd, J=9.6, 2.8 Hz, 1H), 6.54 (d, J=9.7 Hz, 1H), 3.99 (s, 2H), 3.57-3.39 (s, 1H), 1.27 (s, 6H).

Compound 244b. 1-(2-hydroxy-2-methylpropyl)-5-(4,4,5,5-tetramethyl-1,3,2-dioxaborolan-2-yl)pyridin-2(1H)-one To a solution of Compound 244a (500 mg, 2.0 mmol) was added bis(pinacolato)diboron (1.0 g, 4.1 mmol), PdCl$_2$(dppf)-CH$_2$Cl$_2$ adduct (166 mg, 0.200 mmol) and potassium acetate (995 mg, 10.1 mmol). The reaction mixture was heated at 100° C. for 16 hours. The reaction mixture was allowed to cool to room temperature and concentrated under reduced pressure. The residue was purified by silica gel chromatography (eluting with 0-10% MeOH) to give Compound 244b (356 mg, 1.20 mmol, 60% yield). $^1$H NMR (400 MHz, CDCl$_3$) δ 7.83-7.59 (m, 2H), 6.59 (d, J=9.0 Hz, 1H), 4.10-3.94 (m, 2H), 1.46-1.19 (m, 18H).

| Ex. No. | Structure | Name | ¹H NMR | LC/MS RT (min) Method M + H | EL IC$_{50}$ (nM) | HL IC$_{50}$ (nM) |
|---|---|---|---|---|---|---|
| 176 | 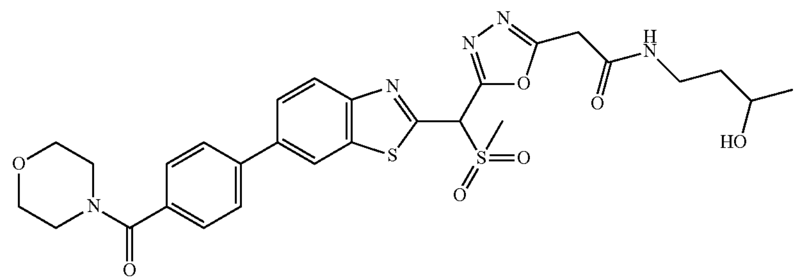 [SMILES: CC(O)CCNC(=O)Cc1nnc(C(c2nc3ccc(-c4ccc(C(=O)N5CCOCC5)cc4)cc3s2)S(C)(=O)=O)o1] | N-(3-hydroxybutyl)-2-(5-((methylsulfonyl)(6-(4-(4-morpholinylcarbonyl)phenyl)-1,3-benzothiazol-2-yl)methyl)-1,3,4-oxadiazol-2-yl)acetamide | ¹H NMR (400 MHz, CD$_3$OD) δ 7.95 (d, J = 1.3 Hz, 1H), 7.75-7.62 (m, 4H), 7.56-7.46 (m, 2H), 3.96-3.89 (m, 2H), 3.87-3.46 (m, 11H), 3.26 (s, 2H), 1.69-1.58 (m, 1H), 1.44-1.36 (m, 1H), 1.23-1.13 (m, 3H) | 1.58 B 614.2 | 10 | 465 |
| 177 | 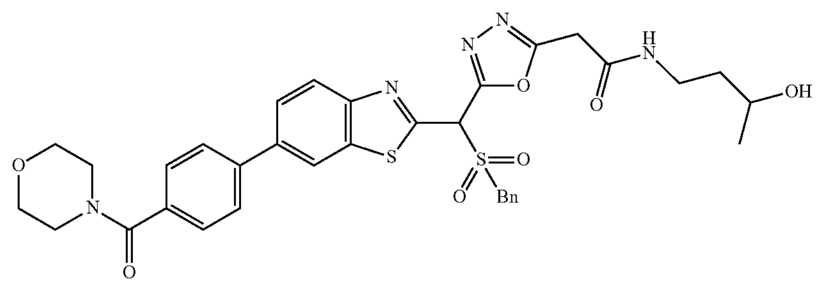 [SMILES: CC(O)CCNC(=O)Cc1nnc(C(c2nc3ccc(-c4ccc(C(=O)N5CCOCC5)cc4)cc3s2)S(=O)(=O)Cc2ccccc2)o1] | 2-(5-((benzylsulfonyl)(6-(4-(4-morpholinylcarbonyl)phenyl)-1,3-benzothiazol-2-yl)methyl)-1,3,4-oxadiazol-2-yl)-N-(3-hydroxybutyl)acetamide | ¹H NMR (400 MHz, CD$_3$OD) δ 7.93 (s, 1H), 7.74 (d, J = 8.4 Hz, 3H), 7.52 (d, J = 8.4 Hz, 2H), 7.32 (d, J = 6.8 Hz, 2H), 7.21 (d, J = 6.8 Hz, 2H), 4.61 (s, 1H), 3.96 (s, 2H), 3.86-3.48 (m, 10H), 1.18 (d, J = 6.2 Hz, 3H) | 1.84 B 690.2 | 14 | 591 |
| 178 | 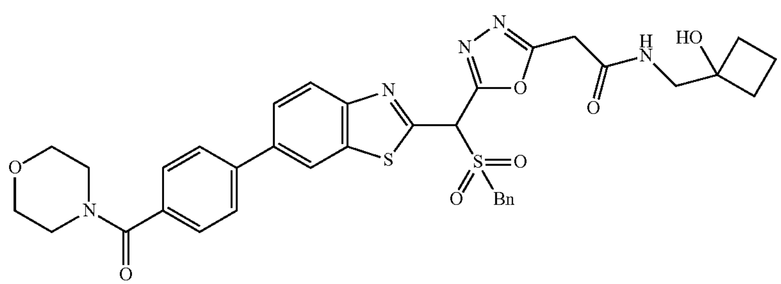 [SMILES: O=C(Cc1nnc(C(c2nc3ccc(-c4ccc(C(=O)N5CCOCC5)cc4)cc3s2)S(=O)(=O)Cc2ccccc2)o1)NCC1(O)CCC1] | 2-(5-((benzylsulfonyl)(6-(4-(4-morpholinylcarbonyl)phenyl)-1,3-benzothiazol-2-yl)methyl)-1,3,4-oxadiazol-2-yl)-N-((1-hydroxycyclobutyl)methyl)acetamide | ¹H NMR (400 MHz, CD$_3$OD) δ 7.76 (s, 1H), 7.69-7.60 (m, 3H), 7.57-7.46 (m, 4H), 7.31-7.25 (m, 2H), 7.20 (d, J = 5.9 Hz, 3H), 3.97 (s, 2H), 3.87-3.51 (m, 7H), 3.47-3.40 (m, 2H), 2.11-1.99 (m, 4H), 1.82-1.68 (m, 1H), 1.63-1.50 (m, 1H) | 1.87 B 707.2 | <10 | 277 |

| Ex. No. | Structure | Name | ¹H NMR | LC/MS RT (min) Method M + H | EL IC₅₀ (nM) | HL IC₅₀ (nM) |
|---|---|---|---|---|---|---|
| 179 | 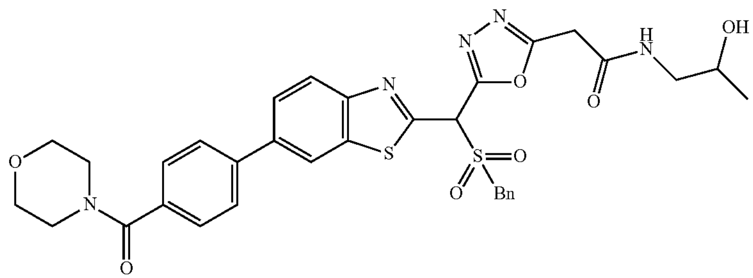 [SMILES: CC(O)CNC(=O)Cc1nnc(C(c2nc3ccc(-c4ccc(C(=O)N5CCOCC5)cc4)cc3s2)S(=O)(=O)Cc2ccccc2)o1] | 2-(5-((benzylsulfonyl)(6-(4-(4-morpholinylcarbonyl)phenyl)-1,3-benzothiazol-2-yl)methyl)-1,3,4-oxadiazol-2-yl)-N-(2-hydroxypropyl)acetamide | ¹H NMR (400 MHz, CD₃OD) δ 7.91 (d, J = 1.5 Hz, 1H), 7.75-7.72 (m, 2H), 7.70-7.66 (m, 1H), 7.63-7.58 (m, 1H), 7.55-7.50 (m, 2H), 7.32 (dd, J = 7.6, 1.7 Hz, 2H), 7.21 (d, J = 7.0 Hz, 2H), 4.62 (s, 2H), 4.01 (s, 2H), 3.90 (td, J = 6.7, 4.6 Hz, 1H), 3.84-3.60 (m, 8H), 3.24-3.18 (m, 1H), 1.20 (d, J = 6.4 Hz, 3H) | 1.78 B 676.2 | <10 | 518 |
| 180 | 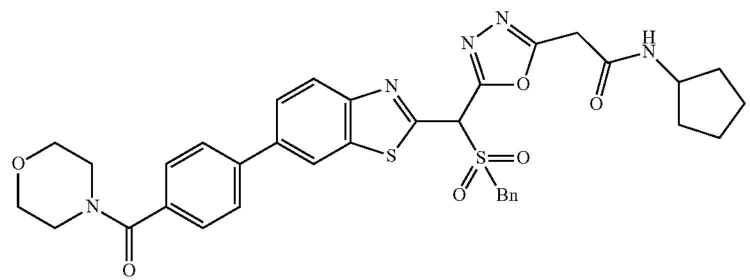 [SMILES: O=C(Cc1nnc(C(c2nc3ccc(-c4ccc(C(=O)N5CCOCC5)cc4)cc3s2)S(=O)(=O)Cc2ccccc2)o1)NC1CCCC1] | 2-(5-((benzylsulfonyl)(6-(4-(4-morpholinylcarbonyl)phenyl)-1,3-benzothiazol-2-yl)methyl)-1,3,4-oxadiazol-2-yl)-N-cyclopentylacetamide | ¹H NMR (400 MHz, CD₃OD) δ 7.72 (d, J = 1.5 Hz, 1H), 7.66-7.59 (m, 3H), 7.56-7.47 (m, 3H), 7.27-7.18 (m, 5H), 4.51 (s, 2H), 3.84-3.63 (m, 9H), 2.11-1.98 (m, 3H), 1.50 (dt, J = 12.2, 6.2 Hz, 3H) | 2.10 B 686.2 | <10 | 44 |
| 184 | 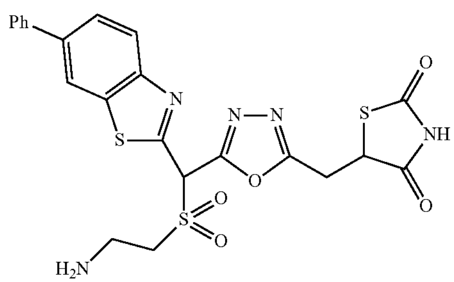 [SMILES: NCCS(=O)(=O)C(c1nnc(CC2SC(=O)NC2=O)o1)c1nc2ccc(-c3ccccc3)cc2s1] | 5-((5-(((2-aminoethyl)sulfonyl)(6-phenyl-1,3-benzothiazol-2-yl)methyl)-1,3,4-oxadiazol-2-yl)methyl)-1,3-thiazolidine-2,4-dione | ¹H NMR (400 MHz, DMF-d₇) δ 8.32 (s, 1H), 8.12 (d, J = 8.6 Hz, 1H), 7.85 (d, J = 8.6 Hz, 1H), 7.80 (d, J = 7.7 Hz, 2H), 7.62-7.48 (m, 2H), 7.43 (s, 1H), 5.21 (d, J = 4.2 Hz, 1H), 4.06 (br. s., 2H), 3.87 (d, J = 4.4 Hz, 1H), 3.79 (d, J = 8.4 Hz, 2H) | 1.12 M 530.0 | <10 | <10 |

| Ex. No. | Structure | Name | ¹H NMR | LC/MS RT (min) Method M + H | EL IC₅₀ (nM) | HL IC₅₀ (nM) |
|---|---|---|---|---|---|---|
| 185 | 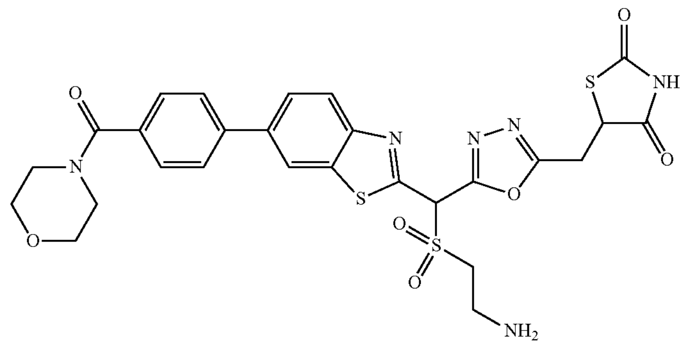 [SMILES: NCCS(=O)(=O)C(c1nnc(CC2SC(=O)NC2=O)o1)c1nc2ccc(-c3ccc(C(=O)N4CCOCC4)cc3)cc2s1] | 5-{[5-(((2-aminoethyl) sulfonyl][6-[4-(4-morpholinylcarbonyl) phenyl]-1,3-benzothiazol-2-yl[methyl]-1,3,4-oxadiazol-2-yl]methyl]-1,3-thiazolidine-2,4-dione | ¹H NMR (400 MHz, CD₃OD) δ 8.10 (s, 1H), 7.78 (dd, J = 5.0, 3.4 Hz, 4H), 7.63-7.44 (m, 2H), 5.00 (dd, J = 7.2, 5.0 Hz, 1H), 3.94-3.43 (m, 18H) | 0.86 M 643.2 | <10 | 70 |
| 186 | 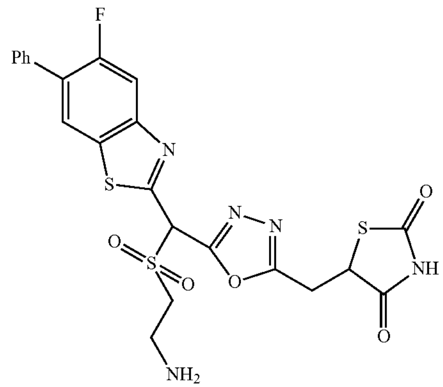 [SMILES: NCCS(=O)(=O)C(c1nnc(CC2SC(=O)NC2=O)o1)c1nc2cc(F)c(-c3ccccc3)cc2s1] | 5-((5-(((2-aminoethyl) sulfonyl)(5-fluoro-6-phenyl-1,3-benzothiazol-2-yl)methyl)-1,3,4-oxadiazol-2-yl)methyl)-1,3-thiazolidine-2,4-dione | ¹H NMR (400 MHz, CD₃OD) δ = 8.01-7.69 (m, 1H), 7.68-7.52 (m, 3H), 7.50-7.37 (m, 3H), 5.00 (dd, J = 7.0, 4.8 Hz, 1H), 4.93-4.86 (m, 1H), 3.85-3.61 (m, 3H), 3.58-3.35 (m, 2H) | 1.84 Q 548.1 | <10 | 49 |
| 187 | 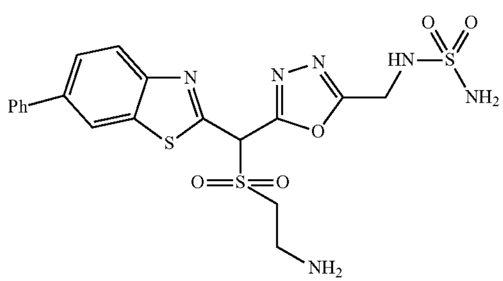 [SMILES: NCCS(=O)(=O)C(c1nnc(CNS(N)(=O)=O)o1)c1nc2ccc(-c3ccccc3)cc2s1] | N-[(5-{[(2-aminoethyl) sulfonyl](6-phenyl-1,3-benzothiazol-2-yl)methyl]-1,3,4-oxadiazol-2-yl)methyl] sulfuric diamide | ¹H NMR (500 MHz, DMSO-d₆) δ 8.24 (br. s., 1H), 8.06-7.86 (m,4H), 7.77 (d, J = 8.0 Hz, 1H), 7.71 (d, J = 7.4 Hz, 2H), 7.56-7.45 (m, 3H), 7.41 (d, J = 7.2 Hz, 1H), 6.82 (s, 2H), 4.40 (d, J = 5.5 Hz, 2H), 3.74 (br. s., 2H), 3.25 (br. s., 2H) | 1.36 N 509.2 | <10 | 12 |

| Ex. No. | Structure | Name | ¹H NMR | LC/MS RT (min) Method M+H | EL IC₅₀ (nM) | HL IC₅₀ (nM) |
|---|---|---|---|---|---|---|
| 193 | 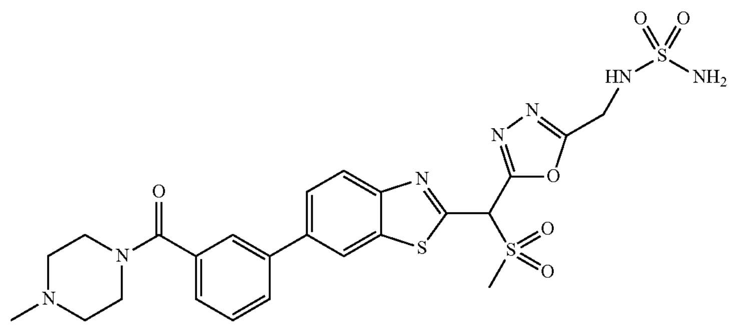 [SMILES: CN1CCN(C(=O)c2cccc(-c3ccc4nc(C(c5nnc(CNS(N)(=O)=O)o5)S(C)(=O)=O)sc4c3)c2)CC1] | N-((5-(6-(3-((4-methyl-1-piperazinyl)carbonyl)phenyl)-1,3-benzothiazol-2-yl)(methylsulfonyl)methyl)-1,3,4-oxadiazol-2-yl)methyl)sulfamide | ¹H NMR (400 MHz, CD₃OD) δ 7.96 (s, 1H), 7.85 (d, J = 13.2 Hz, 1H), 7.80-7.73 (m, 1H), 7.68-7.44 (m, 4H), 4.51 (s, 2H), 3.35 (s, 7H), 3.28 (s, 3H), 2.98 (s, 3H) | 1.26 B 606.0 | <10 | 105 |
| 194 | 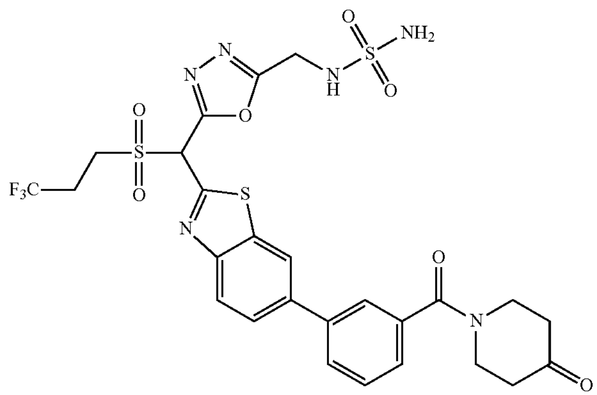 [SMILES: NS(=O)(=O)NCc1nnc(C(c2nc3ccc(-c4cccc(C(=O)N5CCC(=O)CC5)c4)cc3s2)S(=O)(=O)CCC(F)(F)F)o1] | N-((5-(6-(3-((4-oxo-1-piperidinyl)carbonyl)phenyl)-1,3-benzothiazol-2-yl)(3,3,3-trifluoropropyl)sulfonyl)methyl)-1,3,4-oxadiazol-2-yl)methyl)sulfamide | ¹H NMR (400 MHz, CDCl₃) δ 7.85 (s, 1H), 7.73-7.66 (m, 3H), 7.64-7.54 (m, 3H), 7.48 (d, J = 7.5 Hz, 1H), 5.15 (m, 1H), 4.67 (m, 2H), 4.06 (m, 1H), 3.94-3.74 (m, 2H), 3.61-3.47 (m, 2H), 2.79-2.37 (m, 6H) | 1.86 B 687.1 | <10 | 171 |

| Ex. No. | Structure | Name | ¹H NMR | LC/MS RT (min) Method M+H | EL IC₅₀ (nM) | HL IC₅₀ (nM) |
|---|---|---|---|---|---|---|
| 195 | 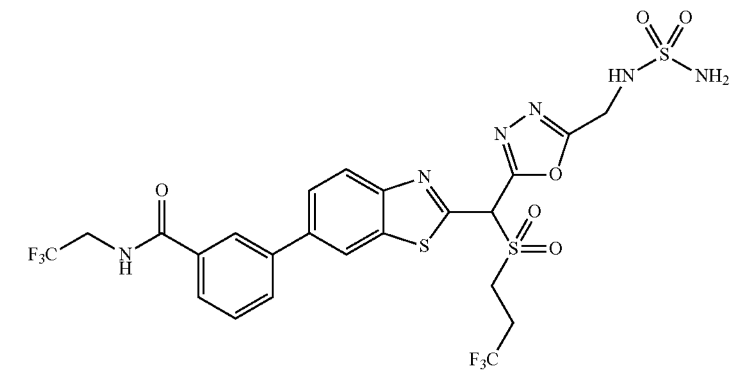 [SMILES: NS(=O)(=O)NCc1nnc(C(c2nc3ccc(-c4cccc(C(=O)NCC(F)(F)F)c4)cc3s2)S(=O)(=O)CCC(F)(F)F)o1] | 3-(2-((5-(((sulfamoylamino)methyl)-1,3,4-oxadiazol-2-yl)((3,3,3-trifluoropropyl)sulfonyl)methyl)-1,3-benzothiazol-6-yl)-N-(2,2,2-trifluoroethyl)benzamide | ¹H NMR (500 MHz, DMSO-d₆) δ 9.21 (br. s., 1H), 8.28 (br. s., 1H), 8.21 (br. s., 1H), 7.90 (m, 2H), 7.82 (d, J = 7.2 Hz, 1H), 7.65-7.59 (m, 1H), 7.48 (br. s., 1H), 6.77 (m, 2H), 4.38 (m, 2H), 4.18-4.10 (m, 2H), 3.70 (m, 2H) | 1.73 O 687.0 | <10 | 336 |
| 196 | 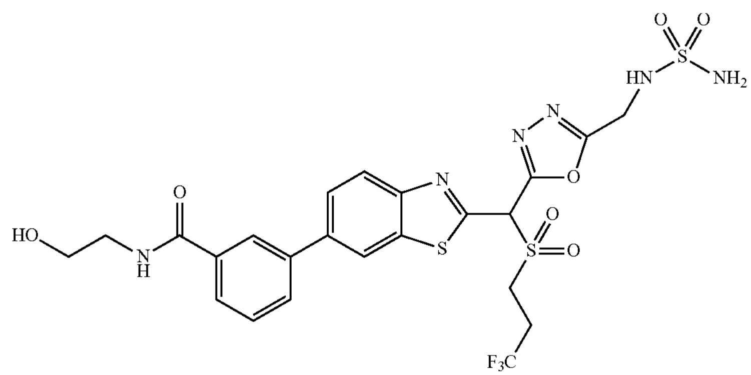 [SMILES: NS(=O)(=O)NCc1nnc(C(c2nc3ccc(-c4cccc(C(=O)NCCO)c4)cc3s2)S(=O)(=O)CCC(F)(F)F)o1] | N-(2-hydroxyethyl)-3-(2-((5-(((sulfamoylamino)methyl)-1,3,4-oxadiazol-2-yl)((3,3,3-trifluoropropyl)sulfonyl)methyl)-1,3-benzothiazol-6-yl)benzamide | ¹H NMR (500 MHz, DMSO-d₆) δ 8.61-8.52 (m, 1H), 8.16 (br. s., 1H), 7.82 (m, 2H), 7.61-7.38 (m, 2H), 6.80 (m, 2H), 4.81-4.71 (m, 1H), 4.42-4.28 (m, 2H), 3.90 (s, 6H) | 1.46 O 649.1 | <10 | 209 |

| Ex. No. | Structure | Name | $^1$H NMR | LC/MS RT (min) Method M+H | EL IC$_{50}$ (nM) | HL IC$_{50}$ (nM) |
|---|---|---|---|---|---|---|
| 197 | 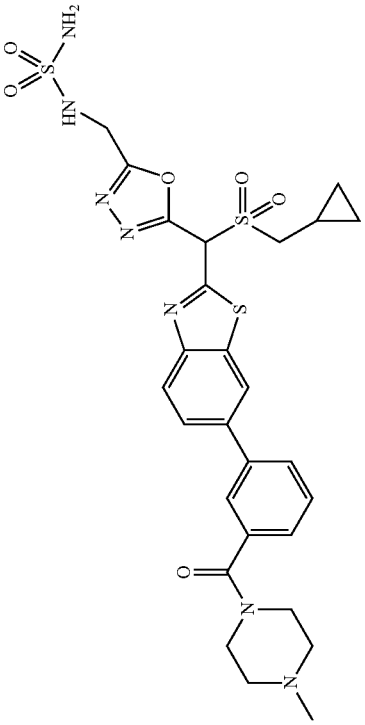 | N-((5-(((cyclopropylmethyl)sulfonyl)(6-(3-((4-methyl-1-piperazinyl)carbonyl)phenyl)-1,3-benzothiazol-2-yl)methyl)-1,3,4-oxadiazol-2-yl)methyl)sulfamide | $^1$H NMR (500 MHz, DMSO-$d_6$) δ 8.23 (s, 1H), 7.97 (d, J = 8.5 Hz, 1H), 7.83 (d, J = 7.7 Hz, 1H), 7.75 (d, J = 1.1 Hz, 1H), 7.60 (m, 1H), 7.54-7.43 (m, 2H), 6.78 (m, 2H), 4.39 (m, 2H), 3.54-3.05 (m, 8H), 2.85 (s, 3H), 1.01 (m, 1H), 0.46 (d, J = 7.4 Hz, 3H), 0.25 (d, J = 4.4 Hz, 3H) | 1.42 B 646.2 | <10 | 2566 |
| 198 | 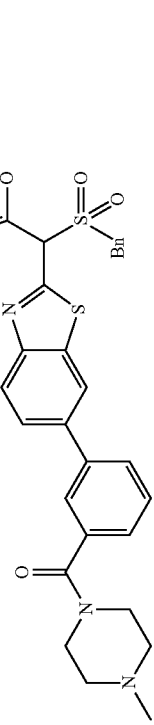 | N-((5-((benzylsulfonyl)(6-(3-((4-methyl-1-piperazinyl)carbonyl)phenyl)-1,3-benzothiazol-2-yl)methyl)-1,3,4-oxadiazol-2-yl)methyl)sulfamide | $^1$H NMR (500 MHz, DMSO-$d_6$) δ 7.89 (d, J = 8.0 Hz, 1H), 7.78 (d, J = 8.0 Hz, 1H), 7.73-7.67 (m, 2H), 7.58 (m, 2H), 7.44 (d, J = 7.4 Hz, 1H), 7.30 (m, 1H), 7.24 (m, 2H), 4.72 (m, 2H), 4.42 (m,, 2H), 2.90 (s, 3H), 3.62-2.92 (m, 8H) | 1.48 B 682.2 | <10 | 9180 |

| Ex. No. | Structure | Name | LC/MS RT (min) Method M+H | EL IC$_{50}$ (nM) | HL IC$_{50}$ (nM) |
|---|---|---|---|---|---|
| 199 | 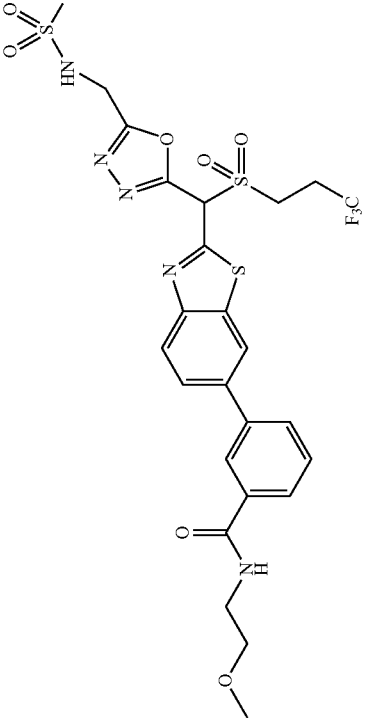 | N-(2-methoxyethyl)-3-(2-((5-((sulfamoyl)amino)methyl)-1,3,4-oxadiazol-2-yl)(3,3,3-trifluoropropyl)sulfonyl)methyl)-1,3-benzothiazol-6-yl)benzamide | 1.82 B 663.1 | <10 | 1025 |
| | | $^1$H NMR (500 MHz, DMSO-d$_6$) δ 8.70-8.62 (m, 1H), 8.27 (s, 1H), 8.17 (s, 1H), 7.95 (d, J = 8.3 Hz, 1H), 7.87-7.79 (m, 3H), 7.57 (m, 1H), 7.49 (m, 1H), 6.77 (br. s., 2H), 4.38 (m, 2H), 3.69 (m, 3H), 3.50-3.43 (m, 5H), 3.28 (s, 3H) | | | |
| 200 | 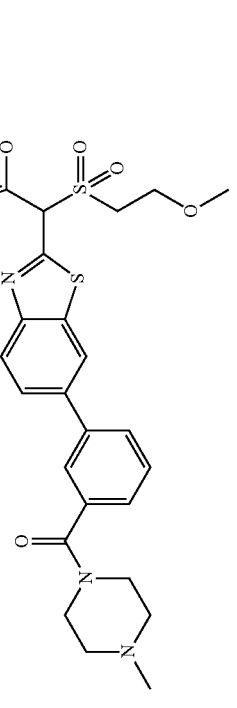 | N-((5-(((2-methoxyethyl)sulfonyl)(6-(3-((4-methyl-1-piperazinyl)carbonyl)phenyl)-1,3-benzothiazol-2-yl)methyl)-1,3,4-oxadiazol-2-yl)methyl)sulfamide | 1.04 O 650.1 | <10 | 201 |
| | | $^1$H NMR (500 MHz, DMSO-d$_6$) δ 8.25-8.13 (m, 1H), 7.80 (m, 2H), 7.69 (m, 2H), 7.60-7.47 (m, 3H), 7.38 (m, 1H), 6.85 (m, 2H), 4.36 (m, 2H), 3.71 (m, 8H), 3.15 (s, 3H), 2.32 (m, 4H), 1.92 (s, 3H) | | | |

| Ex. No. | Structure | Name | ¹H NMR | LC/MS RT (min) Method M+H | EL IC₅₀ (nM) | HL IC₅₀ (nM) |
|---|---|---|---|---|---|---|
| 201 | 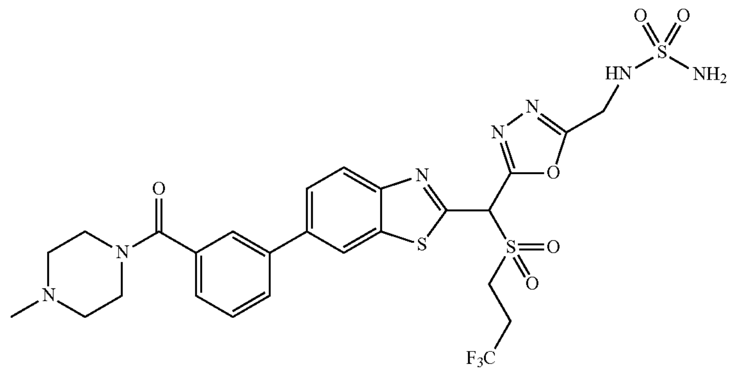 [SMILES: CN1CCN(C(=O)c2cccc(-c3ccc4nc(C(c5nnc(CNS(N)(=O)=O)o5)S(=O)(=O)CCC(F)(F)F)sc4c3)c2)CC1] | N-((5-(6-(3-((4-methyl-1-piperazinyl)carbonyl)phenyl)-1,3-benzothiazol-2-yl)(3,3,3-trifluoropropyl)sulfonyl)methyl)-1,3,4-oxadiazol-2-yl)methyl)sulfamide | ¹H NMR (500 MHz, DMSO-d₆) δ 8.27 (s, 1H), 7.96 (m, 2H), 7.84 (d, J = 8.0 Hz, 1H), 7.79 (d, J = 9.4 Hz, 1H), 7.76 (s, 1H), 7.62 (m, 1H), 7.53 (m, 1H), 7.48 (s, 1H), 6.82 (m, 2H), 4.40 (s, 2H), 3.71 (m, 4H), 3.29-3.02 (m, 4H), 2.84 (s, 3H), 2.86-2.75 (m, 3H) | 1.30 O 688.1 | <10 | 365 |
| 202 | 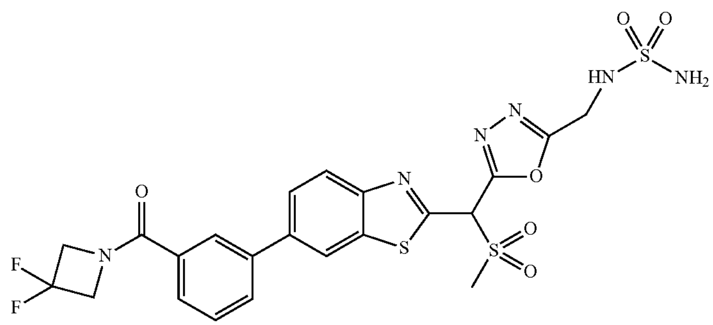 [SMILES: CS(=O)(=O)C(c1nnc(CNS(N)(=O)=O)o1)c1nc2ccc(-c3cccc(C(=O)N4CC(F)(F)C4)c3)cc2s1] | N-((5-(6-(3-((3,3-difluoro-1-azetidinyl)carbonyl)phenyl)-1,3-benzothiazol-2-yl)(methylsulfonyl)(methyl)methyl)-1,3,4-oxadiazol-2-yl)methyl)sulfamide | ¹H NMR (400 MHz, CDCl₃) δ 7.90 (br. s., 1H), 7.84 (s, 1H), 7.73 (m, 1H), 7.69-7.64 (m, 1H), 7.62-7.51 (m, 3H), 4.73-4.55 (m, 6H), 4.16 (8, 3H) | 1.69 B 599.0 | <10 | 35 |
| 203 | 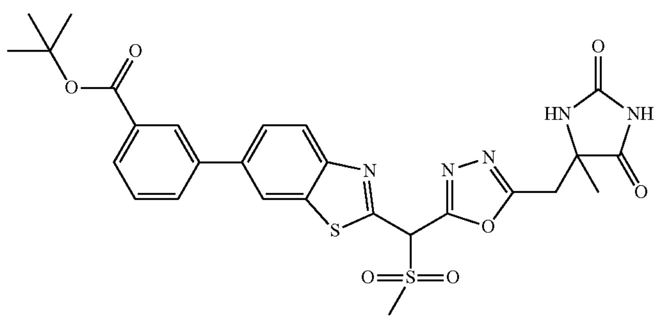 [SMILES: CC(C)(C)OC(=O)c1cccc(-c2ccc3nc(C(c4nnc(CC5(C)NC(=O)NC5=O)o4)S(C)(=O)=O)sc3c2)c1] | tert-butyl 3-{2-[methanesulfonyl({5-[(4-methyl-2,5-dioxoimidazolidin-4-yl)methyl]-1,3,4-oxadiazol-2-yl}methyl)]-1,3-benzothiazol-6-yl}benzoate | ¹H NMR (500 MHz, DMSO-d₆) δ 10.75-10.69 (m, 1H), 8.26 (d, J = 9.6 Hz, 1H), 8.20-8.01 (m, 2H), 8.01-7.89 (m, 3H), 7.82-7.54 (m, 2H), 3.40 (d, J = 6.9 Hz, 2H), 3.31-3.22 (m, 3H), 1.60 (s, 9H), 1.47 (s, 3H) | 1.96 O 598.2 | 33 | 2 |

| Ex. No. | Structure | Name | ¹H NMR | LC/MS RT (min) Method M+H | EL IC₅₀ (nM) | HL IC₅₀ (nM) |
|---|---|---|---|---|---|---|
| 204 | 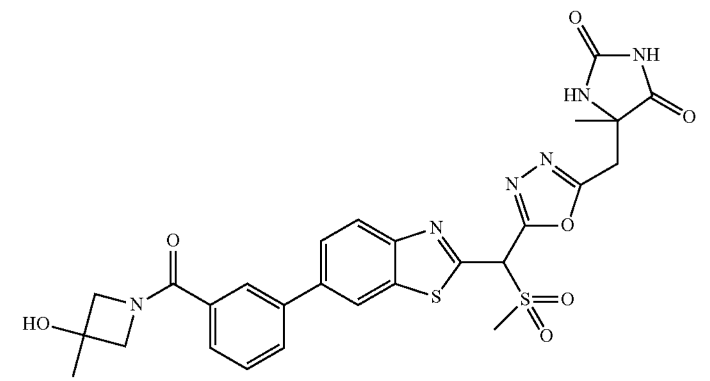 [SMILES: CC1(O)CN(C(=O)c2cccc(-c3ccc4nc(C(c5nnc(CC6(C)NC(=O)NC6=O)o5)S(C)(=O)=O)sc4c3)c2)C1] | 5-[{5-({6-[3-(3-hydroxy-3-methylazetidine-1-carbonyl)phenyl]-1,3-benzothiazol-2-yl}(methanesulfonyl(methyl))-1,3,4-oxadiazol-2-yl]methyl}-5-methyl imidazolidine-2,4-dione | ¹H NMR (500 MHz, DMSO-d₆) δ 12.71-8.45 (m, 2H), 8.32- 8.16 (m, 1H), 8.13-8.04 (m, 1H), 7.98-7.81 (m, 3H), 7.78-7.54 (m, 3H), 5.69 (s, 1H), 4.28-4.10 (m, 2H), 4.01-3.88 (m, 3H), 3.40 (d, J = 6.6 Hz, 1H), 3.30-3.27 (m, 2H), 1.48-1.45 (m, 2H), 1.43 (s, 3H) | 1.23 O 611.1 | 17 | 783 |
| 205 | 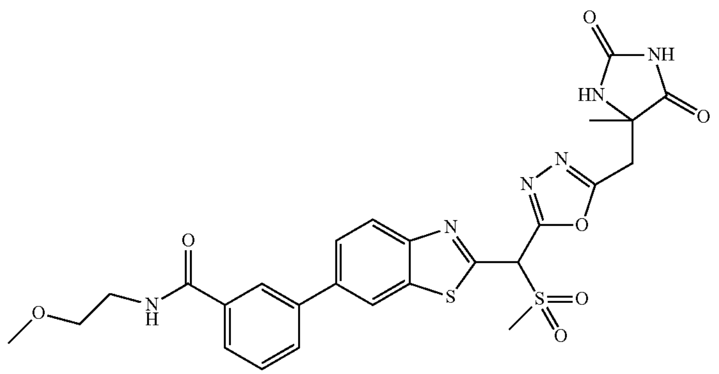 [SMILES: COCCNC(=O)c1cccc(-c2ccc3nc(C(c4nnc(CC5(C)NC(=O)NC5=O)o4)S(C)(=O)=O)sc3c2)c1] | 3-{2-[methanesulfonyl({5-[(4-methyl-2,5-dioxoimidazolidin-4-yl)methyl]-1,3,4-oxadiazol-2-yl})methyl]-1,3-benzothiazol-6-yl}-N-(2-methoxyethyl)benzamide | ¹H NMR (500 MHz, DMSO-d₆) δ 11.14-10.55 (m, 1H), 8.77-8.54 (m, 1H), 8.37-8.16 (m, 2H), 8.13-8.06 (m, 1H), 8.04-7.78 (m, 4H), 7.66-7.55 (m, 1H), 3.92 (s, 1H), 3.54-3.35 (m, 4H), 3.33-3.26 (m, 5H), 1.66-1.31 (m, 3H) | 1.28 O 599.1 | 18 | 449 |

| Ex. No. | Structure | Name | ¹H NMR | LC/MS RT (min) Method M + H | EL IC₅₀ (nM) | HL IC₅₀ (nM) |
|---|---|---|---|---|---|---|
| 206 | 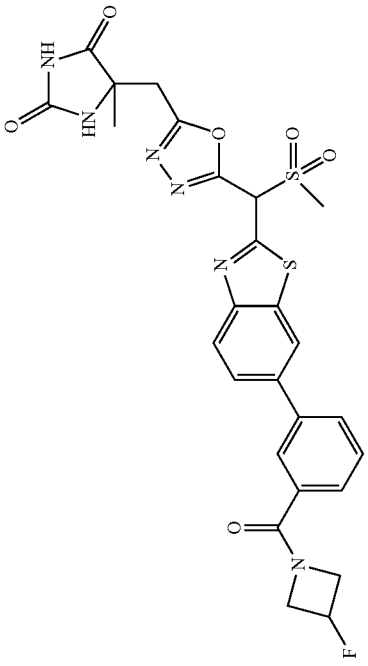 | 5-{[5-({6-[3-(3-fluoroazetidine-1-carbonyl)phenyl]-1,3-benzothiazol-2-yl}methanesulfonyl)methyl]-1,3,4-oxadiazol-2-yl]methyl}-5-methyl imidazolidine-2,4-dione | ¹H NMR (500 MHz, DMSO-d₆) δ 12.99-8.40 (m, 2H), 8.36-8.19 (m, 1H), 8.09 (br. s., 1H), 8.03-7.52 (m, 9H), 4.76-4.04 (m, 4H), 3.91 (br. s., 2H), 1.55-1.40 (m, 4H) | 1.24 O 599.1 | 16 | 125 |
| 207 | 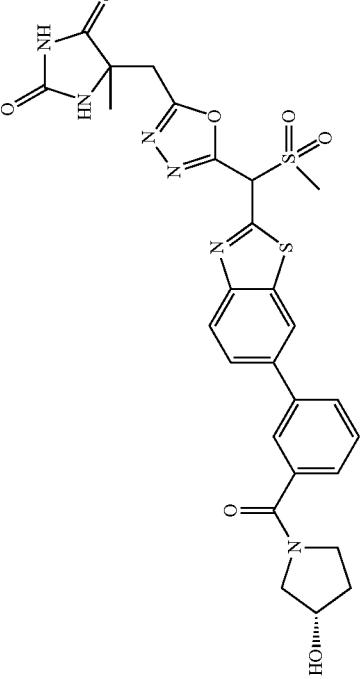 | 5-({5-[6-[(3S)-3-hydroxypyrrolidine-1-carbonyl]phenyl}-1,3-benzothiazol-2-yl)(methanesulfonyl)methyl]-1,3,4-oxadiazol-2-yl}methyl)-5-methyl imidazolidine-2,4-dione | ¹H NMR (500 MHz, DMSO-d₆) δ 13.03-8.53 (m, 2H), 8.31-8.20 (m, 1H), 8.15-8.04 (m, 1H), 8.01-7.86 (m, 2H), 7.84-7.73 (m, 2H), 7.65-7.46 (m, 2H), 4.52-4.20 (m, 1H), 3.92 (s, 2H), 3.70-3.56 (m, 3H), 3.41-3.34 (m, 4H), 3.31-3.23 (m, 3H), 1.55-1.39 (m, 3H) | 1.06 O 611.2 | 22 | 370 |

| Ex. No. | Structure | Name | ¹H NMR | LC/MS RT (min) Method M + H | EL IC₅₀ (nM) | HL IC₅₀ (nM) |
|---|---|---|---|---|---|---|
| 208 | 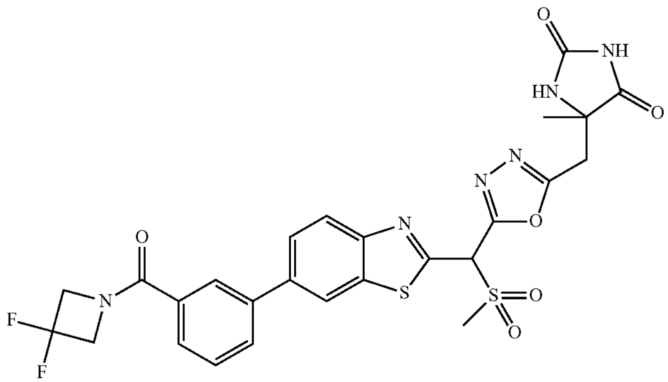 [SMILES: CC1(Cc2nnc(C(c3nc4ccc(-c5cccc(C(=O)N6CC(F)(F)C6)c5)cc4s3)S(C)(=O)=O)o2)NC(=O)NC1=O] | 5-{[5-({6-[3-(3,3-difluoroazetidine-1-carbonyl)phenyl]-1,3-benzothiazol-2-yl}methanesulfonyl)(methyl)-1,3,4-oxadiazol-2-yl]methyl}-5-methyl imidazolidine-2,4-dione | ¹H NMR (500 MHz, DMSO-d₆) δ 13.09-8.53 (m, 2H), 8.31-8.19 (m, 1H), 8.12-7.88 (m, 5H), 7.81-7.55 (m, 3H), 4.88 (br. s., 2H), 4.54 (br. s., 2H), 3.92 (s, 1H), 3.30-3.26 (m, 3H), 1.47 (br. s., 3H) | 1.35 O 617.1 | 177 | 131 |
| 209 | 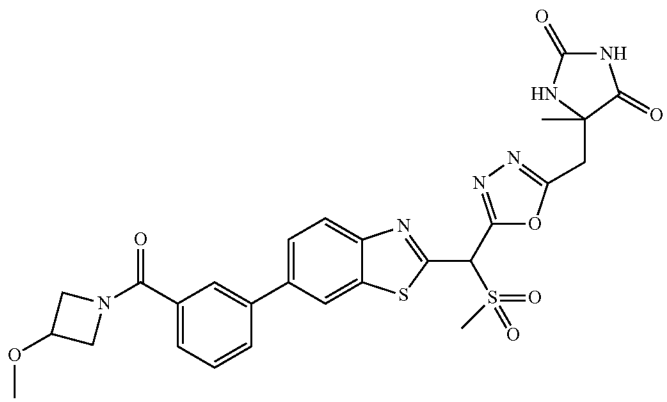 [SMILES: COC1CN(C(=O)c2cccc(-c3ccc4nc(C(c5nnc(CC6(C)NC(=O)NC6=O)o5)S(C)(=O)=O)sc4c3)c2)C1] | 5-({5-[methanesulfonyl({6-[3-(3-methoxyazetidine-1-carbonyl)phenyl]-1,3-benzothiazol-2-yl})methyl]-1,3,4-oxadiazol-2-yl}methyl)-5-methyl imidazolidin-2,4-dione | ¹H NMR (500 MHz, DMSO-d₆) δ 12.97-8.46 (m, 2H), 8.32-8.18 (m, 1H), 8.14-8.04 (m, 1H), 8.01-7.76 (m, 4H), 7.69-7.53 (m, 2H), 4.56-4.47 (m, 1H), 4.33-4.25 (m, 2H), 4.24-4.16 (m, 1H), 3.95-3.84 (m, 2H), 3.41-3.38 (m, 1H), 3.30-3.27 (m, 2H), 3.26-3.24 (m, 3H), 1.49-1.42 (m, 3H) | 1.20 O 611.2 | 18 | 227 |

-continued

| Ex. No. | Structure | Name | ¹H NMR | LC/MS RT (min) Method M + H | EL IC₅₀ (nM) | HL IC₅₀ (nM) |
|---|---|---|---|---|---|---|
| 210 | 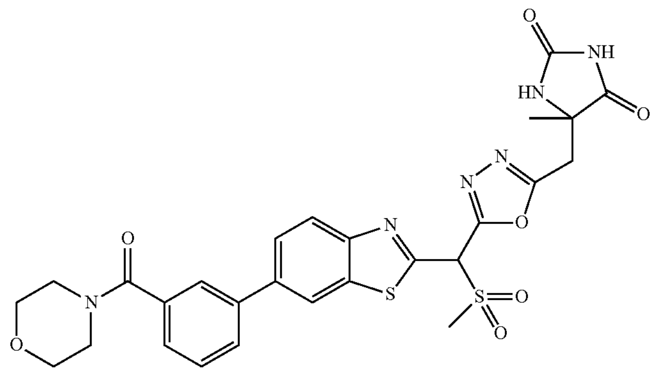 [SMILES: CC1(Cc2nnc(C(c3nc4ccc(-c5cccc(C(=O)N6CCOCC6)c5)cc4s3)S(C)(=O)=O)o2)NC(=O)NC1=O] | 5-({5-[methanesulfonyl({6-[3-(morpholine-4-carbonyl)phenyl]-1,3-benzothiazol-2-yl})methyl]-1,3,4-oxadiazol-2-yl}methyl)-5-methyl imidazolidine-2,4-dione | ¹H NMR (500 MHz, DMSO-d₆) δ 13.17-8.47 (m, 2H), 8.28-8.19 (m, 1H), 8.12-8.05 (m, 1H), 7.98-7.83 (m, 2H), 7.82-7.75 (m, 2H), 7.74-7.70 (m, 1H), 7.64-7.54 (m, 1H), 7.48-7.39 (m, 1H), 3.66 (br. s., 8H), 3.41-3.38 (m, 1H), 3.28 (br. s., 3H), 1.49-1.41 (m, 3H). | 1.23 O 611.1 | 9 | 365 |
| 211 | 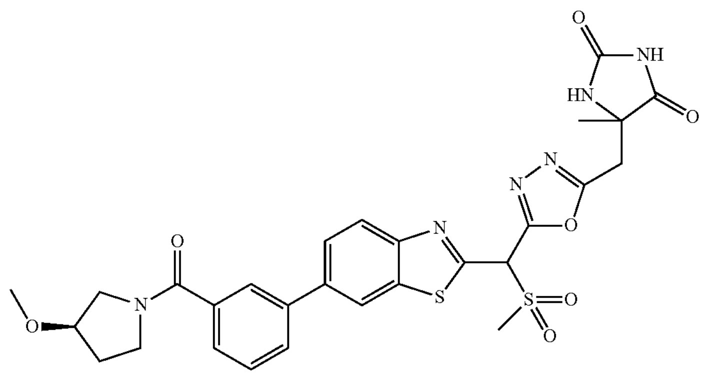 [SMILES: CO[C@@H]1CCN(C(=O)c2cccc(-c3ccc4nc(C(c5nnc(CC6(C)NC(=O)NC6=O)o5)S(C)(=O)=O)sc4c3)c2)C1] | 5-({5-[methanesulfonyl(6-{3-[(3R)-3-methoxy pyrrolidine-1-carbonyl]phenyl}-1,3-benzothiazol-2-yl)methyl]-1,3,4-oxadiazol-2-yl}methyl )-5-methyl imidazolidine-2,4-dione | ¹H NMR (500 MHz, DMSO-d₆) δ 10.76-10.69 (m, 1H), 8.28 (s, 1H), 8.09 (br. s., 1H), 7.97 (br. s., 2H), 7.81 (br. s., 2H), 7.64-7.54 (m, 3H), 4.09-4.01 (m, 1H), 4.00-3.94 (m, 1H), 3.42-3.35 (m, 4H), 3.30 (br. s., 3H) 3.21-3.15 (m, 3H), 2.12-1.89 (m, 3H), 1.46-1.46 (m, 3H). | 1.22 O 625.2 | 2 | 575 |

-continued

| Ex. No. | Structure | Name | LC/MS RT (min) Method M+H | EL IC$_{50}$ (nM) | HL IC$_{50}$ (nM) |
|---|---|---|---|---|---|
| 212 | 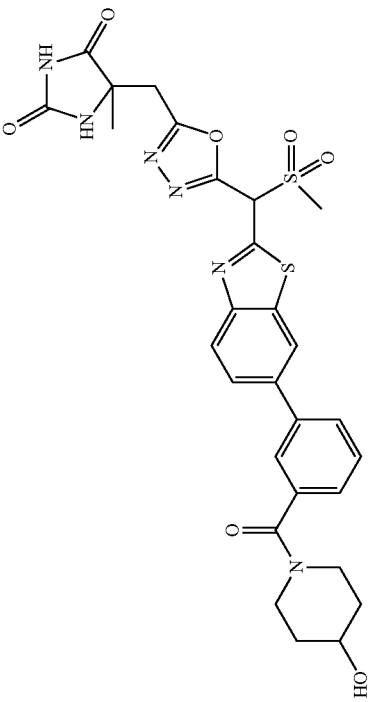 | 5-{[5-({6-[3-(4-hydroxypiperidine-1-carbonyl)phenyl]-1,3-benzothiazol-2-yl}(methanesulfonyl)methyl)-1,3,4-oxadiazol-2-yl]methyl}-5-methylimidazolidine-2,4-dione | 1.09 O 625.1 | 2 | 1105 |
| | | $^1$H NMR (500 MHz, DMSO-d$_6$) δ 10.84-10.69 (m, 1H), 8.64-8.04 (m, 3H), 8.00-7.73 (m, 4H), 7.71-7.53 (m, 2H), 5.71 (br. s., 1H), 4.32-4.11 (m, 2H), 3.93 (d, J=15.7 Hz, 3H), 3.29-3.23 (m, 3H), 1.53-1.37 (m, 6H). | | | |
| 218 | 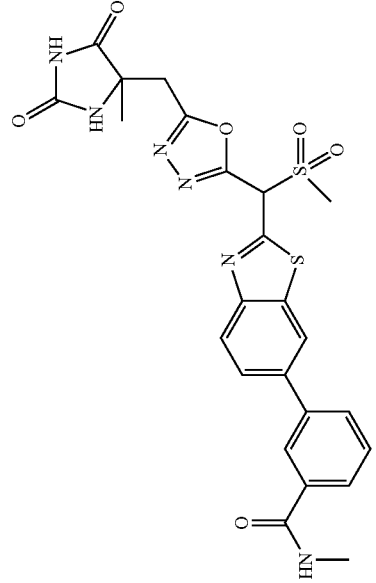 | 3-{2-[methanesulfonyl({5-[(4-methyl-2,5-dioxoimidazolidin-4-yl)methyl]-1,3,4-oxadiazol-2-yl})methyl]-1,3-benzothiazol-6-yl}-N-methylbenzamide | 1.06 O 555.1 | 10 | 262 |
| | | $^1$H NMR (500 MHz, DMSO-d$_6$) δ 10.82-10.70 (m, 1H), 8.65-8.13 (m, 5H), 8.10-8.04 (m, 1H), 8.02-7.91 (m, 2H), 7.90-7.77 (m, 2H), 7.69-7.54 (m, 1H), 3.70-3.59 (m, 2H), 3.20-3.10 (m, 2H), 2.87-2.81 (m, 3H), 1.55-1.41 (m, 3H). | | | |

| Ex. No. | Structure | Name | ¹H NMR | LC/MS RT (min) Method M + H | EL IC₅₀ (nM) | HL IC₅₀ (nM) |
|---|---|---|---|---|---|---|
| 219 | 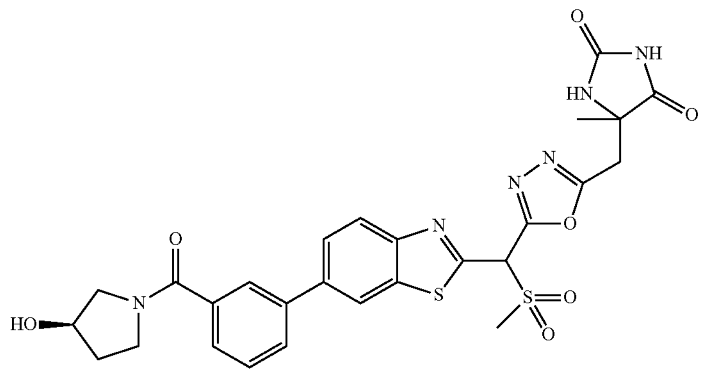 | 5-({5-[(6-{3-[(3R)-3-hydroxypyrrolidine-1-carbonyl]phenyl}-1,3-benzothiazol-2-yl)(methanesulfonyl)methyl]-1,3,4-oxadiazol-2-yl}methyl)-5-methylimidazolidine-2,4-dione | ¹H NMR (500 MHz, DMSO-d₆) δ 10.74 (br. s., 1H), 8.28 (br. s., 1H), 8.11-8.08 (m, 1H), 7.99-7.95 (m, 2H), 7.88 (br. s., 1H), 7.82-7.78 (m, 2H), 7.59-7.54 (m, 2H), 3.98-3.87 (m, 1H), 3.70-3.53 (m, 5H), 3.31-3.25 (m, 3H), 2.04-1.91 (m, 2H), 1.90-1.78 (m, 2H), 1.49-1.46 (m, 3H). | 1.00 O 611.2 | 2 | 2304 |
| 221 | 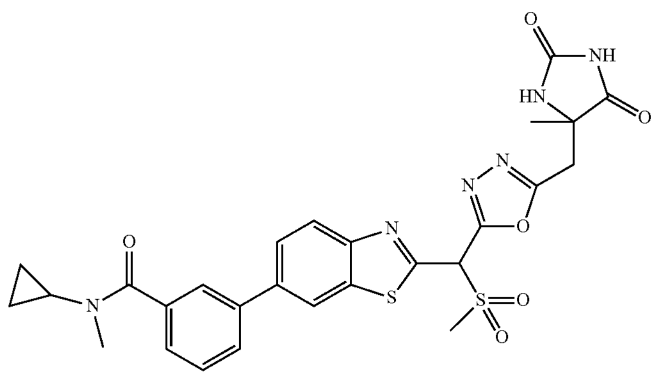 [SMILES: CN(C(=O)c1cccc(-c2ccc3nc(C(c4nnc(CC5(C)NC(=O)NC5=O)o4)S(C)(=O)=O)sc3c2)c1)C1CC1] | N-cyclopropyl-3-{2-[methanesulfonyl({5-[(4-methyl-2,5-dioxoimidazolidin-4-yl)methyl]-1,3,4-oxadiazol-2-yl}methyl)-1,3-benzothiazol-6-yl]-N-methylbenzamide | ¹H NMR (500 MHz, DMSO-d₆) δ 12.99-8.47 (m, 2H), 8.33-8.19 (m, 1H), 8.13-8.05 (m, 1H), 7.99-7.83 (m, 2H), 7.83-7.74 (m, 2H), 7.62-7.42 (m, 2H), 3.92 (s, 2H), 3.42-3.38 (m, 1H), 3.31-3.22 (m, 3H), 3.02 (br. s., 3H), 1.58-1.35 (m, 3H), 0.65-0.31 (m, 4H). | 1.39 O 595.1 | 1 | 25 |

| Ex. No. | Structure | Name | ¹H NMR | LC/MS RT (min) Method M + H | EL IC₅₀ (nM) | HL IC₅₀ (nM) |
|---|---|---|---|---|---|---|
| 222 | 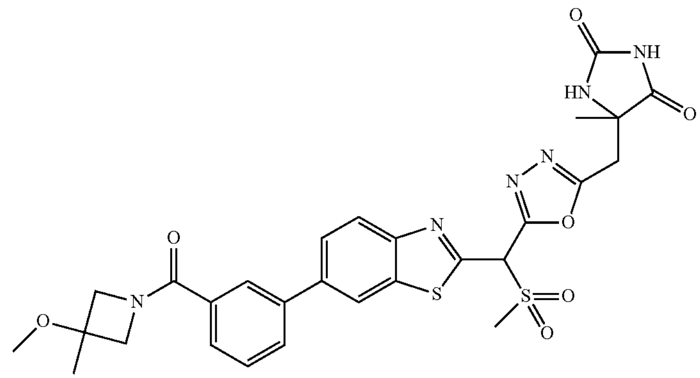 [SMILES: COC1(C)CN(C(=O)c2cccc(-c3ccc4nc(C(c5nnc(CC6(C)NC(=O)NC6=O)o5)S(C)(=O)=O)sc4c3)c2)C1] | 5-({5-[methanesulfonyl({6-[3-(3-methoxy-3-methyl azetidine-1-carbonyl) phenyl]-1,3-benzothiazol-2-yl}methyl)]-1,3,4-oxadiazol-2-yl}methyl)-5-methyl imidazolidine-2,4-dione | ¹H NMR (500 MHz, DMSO-d₆) δ 12.94-8.50 (m, 2H), 8.32-8.19 (m, 1H), 8.14-8.06 (m, 1H), 8.02-7.88 (m, 2H), 7.87-7.84 (m, 1H), 7.80-7.68 (m, 1H), 7.67-7.55 (m, 2H), 4.31 (d, J = 9.1 Hz, 1H), 4.17 (d, J = 9.1 Hz, 1H), 4.01 (d, J = 10.2 Hz, 1H), 3.94-3.86 (m, 3H), 3.40 (d, J = 7.4 Hz, 1H), 3.32-3.26 (m, 2H), 3.21 (s, 3H), 1.49-1.42 (m, 6H). | 1.34 O 625.1 | 8 | 162 |
| 223 | 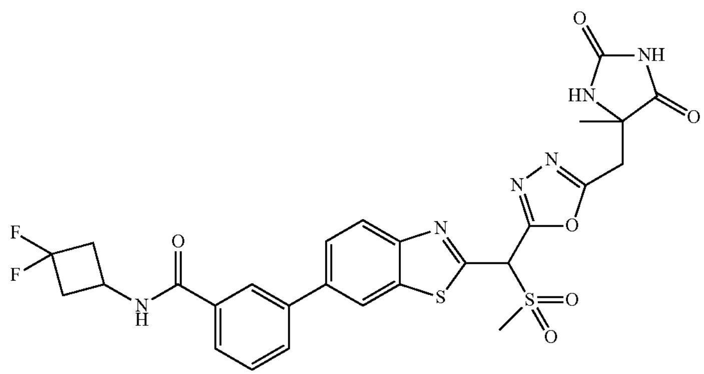 | N-(3,3-difluorocyclobutyl)-3-{2-[methanesulfonyl({5-[(4-methyl-2,5-dioxo imidazolidin-4-yl)methyl]-1,3,4-oxadiazol-2-yl})methyl]-1,3-benzothiazol-6-yl}benzamide | ¹H NMR (500 MHz, DMSO-d₆) δ 12.80-10.64 (m, 2H), 9.16-8.84 (m, 1H), 8.28-8.23 (m, 1H), 8.18-8.08 (m, 2H), 8.06-7.76 (m, 4H), 7.68-.53 (m, 1H), 4.48-4.26 (m, 1H), 3.92 (s, 1H), 3.41-3.38 (m, 1H), 3.32-3.25 (m, 3H), 3.07-2.95 (m, 2H), 2.87-2.76 (m, 2H), 1.46 (s, 3H). | 1.46 O 631.1 | 32 | 55 |

| Ex. No. | Structure | Name | $^1$H NMR | LC/MS RT (min) Method M+H | EL IC$_{50}$ (nM) | HL IC$_{50}$ (nM) |
|---|---|---|---|---|---|---|
| 224 | 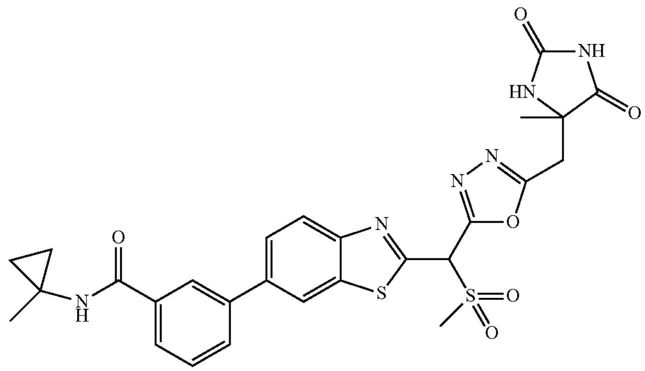 [SMILES: CC1(NC(=O)c2cccc(-c3ccc4nc(C(c5nnc(CC6(C)NC(=O)NC6=O)o5)S(C)(=O)=O)sc4c3)c2)CC1] | 3-{2-[methanesulfonyl({5-[(4-methyl-2,5-dioxo imidazolidin-4-yl) methyl]-1,3,4-oxadiazol-2-yl})methyl]-1,3-benzothiazol-6-yl]-N-(1-methylcyclopropyl) benzamide | $^1$H NMR (500 MHz, DMSO-d$_6$) δ 12.80-10.69 (m, 2H), 8.96-8.77 (m, 1H), 8.29-8.20 (m, 1H), 8.13 (s, 2H), 8.02-7.90 (m, 1H), 7.89-7.76 (m, 2H), 7.62-7.50 (m, 1H), 3.92 (s, 1H), 3.42-3.38 (m, 1H), 3.29 (br. s., 3H), 1.41 (s, 6H), 0.78 (br. s., 2H), 0.65 (br. s., 2H) | 1.37 O 595.1 | 11 | 76 |
| 225 | 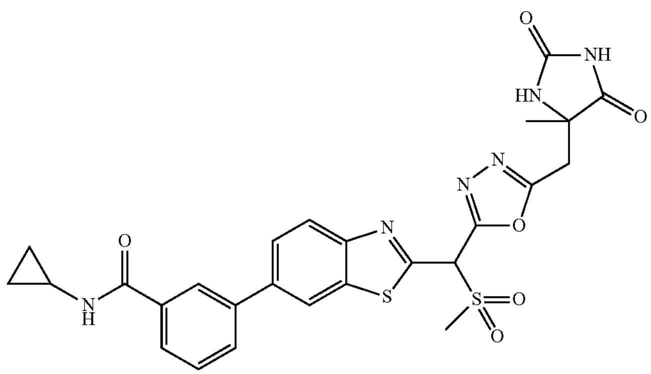 [SMILES: CC1(Cc2nnc(C(c3nc4ccc(-c5cccc(C(=O)NC6CC6)c5)cc4s3)S(C)(=O)=O)o2)NC(=O)NC1=O] | N-cyclopropyl-3-{2-[methanesulfonyl({5-[(4-methyl-2,5-dioxo imidazolidin-4-yl)methyl]-1,3,4-oxadiazol-2-yl})methyl]-1,3-benzothiazol-6-yl}benzamide | $^1$H NMR (500 MHz, DMSO-d$_6$) δ 10.94-10.60 (m, 1H), 8.67-8.52 (m, 1H), 8.30-8.18 (m, 1H), 8.14-8.07 (m, 2H), 8.03-7.91 (m, 2H), 7.89-7.77 (m, 2H), 7.65-7.53 (m, 1H), 3.96-3.86 (m, 2H), 3.31-3.27(m, 2H), 2.94-2.84 (m, 2H), 2.78-2.70 (m, 1H), 1.49-1.40 (m, 3H), 0.77-0.71 (m, 2H), 0.65-0.58 (m, 2H) | 1.28 O 581.2 | 5 | 51 |

| Ex. No. | Structure | Name | ¹H NMR | LC/MS RT (min) Method M+H | EL IC₅₀ (nM) | HL IC₅₀ (nM) |
|---|---|---|---|---|---|---|
| 226 | 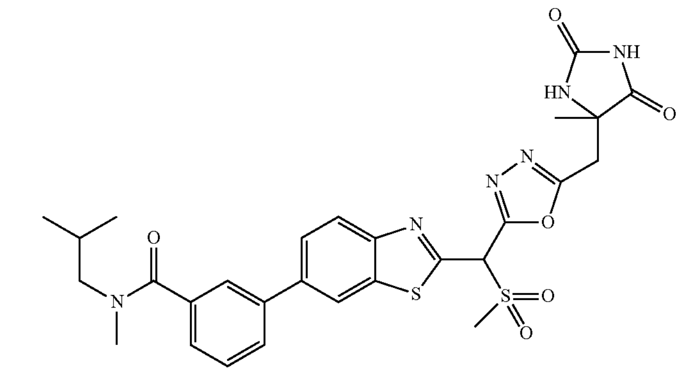 [SMILES: CC(C)CN(C)C(=O)c1cccc(-c2ccc3nc(C(c4nnc(CC5(C)NC(=O)NC5=O)o4)S(C)(=O)=O)sc3c2)c1] | 3-{2-[methanesulfonyl({5-[(4-methyl-2,5-dioxo imidazolidin-4-yl)methyl]-1,3,4-oxadiazol-2-yl})methyl]-1,3-benzothiazol-6-yl}-N-methyl-N-(2-methylpropyl)benzamide | ¹H NMR (500 MHz, DMSO-d₆) δ 10.85-10.70 (m, 1H), 8.31-8.19 (m, 1H), 8.16-8.03 (m, 1H), 8.00-7.69 (m, 3H), 7.68-7.52 (m, 2H), 7.46-7.30 (m, 1H), 3.92 (s, 1H), 3.40 (d, J = 7.2 Hz, 1H), 3.31-3.25 (m, 3H), 3.12 (d, J = 5.8 Hz, 1H), 3.03-2.92 (m, 4H), 2.16-1.81 (m, 1H), 1.46 (s, 3H), 0.96 (d, J = 6.3 Hz, 3H), 0.72 (d, J = 5.8 Hz, 3H) | 1.57 O 611.2 | 35 | 53 |
| 227 | 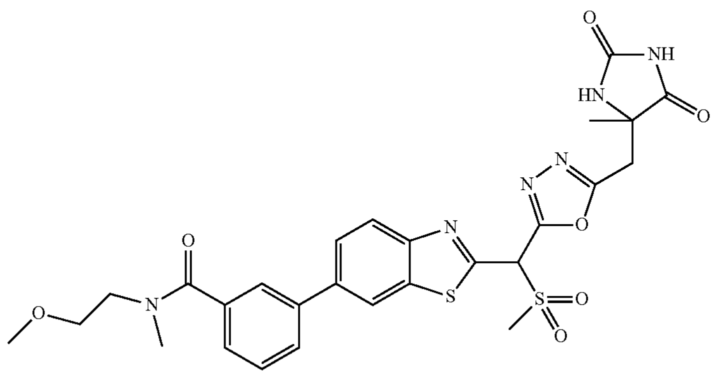 [SMILES: COCCN(C)C(=O)c1cccc(-c2ccc3nc(C(c4nnc(CC5(C)NC(=O)NC5=O)o4)S(C)(=O)=O)sc3c2)c1] | 3-{2-[methanesulfonyl({5-[(4-methyl-2,5-dioxo imidazolidin-4-yl)methyl]-1,3,4-oxadiazol-2-yl})methyl]-1,3-benzothiazol-6-yl}-N-(2-methoxyethyl)-N-methylbenzamide | ¹H NMR (500 MHz, DMSO-d₆) δ 10.87-10.69 (m, 1H), 8.57 (br. s., 1H), 8.35-8.19 (m, 1H), 8.12 (s, 1H), 7.99-7.91 (m, 1H), 7.88-7.66 (m, 3H), 7.62-7.51 (m, 1H), 7.46-7.36 (m, 1H), 3.70-3.56 (m, 2H), 3.49-3.44 (m, 3H), 3.34-3.26 (m, 5H), 3.23-3.16 (m, 2H), 3.02 (br. s., 3H), 1.47 (s, 3H). | 1.29 O 613.2 | 38 | 356 |

| Ex. No. | Structure | Name | $^1$H NMR | LC/MS RT (min) Method M+H | EL IC$_{50}$ (nM) | HL IC$_{50}$ (nM) |
|---|---|---|---|---|---|---|
| 228 | 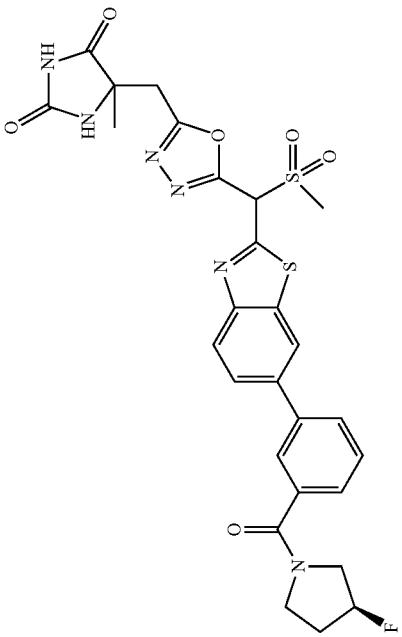 | 5-({5-[(6-{3-[(3S)-3-fluoropyrrolidine-1-carbonyl]phenyl}-1,3-benzothiazol-2-yl)(methanesulfonyl)methyl]-1,3,4-oxadiazol-2-yl}methyl)-5-methyl imidazolidine-2,4-dione | $^1$H NMR (500 MHz, DMSO-$d_6$) δ 11.14-10.70 (m, 1H), 8.37-7.47 (m, 10H), 5.57-5.12 (m, 1H), 3.92 (s, 2H), 3.83-3.55 (m, 4H), 3.23-3.14 (m, 3H), 2.26-2.01 (m, 3H), 1.42 (s, 3H). | 1.30 O 613.2 | 114 | 170 |
| 232 | 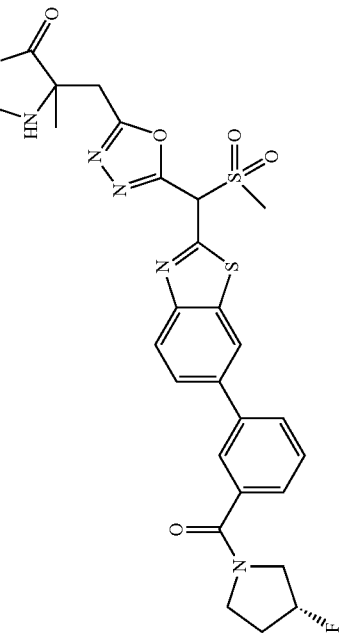 | 5-({5-[(6-{3-[(3R)-3-fluoropyrrolidine-1-carbonyl]phenyl}-1,3-benzothiazol-2-yl)(methanesulfonyl)methyl]-1,3,4-oxadiazol-2-yl}methyl)-5-methyl imidazolidine-2,4-dione | $^1$H NMR (500 MHz, DMSO-$d_6$) δ 12.66-8.54 (m, 2H), 8.34-8.06 (m, 2H), 7.97 (s, 4H), 7.65-7.45 (m, 2H), 5.73-5.04 (m, 1H), 3.92 (s, 1H), 3.50 (br.s., 6H), 3.28 (s, 2H), 2.28-2.02 (m, 2H), 1.47 (s, 3H), | 1.39 O 613.0 | 1 | 54 |

-continued

| Ex. No. | Structure | Name | ¹H NMR | LC/MS RT (min) Method M + H | EL IC₅₀ (nM) | HL IC₅₀ (nM) |
|---|---|---|---|---|---|---|
| 233 | 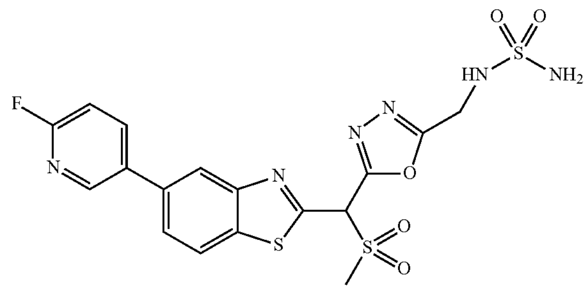 [SMILES: CS(=O)(=O)C(c1nnc(CNS(N)(=O)=O)o1)c1nc2cc(-c3ccc(F)nc3)ccc2s1] | N-[(5-[[5-(6-fluoropyridin-3-yl)-1,3-benzothiazol-2-yl](methanesulfonyl)methyl]-1,3,4-oxadiazol-2-yl)methyl]aminosulfonamide | ¹H NMR (500 MHz, DMSO-d₆) δ 8.74-8.59 (m, 1H), 8.53-8.40 (m, 1H), 8.35 (d, J = 8.4 Hz, 1H), 8.05-7.88 (m, 1H), 7.71-7.59 (m, 1H), 7.51 (d, J = 6.4 Hz, 1H), 7.40-7.28 (m, 1H), 6.79 (m, 2H), 4.43 (m, 2H), 3.44 (s, 3H) | 1.52 B 499.0 | 1 | 18 |
| 234 | 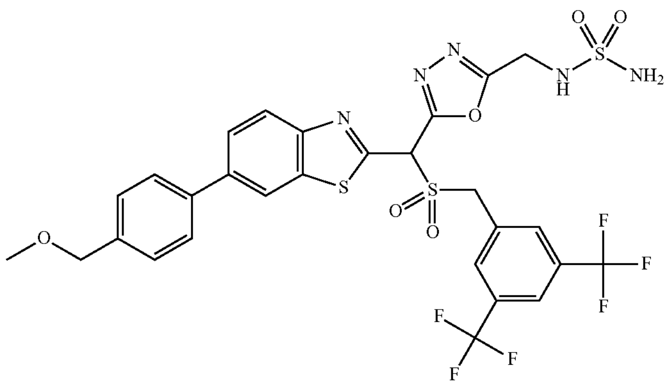 [SMILES: COCc1ccc(-c2ccc3nc(C(c4nnc(CNS(N)(=O)=O)o4)S(=O)(=O)Cc4cc(C(F)(F)F)cc(C(F)(F)F)c4)sc3c2)cc1] | N-[(5-[[3,5-bis(trifluoromethyl)phenyl]methanesulfonyl]({6-[4-(methoxymethyl)phenyl]-1,3-benzothiazol-2-yl})methyl]-1,3,4-oxadiazol-2-yl)methyl]aminosulfonamide | ¹H NMR (500 MHz, DMSO-d₆) δ 12.59 (br. s., 1H), 8.10 (d, J = 9.9 Hz, 1H), 8.04 (br. s., 3H), 7.88 (br. s., 1H), 7.71 (d, J = 8.5 Hz, 1H), 7.66 (d, J = 8.0 Hz, 2H), 7.56 (br. s., 1H), 7.43 (d, J = 8.0 Hz, 2H), 6.84 (s, 2H), 5.00 (br. s., 2H), 4.47 (s, 2H), 4.44 (d, J = 5.0 Hz, 2H) | 2.13 N 736.1 | 4 | 17 |

| Ex. No. | Structure | Name | ¹H NMR | LC/MS RT (min) Method M+H | EL IC₅₀ (nM) | HL IC₅₀ (nM) |
|---|---|---|---|---|---|---|
| 235 | 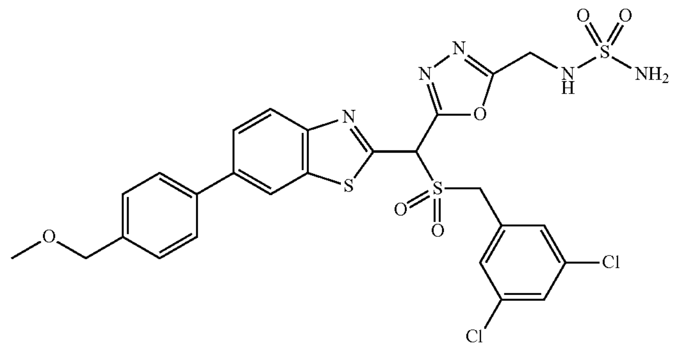 [SMILES: COCc1ccc(-c2ccc3nc(C(c4nnc(CNS(N)(=O)=O)o4)S(=O)(=O)Cc4cc(Cl)cc(Cl)c4)sc3c2)cc1] | N-({5-[(3,5-dichlorophenyl)methanesulfonyl({6-[4-(methoxymethyl)phenyl]-1,3-benzothiazol-2-yl}methyl)]-1,3,4-oxadiazol-2-yl}methyl)aminosulfonamide | ¹H NMR (500 MHz, DMSO-d₆) δ 8.16 (br. s., 1H), 8.06 (d, J = 8.3 Hz, 1H), 7.99-7.84 (m, 1H), 7.72 (d, J = 8.0 Hz, 1H), 7.68 (d, J = 8.0 Hz, 2H), 7.62-7.50 (m, 2H), 7.43 (d, J = 8.3 Hz, 4H), 6.84 (s, 2H), 4.79 (br. s., 2H), 4.47 (s, 2H), 4.44 (br. s., 2H), 3.33 (s, 3H) | 2.08 N 668.1 | 4 | 6 |
| 236 | 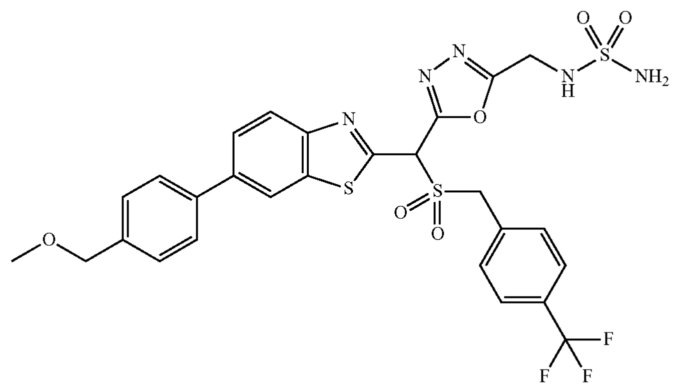 [SMILES: COCc1ccc(-c2ccc3nc(C(c4nnc(CNS(N)(=O)=O)o4)S(=O)(=O)Cc4ccc(C(F)(F)F)cc4)sc3c2)cc1] | N-{[5-({6-[4-(methoxymethyl)phenyl]-1,3-benzothiazol-2-yl}[4-(trifluoromethyl)phenyl]methanesulfonylmethyl)-1,3,4-oxadiazol-2-yl]methyl}aminosulfonamide | ¹H NMR (500 MHz, DMSO-d₆) δ 8.10 (br. s., 1H), 7.87 (br. s., 1H), 7.70 (d, J = 8.3 Hz, 1H), 7.66 (d, J = 8.0 Hz, 4H), 7.61-7.55 (m, 3H), 7.43 (d, J = 8.0 Hz, 2H), 6.84 (s, 2H), 4.88 (br. s., 2H), 4.47 (s, 2H), 4.44 (d, J = 4.4 Hz, 2H), 3.33 (s, 3H) | 1.99 N 668.1 | 1 | 1 |

| Ex. No. | Structure | Name | LC/MS RT (min) Method M+H | EL IC$_{50}$ (nM) | HL IC$_{50}$ (nM) |
|---|---|---|---|---|---|
| 237 | 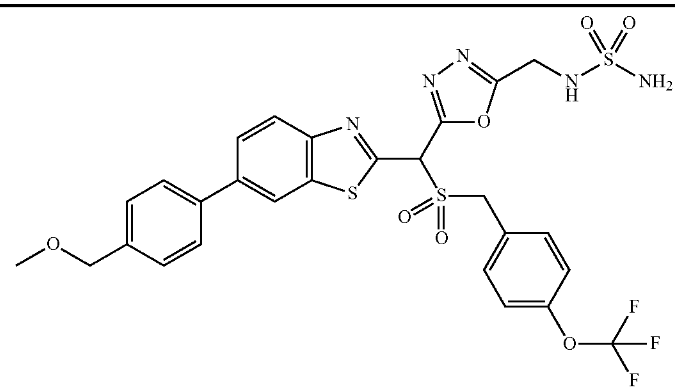 | N-{[5-({6-[4-(methoxymethyl)phenyl]-1,3-benzothiazol-2-yl}[4-(trifluoromethoxy)phenyl]methanesulfonylmethyl)-1,3,4-oxadiazol-2-yl]methyl}aminosulfonamide | 2.04 N 684.2 | 1 | 2 |
| 238 | 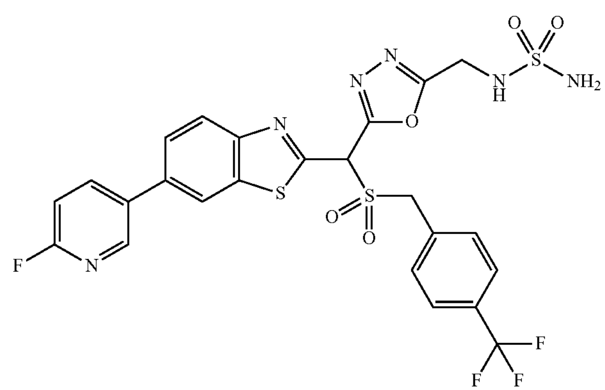 | N-[(5-{[6-(6-fluoropyridin-3-yl)-1,3-benzothiazol-2-yl][4-(trifluoromethyl)phenyl]methanesulfonylmethyl}-1,3,4-oxadiazol-2-yl)methyl]aminosulfonamide | 1.79 N 643.1 | 4 | 18 |

¹H NMR (Ex. 237): ¹H NMR (500 MHz, DMSO-d$_6$) δ 8.08 (br. s., 1H), 7.86 (br. s., 1H), 7.69 (d, J = 8.3 Hz, 1H), 7.65 (d, J = 8.0 Hz, 2H), 7.59 (br. s., 1H), 7.46 (d, J = 7.4 Hz, 2H), 7.42 (d, J = 8.0 Hz, 2H), 7.26 (d, J = 8.3 Hz, 2H), 6.84 (s, 2H), 4.79 (br. s., 2H), 4.47 (s, 2H), 4.44 (d, J = 5.0 Hz, 2H), 3.33 (s, 3H)

¹H NMR (Ex. 238): ¹H NMR (500 MHz, DMSO-d$_6$) δ 8.55 (s, 1H), 8.33-8.24 (m, 1H), 7.97 (s, 1H), 7.90 (br. s., 1H), 7.75 (d, J = 8.5 Hz, 1H), 7.68-7.61 (m, 2H), 7.61-7.52 (m, 3H), 7.32 (dd, J = 8.5, 1.9 Hz, 1H), 6.85 (s, 2H), 4.89 (br. s., 2H), 4.44 (d, J = 4.4 Hz, 2H)

| Ex. No. | Structure | Name | ¹H NMR | LC/MS RT (min) Method M+H | EL IC$_{50}$ (nM) | HL IC$_{50}$ (nM) |
|---|---|---|---|---|---|---|
| 239 | 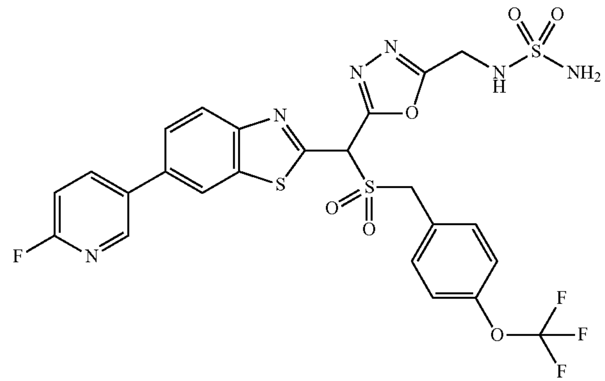 | N-[(5-[6-(6-fluoropyridin-3-yl)-1,3-benzothiazol-2-yl][4-(trifluoromethoxy)phenyl]methanesulfonyl)methyl]-1,3,4-oxadiazol-2-yl)methyl]aminosulfonamide | ¹H NMR (500 MHz, DMSO-d$_6$) δ 8.54 (s, 1H), 8.39-8.22 (m, 1H), 8.14 (br. s., 1H), 7.91 (br. s., 1H), 7.75 (d, J = 8.3 Hz, 1H), 7.60 (br. s., 1H), 7.46 (d, J = 7.4 Hz, 2H), 7.32 (dd, J = 8.5, 2.5 Hz, 1H), 7.27 (d, J = 8.0 Hz, 2H), 6.84 (s, 2H), 4.80 (br. s., 2H), 4.45 (d, J = 4.4 Hz, 2H) | 1.92 O 659.1 | 4 | 9 |
| 240 | 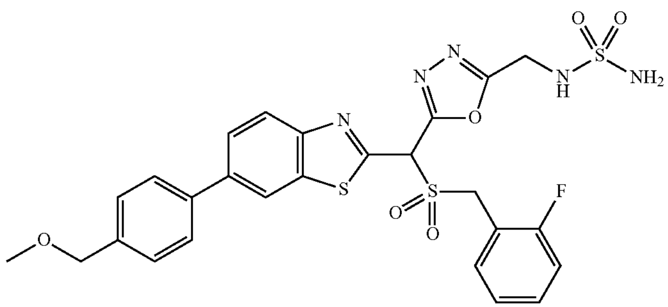 | N-({5-[((2-fluorophenyl)methanesulfonyl({6-[4-(methoxymethyl)phenyl]-1,3,4-oxadiazol-2-yl}methyl)methyl]-1,3,4-oxadiazol-2-yl}methyl)aminosulfonamide | ¹H NMR (500 MHz, DMSO-d$_6$) δ 8.11 (br. s., 1H), 7.92-7.69 (m, 3H), 7.66 (d, J = 7.7 Hz, 2H), 7.58-7.46 (m, 2H), 7.42 (d, J = 7.7 Hz, 2H), 7.40-7.25 (m, 2H), 7.19-7.00 (m, 2H), 6.81 (s, 2H), 4.78 (br. s., 2H), 4.58-4.49 (m, 1H), 4.47 (s, 2H), 4.41 (br. s., 2H), 3.33 (s, 3H) | 1.86 N 618.1 | 2 | 3 |
| 241 | 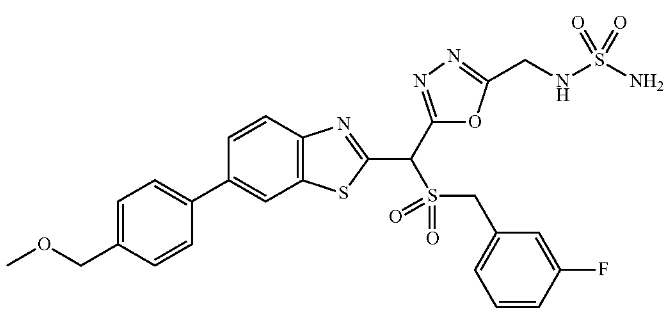 | N-({5-[(3-fluorophenyl)methanesulfonyl({6-[4-(methoxymethyl)phenyl]-1,3-benzothiazol-2-yl}methyl)methyl]-1,3,4-oxadiazol-2-yl}methyl)aminosulfonamide | ¹H NMR (500 MHz, DMSO-d$_6$) δ 8.12 (br. s., 1H), 7.88 (d, J = 8.0 Hz, 1H), 7.70 (d, J = 8.5 Hz, 1H), 7.66 (d, J = 7.7 Hz, 2H), 7.60 (d, J = 2.8 Hz, 1H), 7.42 (d, J = 7.4 Hz, 2H), 7.19 (d, J = 12.1 Hz, 2H), 7.10 (br. s., 1H), 6.85 (br. s., 2H), 4.79 (br. s., 2H), 4.46 (s, 4H), 3.32 (s, 3H) | 1.92 N 618.1 | 1 | 1 |

| Ex. No. | Structure | Name | ¹H NMR | LC/MS RT (min) Method M+H | EL IC₅₀ (nM) | HL IC₅₀ (nM) |
|---|---|---|---|---|---|---|
| 242 | 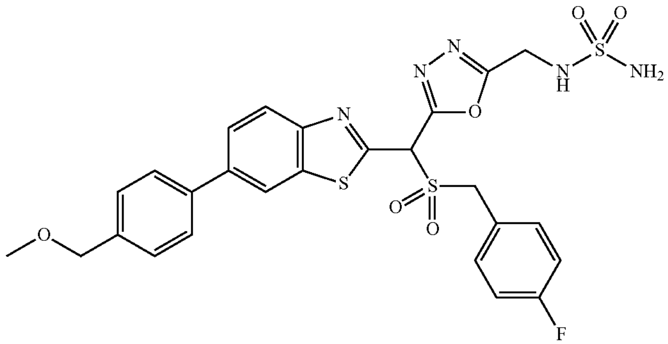 | N-({5-[(4-fluorophenyl)methanesulfonyl({6-[4-(methoxymethyl)phenyl]-1,3-benzothiazol-2-yl})methyl]-1,3,4-oxadiazol-2-yl}methyl)aminosulfonamide | ¹H NMR (500 MHz, DMSO-d₆) δ 7.85 (d, J = 7.7 Hz, 1H), 7.70 (d, J = 8.5 Hz, 1H), 7.66 (d, J = 7.7 Hz, 2H), 7.58 (br. s., 1H), 7.42 (d, J = 7.7 Hz, 2H), 7.37 (br. s., 2H), 7.11 (t, J = 8.5 Hz, 2H), 6.84 (s, 2H), 4.74 (br. s., 2H), 4.47 (s, 2H), 4.44 (br. s., 2H), 3.33 (s. 3H) | 1.86 N 618.2 | 1 | 1 |
| 243 | 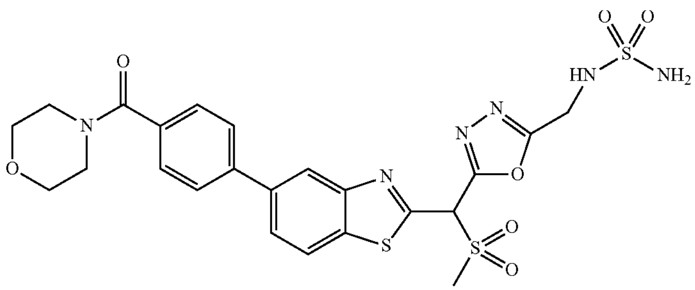 [SMILES: CS(=O)(=O)C(c1nnc(CNS(N)(=O)=O)o1)c1nc2cc(-c3ccc(C(=O)N4CCOCC4)cc3)ccc2s1] | N-({5-[methanesulfonyl({5-[4-(morpholine-4-carbonyl)phenyl]-1,3-benzothiazol-2-yl})methyl]-1,3,4-oxadiazol-2-yl}methyl)aminosulfonamide | ¹H NMR (500 MHz, DMSO-d₆) δ 8 8.38-8.26 (m, 1H), 8.02-7.95 (m, 2H), 7.91 (d, J = 8.5 Hz, 1H), 7.82 (d = 7.4 Hz, 1H), 7.62 (s, 1H), 7.56 (m, 3H), 6.80 (m, 2H), 4.43 (m, 2H), 3.64 (m, 8H), 2.91 (s, 3H) | 1.28 N 593.1 | 5 | 119 |
| 244 | 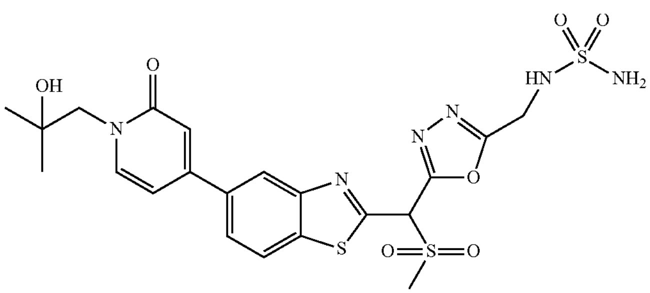 [SMILES: CC(C)(O)Cn1ccc(-c2ccc3sc(C(c4nnc(CNS(N)(=O)=O)o4)S(C)(=O)=O)nc3c2)cc1=O] | N-{[5-({5-[1-(2-hydroxy-2-methylpropyl)-2-oxo-1,2-dihydropyridin-4-yl]-1,3-benzothiazol-2-yl}(methanesulfonyl)methyl]-1,3,4-oxadiazol-2-yl]methyl}aminosulfonamide | ¹H NMR (500 MHz, DMSO-d₆) δ 7.96 (br. s., 1H), 7.80-7.69 (m, 1H), 7.58-7.45 (m, 1H), 6.89-6.73 (m, 3H), 6.68-6.58 (m, 1H), 4.46-4.36 (m, 2H), 3.95 (m, 4H), 1.13 (s, 9H) | 1.18 N 569.1 | 6 | 737 |

Prepared by the general procedures given for Example 46 using Compound 244b

| Ex. No. | Structure | Name | $^1$H NMR | LC/MS RT (min) Method M+H | EL IC$_{50}$ (nM) | HL IC$_{50}$ (nM) |
|---|---|---|---|---|---|---|
| 245 | 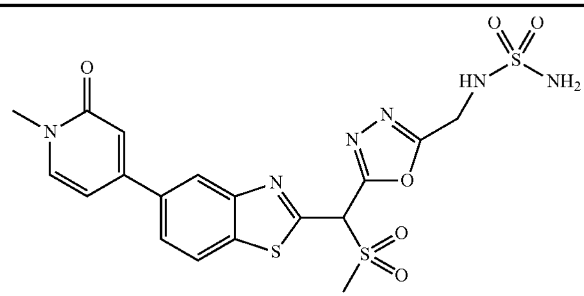 | N-[(5-[methanesulfonyl[5-(1-methyl-2-oxo-1,2-dihydropyridin-4-yl)]methyl]-1,3-benzothiazol-2-yl]methyl]-1,3,4-oxadiazol-2-yl)methyl]aminosulfonamide | $^1$H NMR (500 MHz, DMSO-d$_6$) δ 7.95 (m, 2H), 7.83 (m, 2H), 7.62 (m, 2H), 7.55-7.44 (m, 2H), 6.64-6.56 (m, 1H), 4.46-4.40 (m, 2H), 3.48 (br. s., 6H) | 1.04 N 511.1 | 8 | 72 |
| 246 | 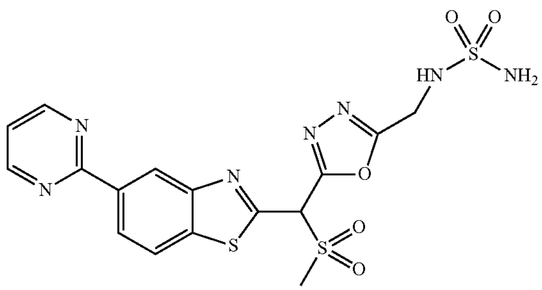 [SMILES: CS(=O)(=O)C(c1nnc(CNS(N)(=O)=O)o1)c1nc2cc(-c3ncccn3)ccc2s1] | N-[(5-[methanesulfonyl[5-(pyrimidin-2-yl)-1,3-benzothiazol-2-yl]methyl]-1,3,4-oxadiazol-2-yl)methyl]aminosulfonamide | $^1$H NMR (500 MHz, DMSO-d$_6$) δ 9.31 (s, 1H), 9.22 (m, 2H), 8.10-8.00 (m, 1H), 7.52 (d, J = 5.2 Hz, 1H), 6.80 (m, 2H), 4.42 (m, 2H), 2.91 (s, 3H) | 1.02 N 482.0 | 9 | 6 |
| 247 | 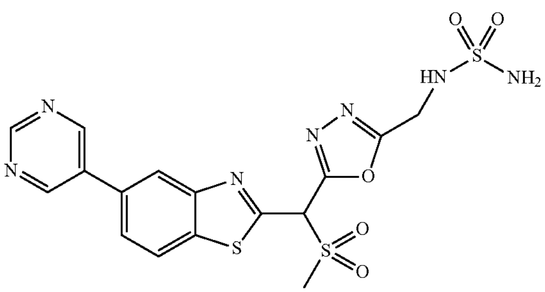 [SMILES: CS(=O)(=O)C(c1nnc(CNS(N)(=O)=O)o1)c1nc2cc(-c3cncnc3)ccc2s1] | N-[(5-[methanesulfonyl[5-(pyrimidin-5-yl)-1,3-benzothiazol-2-yl]methyl]-1,3,4-oxadiazol-2-yl)methyl]aminosulfonamide | $^1$H NMR (500 MHz, DMSO-d$_6$) δ 9.36 (s, 1H), 8.53 (d, J = 8.5 Hz, 1H), 8.19 (d, J = 8.8 Hz, 1H), 8.09-8.01 (m, 1H), 7.60-7.46 (m, 1H), 6.80 (m, 2H), 4.48-4.37 (m, 2H), 2.91 (s, 3H) | 1.02 N 482.0 | 4 | 43 |

| Ex. No. | Structure | Name | ¹H NMR | LC/MS RT (min) Method M+H | EL IC₅₀ (nM) | HL IC₅₀ (nM) |
|---|---|---|---|---|---|---|
| 248 | 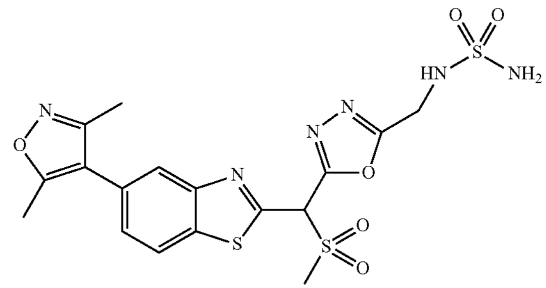 [SMILES: Cc1noc(C)c1-c1ccc2sc(C(c3nnc(CNS(N)(=O)=O)o3)S(C)(=O)=O)nc2c1] | N-[(5-{[5-(dimethyl-1,2-oxazol-4-yl)-1,3-benzothiazol-2-yl](methanesulfonyl)methyl]-1,3,4-oxadiazol-2-yl)methyl]aminosulfonamide | ¹H NMR (500 MHz, DMSO-d₆) δ 7.95 (s, 1H), 7.62-7.54 (m, 1H), 7.48 (d, J = 5.8 Hz, 1H), 6.85-6.75 (m, 2H), 4.44-4.32 (m, 2H), 3.24 (s, 3H), 2.44 (s, 3H), 2.27 (s, 3H) | 1.30 N 499.1 | 5 | 26 |
| 249 | 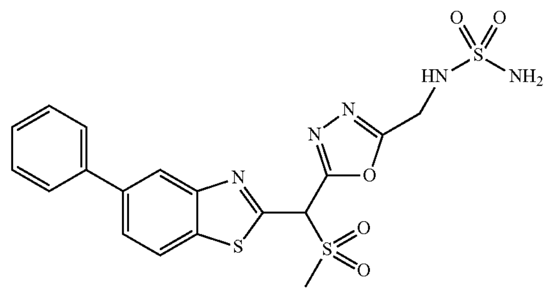 [SMILES: CS(=O)(=O)C(c1nnc(CNS(N)(=O)=O)o1)c1nc2cc(-c3ccccc3)ccc2s1] | N-({5-[methanesulfonyl(5-phenyl-1,3-benzothiazol-2-yl)methyl]-1,3,4-oxadiazol-2-yl}methyl)aminosulfonamide | ¹H NMR (500 MHz, DMSO-d₆) δ 7.99-7.93 (m, 1H), 7.87 (d, J = 8.5 Hz, 1H), 7.80 (dd, J = 7.6, 2.9 Hz, 1H), 7.70 (m, 2H), 7.54-7.45 (m, 3H), 7.38 (s, 1H), 6.80 (m, 2H), 4.35 (m, 2H), 3.24 9s, 3H) | 1.66 N 480.0 | 1 | 1 |
| 250 | 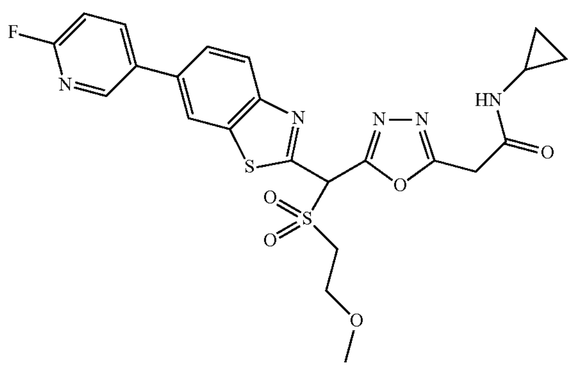 [SMILES: COCCS(=O)(=O)C(c1nnc(CC(=O)NC2CC2)o1)c1nc2ccc(-c3ccc(F)nc3)cc2s1] | N-cyclopropyl-2-(5-{[6-(6-fluoropyridin-3-yl)-1,3-benzothiazol-2-yl](2-methoxyethanesulfonyl)methyl}-1,3,4-oxadiazol-2-yl)acetamide | ¹H NMR (400 MHz, CDCl₃) δ 8.43 (d, J = 2.6 Hz, 1H), 8.02 (m, 1H), 7.79 (s, 1H), 7.60 (d, J = 1.3 Hz, 2H), 7.08 (m, 1H), 3.87 (m, 2H), 3.82 (m, 2H), 3.58 (m, 2H), 3.21 (s, 3H), 2.75 (mm 1H), 0.83-0.76 (m, 2H), 0.57 (m, 2H) | 1.70 B 532.1 | 194 | 306 |

| Ex. No. | Structure | Name | ¹H NMR | LC/MS RT (min) Method M + H | EL IC₅₀ (nM) | HL IC₅₀ (nM) |
|---|---|---|---|---|---|---|
| 251 | 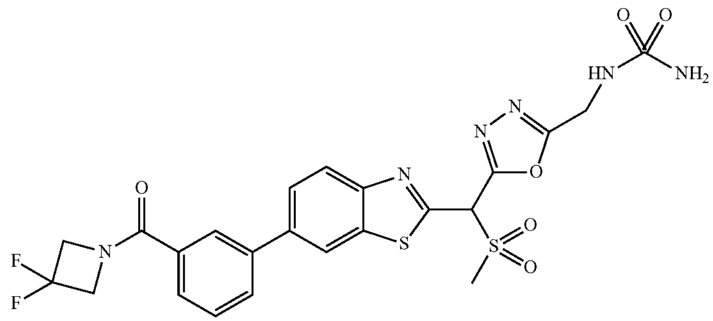 | N-{[5-({6-[3-(3,3-difluoroazetidine-1-carbonyl)phenyl]-1,3-benzothiazol-2-yl}(methanesulfonyl)methyl)-1,3,4-oxadiazol-2-yl]methyl}aminosulfonamide | ¹H NMR (500 MHz, DMSO-d₆) δ 8.30-8.17 (m, 1H), 8.03-7.84 (m, 3H), 7.59 (s, 3H), 7.54-7.47 (m, 1H), 4.87 (m, 2H), 4.51 (m, 2H), 4.44-4.34 (m, 2H), 3.42 (s, 3H) | 1.61 B 599.0 | 9 | 21 |
| 252 | 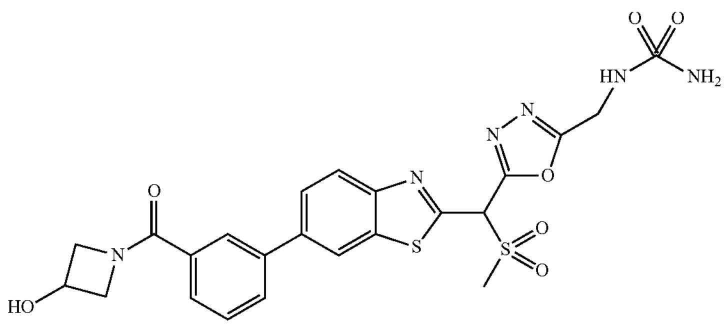 | N-{[5-({6-[3-(3-hydroxyazetidine-1-carbonyl)phenyl]-1,3-benzothiazol-2-yl}(methanesulfonyl)methyl)-1,3,4-oxadiazol-2-yl]methyl](amine-sulfonamide | ¹H NMR (500 MHz, DMSO-d₆) δ 8.29-8.17 (m, 1H), 7.99-7.81 (m, 3H), 7.75 (d, J = 8.2 Hz, 1H), 7.67-7.48 (m, 3H), 6.80 (m, 2H) 5.79 (d, J = 5.2 Hz, 1H), 4.52 (m, 2H), 4.45-4.36 (m, 2H), 4.10-4.28 (m, 2H), 3.41 (s, 3H) | 1.71 S 579.2 | 10 | 22 |
| 253 | 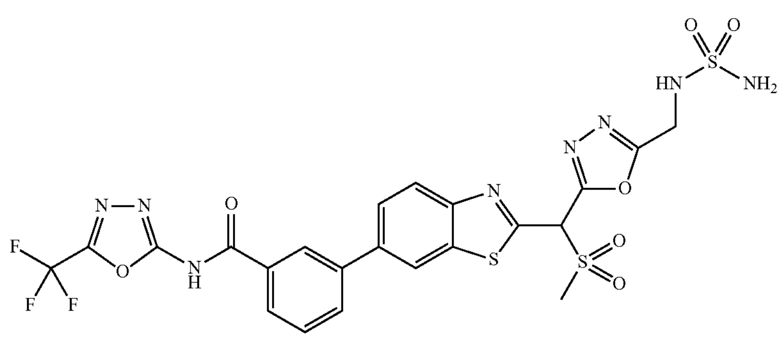 [SMILES: CS(=O)(=O)C(c1nnc(CNS(N)(=O)=O)o1)c1nc2ccc(-c3cccc(C(=O)Nc4nnc(C(F)(F)F)o4)c3)cc2s1] | 3-{2-[methanesulfonyl({5-[(sulfamoylamino)methyl]-1,3,4-oxadiazol-2-yl})methyl]-1,3-benzothiazol-6-yl}-N-[5-(trifluoromethyl)-1,3,4-oxadiazol-2-yl]benzamide | ¹H NMR (500 MHz, DMSO-d₆) δ 8.48-8.34 (m, 1H), 8.27 (s, 1H), 8.01 (m, 2H), 7.95 (m, 2H), 7.71-7.58 (m, 2H), 7.55-7.48 (m, 1H), 6.79 (m, 2H), 4.46-4.32 (m, 2H), 3.42 (s, 3H) | 1.98 S 659.0 | 7 | 62 |

| Ex. No. | Structure | Name | ¹H NMR | LC/MS RT (min) Method M + H | EL IC₅₀ (nM) | HL IC₅₀ (nM) |
|---|---|---|---|---|---|---|
| 254 | 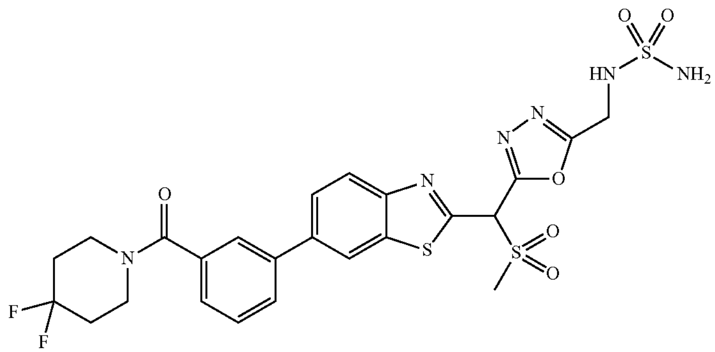 [SMILES: CS(=O)(=O)C(c1nnc(CNS(N)(=O)=O)o1)c1nc2ccc(-c3cccc(C(=O)N4CCC(F)(F)CC4)c3)cc2s1] | N-[{5-[{6-[3-(4,4-difluoropiperidine-1-carbonyl)phenyl]-1,3-benzothiazol-2-yl}(methanesulfonyl)methyl]-1,3,4-oxadiazol-2-yl]methyl}aminosulfonamide | ¹H NMR (500 MHz, DMSO-d₆) δ 8.21 (d, J = 18.6 Hz, 1H), 7.98-7.72 (m, 4H), 7.66-7.39 (m, 4H), 6.80 (m, 2H), 4.46-4.34 (m, 2H), 3.84-3.69 (m, 2H), 3.65-3.56 (m, 2H), 3.53-3.43 (m, 2H), 3.41 (s, 3H), 3.24-3.04 (m, 2H) | 2.49 S 627.1 | 5 | 17 |
| 255 | 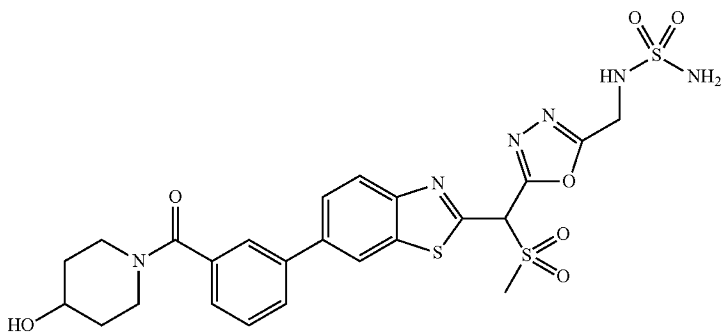 [SMILES: CS(=O)(=O)C(c1nnc(CNS(N)(=O)=O)o1)c1nc2ccc(-c3cccc(C(=O)N4CCC(O)CC4)c3)cc2s1] | N-[{5-[{6-[3-(4-hydroxypiperidine-1-carbonyl)phenyl]-1,3-benzothiazol-2-yl}(methanesulfonyl)methyl]-1,3,4-oxadiazol-2-yl]methyl}aminosulfonamide | ¹H NMR (500 MHz, DMSO-d₆) δ 8.28 -8.16 (m, 1H), 7.93 (d, J = 10.1 Hz, 1H), 7.75 (m, 2H), 7.66 (s, 1H), 7.61-7.48 (m, 2H), 7.36 (m, 1H), 6.80 (m, 2H), 4.81 (m, 1H), 4.40 (m, 2H), 3.75 (m, 1H), 3.53 (m, 1H), 3.41 (s, 3H), 3.28-3.14 (m, 2H), 1.89-1.65 (m, 2H), 1.48-1.21 (m, 2H) | 1.74 S 607.2 | 2 | 46 |
| 256 | 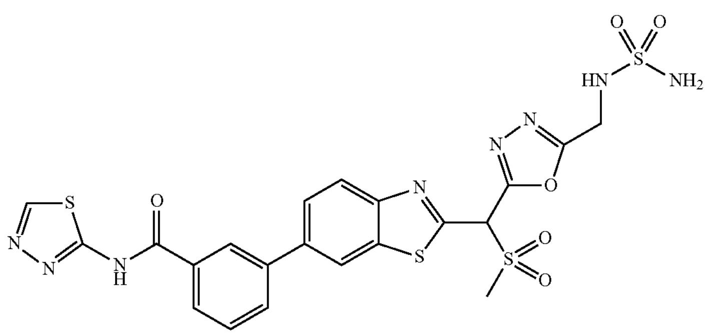 [SMILES: CS(=O)(=O)C(c1nnc(CNS(N)(=O)=O)o1)c1nc2ccc(-c3cccc(C(=O)Nc4nncs4)c3)cc2s1] | 3-{2-[methanesulfonyl({5-[(sulfamoyl)amino)methyl]-1,3,4-oxadiazol-2-yl})methyl]-1,3-benzothiazol-6-yl}-N-(1,3,4-thiadiazol-2-yl)benzamide | ¹H NMR (500 MHz, DMSO-d₆) δ 9.14-9.02 (m, 1H), 8.26 (br. s., 1H), 8.18 (s, 1H), 7.95 (m, 3H), 7.86 (m, 2H), 7.80 (d, J = 8.9 Hz, 1H), 7.60 (s, 1H), 6.80 (m, 2H), 4.44-4.37 (m, 2H), 4.11 (m, 2H), 3.42 (s, 3H) | 2.05 S 607.3 | 2 | 16 |

-continued

| Ex. No. | Structure | Name | ¹H NMR | LC/MS RT (min) Method M + H | EL IC₅₀ (nM) | HL IC₅₀ (nM) |
|---|---|---|---|---|---|---|
| 257 | 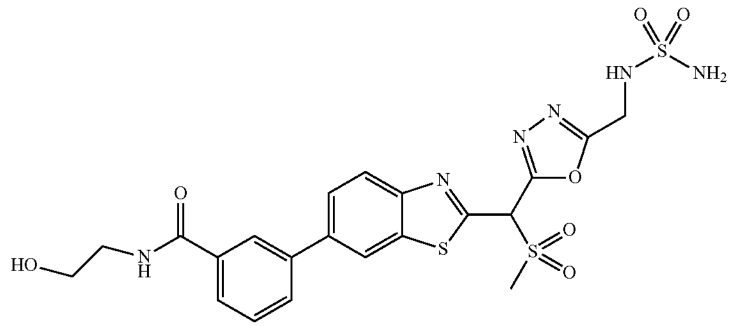 [SMILES: CS(=O)(=O)C(c1nnc(CNS(N)(=O)=O)o1)c1nc2ccc(-c3cccc(C(=O)NCCO)c3)cc2s1] | N-(2-hydroxyethyl)-3-{2-[methanesulfonyl({5-[(sulfamoylamino)methyl]-1,3,4-oxadiazol-2-yl})methyl]-1,3-benzothiazol-6-yl}benzamide | ¹H NMR (500 MHz, DMSO-d₆) δ 8.62-8.57 (m, 1H), 8.25 (br. s., 1H), 7.94 (m, 3H), 7.88-7.78 (m, 2H), 7.64-7.55 (m, 1H), 7.54-7.46 (m, 1H), 6.84-6.77 (m, 2H), 4.88-4.78 (m, 1H), 4.41 (m, 2H), 3.58-3.54 (s, 3H), 3.41 -3.37 (m, 2H), 3.35- 3.29 (m, 2H) | 1.69 S 567.1 | 10 | 29 |
| 258 | 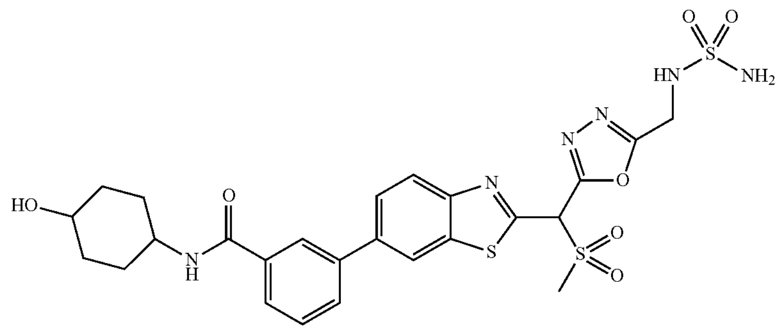 [SMILES: CS(=O)(=O)C(c1nnc(CNS(N)(=O)=O)o1)c1nc2ccc(-c3cccc(C(=O)NC4CCC(O)CC4)c3)cc2s1] | N-(4-hydroxycyclohexyl)-3-{2-[methanesulfonyl({5-[(sulfamoylamino)methyl]-1,3,4-oxadiazol-2-yl})methyl]-1,3-benzothiazol-6-yl}benzamide | ¹H NMR (500 MHz, DMSO-d₆) δ 8.38-8.29 (m, 1H), 8.26-8.17 (m, 1H), 8.01-7.89 (m, 4H), 7.88-7.76 (m, 2H), 7.63-7.48 (m, 2H), 6.81 (m, 2H), 4.73-4.62 (m, 1H), 4.47-4.36 (m, 2H), 3.84-3.69 (m, 2H), 3.42-3.40 (s, 3H), 1.93-1.80 (m, 4H), 1.45-1.19 (m, 4H) | 1.85 S 621.1 | 8 | 35 |
| 259 | 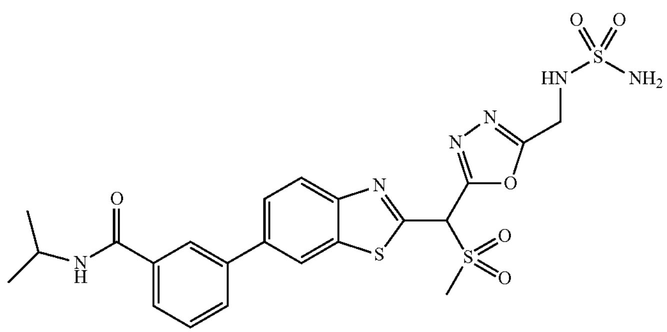 [SMILES: CC(C)NC(=O)c1cccc(-c2ccc3nc(C(c4nnc(CNS(N)(=O)=O)o4)S(C)(=O)=O)sc3c2)c1] | 3-{2-[methanesulfonyl({5-[(sulfamoylamino)methyl]-1,3,4-oxadiazol-2-yl})methyl]-1,3-benzothiazol-6-yl}-N-( propan-2-yl) benzamide | ¹H NMR (500 MHz, DMSO-d₆) δ 8.34 (d, J = 7.6 Hz, 1H), 8.28-8.21 (m, 1H), 8.14 (s, 1H), 7.96 (br. s., 1H), 7.94-7.87 (m, 1H), 7.84 (m, 2H), 7.64-7.49 (m, 2H), 6.81 (m, 2H), 4.47-4.37 (m, 2H), 4.19-4.08 (m, 1H), 3.43 (s, 3H), 1.24-1.18 (s, 6H) | 2.22 S 565.2 | 8 | 37 |

-continued

| Ex. No. | Structure | Name | ¹H NMR | LC/MS RT (min) Method M + H | EL IC₅₀ (nM) | HL IC₅₀ (nM) |
|---|---|---|---|---|---|---|
| 260 | 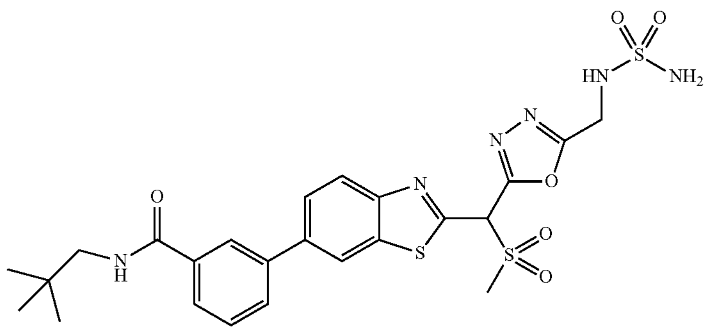 [SMILES: CC(C)(C)CNC(=O)c1cccc(-c2ccc3nc(C(c4nnc(CNS(N)(=O)=O)o4)S(C)(=O)=O)sc3c2)c1] | N-(2,2-dimethylpropyl)-3-{2-[methanesulfonyl({5-[(sulfamoylamino)methyl]-1,3,4-oxadiazol-2-yl})methyl]-1,3-benzothiazol-6-yl}benzamide | ¹H NMR (500 MHz, DMSO-d₆) δ 8.47 (s, 1H), 8.29-8.19 (m, 2H), 7.96 (m, 2H), 7.85 (m, 2H), 7.61 (m, 2H), 6.81 (d, J = 7.0 Hz, 2H), 4.46-4.36 (m, 2H), 3.20 (m, 2H), 2.90 (s, 3H), 0.93 (s, 9H) | 2.54 S 593.3 | 3 | 7 |
| 261 | 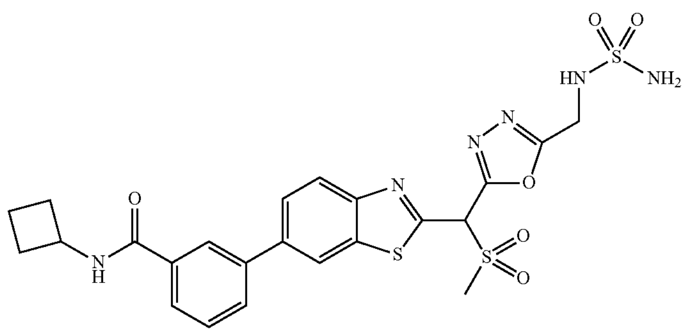 [SMILES: CS(=O)(=O)C(c1nnc(CNS(N)(=O)=O)o1)c1nc2ccc(-c3cccc(C(=O)NC4CCC4)c3)cc2s1] | N-cyclobutyl-3-{2-[methanesulfonyl({5-[(sulfamoylamino)methyl]-1,3,4-oxadiazol-2-yl})methyl]-1,3-benzothiazol-6-yl}benzamide | ¹H NMR (500 MHz, DMSO-d₆) δ 8.80-8.67 (m, 1H), 8.31-8.08 (m, 2H), 8.03-7.91 (m, 2H), 7.88-7.77 (m, 2H), 7.59 (m, 2H), 6.81 (m, 2H), 4.43 (m, 3H), 2.90 (s, 3H), 2.25 (m, 2H), 2.11 (m, 2H), 1.70 (m, 2H) | 2.35 S 577.2 | 3 | 5 |
| 262 | 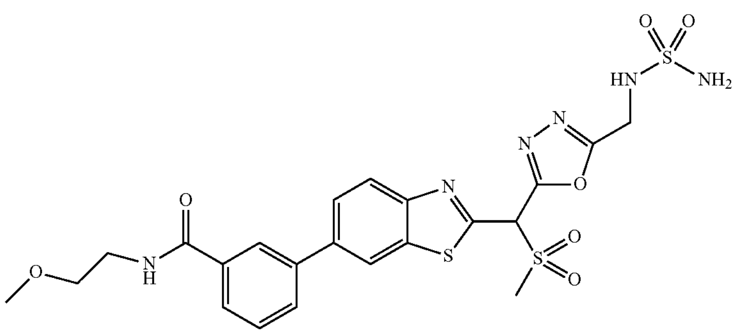 [SMILES: COCCNC(=O)c1cccc(-c2ccc3nc(C(c4nnc(CNS(N)(=O)=O)o4)S(C)(=O)=O)sc3c2)c1] | 3-{2-[methanesulfonyl({5-[(sulfamoylamino)methyl]-1,3,4-oxadiazol-2-yl})methyl]-1,3-benzothiazol-6-yl}-N-(2-methoxyethyl)benzamide | ¹H NMR (500 MHz, DMSO-d₆) δ 8.76-8.64 (m, 1H), 8.30-8.15 (m, 2H), 7.96 (m, 2H), 7.85 (m, 2H), 7.66-7.49 (m, 2H), 6.81 (m, 2H), 4.47-4.37 (m, 2H), 3.49 (m, 4H), 3.29 (s, 3H), 2.90 (s, 3H) | 2.03 S 581.2 | 14 | 45 |

| Ex. No. | Structure | Name | ¹H NMR | LC/MS RT (min) Method M + H | EL IC₅₀ (nM) | HL IC₅₀ (nM) |
|---|---|---|---|---|---|---|
| 263 | 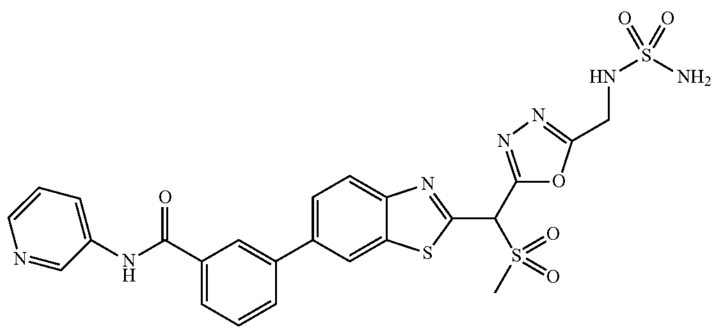 [SMILES: CS(=O)(=O)C(c1nnc(CNS(N)(=O)=O)o1)c1nc2ccc(-c3cccc(C(=O)Nc4cccnc4)c3)cc2s1] | 3-{2-[methanesulfonyl({5-[(sulfamoylamino)methyl]-1,3,4-oxadiazol-2-yl}methyl)]-1,3-benzothiazol-6-yl}-N-(pyridin-3-yl)benzamide | ¹H NMR (500 MHz, DMSO-d₆) δ 8.43-8.36 (m, 2H), 8.31 (d, J = 8.9 Hz, 1H), 7.96 (m, 6H), 7.77-7.59 (m, 3H), 7.53 (m, 1H), 6.81 (m, 2H), 4.47-4.35 (m, 4H), 2.90 (s, 3H) | 2.23 S 600.2 | 4 | 26 |
| 264 | 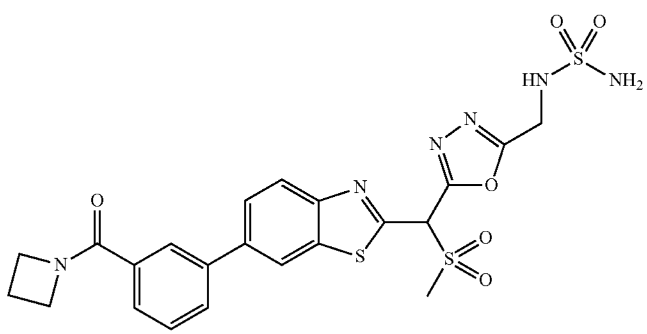 [SMILES: CS(=O)(=O)C(c1nnc(CNS(N)(=O)=O)o1)c1nc2ccc(-c3cccc(C(=O)N4CCC4)c3)cc2s1] | N-{[5-({6-[3-(azetidine-1-carbonyl)phenyl]-1,3-benzothiazol-2-yl}(methanesulfonyl)methyl)-1,3,4-oxadiazol-2-yl]}aminosulfonamide | ¹H NMR (500 MHz, DMSO-d₆) δ 8.33-8.16 (m, 1H), 7.98-7.88 (m, 3H), 7.86-7.74 (m, 1H), 7.69-7.46 (m, 3H), 6.81 (m, 2H), 4.48-4.29 (m, 4H), 4.09 (m, 2H), 2.90 (s, 3H), 2.35-2.23 (m, 2H) | 2.20 S 563.2 | 19 | 37 |
| 265 | 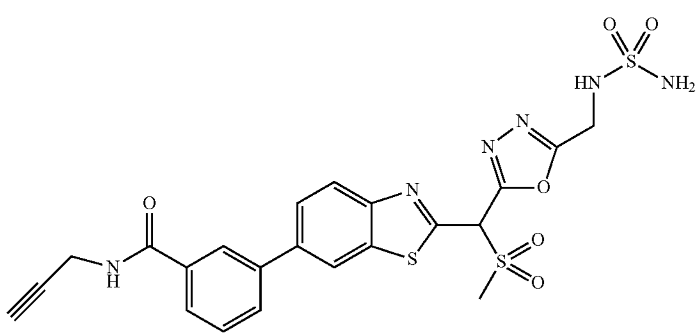 [SMILES: C#CCNC(=O)c1cccc(-c2ccc3nc(C(c4nnc(CNS(N)(=O)=O)o4)S(C)(=O)=O)sc3c2)c1] | 3-{2-[methanesulfonyl({5-[(sulfamoylamino)methyl]-1,3,4-oxadiazol-2-yl}methyl)]-1,3-benzothiazol-6-yl}-N-(prop-2-yn-1-yl)benzamide | ¹H NMR (500 MHz, DMSO-d₆) δ 9.15-9.03 (m, 1H), 8.30-8.16 (m, 2H), 7.96 (s, 3H), 7.87 (m, 2H), 7.81 (d, J = 8.9 Hz, 1H), 7.60 (d, J = 4.9 Hz, 1H), 6.80 (s, 2H), 4.47-4.37 (m, 2H), 4.12 (m, 2H), 3.43 (s, 3H) | 2.17 S 561.2 | 6 | 19 |

| Ex. No. | Structure | Name | ¹H NMR | LC/MS RT (min) Method M + H | EL IC₅₀ (nM) | HL IC₅₀ (nM) |
|---|---|---|---|---|---|---|
| 266 | 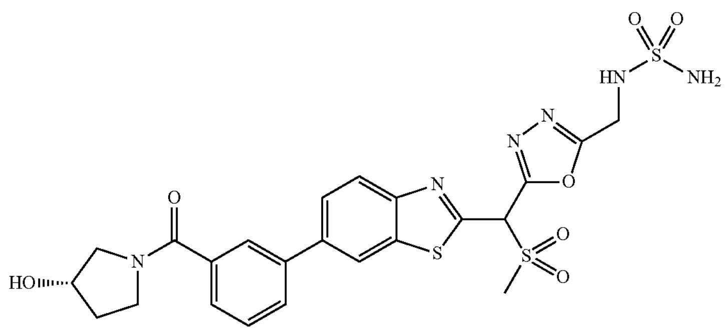 [SMILES: CS(=O)(=O)C(c1nnc(CNS(N)(=O)=O)o1)c1nc2ccc(-c3cccc(C(=O)N4CC[C@H](O)C4)c3)cc2s1] | N-({5-[(6-{3-[(3S)-3-hydroxypyrrolidine-1-carbonyl]phenyl}-1,3-benzothiazol-2-yl)(methanesulfonyl)methyl]-1,3,4-oxadiazol-2-yl}methyl)aminosulfonamide | ¹H NMR (500 MHz, DMSO-d₆) δ 7.96 (s, 2H), 7.87 (br. s., 1H), 7.79 (m, 2H), 7.64-7.46 (m, 4H), 6.81 (m, 2H), 4.42 (m, 2H), 4.37-4.20 (m, 2H), 3.69-3.45 (m, 4H), 3.26 (m, 1H), 2.90 (s, 3H) | 1.95 S 593.2 | 13 | 94 |
| 267 | 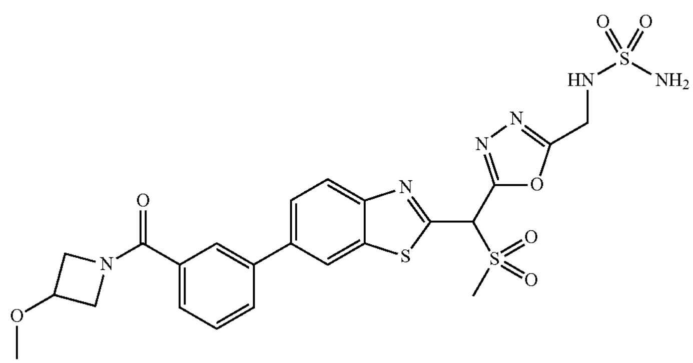 [SMILES: COC1CN(C(=O)c2cccc(-c3ccc4nc(C(c5nnc(CNS(N)(=O)=O)o5)S(C)(=O)=O)sc4c3)c2)C1] | N-({5-[methanesulfonyl{(6-[3-(3-methoxyazetidine-1-carbonyl)phenyl]-1,3-benzothiazol-2-yl})methyl]-1,3,4-oxadiazol-2-yl}methyl)aminosulfonamide | ¹H NMR (500 MHz, DMSO-d₆) δ 8.31-8.18 (m, 1H), 8.00-7.89 (m, 3H), 7.87-7.75 (m, 1H), 7.71-7.47 (m, 3H), 6.81 (m, 2H), 4.52 (br. s., 1H), 4.42 (m, 2H), 4.32-4.19 (m, 3H), 3.90 (m, 1H), 3.24 (s, 3H) | 2.19 S 593.2 | 14 | 41 |

Reference 1

N-((5-(1-(Methylsulfonyl)-1-(6-phenyl-1,3-benzothiazol-2-yl)ethyl)-1,3,4-oxadiazol-2-yl)methyl)sulfamide (Isomer A) and (Isomer B)

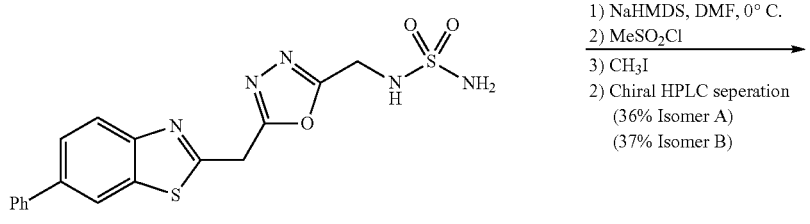

46b

1) NaHMDS, DMF, 0° C.
2) MeSO$_2$Cl
3) CH$_3$I
2) Chiral HPLC seperation
   (36% Isomer A)
   (37% Isomer B)

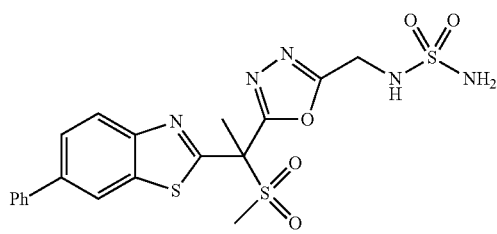

Reference 1
Isomer A and Isomer B

To a solution of Compound 46b (100 mg, 0.25 mmol) in DMF (3 mL) at 0° C. was added 1M NaHMDS in THF (0.55 mL, 0.55 mmol) and the mixture stirred for 10 min. Methanesulfonyl chloride (0.025 mL, 0.32 mmol) was added and the mixture stirred for 5 min then 2M iodomethane in tert-butyl methyl ether (0.22 mL, 0.45 mmol) was added and the reaction stirred for 1 h. Additional 2M iodomethane in tert-butyl methyl ether (0.080 mL, 0.16 mmol) was added and the reaction stirred for 1 h then quenched with acetic acid (0.043 mL, 0.75 mmol). The mixture was diluted with MeOH and purified by prep HPLC (Method B, gradient elution of 10-100% solvent B). Fractions containing product were made basic by the addition of 1.5 M phosphate buffer, evaporated under reduced pressure to remove most of the ACN, acidified by the addition of satd. NH$_4$Cl and extracted with DCM (3×), dried (Na$_2$SO$_4$), filtered and concentrated under reduced pressure to afford the racemic product. The material was further purified by silica gel chromatography eluting with 0-100% EtOAc/hexane to afford the racemic product. The enantiomers were separated by chiral preparative chiral HPLC (Whelko 4.6×250 mm ID, 10 μm, 20 mL/min, 25% MeOH/EtOH (1:1) in heptane) to afford Reference 1, Isomer A (RT=14.3 min, 22 mg, 36% yield), LCMS=0.90 min using analytical method (M), 493.9 (M+H), $^1$H NMR (400 MHz, CDCl$_3$) δ 8.05 (d, J=8.5 Hz, 1H), 8.01 (d, J=1.5 Hz, 1H), 7.68 (dd, J=8.8, 1.8 Hz, 1H), 7.56 (d, J=7.0 Hz, 2H), 7.47-7.40 (m, 2H), 7.39-7.31 (m, 1H), 5.73 (br. s., 2H), 4.67 (s, 2H), 3.20 (s, 3H), 2.44 (s, 3H), EL IC$_{50}$=3751 nM; and Reference 1, Isomer B (RT=15.5 min, 23 mg, 37% yield), LCMS=0.90 min using analytical method (M), 493.9 (M+H), $^1$H NMR (400 MHz, CDCl$_3$) δ 8.04 (d, J=8.8 Hz, 1H), 8.00 (d, J=1.3 Hz, 1H), 7.67 (dd, J=8.5, 1.5 Hz, 1H), 7.56 (d, J=7.0 Hz, 2H), 7.47-7.39 (m, 2H), 7.37-7.32 (m, 1H), 5.61 (br. s., 2H), 4.67 (s, 2H), 3.20 (s, 3H), 2.44 (s, 3H), EL IC$_{50}$=5202 nM.

Reference 2

N-((5-(1-(Benzylsulfonyl)-1-(6-phenyl-1,3-benzothiazol-2-yl)ethyl)-1,3,4-oxadiazol-2-yl)methyl)sulfamide (Isomer A) and (Isomer B)

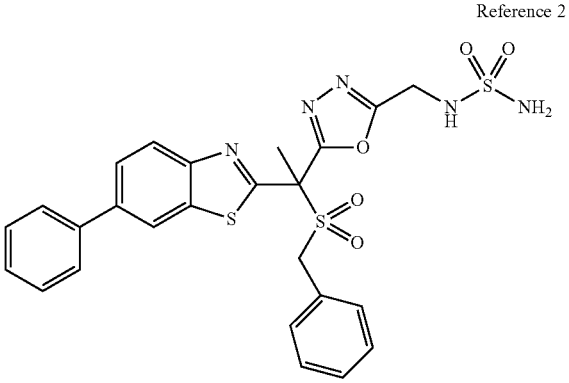

Isomer A and Isomer B

Reference 2, Isomer A and Reference 2, Isomer B were prepared by the general procedure described for Example 98 and Example 99. Reference 2, Isomer A (RT=15.8 min, 28% yield) LCMS=1.00 min using analytical method (M), 570.0

267

(M+H), $^1$H NMR (400 MHz, CDCl$_3$) δ 8.11 (d, J=8.8 Hz, 1H), 8.06 (d, J=1.5 Hz, 1H), 7.75 (dd, J=8.7, 1.6 Hz, 1H), 7.66-7.59 (m, 2H), 7.48 (t, J=7.4 Hz, 2H), 7.42-7.37 (m, 1H), 7.29-7.21 (m, 5H), 4.85 (d, J=13.6 Hz, 1H), 4.63 (s, 2H), 4.58 (d, J=13.6 Hz, 1H), 2.51 (s, 3H), EL IC$_{50}$>25000 nM; and Reference 2, Isomer B (RT=16.9 min, 35% yield), LCMS=1.01 min using analytical method (M), 570.1 (M+H), $^1$H NMR (400 MHz, CDCl$_3$) δ 8.11 (d, J=8.8 Hz, 1H), 8.07 (s, 1H), 7.79-7.71 (m, 1H), 7.67-7.57 (m, 2H), 7.48 (t, J=7.4 Hz, 2H), 7.43-7.35 (m, 1H), 7.29-7.21 (m, 5H), 4.85 (d, J=13.6 Hz, 1H), 4.63 (s, 2H), 4.58 (d, J=13.6 Hz, 1H), 2.51 (s, 3H), EL IC$_{50}$=713 nM.

268

Reference 3

N-((5-(1-(6-(6-Fluoro-3-pyridinyl)-1,3-benzothiazol-2-yl)ethyl)-1,3,4-oxadiazol-2-yl)methyl)sulfamide and Reference 4

N-((5-(1-(6-(6-Fluoro-3-pyridinyl)-1,3-benzothiazol-2-yl)-1-hydroxyethyl)-1,3,4-oxadiazol-2-yl)methyl)sulfamide

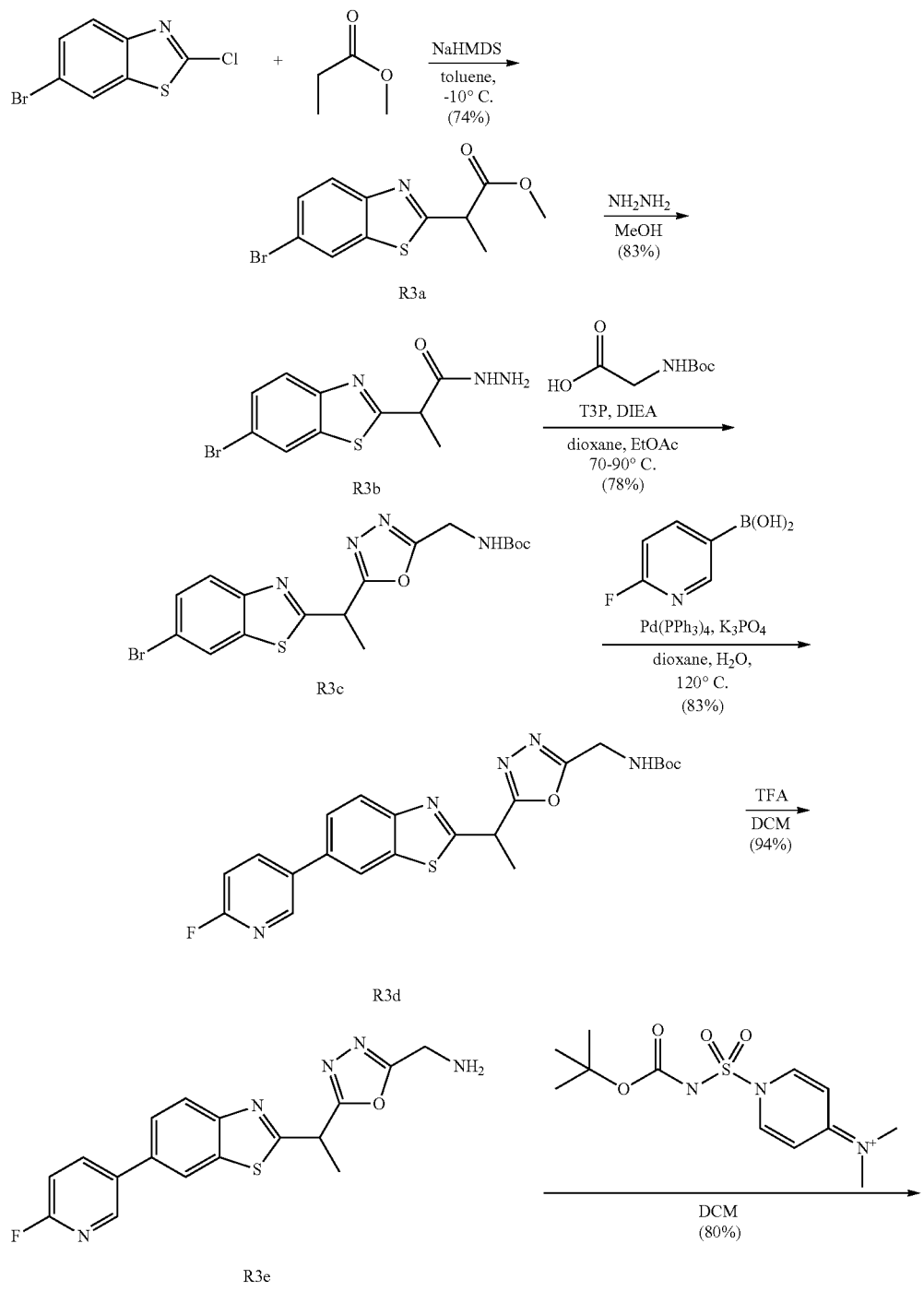

-continued

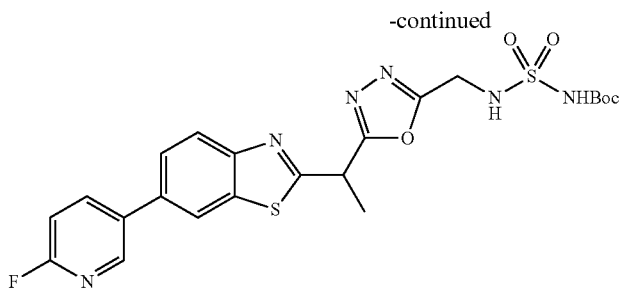

R3f

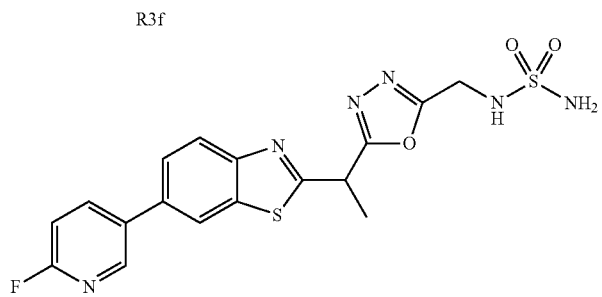

Reference 3

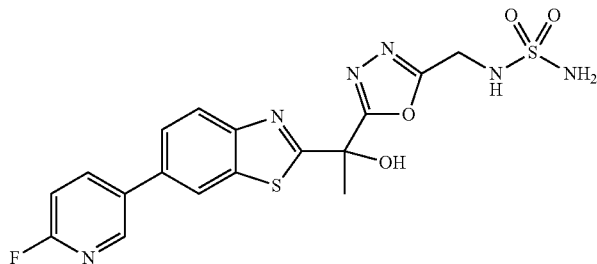

Reference 4

Compound R3a. Methyl 2-(6-bromobenzo[d]thiazol-2-yl)propanoate

To a solution of methyl propionate (0.088 mL, 0.89 mmol) and 6-bromo-2-chlorobenzo[d]thiazole (221 mg, 0.89 mmol) in degassed toluene (5 mL) at brine/ice bath temperature was slowly added 1.0 M NaHMDS in THF (2.22 mL, 2.22 mmol). After the addition was complete, the reaction was stirred for 10 min. The mixture was then quenched with satd. $NH_4Cl$ (15 mL) then extracted with EtOAc (2×20 mL). The organic extracts were dried over $Na_2SO_4$, filtered and concentrated in vacuo. The residue was purified by silica gel chromatography eluting with 0-100% EtOAc/hexane to give Compound R3a (198 mg, 0.66 mmol, 74% yield) as a yellow solid. LCMS=1.0 min using analytical method (M), 302.0 (M+H). $^1$H NMR (400 MHz, $CDCl_3$) δ 8.02 (d, J=1.8 Hz, 1H), 7.87 (d, J=8.8 Hz, 1H), 7.58 (dd, J=8.7, 1.9 Hz, 1H), 4.30 (q, J=7.3 Hz, 1H), 3.78 (s, 3H), 1.75 (d, J=7.3 Hz, 3H).

Compound R3b. 2-(6-Bromobenzo[d]thiazol-2-yl)propanehydrazide

To a solution of Compound R3a (192 mg, 0.64 mmol) in MeOH (2 mL) and DCM (2 mL) was added hydrazine (0.20 mL, 6.4 mmol) and the mixture stirred for 16 h (overnight). The reaction mixture was diluted with diethyl ether and the solid collected by filtration to give Compound R3b (160 mg, 0.53 mmol, 83% yield) as light yellow solid. LCMS=1.4 min using analytical method (B), 288.0 (M+H). $^1$H NMR (400 MHz, DMSO-$d_6$) δ 9.51 (s, 1H), 8.36 (d, J=1.8 Hz, 1H), 7.89 (d, J=8.5 Hz, 1H), 7.64 (dd, J=8.5, 2.0 Hz, 1H), 4.38 (br. s., 2H), 4.13 (q, J=7.0 Hz, 1H), 1.53 (d, J=7.0 Hz, 3H).

Compound R3c. tert-Butyl (5-(1-(6-bromobenzo[d]thiazol-2-yl)ethyl)-1,3,4-oxadiazol-2-yl)methylcarbamate Compound R3c was prepared from Compound R3b and 2-((tert-butoxycarbonyl)amino)acetic acid in 78% yield using the general procedure given for Compound 1b. LCMS=2.0 min using analytical method (B), 441.0 (M+H).

Compound R3d. tert-Butyl (5-(1-(6-(6-fluoropyridin-3-yl)benzo[d]thiazol-2-yl)ethyl)-1,3,4-oxadiazol-2-yl)methylcarbamate Compound R3d (125 mg, 83% yield) was prepared from Compound R3c in 83% yield using the general procedure given for Compound 1c. LCMS=1.9 min using analytical method (B), 456.1 (M+H). $^1$H NMR (400 MHz, $CDCl_3$) δ 8.47 (d, J=2.8 Hz, 1H), 8.14-8.07 (m, 1H), 8.06-7.98 (m, 2H), 7.73-7.63 (m, 2H), 7.09-7.02 (m, 1H), 4.95 (q, J=7.3 Hz, 1H), 4.55 (d, J=5.8 Hz, 2H), 2.00 (d, J=7.0 Hz, 3H), 1.56 (s, 9H).

Compound R3e. (5-(1-(6-(6-Fluoropyridin-3-yl)benzo[d]thiazol-2-yl)ethyl)-1,3,4-oxadiazol-2-yl)methanamine Compound R3e (112 mg, 94%) was prepared from Compound R3d in 94% yield using the general procedure given for Compound 46b. LCMS=1.4 min using analytical method (B), 356.0 (M+H). $^1$H NMR (400 MHz, CDCl$_3$) δ 8.44 (s, 1H), 8.16-8.04 (m, 1H), 8.03-7.93 (m, 2H), 7.67-7.59 (m, 1H), 7.10-7.01 (m, 1H), 4.93 (q, J=7.1 Hz, 1H), 4.16 (s, 2H), 1.98 (d, J=7.3 Hz, 4H).

Compound R3f. tert-Butyl N-((5-(1-(6-(6-fluoropyridin-3-yl)benzo[d]thiazol-2-yl)ethyl)-1,3,4-oxadiazol-2-yl)methyl)sulfamoylcarbamate Compound R3f (151 mg, 80%) was prepared Compound R3e in 80% yield using the general procedure given for Compound 46a. LCMS=1.9 min using analytical method (B), 535.0 (M+H). $^1$H NMR (400 MHz, CDCl$_3$) δ 8.77-8.66 (m, 1H), 8.48 (d, J=2.0 Hz, 1H), 8.15-8.08 (m, 1H), 8.05-7.97 (m, 2H), 7.73-7.62 (m, 1H), 7.13-7.02 (m, 1H), 6.81-6.61 (m, 1H), 4.97 (q, J=7.2 Hz, 1H), 4.66-4.56 (m, 2H), 2.04-1.98 (m, 3H), 1.36 (s, 9H).

Reference 3 and Reference 4

To a solution of Compound R3f (112 mg, 0.21 mmol) in DCM (2 mL) was added TFA (2 mL). The mixture was stirred at rt for 15 min. The reaction mixture was concentrated under reduced pressure and coevaporated with toluene and DCM under reduced pressure. The residue was dissolved in DCM and washed with 1.5 M K$_3$PO$_4$ solution. The organic layer was concentrated under reduced pressure. The residue was purified by silica gel flash chromatography eluting with 0-10% MeOH/DCM to give Reference 3 (19 mg, 21% yield) Reference 4 (10 mg, 10% yield) as light yellow solids. Reference 3: LCMS=1.5 min using analytical method (B), 435.0 (M+H). $^1$H NMR (400 MHz, CD$_3$OD) δ 8.46 (d, J=2.0 Hz, 1H), 8.12-8.03 (m, 3H), 7.68 (dd, J=8.7, 1.6 Hz, 1H), 7.13-7.06 (m, 1H), 4.99 (q, J=7.3 Hz, 1H), 3.43-3.34 (m, 2H), 2.01 (d, J=7.3 Hz, 3H), EL IC$_{50}$=6518 nM. Reference 4: LCMS=1.5 min using analytical method (B), 451.0 (M+H). $^1$H NMR (400 MHz, CD$_3$OD) δ 8.51-8.44 (m, 1H), 8.18-8.14 (m, 1H), 8.14-8.10 (m, 1H), 8.07-8.03 (m, 1H), 7.71-7.67 (m, 1H), 7.15-7.09 (m, 1H), 4.48 (s, 2H), 3.40-3.39 (m, 1H), 2.22 (s, 3H), EL IC$_{50}$=14880 nM.

What is claimed is:

1. A compound of Formula (I):

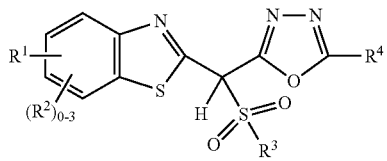

(I)

or a stereoisomer, a tautomer, or a pharmaceutically acceptable salt thereof, wherein:

$R^1$ is independently selected from: halogen, CN, —CO—$R^j$, —CONH—(CH$_2$)$_m$—$R^j$, phenyl substituted with 0-3 $R^a$, and a 5- to 6-membered heterocycle comprising carbon atoms and 1-4 heteroatoms selected from N, NR$^c$, O, and S(O)$_p$; wherein heterocycle is substituted with 0-3 $R^{a1}$;

$R^2$ is, independently at each occurrence, selected from: halogen, OH, C$_{1-4}$ alkyl, C$_{1-4}$ alkoxy, C$_{1-4}$ haloalkyl, C$_{1-4}$ haloalkoxy, CN, NH$_2$, NO$_2$, NH(C$_{1-4}$ alkyl), N(C$_{1-4}$ alkyl)$_2$, CO$_2$H, CO$_2$(C$_{1-4}$ alkyl), and CONH$_2$;

$R^3$ is independently selected from: C$_{1-6}$ alkyl substituted with 0-2 $R^7$, C$_{2-6}$ alkenyl, C$_{1-6}$ haloalkyl, C$_{1-6}$ alkoxy, —(CH$_2$)$_m$—(O)$_n$—(C$_{3-6}$ carbocycle substituted with 0-3 $R^b$), —(CH$_2$)$_m$—(O)$_n$-(5- to 6-membered heterocycle comprising carbon atoms and 1-4 heteroatoms selected from N, NR$^c$, O, and S(O)$_p$; wherein said heterocycle is substituted with 0-2 $R^b$);

$R^4$ independently selected from:

$R^5$ is independently selected from: CO$_2$(C$_{1-4}$ alkyl), NH$_2$, NH(C$_{1-4}$ alkyl), N(C$_{1-4}$ alkyl)$_2$, CONH$_2$, CONH(C$_{1-4}$ alkyl), CON(C$_{1-4}$ alkyl)$_2$, NHCOR$^8$, NHCONH(C$_{1-4}$ alkyl), SO$_2$R$^9$, NHSO$_2$NH$_2$, SO$_2$NHCO(C$_{1-4}$ alkyl), NHSO$_2$(C$_{1-4}$ alkyl), NHSO$_2$NHCO$_2$(C$_{1-4}$ alkyl), NHSO$_2$NHR$^j$, SO$_2$NHSO$_2$(C$_{1-4}$ haloalkyl), N(C$_{1-4}$ alkyl)SO$_2$NH$_2$, N(CO$_2$C$_{1-4}$ alkyl)SO$_2$(C$_{1-4}$ alkyl), CONH(C$_{3-6}$ cycloalkyl),

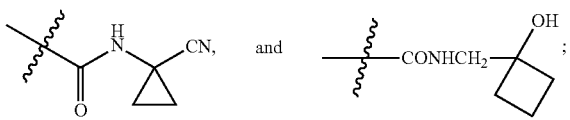

$R^6$ is independently selected from:

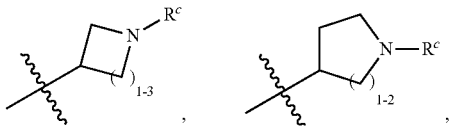

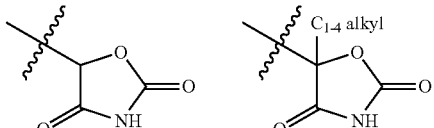

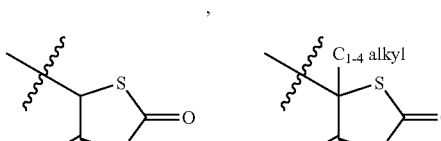

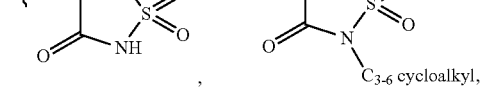

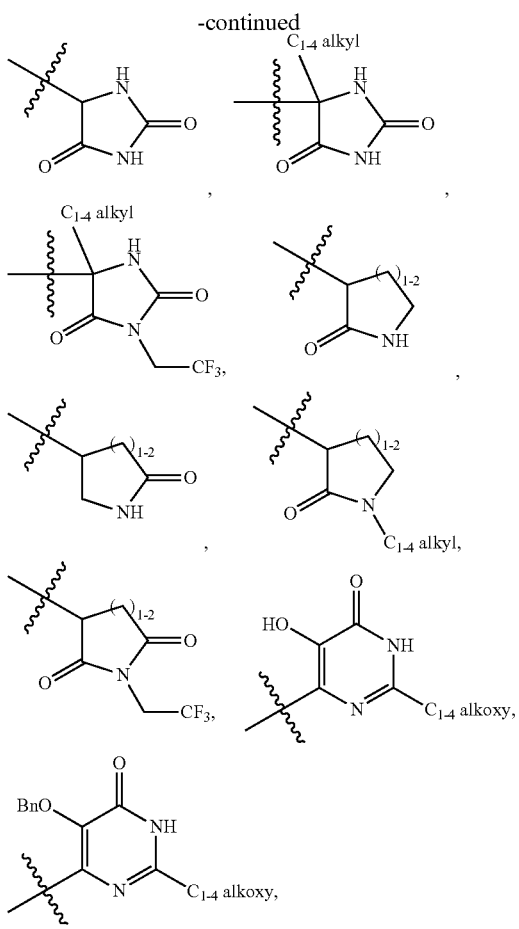

phenyl and a 5- to 6-membered heteroaryl comprising carbon atoms and 1-4 heteroatoms selected from N, $NR^c$, O, and $S(O)_p$; wherein said phenyl and heteroaryl are is substituted with 0-2 $R^{11}$;

$R^7$ is independently selected from: halogen, $C_{1-4}$ alkoxy, $C_{1-4}$ haloalkyl, $C_{1-4}$ haloalkoxy, $NH_2$, $CO_2H$, $CO_2(C_{1-4}$ alkyl), $SO_3H$, $CONHR^d$, $NHCONHR^d$, $NHCO_2R^d$,

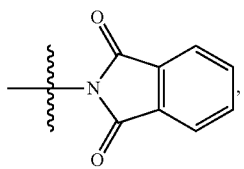 [SMILES: *N1C(=O)c2ccccc2C1=O]

and 5- to 6-membered heterocycle comprising carbon atoms and 1-4 heteroatoms selected from N, $NR^g$, O, and $S(O)_p$;

$R^8$ is, independently selected from: $C_{1-4}$ alkyl, $-(CH_2)_{0-3}C_{1-4}$ alkoxy, $-CH(OH)(C_{1-4}$ alkyl), $-CH(OCON(C_{1-4}$ alkyl$)_2)(C_{1-4}$ alkyl), and $-(CH_2)_{1-3}CH(OH)(C_{1-4}$ alkyl);

$R^9$ is independently selected from: OH, $C_{1-6}$ alkyl, $C_{2-6}$ alkenyl, $NH_2$, $NH(C_{1-6}$ alkyl), $NH(C_{2-6}$ alkenyl), $NH(C_{1-4}$ haloalkyl), NHPh, and phenyl substituted with 0-2 halogens;

$R^a$ is, independently at each occurrence, selected from: halogen, $C_{1-6}$ alkyl substituted with 0-1 $R^f$, $C_{1-4}$ alkoxy substituted with 0-1 $R^f$, $C_{1-6}$ haloalkyl, $C_{1-6}$ haloalkoxy, OH, CN, $NO_2$, $CO_2H$, $CO_2(C_{1-4}$ alkyl), $NR^gR^h$, $CONR^gR^h$, $CONR^gR^j$, $NHCOR^i$, $NHCO_2R^i$, $SO_2NR^gR^h$, $-(O)_n-(CH_2)_t-R^j$, and $-CO-R^j$;

$R^{a1}$ is, independently selected from: $=O$ and $R^a$;

$R^b$ is, independently at each occurrence, selected from: halogen, $C_{1-4}$ alkyl, $C_{1-4}$ alkoxy, $C_{1-4}$ haloalkyl, $C_{1-4}$ haloalkoxy, OH, CN, $NH_2$, $NO_2$, $NH(C_{1-4}$ alkyl), $N(C_{1-4}$ alkyl$)_2$, $CO_2H$, $CO_2(C_{1-4}$ alkyl), $SO_2(C_{1-4}$ alkyl), $SO_2NH_2$, $CONH_2$, and $CONH(C_{1-4}$ alkyl);

$R^c$ is, independently at each occurrence, selected from: H, $C_{1-6}$ alkyl substituted with 0-1 $R^e$, $CO(C_{1-4}$ alkyl), $CO_2(C_{1-4}$ alkyl), COBn, $CO_2Bn$, $-(CH_2)_t$-piperidinyl, $-(CH_2)_t$-morpholinyl, $-(CH_2)_t$-piperazinyl, pyrimidinyl and $-(CH_2)_t-(C_{3-6}$ carbocycle substituted with 0-2 $R^e$);

$R^d$ is, independently at each occurrence, selected from: $C_{1-6}$ alkyl and $-(CH_2)_t$-(phenyl substituted with 0-2 $R^e$);

$R^e$ is, independently at each occurrence, selected from: halogen, $C_{1-4}$ alkyl, $C_{1-4}$ alkoxy, $C_{1-4}$ haloalkyl, and $C_{1-4}$ haloalkoxy;

$R^f$ is, independently at each occurrence, selected from: OH, halogen, $C_{1-4}$ alkyl, $C_{1-4}$ alkoxy, $C_{1-4}$ haloalkyl, and $C_{1-4}$ haloalkoxy;

$R^g$ is, independently at each occurrence, selected from: H and $C_{1-4}$ alkyl;

$R^h$ is, independently at each occurrence, selected from: H, $C_{1-6}$ haloalkyl and $C_{1-6}$ alkyl substituted with 0-1 $R^f$;

$R^i$ is, independently at each occurrence, selected from: $C_{1-4}$ haloalkyl and $C_{1-4}$ alkyl substituted with 0-1 $R^f$;

$R^j$ is, independently at each occurrence: $C_{3-6}$ carbocycle or a 4- to 6-membered heterocycle comprising carbon atoms and 1-4 heteroatoms selected from N, $NR^g$, O, and $S(O)_p$; wherein said carbocycle and heterocycle are substituted with 0-2 $R^f$;

m and t are, independently at each occurrence, selected from 0, 1, 2, and 3;

n is, independently at each occurrence, selected from 0 and 1;

p is, independently at each occurrence, selected from 0, 1, and 2; and s is, independently at each occurrence, selected from 1, 2, and 3.

2. A compound according to claim 1, wherein the compound is of Formula (IIa) or (IIb):

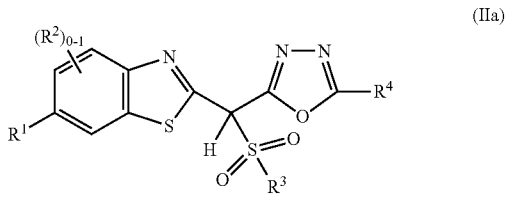

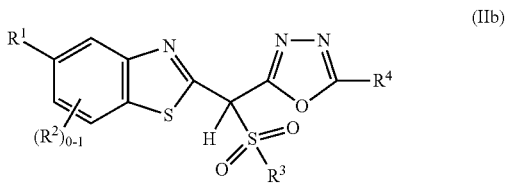

or a stereoisomer, a tautomer, or a pharmaceutically acceptable salt thereof, wherein:

$R^2$ is independently selected from: halogen, $C_{1-4}$ alkyl, $C_{1-4}$ alkoxy and $C_{1-4}$ haloalkyl.

3. A compound according to claim 1, wherein the compound is of Formula (IIIa) or (IIIb):

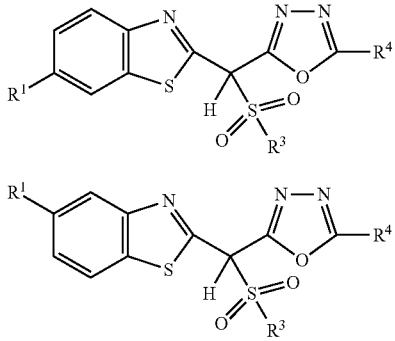

(IIIa)

(IIIb)

or a stereoisomer, a tautomer, or a pharmaceutically acceptable salt thereof.

4. A compound according to claim 3, wherein:

$R^1$ is independently selected from: phenyl substituted with 0-2 $R^a$, pyridyl substituted with 0-2 $R^a$, pyrimidinyl substituted with 0-2 $R^a$,

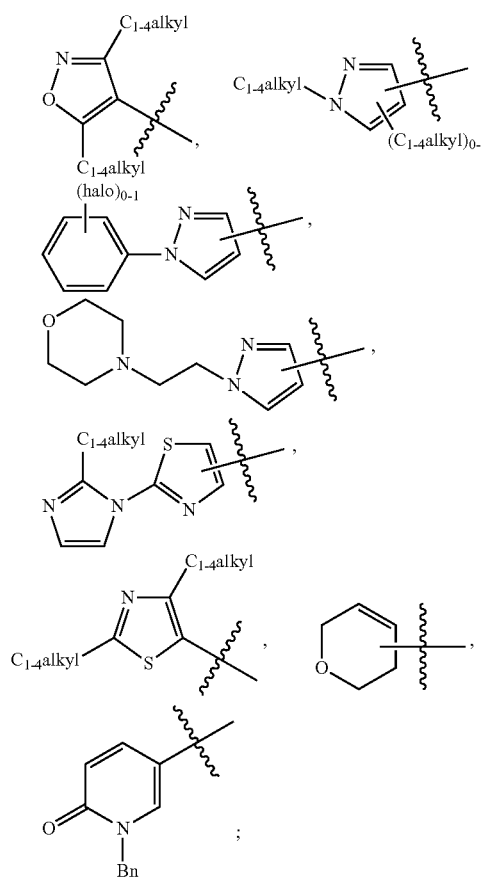

$R^3$ is independently selected from: $C_{1-4}$ alkyl substituted with 0-2 $R^7$, $C_{2-4}$ alkenyl, $C_{1-4}$ haloalkyl, —$(CH_2)_{0-1}$—($C_{3-6}$ cycloalkyl), —$(CH_2)_{0-3}$—$(O)_{0-1}$-(phenyl substituted with 0-2 $R^b$), —$(CH_2)_{0-3}$—$(O)_{0-1}$-(pyridyl substituted with 0-2 $R^b$),

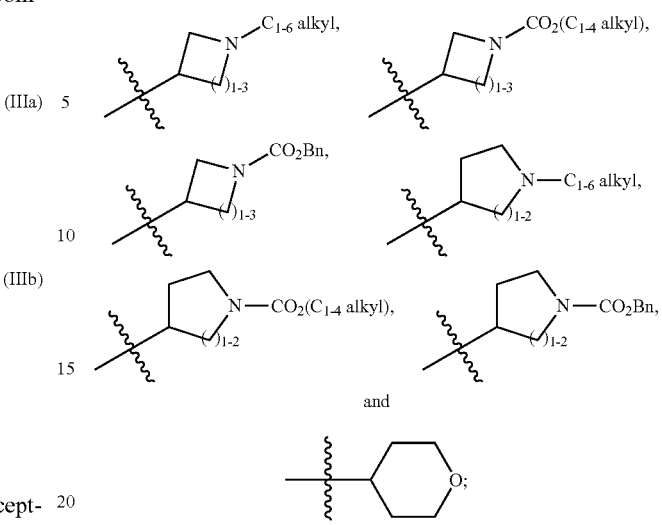

and $R^4$ independently selected from:

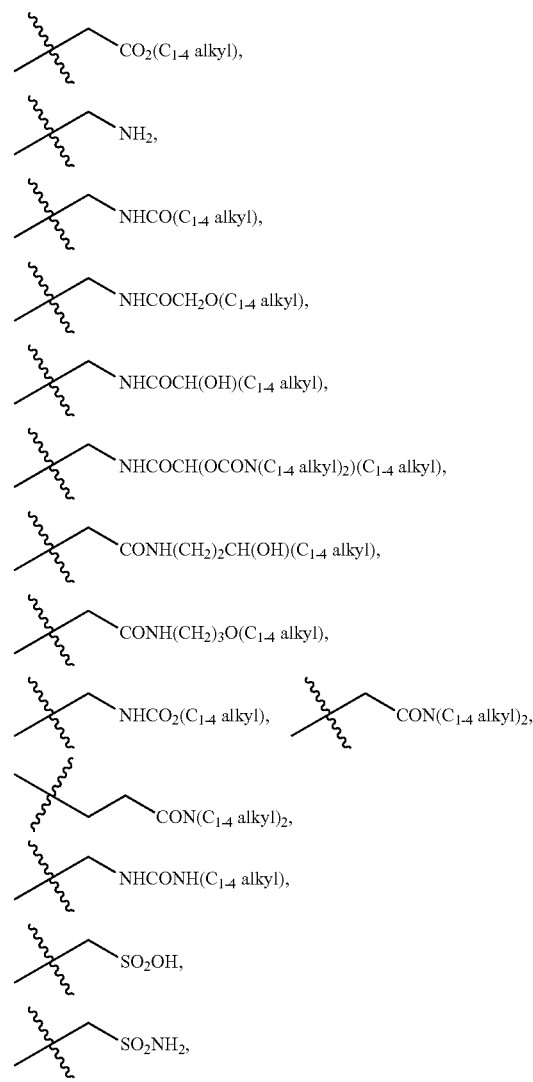

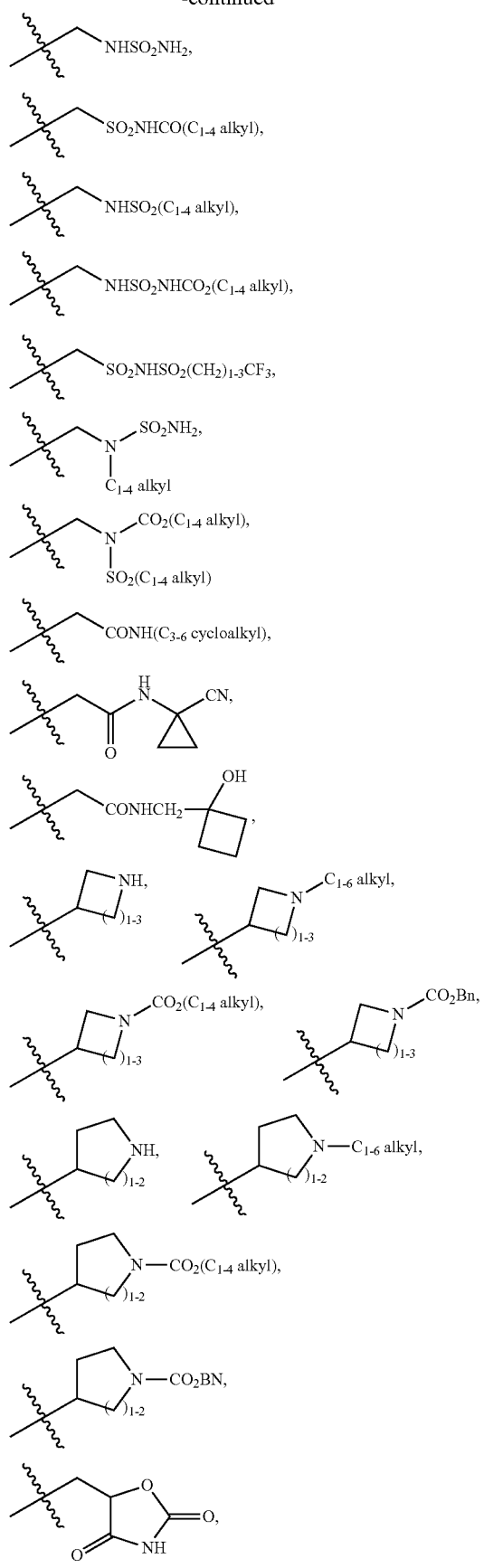
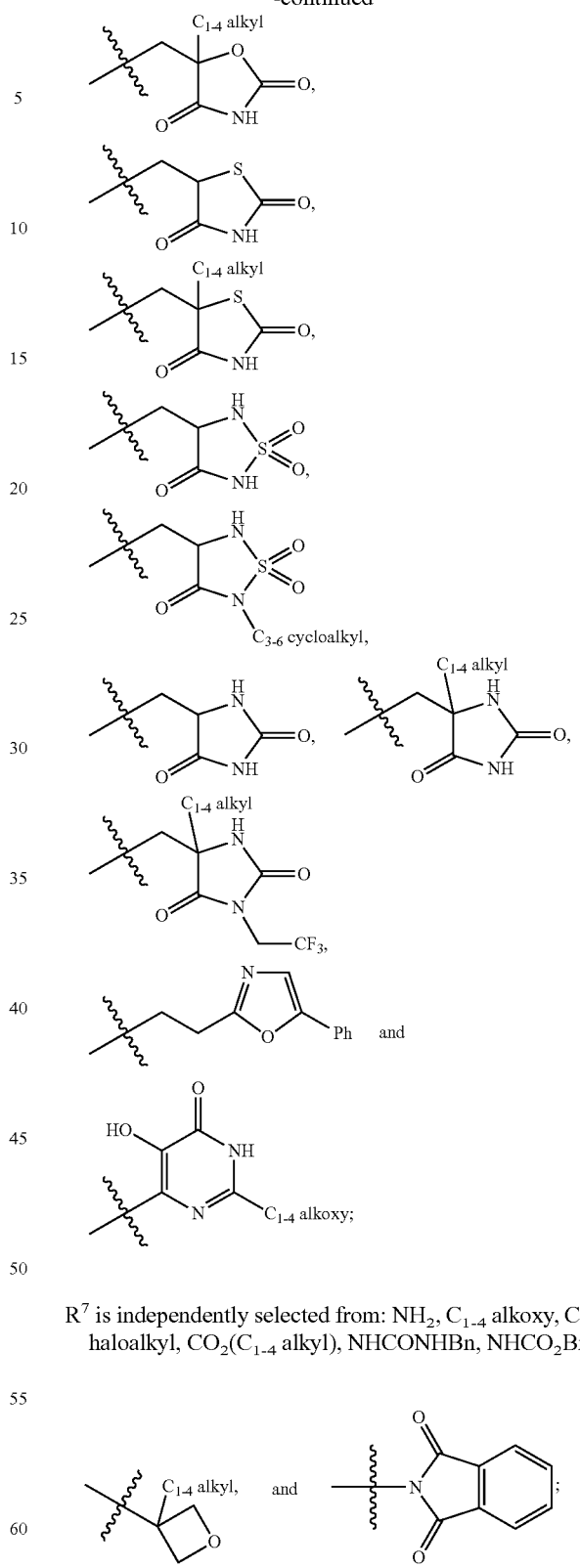
$R^7$ is independently selected from: $NH_2$, $C_{1-4}$ alkoxy, $C_{1-4}$ haloalkyl, $CO_2(C_{1-4}$ alkyl), $NHCONHBn$, $NHCO_2Bn$,
$R^a$ is, independently at each occurrence, selected from: OH, halogen, $C_{1-4}$ alkyl, $C_{1-4}$ alkoxy, $C_{1-4}$ haloalkyl, $CO_2H$, $CON(C_{1-4}$ alkyl$)_2$, $CONH(CH_2)_2OH$, $CONH(CH_2)_2O(C_{1-4}$ alkyl$)$, $CONH(C_{1-4}$ haloalkyl$)$, benzoxy,

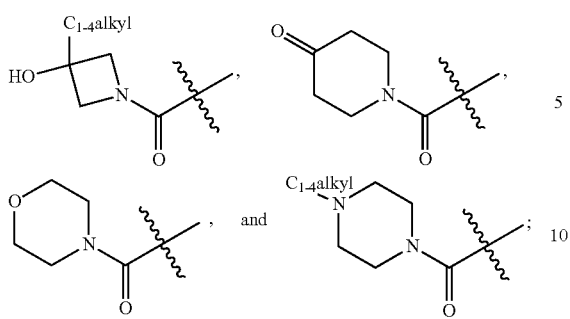

$R^b$ is independently selected from: halogen, $C_{1-4}$ alkyl, $C_{1-4}$ alkoxy, and $C_{1-4}$ haloalkyl.

5. A compound according to claim 4, wherein:

$R^1$ independently selected from: Ph, 3-halo-Ph, 4-halo-Ph, 4-$C_{1-4}$ haloalkyl-Ph, pyrimidinyl,

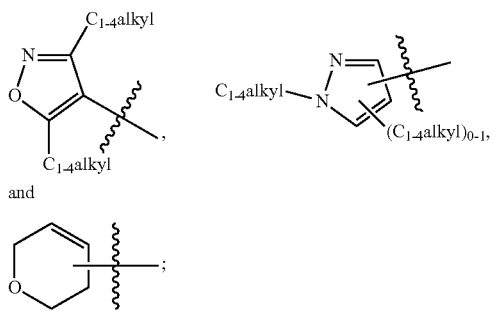

$R^3$ independently selected from: $C_{1-4}$ alkyl substituted with 0-2 $R^7$, $C_{2-4}$ alkenyl, —$(CH_2)_{0-3}$—$C_{3-6}$ cycloalkyl, —$(CH_2)_{1-3}$—$(O)_{0-1}$-(phenyl substituted with 0-2 $R^b$),

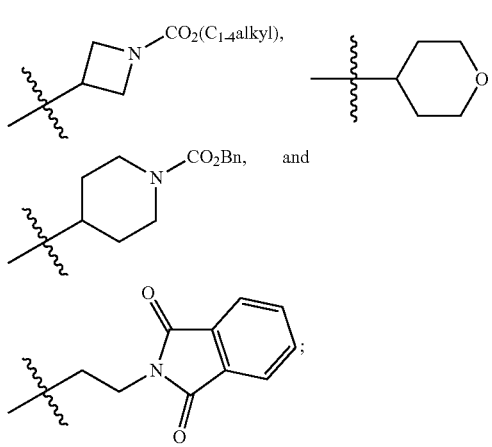

and $R^4$ is independently selected from:

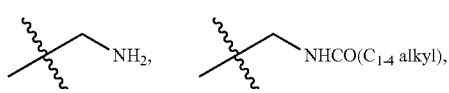

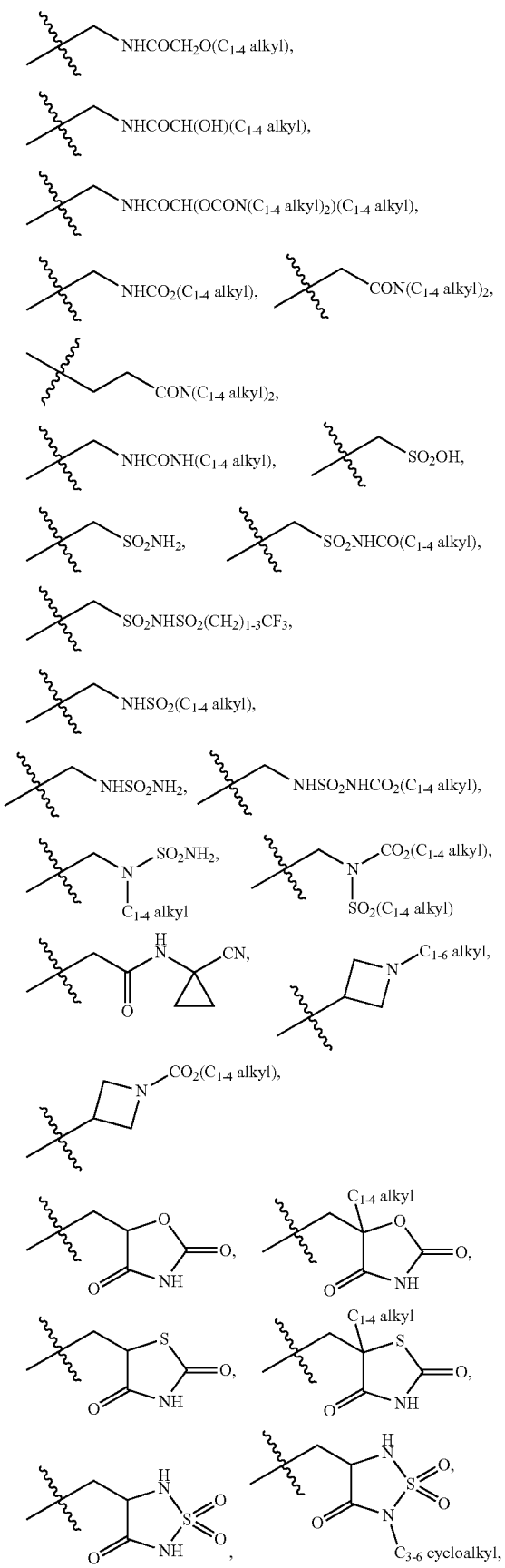

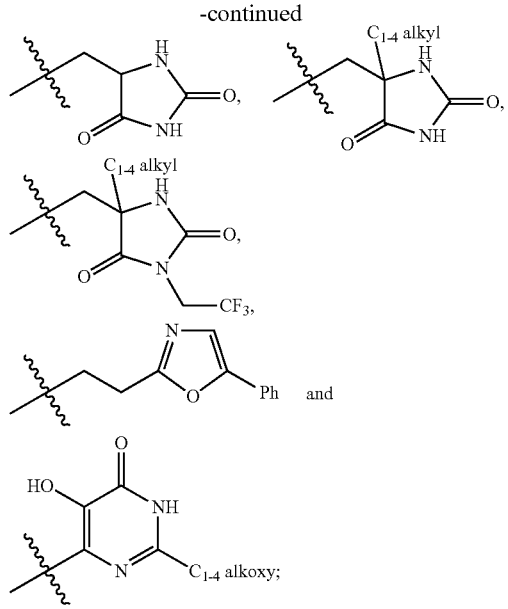

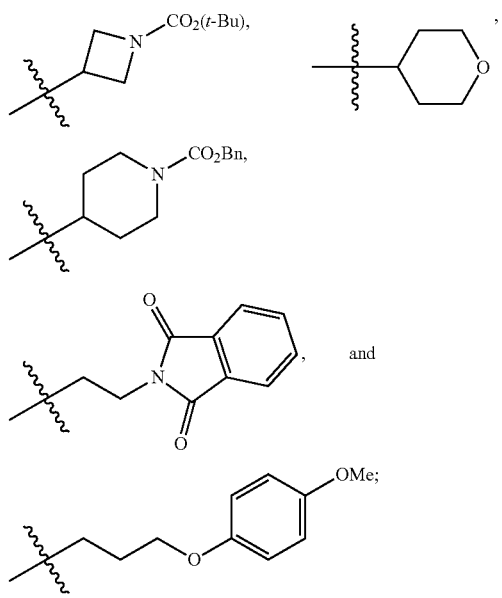

$R^b$ is independently selected from: halogen, $C_{1-4}$ alkyl, $C_{1-4}$ alkoxy, and $C_{1-4}$ haloalkyl; and $R^7$ is independently selected from: OH, $NH_2$, $C_{1-4}$ alkoxy, $C_{1-4}$ haloalkyl, $CO_2H$, $CO_2(C_{1-4}$ alkyl), and $NHCO_2Bn$.

6. A compound according to claim 5, wherein:

$R^1$ independently selected from: Ph, 4-F-Ph, 3-Cl-Ph, 4-Cl-Ph, 4-CF$_3$-Ph, pyrimidin-5-yl,

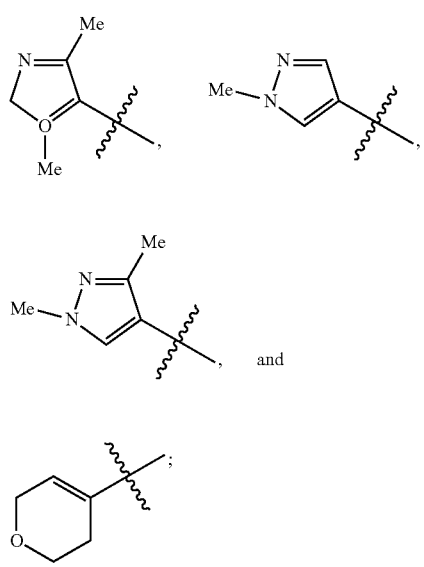

$R^3$ is independently selected from: Me, Et, Pr, i-Pr, i-Bu, —CH$_2$—CH=CH$_2$, —CH$_2$CH(OH)Me, —CH$_2$CH(OH)CH$_2$OH, —(CH$_2$)$_2$OMe, —(CH$_2$)$_{2-3}$CF$_3$, —(CH$_2$)$_2$NH$_2$, —(CH$_2$)$_2$CO$_2$H, —(CH$_2$)$_2$CO$_2$Me, —(CH$_2$)$_2$NHCO$_2$Bn, cyclopropyl, cyclopropylmethyl, cyclopentyl, cyclohexylmethyl, Bn, 2-Me-Bn, 3-Me-Bn, 2-F-Bn, 3-F-Bn, 4-F-Bn, 3-Cl-Bn, 4-Cl-Bn, 3-Br-Bn, 3-CF$_3$-Bn, 4-CF$_3$-Bn, 3,4-diCl-Bn, 3,5-diCl-Bn, 3-CF$_3$-5-CF$_3$-Bn, —CH$_2$CH$_2$CH$_2$Ph, $R^4$ is independently selected from:

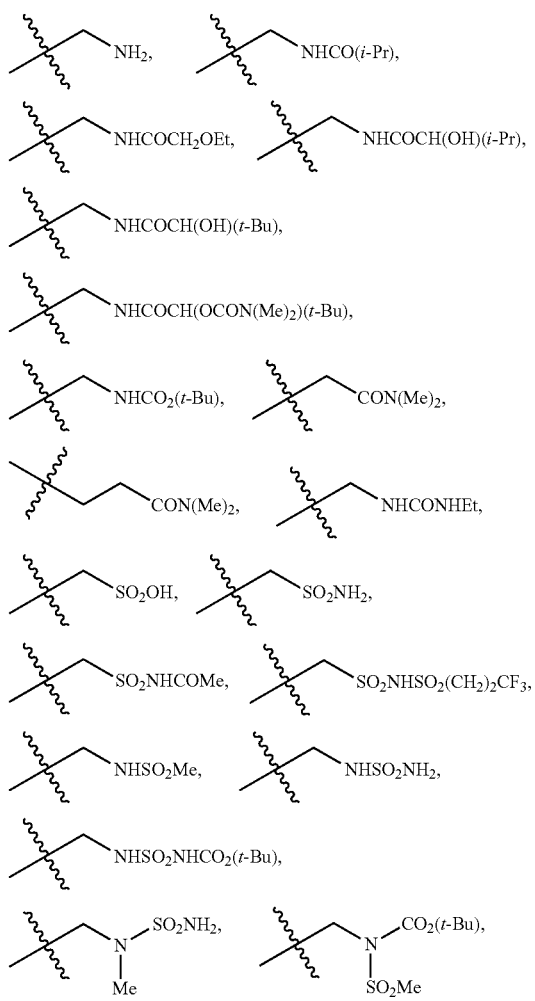

-continued

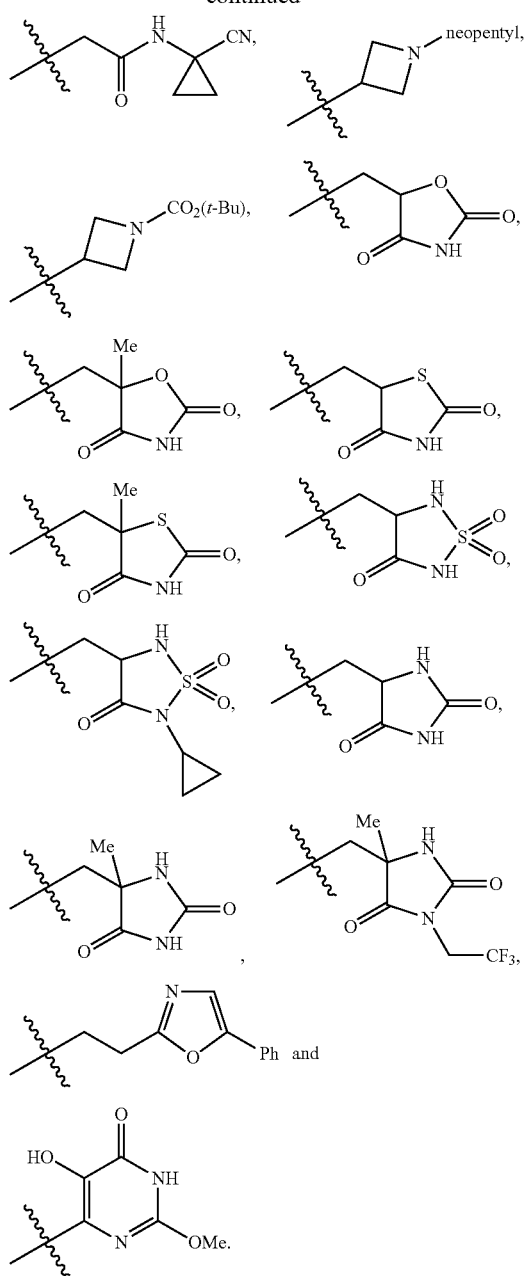

7. A compound according to claim 4, wherein:

R$^1$ is independently selected from: 3-CO$_2$H-Ph, 3-CONH(CH$_2$)$_2$OH-Ph, 3-CONH(CH$_2$)$_2$O(C$_{1-4}$ alkyl)-Ph, 3-halo-4-halo-Ph, 3-halo-5-halo-Ph, 3-halo-4-CON(C$_{1-4}$ alkyl)-2-Ph, 6-OH-pyrid-3-yl, 6-halo-pyrid-3-yl, 2-C$_{1-4}$ alkoxy-pyrid-4-yl, 2-halo-6-halo-pyrid-4-yl,

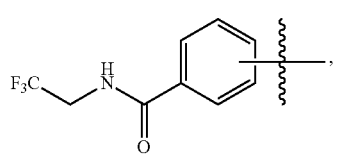

-continued

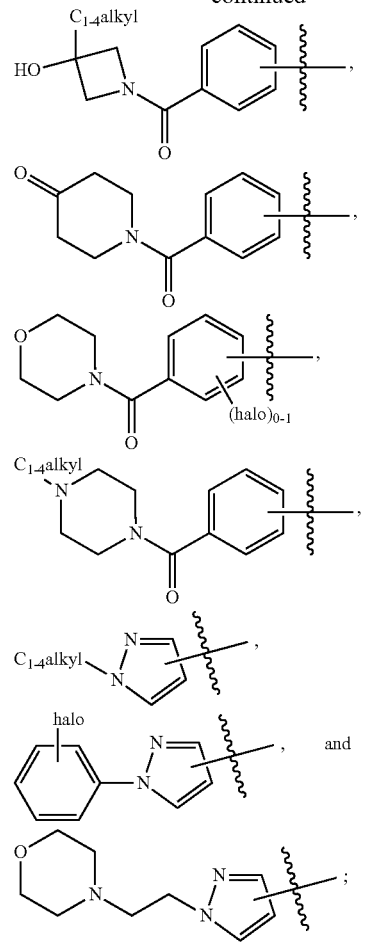

R$^3$ is independently selected from: C$_{1-4}$ alkyl substituted with 0-1 R$^7$, C$_{2-4}$ alkenyl, —CH$_2$—C$_{3-6}$ cycloalkyl, Bn, (6-halo-pyrid-3-yl)methyl, (6-CF$_3$-pyrid-3-yl)methyl, and

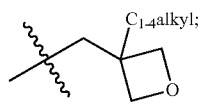

R$^4$ is independently selected from:

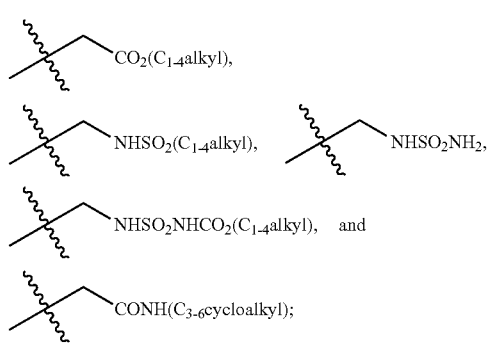

and

R$^7$ is independently selected from: NH$_2$, C$_{1-4}$ alkoxy, C$_{1-4}$ haloalkyl, and NHCO$_2$Bn.

8. A compound according to claim 7, wherein:

R$^1$ is independently selected from: 3-CO$_2$H-Ph, 3-CONH(CH$_2$)$_2$OH-Ph, 3-CONH(CH$_2$)$_2$OMe-Ph, 3-CONHCH$_2$CF$_3$-Ph, 3-F-4-Cl-Ph, 3-Cl-4-F-Ph, 3-Cl-4-Cl-Ph, 3-Cl-5-F-Ph, 3-Cl-5-Cl-Ph, 3-Cl-4-CON(Me)-2-Ph, 6-OH-pyrid-3-yl, 6-F-pyrid-3-yl, 2-OMe-pyrid-4-yl, 2,6-diF-pyrid-4-yl,

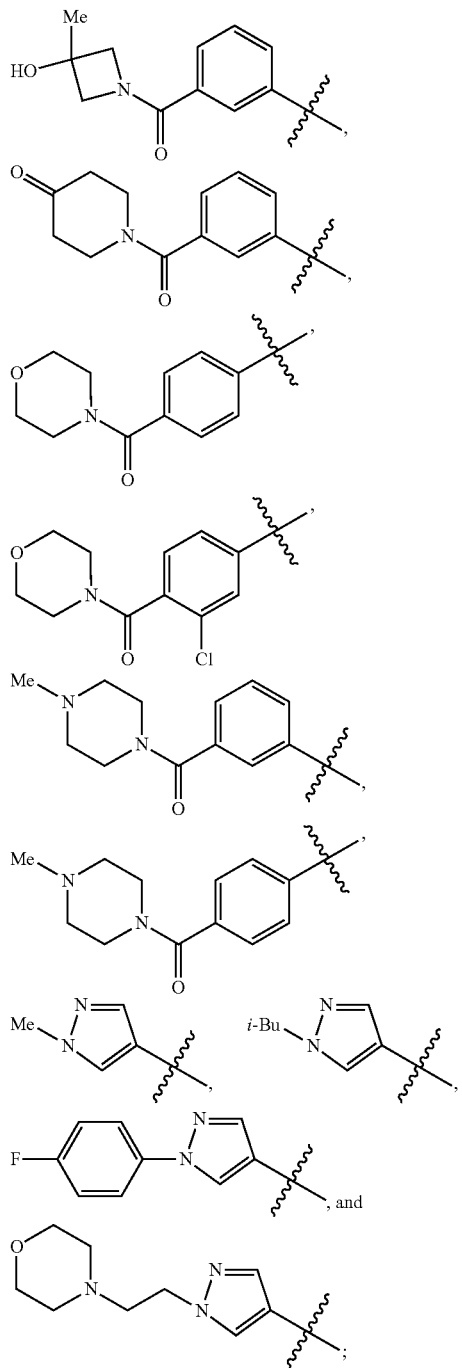

R$^3$ is independently selected from: Me, —CH$_2$—CH═CH$_2$, —(CH$_2$)$_2$OMe, —(CH$_2$)$_2$NH$_2$, —(CH$_2$)$_2$CF$_3$, —(CH$_2$)$_2$NHCO$_2$Bn, cyclopropylmethyl, Bn, (6-F-pyrid-3-yl)methyl, (6-CF$_3$-pyrid-3-yl)methyl,

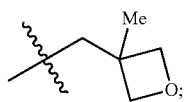 [SMILES: *CC1(C)COC1]

and

R$^4$ is independently selected from:

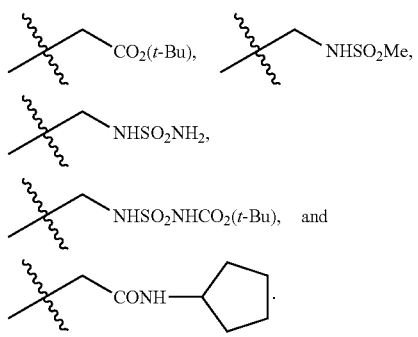

9. A compound according to claim 4, wherein:

R$^1$ is independently selected from: 4-OBn-Ph, 4-CO$_2$Bn-Ph, 2-halo-pyrid-4-yl, 6-halo-pyrid-3-yl, 2-CN-pyrid-4-yl, —CO-morpholinyl,

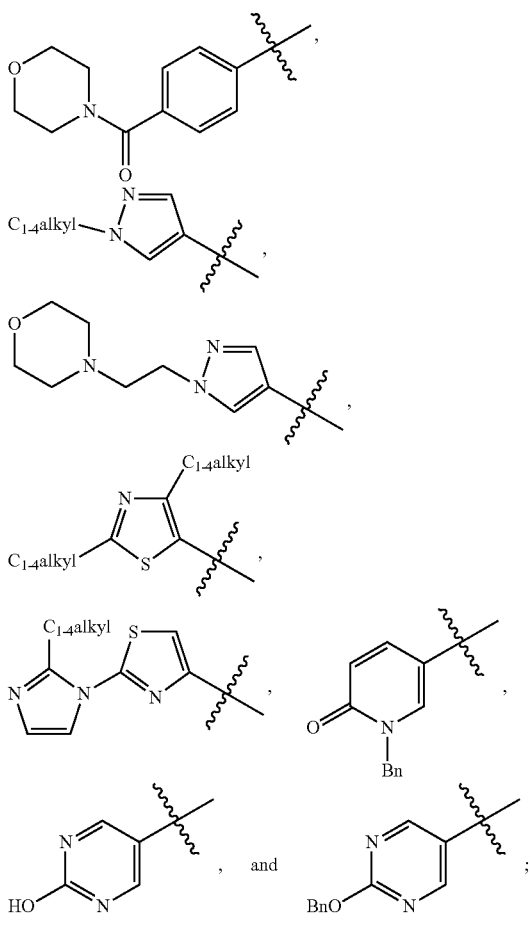

$R^3$ is independently selected from: $C_{1-4}$ alkyl substituted with 0-1 $R^7$, Bn and

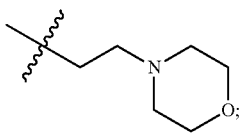 [SMILES: *CCN1CCOCC1]

$R^4$ is independently selected from:

 CONH(CH$_2$)$_{1-3}$CH(OH)(C$_{1-4}$alkyl),

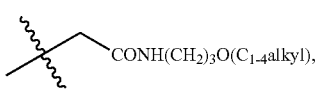 CONH(CH$_2$)$_3$O(C$_{1-4}$alkyl),

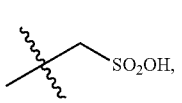 SO$_2$OH,  CONHCH$_2$—

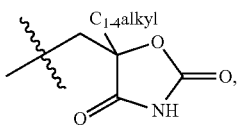 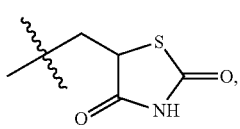

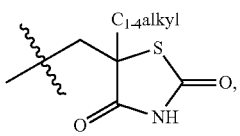 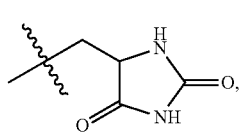

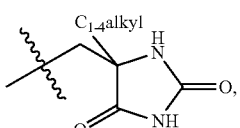 and

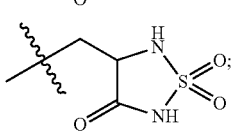

$R^7$ is independently selected from: NH$_2$ and C$_{1-4}$ haloalkyl.

10. A compound according to claim 9, wherein:

$R^1$ is independently selected from: 4-OBn-Ph, 4-CO$_2$Bn-Ph, 2-F-pyrid-4-yl, 6-F-pyrid-3-yl, 2-CN-pyrid-4-yl, —CO-morpholinyl,

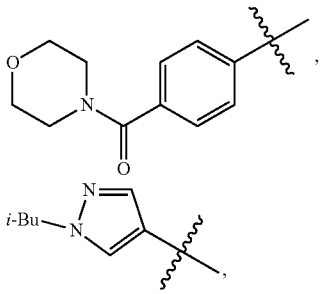

-continued

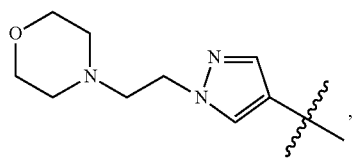

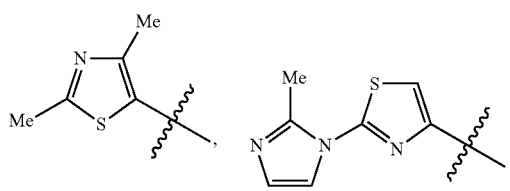

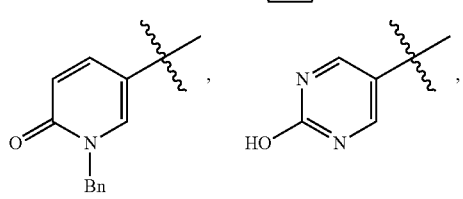

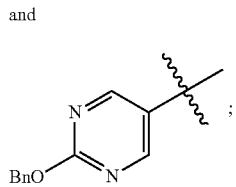

and

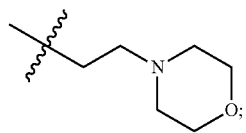 [SMILES: *CCN1CCOCC1]

$R^3$ is independently selected from: Me, —(CH$_2$)$_2$NH$_2$, —(CH$_2$)$_2$CF$_3$, Bn, and

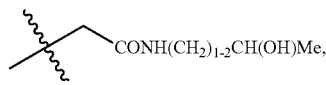

and $R^4$ is independently selected from:

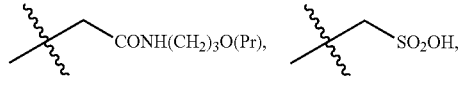 CONH(CH$_2$)$_{1-2}$CH(OH)Me,

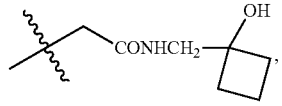 CONH(CH$_2$)$_3$O(Pr), SO$_2$OH,

CONHCH$_2$—

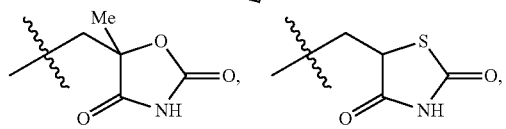

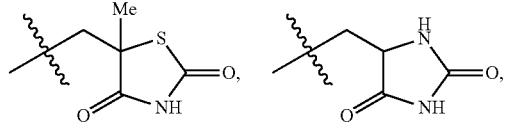

-continued
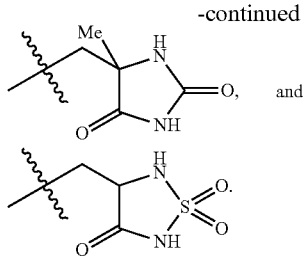
and
11. A compound selected from the exemplified examples 1-267 or a stereoisomer, a tautomer, or a pharmaceutically acceptable salt thereof.
12. A pharmaceutical composition, comprising a pharmaceutically acceptable carrier and a compound of claim 1, or a stereoisomer, a tautomer, or a pharmaceutically acceptable salt thereof.
* * * * *

UNITED STATES PATENT AND TRADEMARK OFFICE
CERTIFICATE OF CORRECTION

PATENT NO. : 8,680,090 B2
APPLICATION NO. : 13/936311
DATED : March 25, 2014
INVENTOR(S) : James A. Johnson et al.

It is certified that error appears in the above-identified patent and that said Letters Patent is hereby corrected as shown below:

On the Title Page

Page 2 Column 1 Item (56)
Line 23, "Glycylaminobenzoyloxyrnethyl" should read -- Glycylaminobenzoyloxymethyl --; and
Line 25, "carboxlyic" should read -- carboxylic --.

Page 2 Column 2 Item (56)
Line 18, "[44-" should read -- [4- --; and
Line 19, "dihydropyridina" should read -- dihydropyridin --.

In the Claims

Column 283
Lines 58, "($C_{1-4}$ alkyl)-2-Ph," should read -- ($C_{1-4}$ alkyl)$_2$-Ph, --.

Column 285
Lines 5-6, "3-Cl-4-CON(Me)-2-Ph," should read -- 3-Cl-4-CON(Me)$_2$-Ph, --.

Column 289
Line 12-13, "the exemplified examples 1-267" should read -- examples 1-267, --.

Signed and Sealed this
Fourteenth Day of October, 2014

Michelle K. Lee
*Deputy Director of the United States Patent and Trademark Office*